(12) United States Patent  
Prakash et al.

(10) Patent No.: US 11,584,769 B2  
(45) Date of Patent: Feb. 21, 2023

(54) DITERPENE GLYCOSIDES, COMPOSITIONS AND PURIFICATION METHODS

(71) Applicant: The Coca-Cola Company, Atlanta, GA (US)

(72) Inventors: Indra Prakash, Alpharetta, GA (US); Cynthia Bunders, Minneapolis, MN (US)

(73) Assignee: The Coca-Cola Company, Atlanta, GA (US)

( * ) Notice: Subject to any disclaimer, the term of this patent is extended or adjusted under 35 U.S.C. 154(b) by 1055 days.

(21) Appl. No.: 15/529,349

(22) PCT Filed: Nov. 30, 2015

(86) PCT No.: PCT/US2015/062963  
§ 371 (c)(1),  
(2) Date: May 24, 2017

(87) PCT Pub. No.: WO2016/086233  
PCT Pub. Date: Jun. 2, 2016

(65) Prior Publication Data  
US 2017/0275325 A1    Sep. 28, 2017

Related U.S. Application Data

(60) Provisional application No. 62/138,103, filed on Mar. 25, 2015, provisional application No. 62/085,513, filed on Nov. 29, 2014.

(51) Int. Cl.  
*C07H 15/256* (2006.01)  
*A23L 2/60* (2006.01)  
*A23L 27/30* (2016.01)  
*A23L 27/00* (2016.01)  
*A23L 2/56* (2006.01)

(52) U.S. Cl.  
CPC .............. *C07H 15/256* (2013.01); *A23L 2/56* (2013.01); *A23L 2/60* (2013.01); *A23L 27/36* (2016.08); *A23L 27/88* (2016.08); *A23V 2002/00* (2013.01)

(58) Field of Classification Search  
CPC ....... C07H 15/256; A23L 27/88; A23L 27/36; A23L 2/56; A23L 2/60; A23V 2002/00  
USPC .................................................. 426/590, 548  
See application file for complete search history.

(56) References Cited

U.S. PATENT DOCUMENTS

| | | | |
|---|---|---|---|
| 4,361,697 A † | 11/1982 | Dobberstein | |
| 4,612,942 A † | 9/1986 | Dobberstein | |
| 2007/0082106 A1 | 4/2007 | Lee et al. | |
| 2007/0029258 A1 | 12/2007 | Prakash et al. | |
| 2007/0292582 A1 | 12/2007 | Prakash et al. | |
| 2011/0183056 A1 | 7/2011 | Morita et al. | |
| 2014/0171519 A1 | 6/2014 | Prakash et al. | |
| 2014/0227421 A1† | 8/2014 | Markosyan | |

FOREIGN PATENT DOCUMENTS

| | | |
|---|---|---|
| WO | 2012/129451 A1 † | 9/2012 |
| WO | WO 2014/146135 | 9/2014 |
| WO | WO 2014/172055 | 10/2014 |

OTHER PUBLICATIONS

Extended European Search Report for EP 15864043.3, dated Jun. 20, 2018.  
Mizutani, et al., Study on Improvement of Sweetness of Steviol Bioglycosides Selective Enzymic Transglucosylation of the 13-O-Glycosyl Moiety, Agric. Biol. Chem., vol. 53, No. 2, Jan. 1, 1989, pp. 395-398.  
Prakash, et al., "Development of Next Generation Stevia Sweetener: Rebaudioside M", Foods, vol. 3., No. 1, Feb. 27, 2004, pp. 162-175.  
International Search Report for PCT/US2015/062963, dated Feb. 4, 2016.  
Clinton C. Shock, "Rebaudi's stevia: natural noncaloric sweetener", California Agriculture, 1982, 36(9), pp. 4-5.

† cited by third party

*Primary Examiner* — Leslie A Wong  
(74) *Attorney, Agent, or Firm* — King & Spalding

(57) ABSTRACT

Novel diterpene glycosides and methods for purifying the same are provided herein. In addition, compositions comprising the novel diterpene glycosides, as well as methods of using the diterpene glycosides are provided.

7 Claims, 65 Drawing Sheets

= $^1$H-$^{13}$C HMBC correlations
= $^1$H-$^1$H COSY correlations $^1H$-$^{13}C$ HMBC Correlations $^1H$-$^1H$ COSY Correlations ↷ $^1H$-$^{13}C$ HMBC Correlations
↔ $^1H$-$^1H$ COSY Correlations = $^1$H-$^{13}$C HMBC correlations
= $^1$H-$^1$H COSY correlations

DITERPENE GLYCOSIDES, COMPOSITIONS AND PURIFICATION METHODS

CROSS REFERENCE TO RELATED APPLICATIONS

This application is a national phase application under 35 U.S.C. § 371 of International Application No. PCT/US2015/062963, filed on Nov. 30, 2015, which claims priority to U.S. Provisional Patent Application No. 62/085,513, filed Nov. 29, 2014 and U.S. Provisional Patent Application No. 62/138,103, filed Mar. 25, 2015. The content of each of the above-identified applications is hereby fully incorporated herein by reference.

FIELD OF THE INVENTION

The present invention relates generally to novel diterpene glycosides, compositions (e.g., consumables) comprising said novel diterpene glycosides, and methods for their purification.

BACKGROUND OF THE INVENTION

Natural caloric sugars, such as sucrose, fructose and glucose, are utilized to provide a pleasant taste to beverages, foods, pharmaceuticals, and oral hygienic/cosmetic products. Sucrose, in particular, imparts a taste preferred by consumers. Although sucrose provides superior sweetness characteristics, it is disadvantageously caloric.

Non-caloric or low caloric sweeteners have been introduced to satisfy consumer demand. However, non- and low caloric sweeteners taste different from natural caloric sugars in ways that frustrate consumers. On a taste basis, non-caloric or low caloric sweeteners exhibit a temporal profile, maximal response, flavor profile, mouth feel, and/or adaptation behavior that differ from sugar. Specifically, non-caloric or low caloric sweeteners exhibit delayed sweetness onset, lingering sweet aftertaste, bitter taste, metallic taste, astringent taste, cooling taste and/or licorice-like taste. On a source basis, many non-caloric or low caloric sweeteners are synthetic sweeteners. Consumer desire for natural non-caloric or low caloric sweeteners that tastes like sucrose remains high.

Stevia rebaudiana Bertoni is a perennial shrub of the Asteraceae (Compositae) family native to certain regions of South America. Its leaves have been traditionally used for hundreds of years in Paraguay and Brazil to sweeten local teas and medicines. The plant is commercially cultivated in Japan, Singapore, Taiwan, Malaysia, South Korea, China, Israel, India, Brazil, Australia and Paraguay.

The leaves of the plant contain a mixture containing diterpene glycosides in an amount ranging from about 10% to 15% of the total dry weight. These diterpene glycosides are about 30 to 450 times sweeter than sugar. Structurally, the diterpene glycosides are characterized by a single base, steviol, and differ by the presence of carbohydrate residues at positions C13 and C19. Typically, on a dry weight basis, the four major steviol glycosides found in the leaves of Stevia are dulcoside A (0.3%), rebaudioside C (0.6-1.0%), rebaudioside A (3.8%) and stevioside (9.1%). Other glycosides identified in Stevia extract include rebaudioside B, D, E, and F, steviolbioside and rubusoside. Among these, only stevioside and rebaudioside A are available on a commercial scale.

The use of steviol glycosides has been limited to date by certain undesirable taste properties, including licorice taste, bitterness, astringency, sweet aftertaste, bitter aftertaste, licorice aftertaste, and become more prominent with increase of concentration. These undesirable taste attributes are particularly prominent in carbonated beverages, where full replacement of sugar requires concentrations of steviol glycosides that exceed 600 mg/L. Use of steviol glycosides in such high concentrations results in significant deterioration in the final product taste.

Accordingly, there remains a need to develop natural reduced or non-caloric sweeteners that provide a temporal and flavor profile similar to the temporal and flavor profile of sucrose.

There remains a further need for methods for purifying glycosides from Stevia.

SUMMARY OF THE INVENTION

The present invention relates generally to novel diterpene glycosides and compositions (e.g., consumables) comprising said novel diterpene glycosides, as well as methods for purifying said novel diterpene glycosides, methods for preparing compositions (e.g., consumables) comprising said novel diterpene glycosides and methods for enhancing the flavor or sweetness of consumables using the novel diterpene glycosides.

In one aspect, the present invention provides a diterpene glycoside of formula (A):

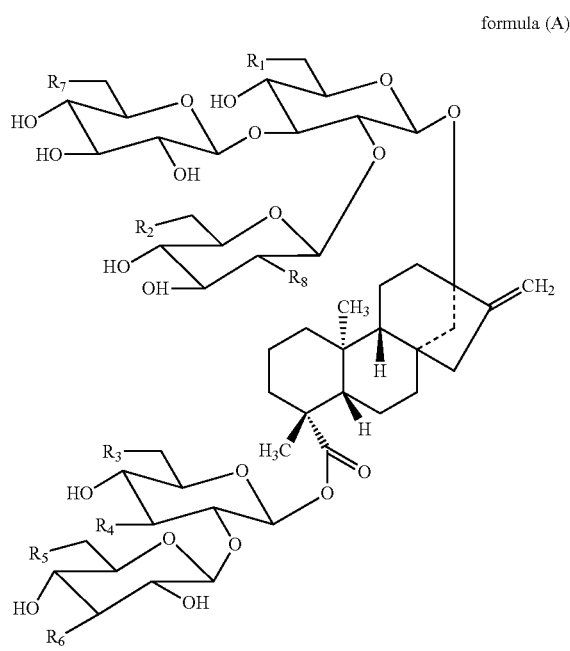

formula (A)

wherein:

$R_1$, $R_2$, $R_3$, $R_5$, $R_6$, $R_7$ and $R_8$ are each independently selected from hydroxyl, an O-linked saccharide and an O-linked oligosaccharide comprising at least two saccharides;

$R_4$ is selected from hydroxyl and an O-linked saccharide; and the diterpene glycoside has at least seven saccharides.

In a particular embodiment, the diterpene glycoside has from seven to twelve saccharides, such as, seven, eight, nine, ten, eleven or twelve saccharides.

In a particular embodiment, the diterpene glycoside of the formulae described herein is isolated and purified.

In some embodiments, a diterpene glycoside of the formulae described herein is sweet. In some embodiments, the diterpene glycoside has a sweetness level of at least about 5 degrees Brix, or at least about 10 degrees Brix.

In a further aspect, the present invention is a composition comprising a diterpene glycoside of the formulae described herein.

In one embodiment, the present invention is a sweetener composition comprising a diterpene glycoside of the formulae described herein.

In another embodiment, the present invention is a flavor enhancing composition comprising a diterpene glycoside of the formulae described herein, wherein the diterpene glycoside is present in the composition in an amount effective to provide a concentration at or below the flavor recognition threshold of the diterpene glycoside when the flavor enhancing composition is added to a consumable.

In yet another embodiment, the present invention is a sweetness enhancing composition comprising a diterpene glycoside of the formulae described herein, wherein the diterpene glycoside is present in the composition in an amount effective to provide a concentration at or below the sweetness recognition threshold of the diterpene glycoside when the sweetness enhancing composition is added to a consumable.

In yet another embodiment, the present invention is a consumable comprising a diterpene glycoside of the formulae described herein. Suitable consumables include, but are not limited to, liquid-based or dry consumables, such as, for example, pharmaceutical compositions, edible gel mixes and compositions, dental compositions, foodstuffs, beverages and beverage products.

In a particular embodiment, the present invention is a beverage comprising a diterpene glycoside of the formulae described herein. In a particular embodiment, a diterpene glycoside of the formulae described herein is present in the beverage at a concentration that is above, at or below the threshold sweetness recognition concentration of the diterpene glycoside.

In another particular embodiment, the present invention is a beverage product comprising a diterpene glycoside of the formulae described herein. In a particular embodiment, the diterpene glycoside is present in the beverage product at a concentration that is above, at or below the threshold flavor recognition concentration of the diterpene glycoside.

In another aspect, the present invention is a method of preparing a consumable comprising (i) providing a consumable matrix and (ii) adding a diterpene glycoside of the formulae described herein to the consumable matrix to provide a consumable.

In a particular embodiment, the present invention is a method of preparing a beverage comprising (i) providing a beverage matrix and (ii) adding a diterpene glycoside of the formulae described herein to the beverage matrix to provide a beverage.

In another aspect, the present invention is a method of enhancing the sweetness of a consumable comprising (i) providing a consumable comprising at least one sweet ingredient and (ii) adding a diterpene glycoside of the formulae described herein to the consumable to provide a consumable with enhanced sweetness, wherein the diterpene glycoside is present in the consumable with enhanced sweetness at a concentration at or below the sweetness recognition threshold of the diterpene glycoside. In a particular embodiment, the consumable is a beverage. In certain embodiments, the compound is added in the form of a composition comprising a diterpene glycoside, as described herein.

In a further aspect, the present invention is a method of enhancing the flavor of a consumable comprising (i) providing a consumable comprising at least one flavor ingredient and (ii) adding a diterpene glycoside of the formulae described herein to the consumable to provide a consumable with enhanced flavor, wherein the diterpene glycoside is present in the consumable with enhanced flavor at a concentration at or below the flavor recognition threshold of the diterpene glycoside. In a particular embodiment, the consumable is a beverage. In certain embodiments, the compound is added in the form of a composition comprising a diterpene glycoside, as described herein.

In some embodiments, the compositions of the present invention comprise one or more sweeteners. In one embodiment, the sweetener is a natural sweetener or a synthetic sweetener. In a particular embodiment, the sweetener is a high intensity sweetener. In a particular embodiment, the sweetener is a high intensity natural sweetener.

In some embodiments, the compositions of the present invention comprise one or more additives. In a particular embodiment, the additive is selected from the group consisting of carbohydrates, polyols, amino acids and their corresponding salts, poly-amino acids and their corresponding salts, sugar acids and their corresponding salts, nucleotides, organic acids, inorganic acids, organic salts including organic acid salts and organic base salts, inorganic salts, bitter compounds, flavorants and flavoring ingredients, astringent compounds, proteins or protein hydrolysates, surfactants, emulsifiers, flavonoids, alcohols, polymers and combinations thereof.

In some embodiments, the compositions of the present invention comprise one or more functional ingredients. In a particular embodiment, the functional ingredient is selected from the group consisting of saponins, antioxidants, dietary fiber sources, fatty acids, vitamins, glucosamine, minerals, preservatives, hydration agents, probiotics, prebiotics, weight management agents, osteoporosis management agents, phytoestrogens, long chain primary aliphatic saturated alcohols, phytosterols and combinations thereof.

In one embodiment, the present invention is a consumable comprising at least one diterpene glycoside of the present invention and one or more sweeteners, additives and/or functional ingredients. In another embodiment, the present invention is a beverage comprising at least one diterpene glycoside of formula of the present invention and one or more sweeteners, additives and/or functional ingredients In one aspect, the present invention is a method for purifying a diterpene glycoside of the present invention comprising (i) passing a solution comprising a source material comprising a diterpene glycoside of the formulae described herein through a HPLC column and (ii) eluting fractions comprising the diterpene glycoside of the formulae described herein to provide a purified diterpene glycoside of the formulae described herein. The method provides a purified diterpene glycoside of the formulae described herein in a purity greater than about 50% by weight on a dry basis.

The HPLC column can be preparative or semi-preparative. The fractions comprising the diterpene glycoside of interest may be eluted by adding an appropriate eluent. The method may optionally comprise additional steps, such as partial or substantially full removal of solvents and/or further purification steps, e.g. extraction, crystallization, chromatography and distillation.

In still other embodiments, the source material can be one fraction, or multiple fractions, containing the diterpene glycoside of interest collected from a previous method or HPLC protocol. The material isolated can be subjected to further methods 2, 3, 4 or more times, each time providing a higher level of purity of the diterpene glycoside. The second and subsequent methods may have different HPLC protocols and different steps following elution.

DETAILED DESCRIPTION OF THE INVENTION

I. Compounds

Figure 1:
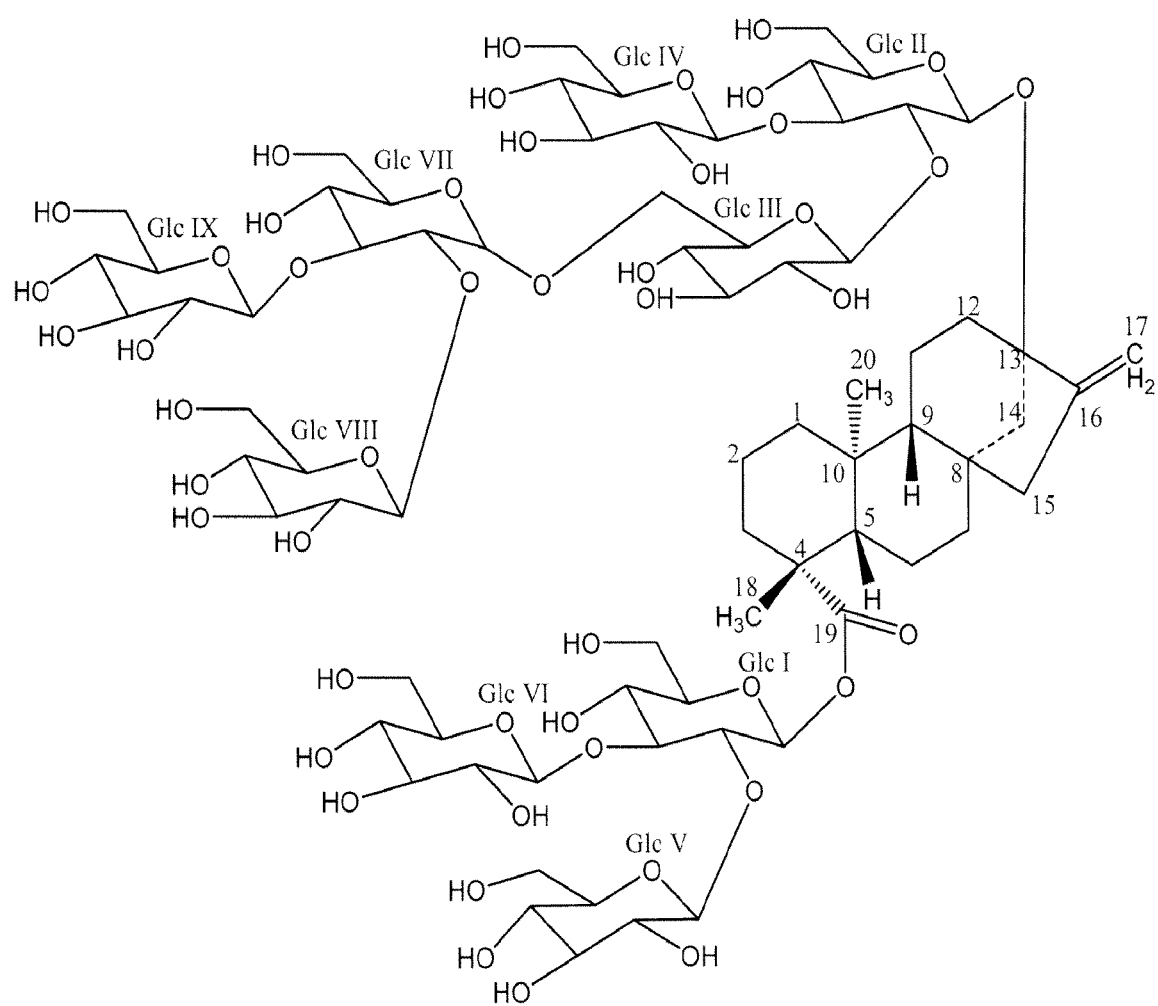
FIG. 1: Shows the structure of diterpene glycoside 1, i.e. (13-[(2-O-(6-O-α-D-glucopyranosyl-(2-O-β-D-glucopyranosyl-3-O-β-D-glucopyranosyl)-β-D-glucopyranosyl-3-O-β-D-glucopyranosyl)-β-D-glucopyranosyl)oxy] ent-kaur-16-en-19-oic acid-[(2-O-β-D-glucopyranosyl-3-O-β-D-glucopyranosyl-β-D-glucopyranosyl) ester].

In one embodiment, the present invention provides a diterpene glycoside of formula (A):

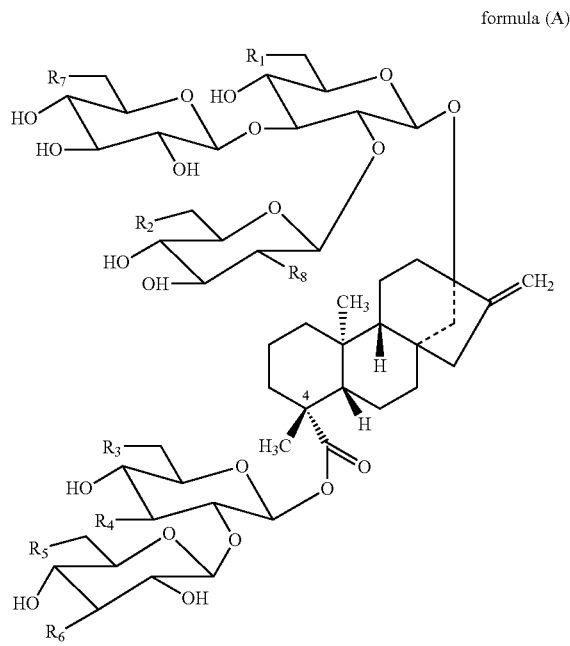

formula (A)

wherein:

$R_1$, $R_2$, $R_3$, $R_5$, $R_6$, $R_7$ and $R_8$ are each independently selected from hydroxyl, an O-linked saccharide and an O-linked oligosaccharide comprising at least two saccharides;

$R_4$ is selected from hydroxyl and an O-linked saccharide; and the diterpene glycoside has at least seven saccharides.

Not wishing to be bound by theory, in certain embodiments it has been found that the number of saccharides at the C4 position of the diterpene glycoside (i.e. the "bottom" portion) influences the compound's negative taste properties (e.g. linger, licorice and bitterness). In particular, it has been found that more than four saccharides at the C4 position, and particularly between six and nine saccharides, maximally reduces the above-referenced negative taste properties.

Not wishing to be bound by theory, in certain embodiments it has been found that perceived sweetness decreases when $R_1$, $R_7$ and $R_8$ are hydroxyl.

The O-linked oligosaccharide comprises at least two saccharides, preferably at least three saccharides. Saccharides include, but are not limited to, glucose, rhamnose, xylose and combinations thereof. The linkages between the saccharides can be α- or β.

In one particular embodiment, the diterpene glycoside has at least seven saccharides. In another particular embodiment, the diterpene glycoside has at least eight saccharides. In still another particular embodiment, the diterpene glycoside has at least nine saccharides. In yet another embodiment, the diterpene glycoside has at least ten saccharides. In a still further embodiment, the diterpene glycoside has at least eleven saccharides. In a further embodiment, the diterpene glycoside has at least twelve saccharides.

In one particular embodiment, the diterpene glycoside has seven saccharides. In another particular embodiment, the diterpene glycoside has eight saccharides. In still another particular embodiment, the diterpene glycoside has nine saccharides. In yet another embodiment, the diterpene glycoside has ten saccharides. In a still further embodiment, the diterpene glycoside has eleven saccharides. In a further embodiment, the diterpene glycoside has twelve saccharides.

In one particular embodiment, the diterpene glycoside has from seven to twelve saccharides, such as, for example, from eight to twelve, from nine to twelve, from ten to twelve or from eleven to twelve. In another particular embodiment, the diterpene glycoside has from eight to twelve saccharides, such as, for example, from eight to twelve, from nine to twelve, from ten to twelve or from eleven to twelve. In still another particular embodiment, the diterpene glycoside has from nine to twelve saccharides, such as, for example, from nine to ten, from nine to eleven or nine to twelve saccharides.

In one embodiment, $R_1$, $R_2$, $R_7$ and $R_8$ are hydroxyl, and $R_4$ is O-glucose, such that the diterpene glycoside belongs to formula (A'):

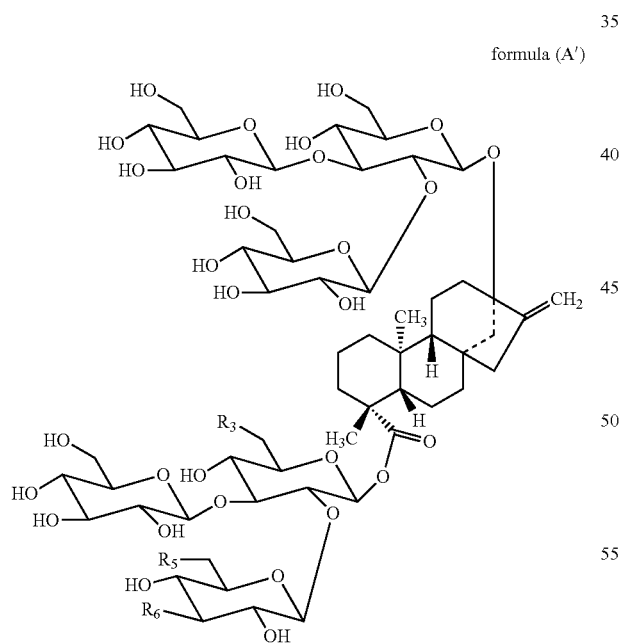

formula (A')

wherein $R_3$, $R_5$ and $R_6$ are each independently selected from hydroxyl and an O-linked oligosaccharide comprising from three to six saccharides, and the diterpene glycoside has at least nine saccharides.

In a particular embodiment, the O-linked oligosaccharide comprises three saccharides. In a more particular embodiment, the O-linked oligosaccharide comprises three glucoses.

In another embodiment, $R_3$, $R_5$ and $R_6$ are hydroxyl and $R_4$ is O-glucose in formula (A), such that the diterpene glycoside belongs to the formula (A"):

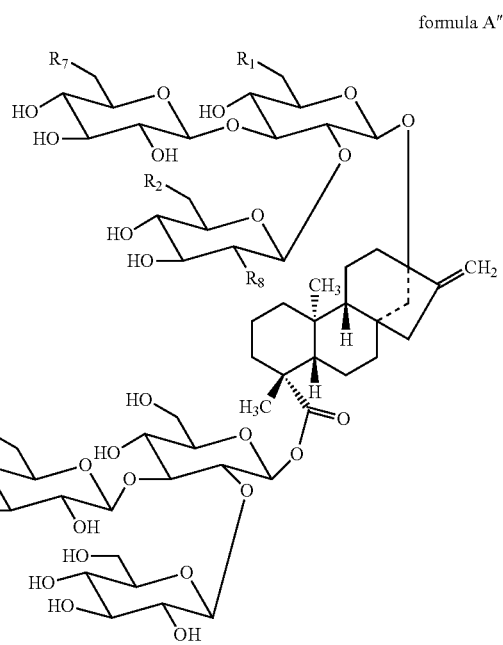

formula A"

wherein:

$R_1$, $R_2$, $R_7$ and $R_8$ are each independently selected from hydroxyl and an O-linked oligosaccharide comprising from three to six saccharides, and the diterpene glycoside has at least nine saccharides.

In a particular embodiment, the O-linked oligosaccharide comprises three saccharides. In a more particular embodiment, the O-linked oligosaccharide comprises three glucoses.

In another embodiment, $R_4$ in formula (A) is O-glucose, such that the diterpene glycoside belongs to formula (A'''):

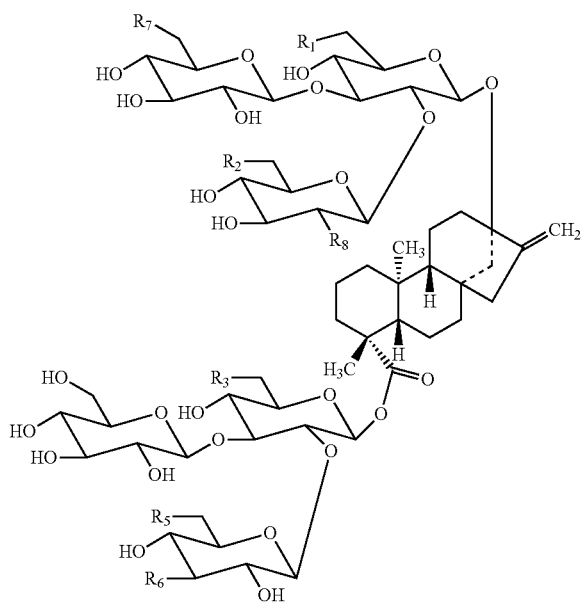

formula A''' wherein $R_1$, $R_2$, $R_3$, $R_5$, $R_6$, $R_7$ and $R_8$ are each independently selected from hydroxyl and an O-linked oligosaccharide comprising from three to six saccharides, and the diterpene glycoside has at least nine saccharides.

In one embodiment, $R_3$ is hydroxyl; $R_5$ is O-linked oligosaccharide and $R_6$ is hydroxyl. In another embodiment, $R_3$ is hydroxyl; $R_5$ hydroxyl is and $R_6$ is O-linked oligosaccharide. In still another embodiment, $R_3$ is O-linked oligosaccharide; $R_5$ hydroxyl is and $R_6$ is hydroxyl.

In other embodiments, $R_3$ is hydroxyl and $R_5$ and $R_6$ are O-linked oligosaccharide. In still other embodiments, $R_5$ is hydroxyl and $R_3$ and $R_6$ are O-lined oligosaccharides. In yet further embodiments, $R_6$ is hydroxyl and $R_3$ and $R_5$ are O-linked oligosaccharides.

In some embodiments, $R_3$, $R_5$ and $R_6$ are all O-linked oligosaccharides.

In a particular embodiment, the O-linked oligosaccharide comprises three saccharides. In a more particular embodiment, the O-linked oligosaccharide comprises three glucoses.

In one embodiment, the present invention is diterpene glycoside 1:

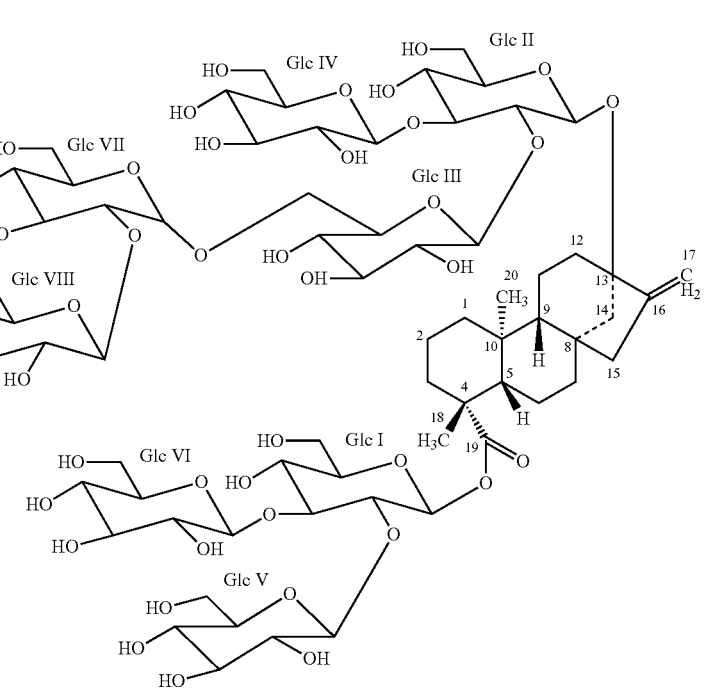

In another embodiment, the present invention is diterpene glycoside 2:
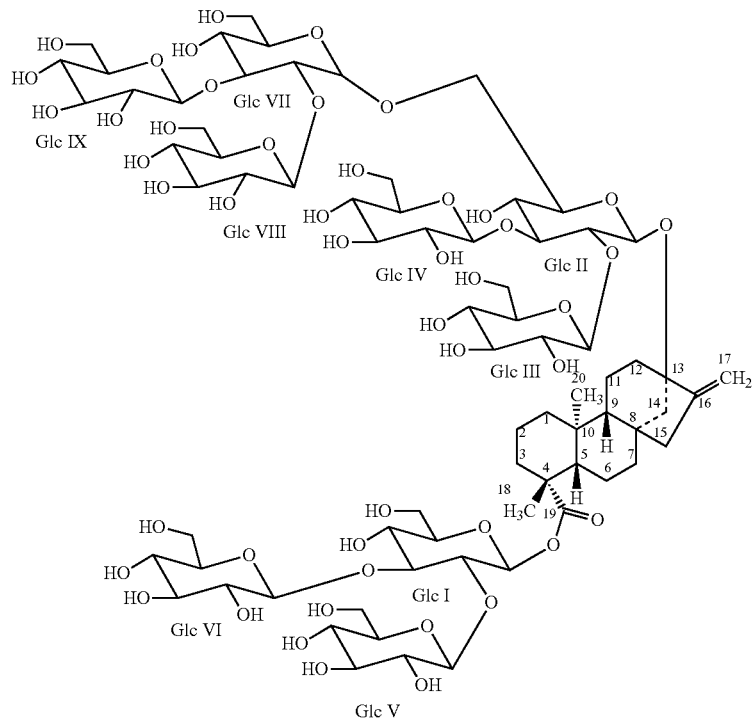
In another embodiment, the present invention is diterpene glycoside 3:
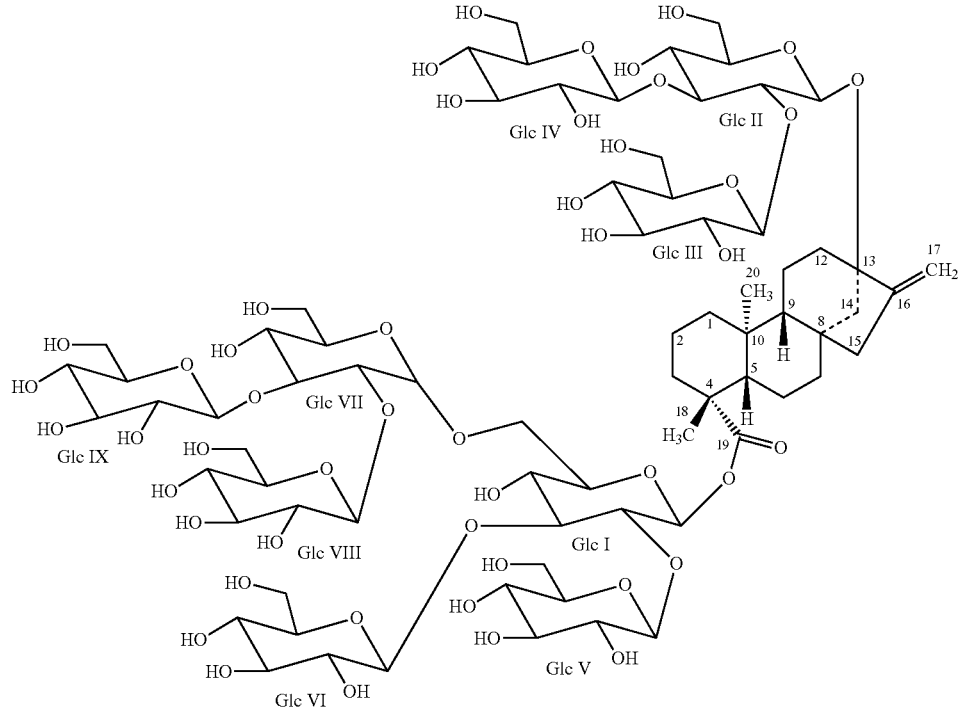

In another embodiment, the present invention is diterpene glycoside 4:
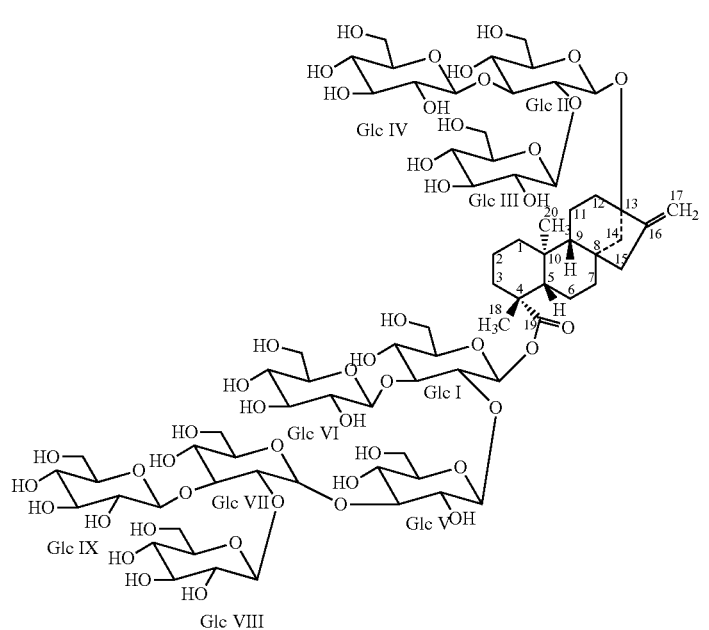
4
In another embodiment, the present invention is diterpene glycoside 5:
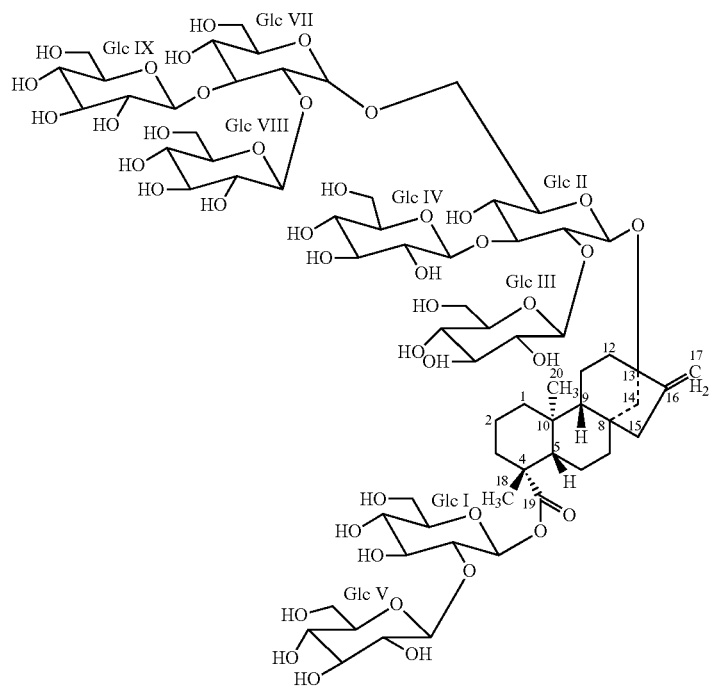
5

In another embodiment, the present invention is diterpene glycoside 6:

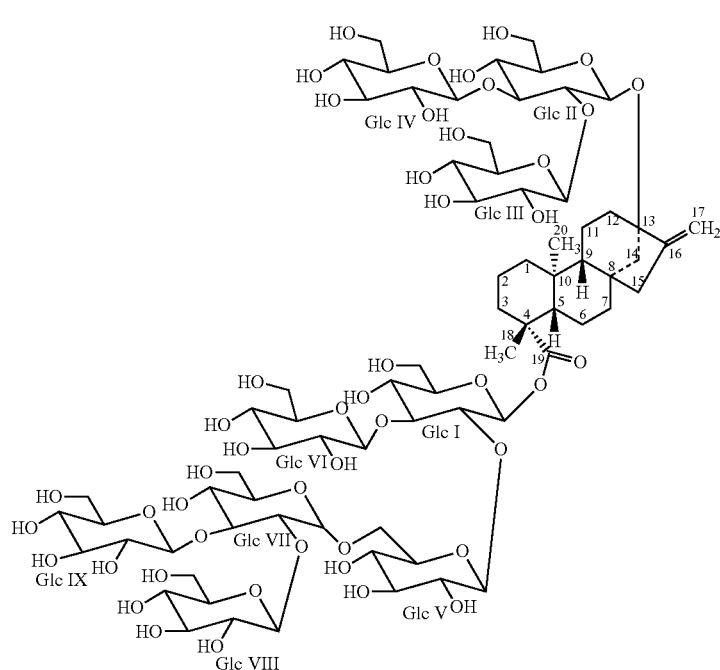

In one embodiment, the diterpene glycoside of the present invention is isolated and purified. The term "isolated and purified", as used herein, means that the compound is about 95% by weight or greater on a dry basis, i.e. is greater than 95% pure. In more specific embodiments, the diterpene glycoside of the formulae described herein has a purity of about 96% or greater, about 97% or greater, about 98% or greater or about 99% or greater.

In some embodiments, the diterpene glycoside of the present invention is sweet. The sweetness of a given composition is typically measured with reference to a solution of sucrose. See generally "A Systematic Study of Concentration-Response Relationships of Sweeteners," G. E. DuBois, D. E. Walters, S. S. Schiffman, Z. S. Warwick, B. J. Booth, S. D. Pecore, K. Gibes, B. T. Carr, and L. M. Brands, in *Sweeteners: Discovery, Molecular Design and Chemoreception*, D. E. Walters, F. T. Orthoefer, and G. E. DuBois, Eds., American Chemical Society, Washington, D C (1991), pp 261-276.

The sweetness of a non-sucrose sweetener can be measured against a sucrose reference by determining the non-sucrose sweetener's sucrose equivalence (SE). Typically, taste panelists are trained to detect sweetness of reference sucrose solutions containing between 1-15% sucrose (w/v). Other non-sucrose sweeteners are then tasted at a series of dilutions to determine the concentration of the non-sucrose sweetener that is as sweet as a given percent sucrose reference. For example, if a 1% solution of a sweetener is as sweet as a 10% sucrose solution, then the sweetener is said to be 10 times as potent as sucrose, and has 10% sucrose equivalence.

In other embodiments, the diterpene glycoside of the present invention is a flavor enhancer when added to a composition (e.g., a consumable) at a concentration at or below its threshold flavor recognition concentration, as described in Section II, herein.

In other embodiment, as described herein, the diterpene glycoside of the present invention is a sweetness enhancer when added to a composition (e.g., a consumable) at a concentration at or below its threshold sweetness recognition concentration, as described in Section II, herein.

I. Compositions

The present invention includes compositions comprising at least one diterpene glycoside of the present invention. "Composition," as the term is used herein, refers to a mixture of at least one diterpene glycoside of the present invention and at least one other substance, wherein the diterpene glycoside is admixed with the at least one other substance. As used herein, "admix" means to mingle or add to something else, but in any case, requires an active step. As such, the compositions contemplated by the present invention do not naturally occur in nature.

In one embodiment, the present invention is a composition comprising at least one diterpene glycoside of the present invention, provided as part of a mixture. In a particular embodiment, the mixture is selected from the group consisting of diterpene glycosides, *Stevia* extract, by-products of other diterpene glycosides' isolation and purification processes, commercially available diterpene extracts or *Stevia* extracts, by-products of biotransformation reactions of other diterpene glycosides, or any combination thereof.

In one embodiment, the mixture contains at least one diterpene glycoside of the present invention in an amount that ranges from about 1% to about 99% by weight on a dry basis, such as, for example, about 5% to about 99% by weight on a dry basis, from about 10% to about 99%, from about 20% to about 99%, from about 30% to about 99%, from about 40% to about 99%, from about 50% to about 99%, from about 60% to about 99%, from about 70% to about 99%, from about 80% to about 99% and from about 90% to about 99%. In a particular embodiment, the mixture contains at least one diterpene glycoside of the present invention in an amount greater than about 90% by weight on a dry basis, for example, greater than about 91%, greater than about 92%, greater than about 93%, greater than about 94%, greater than about 95%, greater than about 96%, greater than about 97%, greater than about 98% and greater than about 99%.

In a particular embodiment, the mixture is an extract of a *Stevia* plant variety. Suitable *Stevia* varieties include, but are not limited to *S. rebaudiana* Bertoni and *S. rebaudiana* Morita.

The *Stevia* extract may contain one or more additional diterpene glycosides, i.e., diterpene glycosides that are not the diterpene glycosides of the present invention, including, but not limited to, stevioside, rebaudioside A, rebaudioside C, dulcoside A, rubusoside, steviolbioside, rebaudioside B, rebaudioside D, rebaudioside F, and combinations thereof.

In one embodiment, the present invention is a composition comprising at least one diterpene glycoside described herein provided as a pure compound, i.e. >99% purity on a dry basis.

The diterpene glycosides of the present invention may be present in the composition in an amount effective to provide a concentration of diterpene glycoside of the present invention from about 1 ppm to about 10,000 ppm when the composition is added to a consumable, such as, for example, from about 1 ppm to about 4,000 ppm, from about 1 ppm to about 3,000 ppm, from about 1 ppm to about 2,000 ppm, from about 1 ppm to about 1,000 ppm.

In another embodiment, the diterpene glycoside of the present invention is present in the composition in an amount effective to provide a concentration of diterpene glycoside of the present invention from about 10 ppm to about 1,000 ppm when the composition is added to a consumable, such as, for example, from about 10 ppm to about 800 ppm, from about 50 ppm to about 800 ppm, from about 50 ppm to about 600 ppm or from about 200 ppm to about 250 ppm. In a particular embodiment, a diterpene glycoside of the present invention is present in the composition in an amount effective to provide a concentration from about 300 ppm to about 600 ppm when the composition is added to a consumable.

Sweetener Compositions

As noted above, in some embodiments, the diterpene glycoside of the present invention is sweet. Accordingly, the present invention also provides a sweetener composition comprising at least one diterpene glycoside of the present invention. "Sweetener composition," as the term is used herein, refers to a mixture of at least one diterpene of the present invention and at least one other substance, wherein the at least one diterpene glycoside is admixed with the at least one other substance. Thus, the sweetener compositions contemplated by the present invention do not occur in nature.

In one embodiment, the diterpene glycoside of the present invention is the sole sweetener in the sweetener composition, i.e. the diterpene glycoside is the only compound present in the sweetener composition that provides a detectable sweetness.

In further embodiments, the sweetener composition comprising at least one diterpene glycoside of the present invention in combination with one or more additional sweetener compounds.

The amount of diterpene glycoside of the present invention in the sweetener composition may vary. In one embodiment, the diterpene glycoside of the present invention is present in a sweetener composition in any amount to impart the desired sweetness when the sweetener composition is added to a sweetenable composition or sweetenable consumable. In a particular embodiment, the diterpene glycoside of the present invention is present in a concentration above its threshold sweetness recognition concentration.

In one embodiment, the diterpene glycoside of the present invention is present in the sweetener composition in an amount effective to provide a sucrose equivalence of greater than about 2% (w/v) when the sweetener composition is added to a sweetenable composition or sweetenable consumable, such as, for example, greater than about 3%, about 4%, about 5%, about 6%, about 7%, about 8%, about 9%, about 10%, about 11%, about 12%, about 13% or about 14%.

The amount of sucrose, and thus another measure of sweetness, in a reference solution may be described in degrees Brix (° Bx). One degree Brix is 1 gram of sucrose in 100 grams of solution and represents the strength of the solution as percentage by weight (% w/w) (strictly speaking, by mass). In one embodiment, a sweetener composition comprises at least one diterpene glycoside of the present invention in an amount effective to provide sweetness equivalent from about 0.50 to 14 degrees Brix of sugar when added to consumable, such as, for example, from about 5 to about 12 degrees Brix, about 7 to 10 degrees Brix, or above 10 degrees Brix.

In some embodiments, a diterpene glycoside of the present invention is present in the sweetener composition in an amount that, when added to a consumable, will provide a concentration of the diterpene glycoside of the present invention from about 1 ppm to about 100 ppm, such as, for example, from about 1 ppm to about 90 ppm, from about 5 ppm to about 80 ppm, from about 5 ppm to about 70 ppm, from about 5 ppm to about 60 ppm, from about 5 ppm to about 50 ppm, from about 5 ppm to about 40 ppm, from about 5 ppm to about 30 ppm, from about 5 ppm to about 20 ppm, or 5 ppm to about 15 ppm.

In other embodiments, a diterpene glycoside of the present invention is present in the sweetener composition in an amount that, when added to a consumable, will provide a concentration of the diterpene glycoside of the present invention greater than about 10 ppm, such as, for example, greater than about 20 ppm, about 30 ppm, about 40 ppm, about 50 ppm, about 60 ppm, about 70 ppm, about 80 ppm, about 90 ppm, about 100 ppm, about 200 ppm, about 300 ppm, about 400 ppm, about 500 ppm, about 600 ppm, about 700 ppm, about 800 ppm or about 900 ppm.

In still other embodiments, a diterpene glycoside of the present invention is present in the sweetener composition in an amount that, when added to a consumable, will provide a concentration of the diterpene glycoside of the present invention from about 1 ppm to about 1,000 ppm, such as, for example, from about 10 ppm to about 1,000 ppm, from about 20 ppm to about 1,000 ppm, from about 30 ppm to about 1,000 ppm, from about 30 ppm to about 1,000 ppm, from about 40 ppm to about 1,000 ppm, from about 50 ppm to about 1,000 ppm, from about 60 ppm to about 1,000 ppm, from about 70 ppm to about 1,000 ppm, from about 80 ppm to about 1,000 ppm, from about 90 ppm to about 1,000 ppm, from about 100 ppm to about 1,000 ppm, from about 200 ppm to about 1,000 ppm, from about 300 ppm to about 1,000 ppm, from about 400 ppm to about 1,000 ppm, from about 500 ppm to about 1,000 ppm, from about 600 ppm to about 1,000 ppm, from about 700 ppm to about 1,000 ppm, from about 800 ppm to about 1,000 ppm or from about 900 ppm to about 1,000 ppm.

In one embodiment, a sweetener composition comprises at least one diterpene glycoside of the present invention and at least one flavonoid, isoflavonoid or combination thereof. Not wishing to be bound by theory, it is believed that inclusion of the at least one flavonoid, isoflavonoid or combination thereof improves the sweetness temporal profile and enhances the sweetness of the at least one diterpene glycoside of the present invention.

In one embodiment, the at least one flavonoid or isoflavonoid is present in an amount such that it provides a concentration from about 5 ppm to about 50 ppm when added to a consumable, such as, for example, from about 5 ppm to about 30 ppm, from about 5 ppm to about 15 ppm, from about 15 ppm to about 50 ppm, from about 15 ppm to about 30 ppm and from about 30 ppm to about 50 ppm.

"Flavonoid", as used herein interchangeably with the term "bioflavonoid". Suitable flavonoids include, but are not limited to, flavones, flavanols, flavanones, flavanes and flavanols.

Flavones contain a 2-phenylchromen-4-one (2-phenyl-1-benzopyran-4-one) backbone. Exemplary flavones include apigenin, tangeritin, chrysin, 6-hydroxyflavone, baicalein, scutellarein, wogonin, diosmin, flavoxate and 7,8-dihydroxyflavone.

Flavanones have the same backbone as flavones, but can be glycosylated by a disaccharide, typically rutinose or neohesperidose, at the 7 position. Exemplary aglycone flavanones include butin, hesperetin, naringenin, eriodictyol, homoeriodictyol, sakuranetin, sterubin and isosakuranetin. Exemplary flavanone glycosides include didymin, eriocitrin, hesperidin, narirutin, naringin, neoeriocitrin, neohesperidin, poncirin and sakuranin.

Flavans contain a 2-phenyl-3,4-dihydro-2H-chromene backbone. Flavans include flavan-3-ols, flavan-4-ols and flavan-3,4-diols. Exemplary flavans include catechin, epicatechin gallate, epigallocatechin, epigallocatechin gallate, proanthocyanidins, theaflavins, thearubigins, apiforol, luteoforol, leucocyanidin, leucodelphinidin, leucofisetinidin, leucomalvidin, leucopelargonidin, leucopeonidin, leucorobinetinidin, melacacidin and teracacidin.

Flavonols contain a 3-hydroxy-2-phenylchromen-4-one, and can also be glycosylated. Exemplary aglycone flavonols include 3-hydroxy flavone, azaleatin, fisetin, galangin, gossypetin, kaempferide, kaempfedrol, isorhamnetin, morin, myricetin, natsudaidain, pachypodol, quercetin, rhamnazin and rhamnetin. Exemplary flavonol glycosides include astragalin, azalein, hyperoside, isoquercitin, kaempferitrin, myricitrin, quercitrin, robinin, rutin, spiraeoside, xanthorhamnin, amurensin, icariin and troxerutin Isoflavonoids have a slightly different backbone compared to flavonoids—typically a 3-phenylchromen-4-one backbone. Suitable isoflavonoids include, but are not limited to, isoflavones, isoflavonones, isoflavans, pterocarpans and roetonoids.

Suitable sources of isoflavones for embodiments of this invention include, but are not limited to, soy beans, soy products, legumes, alfalfa sprouts, chickpeas, peanuts, and red clover. Isoflavones include daidzein, genistein, irilone, orobol, pseudobaptigenin, anagyroidisoflavone A and B, biochanin A, calycosin, formononetin, glycitein, irigenin. 5-O-methylgenistein, pratensein, prunetin, psi-tectorigenin, retusin, tectorigenin, daidzein, genistein, iridin, ononin, puerarin, sophoricoside, tectoridin, bidwillol A, derrubone, luteone, 7-O-methylluteone, wighteone, alpinumisoflavone, barbigerone, di-O-methylalpinumisoflavone, 4'-methylalpinumisoflavone and rotenoids.

In one embodiment, the flavonoid or isoflavonoid is selected from the group consisting of naringenin, hesperetin, hesperidin eriodictyol and a combination thereof.

In another embodiment, a sweetener composition comprises at least one diterpene glycoside of the present invention and at least one compound selected from the group consisting of phyllodulcin, taxifolin 3-O-acetate and phloretin. Not wishing to be bound by theory, it is believed that inclusion of these compounds, or a combination thereof, improves the sweetness temporal profile and enhances the sweetness of the at least one diterpene glycoside of the present invention.

In one embodiment, the at least one at least one compound selected from the group consisting of phyllodulcin, taxifolin 3-O-acetate and phloretin is present in an amount such that it provides a concentration from about 5 ppm to about 50 ppm when added to a consumable, such as, for example, from about 5 ppm to about 30 ppm, from about 5 ppm to about 15 ppm, from about 15 ppm to about 50 ppm, from about 15 ppm to about 30 ppm and from about 30 ppm to about 50 ppm.

In another particular embodiment, a sweetener composition comprises at least one diterpene glycoside of the present invention and a compound selected from the group consisting of rebaudioside A, rebaudioside B, rebaudioside D, rebaudioside M, rebaudioside E, glycosylated steviol glycosides, Luo Han Guo, Mogroside V, erythritol, allulose and combinations thereof.

Sweetness Enhancers

In a particular embodiment, the diterpene glycoside of the present invention is a sweetness enhancer. "Sweetness enhancer", as the term is used herein, refers to a compound that enhances, amplifies or potentiates the perception of sweetness of a consumable (e.g. a beverage) when said compound is present in the consumable in a concentration at or below the compound's sweetener recognition threshold, i.e. in a concentration at which compound does not contribute any noticeable sweet taste in the absence of additional sweetener(s). The term "sweetness recognition threshold concentration," as generally used herein, is the lowest known concentration of a compound that is perceivable by the human sense of taste as sweet. The sweetness recognition threshold concentration is specific for a particular compound, and can vary based on temperature, matrix, ingredients and/or flavor system.

The term "sweetness enhancer" is synonymous with the terms "sweet taste potentiator," "sweetness potentiator," "sweetness amplifier," and "sweetness intensifier."

In one embodiment, a diterpene glycoside described herein is a sweetness enhancer.

In one embodiment, a diterpene glycoside of the present invention may be added directly to the consumable, i.e., not provided in the form of a composition but rather as compound, to enhance sweetness. In this embodiment, a diterpene glycoside of the present invention is added to the consumable at a concentration at or below its sweetness recognition threshold concentration, i.e., a sweetness enhancer. In a particular embodiment, a diterpene glycoside of the present invention is added to the consumable at a concentration below its sweetness recognition threshold concentration, i.e., a sweetness enhancer.

In certain embodiments, a diterpene glycoside of the present invention is a sweetness enhancer and is added to the consumable in an amount that will provide a concentration of the diterpene glycoside that is at least about 1%, at least about 5%, at least about 10%, at least about 15%, at least about 20%, at least about 25%, at least about 30%, at least about 35%, at least about 40%, at least about 45% or at least about 50% or more below its sweetness recognition threshold.

In some embodiments, a diterpene glycoside of the present invention is a sweetness enhancer and is added to the consumable in an amount that will provide a concentration of the diterpene glycoside from about 1 ppm to about 100 ppm, such as, for example, from about 1 ppm to about 90 ppm, from about 5 ppm to about 80 ppm, from about 5 ppm to about 70 ppm, from about 5 ppm to about 60 ppm, from about 5 ppm to about 50 ppm, from about 5 ppm to about 40 ppm, from about 5 ppm to about 30 ppm, from about 5 ppm to about 20 ppm, or 5 ppm to about 15 ppm.

In other embodiments, a diterpene glycoside of the present invention is a sweetness enhancer and is added to the consumable in an amount that will provide a concentration of the diterpene glycoside that is greater than about 10 ppm, such as, for example, greater than about 20 ppm, about 30 ppm, about 40 ppm, about 50 ppm, about 60 ppm, about 70 ppm, about 80 ppm, about 90 ppm, about 100 ppm, about 200 ppm, about 300 ppm, about 400 ppm, about 500 ppm, about 600 ppm, about 700 ppm, about 800 ppm or about 900 ppm.

In still other embodiments, a diterpene glycoside of the present invention is a sweetness enhancer and is added to the consumable in an amount that will provide a concentration of the diterpene glycoside from about 1 ppm to about 1,000 ppm, such as, for example, from about 10 ppm to about 1,000 ppm, from about 20 ppm to about 1,000 ppm, from about 30 ppm to about 1,000 ppm, from about 30 ppm to about 1,000 ppm, from about 40 ppm to about 1,000 ppm, from about 50 ppm to about 1,000 ppm, from about 60 ppm to about 1,000 ppm, from about 70 ppm to about 1,000 ppm, from about 80 ppm to about 1,000 ppm, from about 90 ppm to about 1,000 ppm, from about 100 ppm to about 1,000 ppm, from about 200 ppm to about 1,000 ppm, from about 300 ppm to about 1,000 ppm, from about 400 ppm to about 1,000 ppm, from about 500 ppm to about 1,000 ppm, from about 600 ppm to about 1,000 ppm, from about 700 ppm to about 1,000 ppm, from about 800 ppm to about 1,000 ppm or from about 900 ppm to about 1,000 ppm.

In some embodiments, the diterpene glycosides of the present invention enhances the sucrose equivalence (SE) of the consumable by at least about 0.5%, about 0.6%, about 0.7%, about 0.8%, about 0.9%, about 1.0%, about 1.5%, about 2.0%, about 2.5%, about 3.0%, about 4.0% or about 5.0%, when compared to the SE of the consumable in the absence of the diterpene glycoside of the present invention.

In other embodiments, at least one diterpene glycoside of the present invention may be added to the consumable in the form of a sweetness enhancing composition. "Sweetness enhancing composition," as the term is used herein, refers to a composition of the present invention—as described above—wherein the composition enhances, amplifies or potentiates the perception of sweetness of a consumable (e.g. a beverage) when a diterpene glycoside of the present invention is present in the sweetness enhancer composition in an amount that will provide a concentration of the diterpene glycoside that is at or below its sweetness recognition threshold when added to the consumable. In a particular embodiment, the diterpene glycoside of the present invention in an amount that will provide a concentration of the diterpene glycoside of that is below its sweetness recognition threshold.

In certain embodiments, a diterpene glycoside of the present invention is present in the sweetness enhancing composition in an amount effective to provide a concentration of the diterpene glycoside that is at least about 1%, at least about 5%, at least about 10%, at least about 15%, at least about 20%, at least about 25%, at least about 30%, at least about 35%, at least about 40%, at least about 45% or at least about 50% or more below its sweetness recognition threshold when the sweetness enhancing composition is added to a consumable.

In some embodiments, a diterpene glycoside of the present invention is present in the sweetness enhancing composition in an amount that, when added to the consumable, will provide a concentration of the diterpene glycoside from about 1 ppm to about 100 ppm, such as, for example, from about 5 ppm to about 90 ppm, from about 5 ppm to about 80 ppm, from about 5 ppm to about 70 ppm, from about 5 ppm to about 60 ppm, from about 5 ppm to about 50 ppm, from about 5 ppm to about 40 ppm, from about 5 ppm to about 30 ppm, from about 5 ppm to about 20 ppm, or 5 ppm to about 15 ppm.

In other embodiments, a diterpene glycoside of the present invention is present in the sweetness enhancing composition in an amount that, when added to the consumable, will provide a concentration of the diterpene glycoside greater than about 10 ppm, such as, for example, greater than about 20 ppm, about 30 ppm, about 40 ppm, about 50 ppm, about 60 ppm, about 70 ppm, about 80 ppm, about 90 ppm, about 100 ppm, about 200 ppm, about 300 ppm, about 400 ppm, about 500 ppm, about 600 ppm, about 700 ppm, about 800 ppm or about 900 ppm.

In still other embodiments, a diterpene glycoside of the present invention is present in the sweetness enhancing composition in an amount that, when added to the consumable, will provide a concentration of the diterpene glycoside from about 1 ppm to about 1,000 ppm, such as, for example, from about 10 ppm to about 1,000 ppm, from about 20 ppm to about 1,000 ppm, from about 30 ppm to about 1,000 ppm, from about 30 ppm to about 1,000 ppm, from about 40 ppm to about 1,000 ppm, from about 50 ppm to about 1,000 ppm, from about 60 ppm to about 1,000 ppm, from about 70 ppm to about 1,000 ppm, from about 80 ppm to about 1,000 ppm, from about 90 ppm to about 1,000 ppm, from about 100 ppm to about 1,000 ppm, from about 200 ppm to about 1,000 ppm, from about 300 ppm to about 1,000 ppm, from about 400 ppm to about 1,000 ppm, from about 500 ppm to about 1,000 ppm, from about 600 ppm to about 1,000 ppm, from about 700 ppm to about 1,000 ppm, from about 800 ppm to about 1,000 ppm or from about 900 ppm to about 1,000 ppm.

It is contemplated that the sweetness enhancing composition can include one or more sweetness enhancers in addition to at least one diterpene glycoside of the present invention. In one embodiment, the sweetness enhancing composition can include one additional sweetness enhancer. In other embodiments, the composition can include two or more additional sweetness enhancers. In embodiments where two or more sweetness enhancers are utilized, each sweetness enhancer should be present at or below its respective sweetness recognition threshold concentration.

The one or more other sweetness enhancers are selected from, but not limited to, the group consisting of 2-hydroxybenzoic acid, 3-hydroxybenzoic acid, 4-hydroxybenzoic acid, 2,4-dihydroxybenzoic acid, 3,4-dihydroxybenzoic acid, 2,5-dihydroxybenzoic acid, 2,6-dihydroxybenzoic acid, 2,3,4-trihydroxybenzoic acid, 2,4,6-trihydroxybenzoic acid, 3-aminobenzoic acid, 4-aminobenzoic acid, 4-O-β-D-glucosyl-hesperetin dihydrochalcone, MG isomogrosaide V, 4-hydroxycinnamic acid, 4-methoxycinnamic acid, 1-(2-hydroxyphenyl)-3-(4-pyridyl)-1-propanone, 4-ethoxybenzonitrile, 2-methoxy-5-(phenoxymethyl)-phenol, 1-(2,4-dihydroxyphenyl)-2-β-methoxy-4-hydroxyphenyl)-ethanone, hesperetin, 2,3',6-trihydroxy-4'-methoxydihydrochalcone, N-(3'-methoxy-4'-hydroxybenzyl)-2,4,6-trihydroxybenzamide, 3'-7-dihydroxy-4'-methoxyflavan, FEMA GRAS flavor 4469, FEMA GRAS flavor 4701, FEMA GRAS flavor 4720, FEMA GRAS flavor 4774, FEMA GRAS flavor 4708, FEMA GRAS flavor 4728, FEMA GRAS flavor 4601, FEMA GRAS flavor 4802, 4-amino-5-(cyclohexyloxy)-2-methylquinoline-3-carboxylic acid, rebaudioside M, rebaudioside N, rebaudioside O, rebaudioside C and combinations thereof.

In one embodiment, addition of the sweetness enhancer increases the detected sucrose equivalence of the at least one sweetener in a consumable compared to the sucrose equivalence of the same consumable in the absence of the sweetness enhancer.

In a particular embodiment, the consumable is a beverage. According to this embodiment, a diterpene glycoside of the present invention and at least one sweetener is added to a beverage, wherein the diterpene glycoside is present in a concentration at or below its sweetness recognition threshold. In a particular embodiment, the detected sucrose equivalence is increased from about 0.2% to about 5.0%, such as, for example, about 1%, about 2%, about 3%, about 4% or about 5%.

In one embodiment, the sweetener is at least one natural high-potency sweetener. As used herein, the phrase "natural high potency sweetener" refers to any sweetener found naturally in nature and characteristically has a sweetness potency greater than sucrose, fructose, or glucose, yet has less calories. The natural high potency sweetener can be provided as a pure compound or, alternatively, as part of an extract.

In another embodiment, the sweetener is at least one synthetic sweetener. As used herein, the phrase "synthetic sweetener" refers to any composition which is not found naturally in nature and characteristically has a sweetness potency greater than sucrose, fructose, or glucose, yet has less calories.

In still other embodiments, combinations of natural high potency sweeteners and synthetic sweeteners are contemplated.

In other embodiments, the sweetener is at least one carbohydrate sweetener. Suitable carbohydrate sweeteners are selected from, but not limited to, the group consisting of sucrose, glyceraldehyde, dihydroxyacetone, erythrose, threose, erythrulose, arabinose, lyxose, ribose, xylose, ribulose, xylulose, allose, altrose, galactose, glucose, gulose, idose, mannose, talose, fructose, psicose, sorbose, tagatose, mannoheptulose, sedoheltulose, octolose, fucose, rhamnose, arabinose, turanose, sialose and combinations thereof.

Other suitable sweeteners include rebaudioside A, rebaudioside B, rebaudioside C, rebaudioside D, rebaudioside E, rebaudioside F, rebaudioside I, rebaudioside H, rebaudioside L, rebaudioside K, rebaudioside J, rebaudioside M, rebaudioside N, rebaudioside O, dulcoside A, dulcoside B, rubusoside, *Stevia*, stevioside, mogroside IV, mogroside V, mogroside VI, Luo han guo, siamenoside, monatin and its salts (monatin SS, RR, RS, SR), curculin, glycyrrhizic acid and its salts, thaumatin, monellin, mabinlin, brazzein, hernandulcin, phyllodulcin, glycyphyllin, phloridzin, trilobatin, baiyunoside, osladin, polypodoside A, pterocaryoside A, pterocaryoside B, mukurozioside, phlomisoside I, periandrin I, abrusoside A, steviolbioside, hesperitin and cyclocarioside I, sugar alcohols such as erythritol, sucralose, potassium acesulfame, acesulfame acid and salts thereof, aspartame, alitame, saccharin and salts thereof, neohesperidin dihydrochalcone, cyclamate, cyclamic acid and salts thereof, neotame, advantame, glucosylated steviol glycosides (GSGs) and combinations thereof.

In a particular embodiment, the sweetener is at least one calorie-providing carbohydrate sweetener. Accordingly, incorporation of the sweetness enhancer reduces the quantity of the calorie-providing carbohydrate sweetener that must be used in a given consumable to achieve a particular SE, thereby allowing the preparation of reduced-calorie consumables.

In one embodiment, the sweetener is a caloric sweetener or mixture of caloric sweeteners. In another embodiment, the caloric sweetener is selected from sucrose, fructose, glucose, high fructose corn/starch syrup, a beet sugar, a cane sugar, and combinations thereof.

In another embodiment, the sweetener is a rare sugar selected from allulose, sorbose, lyxose, ribulose, xylose, xylulose, D-allose, L-ribose, D-tagatose, L-glucose, L-fucose, L-arabinose, turanose, kojibiose and combinations thereof.

In still another embodiment, the sweetener is a mixture of at least one natural high potency sweeteners and at least one carbohydrate sweetener. In yet another embodiment, the sweetener is a mixture of at least one synthetic sweetener and at least one carbohydrate sweetener. In a further embodiment, the sweetener is at least one natural high potency sweetener, at least one synthetic sweetener and at least one carbohydrate sweetener.

Flavor Enhancers

In another particular embodiment, the diterpene glycoside of the present invention is a flavor enhancer. "Flavor enhancer", as the term is used herein, refers to a compound that enhances, amplifies or potentiates the perceptions of a flavor ingredient (i.e. any substance that provides sweetness, sourness, saltiness, savoriness, bitterness, metallic taste, etc.) when said compound is present in a consumable (e.g. a beverage) in a concentration at or below the compound's flavor recognition threshold, i.e. in a concentration at which compound does not contribute any noticeable flavor in the absence of any flavor ingredient(s). The term "flavor recognition threshold", as generally used herein, is the lowest known concentration of a compound that is perceivable by the human sense of taste as the particular flavor. The flavor recognition threshold concentration is specific for a particular compound, and can vary based on temperature, matrix, ingredients and/or flavor system.

The term "flavor enhancer" is synonymous with the terms "flavor potentiator," "flavor amplifier," and "flavor intensifier."

In one embodiment, at least one diterpene glycoside of the present invention is added directly to the consumable, i.e., not provided in the form of a composition but rather as a compound, to enhance a flavor. In this embodiment, the diterpene glycoside of the present invention is added to the consumable at a concentration at or below its flavor recognition threshold concentration, i.e., a flavor enhancer. In a particular embodiment, the diterpene glycoside of the present invention is added to the consumable at a concentration below its flavor recognition threshold concentration, i.e., a flavor enhancer.

In certain embodiments, a diterpene glycoside of the present invention is a flavor enhancer and is added to the consumable in an amount that will provide a concentration of the diterpene glycoside that is at least about 1%, at least about 5%, at least about 10%, at least about 15%, at least about 20%, at least about 25%, at least about 30%, at least about 35%, at least about 40%, at least about 45% or at least about 50% or more below its sweetness recognition threshold.

In some embodiments, a diterpene glycoside of the present invention is a flavor enhancer and is added to the consumable in an amount that will provide a concentration of the diterpene glycoside from about 1 ppm to about 100 ppm, such as, for example, from about 1 ppm to about 90 ppm, from about 5 ppm to about 80 ppm, from about 5 ppm to about 70 ppm, from about 5 ppm to about 60 ppm, from about 5 ppm to about 50 ppm, from about 5 ppm to about 40 ppm, from about 5 ppm to about 30 ppm, from about 5 ppm to about 20 ppm, or 5 ppm to about 15 ppm.

In other embodiments, a diterpene glycoside of the present invention is a flavor enhancer and is added to the consumable in an amount that will provide a concentration of the diterpene glycoside that is greater than about 10 ppm, such as, for example, greater than about 20 ppm, about 30 ppm, about 40 ppm, about 50 ppm, about 60 ppm, about 70 ppm, about 80 ppm, about 90 ppm, about 100 ppm, about 200 ppm, about 300 ppm, about 400 ppm, about 500 ppm, about 600 ppm, about 700 ppm, about 800 ppm or about 900 ppm.

In still other embodiments, a diterpene glycoside of the present invention is a flavor enhancer and is added to the consumable in an amount that will provide a concentration of the diterpene glycoside from about 1 ppm to about 1,000 ppm, such as, for example, from about 10 ppm to about 1,000 ppm, from about 20 ppm to about 1,000 ppm, from about 30 ppm to about 1,000 ppm, from about 30 ppm to about 1,000 ppm, from about 40 ppm to about 1,000 ppm, from about 50 ppm to about 1,000 ppm, from about 60 ppm to about 1,000 ppm, from about 70 ppm to about 1,000 ppm, from about 80 ppm to about 1,000 ppm, from about 90 ppm to about 1,000 ppm, from about 100 ppm to about 1,000 ppm, from about 200 ppm to about 1,000 ppm, from about 300 ppm to about 1,000 ppm, from about 400 ppm to about 1,000 ppm, from about 500 ppm to about 1,000 ppm, from about 600 ppm to about 1,000 ppm, from about 700 ppm to about 1,000 ppm, from about 800 ppm to about 1,000 ppm or from about 900 ppm to about 1,000 ppm.

The diterpene glycosides of the present invention enhances the flavor of the consumable by at least about 0.5%, about 0.6%, about 0.7%, about 0.8%, about 0.9%, about 1.0%, about 1.5%, about 2.0%, about 2.5%, about 3.0%, about 4.0% or about 5.0%, when compared to the flavor of the consumable in the absence of the diterpene glycosides of the present invention.

In other embodiments, at least one diterpene glycoside of the present invention may be added to the consumable in the form of a flavor enhancing composition. "Flavor enhancing composition," as the term is used herein, refers to a mixture of at least one diterpene glycoside of the present invention and at least one flavor ingredient, wherein the at least one diterpene is admixed with the at least one flavor ingredient—wherein the composition enhances, amplifies or potentiates the perception of the flavor ingredient in a consumable (e.g. a beverage) when the at least one diterpene glycoside of the present invention is present in the flavor enhancer composition in an amount that will provide a concentration of the diterpene glycoside that is at or below its flavor recognition threshold when added to the consumable. Thus, the flavor enhancing compositions contemplated by the present invention do not occur in nature.

Addition of the flavor enhancing composition increases the detected flavor of the at least one flavor ingredient in the consumable compared to the detected flavor of the same ingredient in the consumable in the absence of the flavor enhancer. Without being bound by theory, the flavor enhancing composition likely does not contribute any noticeable taste to the consumable to which it is added because the flavor enhancer is present in the consumable in a concentration at or below the its flavor recognition threshold.

In one embodiment, the flavor enhancing composition comprises at least one diterpene glycoside of the present invention in an amount effective to provide a concentration of the at least one diterpene glycoside that is at or below its flavor recognition threshold when the flavor enhancing composition is added to a consumable.

In a particular embodiment, a diterpene glycoside of the present invention is present in the flavor enhancing composition in an amount effective to provide a concentration of the diterpene glycoside below its flavor recognition threshold when the flavor enhancing composition is added to a consumable.

In certain embodiment, a diterpene glycoside of the present invention is present in the flavor enhancing composition in an amount that, when added to a consumable, is effective to provide a concentration of the compound that is at least about 1%, at least about 5%, at least about 10%, at least about 15%, at least about 20%, at least about 25%, at least about 30%, at least about 35%, at least about 40%, at least about 45% or at least about 50% or more below its flavor recognition threshold.

In some embodiments, a diterpene glycoside of the present invention is present in the flavor enhancing composition in an amount that, when added to the consumable, will provide a concentration ranging from about 0.5 ppm to about 1000 ppm.

For example, a diterpene glycoside of the present invention can be present in the flavor enhancing composition in an amount that, when added to the consumable, will provide a concentration of the diterpene glycoside greater than about 10 ppm, such as, for example, greater than about 20 ppm, about 30 ppm, about 40 ppm, about 50 ppm, about 60 ppm, about 70 ppm, about 80 ppm, about 90 ppm, about 100 ppm, about 200 ppm, about 300 ppm, about 400 ppm, about 500 ppm, about 600 ppm, about 700 ppm, about 800 ppm or about 900 ppm.

In still other embodiments, a diterpene glycoside of the present invention is present in the flavor enhancing composition in an amount that, when added to the consumable, will provide a concentration of the diterpene glycoside from about 1 ppm to about 1,000 ppm, such as, for example, from about 10 ppm to about 1,000 ppm, from about 20 ppm to about 1,000 ppm, from about 30 ppm to about 1,000 ppm, from about 30 ppm to about 1,000 ppm, from about 40 ppm to about 1,000 ppm, from about 50 ppm to about 1,000 ppm, from about 60 ppm to about 1,000 ppm, from about 70 ppm to about 1,000 ppm, from about 80 ppm to about 1,000 ppm, from about 90 ppm to about 1,000 ppm, from about 100 ppm to about 1,000 ppm, from about 200 ppm to about 1,000 ppm, from about 300 ppm to about 1,000 ppm, from about 400 ppm to about 1,000 ppm, from about 500 ppm to about 1,000 ppm, from about 600 ppm to about 1,000 ppm, from about 700 ppm to about 1,000 ppm, from about 800 ppm to about 1,000 ppm or from about 900 ppm to about 1,000 ppm.

A person of skill in the art will be able to select the concentration of the diterpene glycoside of the present invention in the flavor enhancing composition so that it may impart an enhanced flavor to a consumable comprising at least one flavor ingredient.

Suitable flavor ingredients include, but are not limited to, vanillin, vanilla extract, mango extract, cinnamon, citrus, coconut, ginger, viridiflorol, almond, menthol (including menthol without mint), grape skin extract, and grape seed extract. "Flavorant" and "flavoring ingredient" are synonymous and can include natural or synthetic substances or combinations thereof.

Flavorants also include any other substance which imparts flavor and may include natural or non-natural (synthetic) substances which are safe for human or animals when used in a generally accepted range. Non-limiting examples of proprietary flavorants include Dohler™ Natural Flavoring Sweetness Enhancer K14323 (Dohler™, Darmstadt, Germany), Symrise™ Natural Flavor Mask for Sweeteners 161453 and 164126 (Symrise™, Holzminden, Germany), Natural Advantage™ Bitterness Blockers 1, 2, 9 and 10 (Natural Advantage™, Freehold, N.J., U.S.A.), and Sucramask™ (Creative Research Management, Stockton, Calif., U.S.A.).

In another embodiment, the flavor enhancing composition comprising at least one diterpene glycoside of the present invention enhances flavors (either individual flavors or the overall flavor) when added to the consumable. These flavors include, but are not limited to, fruit flavors, including tropical fruit flavors, and vanilla-caramel type flavors.

The compositions described herein can be customized to provide the desired calorie content. For example, compositions can be "full-calorie", such that they impart the desired sweetness when added to a consumable (such as, for example, a beverage) and have about 120 calories per 8 oz serving. Alternatively, compositions can be "mid-calorie", such that they impart the desired sweetness when added to a consumable (such as, for example, as beverage) and have less than about 60 calories per 8 oz serving. In other embodiments, compositions can be "low-calorie", such that they impart the desired sweetness when added to a consumable (such as, for example, as beverage) and have less than 40 calories per 8 oz serving. In still other embodiments, the compositions can be "zero-calorie", such that they impart the desired sweetness when added to a consumable (such as, for example, a beverage) and have less than 5 calories per 8 oz. serving.

Additives

The compositions may comprise, in addition to at least one diterpene glycoside of the present invention, one or more additives, detailed herein below. In some embodiments, the composition contains additives including, but not limited to, carbohydrates, polyols, amino acids and their corresponding salts, poly-amino acids and their corresponding salts, sugar acids and their corresponding salts, nucleotides, organic acids, inorganic acids, organic salts including organic acid salts and organic base salts, inorganic salts, bitter compounds, flavorants and flavoring ingredients, astringent compounds, proteins or protein hydrolysates, surfactants, emulsifiers, weighing agents, gums, antioxidants, colorants, flavonoids, alcohols, polymers and combinations thereof. In some embodiments, the additives act to improve the temporal and flavor profile of the sweetener to provide a sweetener composition with a taste similar to sucrose.

In one embodiment, the compositions further comprise contain one or more polyols. The term "polyol", as used herein, refers to a molecule that contains more than one hydroxyl group. A polyol may be a diol, triol, or a tetraol which contains 2, 3, and 4 hydroxyl groups respectively. A polyol also may contain more than 4 hydroxyl groups, such as a pentaol, hexaol, heptaol, or the like, which contain 5, 6, or 7 hydroxyl groups, respectively. Additionally, a polyol also may be a sugar alcohol, polyhydric alcohol, or polyalcohol which is a reduced form of carbohydrate, wherein the carbonyl group (aldehyde or ketone, reducing sugar) has been reduced to a primary or secondary hydroxyl group.

Non-limiting examples of polyols in some embodiments include erythritol, maltitol, mannitol, sorbitol, lactitol, xylitol, isomalt, propylene glycol, glycerol (glycerin), threitol, galactitol, palatinose, reduced isomalto-oligosaccharides, reduced xylo-oligosaccharides, reduced gentio-oligosaccharides, reduced maltose syrup, reduced glucose syrup, and sugar alcohols or any other carbohydrates capable of being reduced which do not adversely affect the taste of the compositions.

In certain embodiments, the polyol is present in the compositions in an amount effective to provide a concentration from about 100 ppm to about 250,000 ppm when present in a consumable, such as, for example, a beverage. In other embodiments, the polyol is present in the compositions in an amount effective to provide a concentration from about 400 ppm to about 80,000 ppm when present in a consumable, such as, for example, from about 5,000 ppm to about 40,000 ppm.

In other embodiments, a diterpene glycoside of the present invention is present in the composition with the polyol in a weight ratio from about 1:1 to about 1:800, such as, for example, from about 1:4 to about 1:800, from about 1:20 to about 1:600, from about 1:50 to about 1:300 or from about 1:75 to about 1:150.

Suitable amino acid additives include, but are not limited to, aspartic acid, arginine, glycine, glutamic acid, proline, threonine, theanine, cysteine, cystine, alanine, valine, tyrosine, leucine, arabinose, trans-4-hydroxyproline, isoleucine, asparagine, serine, lysine, histidine, ornithine, methionine, carnitine, aminobutyric acid ($\alpha$-, $\beta$-, and/or $\delta$-isomers), glutamine, hydroxyproline, taurine, norvaline, sarcosine, and their salt forms such as sodium or potassium salts or acid salts. The amino acid additives also may be in the D- or L-configuration and in the mono-, di-, or tri-form of the same or different amino acids. Additionally, the amino acids may be $\alpha$-, $\beta$-, $\gamma$- and/or $\delta$-isomers if appropriate. Combinations of the foregoing amino acids and their corresponding salts (e.g., sodium, potassium, calcium, magnesium salts or other alkali or alkaline earth metal salts thereof, or acid salts) also are suitable additives in some embodiments. The amino acids may be natural or synthetic. The amino acids also may be modified. Modified amino acids refers to any amino acid wherein at least one atom has been added, removed, substituted, or combinations thereof (e.g., N-alkyl amino acid, N-acyl amino acid, or N-methyl amino acid). Non-limiting examples of modified amino acids include amino acid derivatives such as trimethyl glycine, N-methyl-glycine, and N-methyl-alanine. As used herein, modified amino acids encompass both modified and unmodified amino acids. As used herein, amino acids also encompass both peptides and polypeptides (e.g., dipeptides, tripeptides, tetrapeptides, and pentapeptides) such as glutathione and L-alanyl-L-glutamine. Suitable polyamino acid additives include poly-L-aspartic acid, poly-L-lysine (e.g., poly-L-$\alpha$-lysine or poly-L-$\varepsilon$-lysine), poly-L-ornithine (e.g., poly-L-$\alpha$-ornithine or poly-L-$\varepsilon$-ornithine), poly-L-arginine, other polymeric forms of amino acids, and salt forms thereof (e.g., calcium, potassium, sodium, or magnesium salts such as L-glutamic acid mono sodium salt). The poly-amino acid additives also may be in the D- or L-configuration. Additionally, the poly-amino acids may be $\alpha$-, $\beta$-, $\gamma$-, $\delta$-, and $\varepsilon$-isomers if appropriate. Combinations of the foregoing poly-amino acids and their corresponding salts (e.g., sodium, potassium, calcium, magnesium salts or other alkali or alkaline earth metal salts thereof or acid salts) also are suitable additives in some embodiments. The poly-amino acids described herein also may comprise co-polymers of different amino acids. The poly-amino acids may be natural or synthetic. The poly-amino acids also may be modified, such that at least one atom has been added, removed, substituted, or combinations thereof (e.g., N-alkyl poly-amino acid or N-acyl poly-amino acid). As used herein, poly-amino acids encompass both modified and unmodified poly-amino acids. For example, modified poly-amino acids include, but are not limited to, poly-amino acids of various molecular weights (MW), such as poly-L-α-lysine with a MW of 1,500, MW of 6,000, MW of 25,200, MW of 63,000, MW of 83,000, or MW of 300,000.

In particular embodiments, the amino acid is present in the composition in an amount effective to provide a concentration from about 10 ppm to about 50,000 ppm when present in a consumable, such as, for example, a beverage. In another embodiment, the amino acid is present in the composition in an amount effective to provide a concentration from about 1,000 ppm to about 10,000 ppm when present in a consumable, such as, for example, from about 2,500 ppm to about 5,000 ppm or from about 250 ppm to about 7,500 ppm.

Suitable sugar acid additives include, but are not limited to, aldonic, uronic, aldaric, alginic, gluconic, glucuronic, glucaric, galactaric, galacturonic, and salts thereof (e.g., sodium, potassium, calcium, magnesium salts or other physiologically acceptable salts), and combinations thereof.

Suitable nucleotide additives include, but are not limited to, inosine monophosphate ("IMP"), guanosine monophosphate ("GMP"), adenosine monophosphate ("AMP"), cytosine monophosphate (CMP), uracil monophosphate (UMP), inosine diphosphate, guanosine diphosphate, adenosine diphosphate, cytosine diphosphate, uracil diphosphate, inosine triphosphate, guanosine triphosphate, adenosine triphosphate, cytosine triphosphate, uracil triphosphate, alkali or alkaline earth metal salts thereof, and combinations thereof. The nucleotides described herein also may comprise nucleotide-related additives, such as nucleosides or nucleic acid bases (e.g., guanine, cytosine, adenine, thymine, uracil).

The nucleotide is present in the composition in an amount effective to provide a concentration from about 5 ppm to about 1,000 ppm when present in consumable, such as, for example, a beverage.

Suitable organic acid additives include any compound which comprises a —COOH moiety, such as, for example, C2-C30 carboxylic acids, substituted hydroxyl C2-C30 carboxylic acids, butyric acid (ethyl esters), substituted butyric acid (ethyl esters), benzoic acid, substituted benzoic acids (e.g., 2,4-dihydroxybenzoic acid), substituted cinnamic acids, hydroxyacids, substituted hydroxybenzoic acids, anisic acid substituted cyclohexyl carboxylic acids, tannic acid, aconitic acid, lactic acid, tartaric acid, citric acid, isocitric acid, gluconic acid, glucoheptonic acids, adipic acid, hydroxycitric acid, malic acid, fruitaric acid (a blend of malic, fumaric, and tartaric acids), fumaric acid, maleic acid, succinic acid, chlorogenic acid, salicylic acid, creatine, caffeic acid, bile acids, acetic acid, ascorbic acid, alginic acid, erythorbic acid, polyglutamic acid, glucono delta lactone, and their alkali or alkaline earth metal salt derivatives thereof. In addition, the organic acid additives also may be in either the D- or L-configuration.

Suitable organic acid additive salts include, but are not limited to, sodium, calcium, potassium, and magnesium salts of all organic acids, such as salts of citric acid, malic acid, tartaric acid, fumaric acid, lactic acid (e.g., sodium lactate), alginic acid (e.g., sodium alginate), ascorbic acid (e.g., sodium ascorbate), benzoic acid (e.g., sodium benzoate or potassium benzoate), sorbic acid and adipic acid. The examples of the organic acid additives described optionally may be substituted with at least one group chosen from hydrogen, alkyl, alkenyl, alkynyl, halo, haloalkyl, carboxyl, acyl, acyloxy, amino, amido, carboxyl derivatives, alkylamino, dialkylamino, arylamino, alkoxy, aryloxy, nitro, cyano, sulfo, thiol, imine, sulfonyl, sulfenyl, sulfinyl, sulfamyl, carboxalkoxy, carboxamido, phosphonyl, phosphinyl, phosphoryl, phosphino, thioester, thioether, anhydride, oximino, hydrazino, carbamyl, phosphor or phosphonato. In particular embodiments, the organic acid additive is present in the composition in an amount effective to provide a concentration from about 10 ppm to about 5,000 ppm when present in a consumable, such as, for example, a beverage.

Suitable inorganic acid additives include, but are not limited to, phosphoric acid, phosphorous acid, polyphosphoric acid, hydrochloric acid, sulfuric acid, carbonic acid, sodium dihydrogen phosphate, and alkali or alkaline earth metal salts thereof (e.g., inositol hexaphosphate Mg/Ca).

The inorganic acid additive is present in the composition in an amount effective to provide a concentration from about 25 ppm to about 25,000 ppm when present in a consumable, such as, for example, a beverage.

Suitable bitter compound additives include, but are not limited to, caffeine, quinine, urea, bitter orange oil, naringin, quassia, and salts thereof.

The bitter compound is present in the composition in an amount effective to provide a concentration from about 25 ppm to about 25,000 ppm when present in a consumable, such as, for example, a beverage.

Suitable flavorants and flavoring ingredient additives include, but are not limited to, vanillin, vanilla extract, mango extract, cinnamon, citrus, coconut, ginger, viridiflorol, almond, menthol (including menthol without mint), grape skin extract, and grape seed extract. "Flavorant" and "flavoring ingredient" are synonymous and can include natural or synthetic substances or combinations thereof. Flavorants also include any other substance which imparts flavor and may include natural or non-natural (synthetic) substances which are safe for human or animals when used in a generally accepted range. Non-limiting examples of proprietary flavorants include Döhler™ Natural Flavoring Sweetness Enhancer K14323 (Döhler™, Darmstadt, Germany), Symrise™ Natural Flavor Mask for Sweeteners 161453 and 164126 (Symrise™, Holzminden, Germany), Natural Advantage™ Bitterness Blockers 1, 2, 9 and 10 (Natural Advantage™, Freehold, N.J., U.S.A.), and Sucramask™ (Creative Research Management, Stockton, Calif., U.S.A.).

The flavorant is present in the composition in an amount effective to provide a concentration from about 0.1 ppm to about 4,000 ppm when present in a consumable, such as, for example, a beverage.

Suitable polymer additives include, but are not limited to, chitosan, pectin, pectic, pectinic, polyuronic, polygalacturonic acid, starch, food hydrocolloid or crude extracts thereof (e.g., gum acacia senegal (Fibergum™), gum acacia seyal, carageenan), poly-L-lysine (e.g., poly-L-α-lysine or poly-L-ε-lysine), poly-L-ornithine (e.g., poly-L-α-ornithine or poly-L-ε-ornithine), polypropylene glycol, polyethylene glycol, poly(ethylene glycol methyl ether), polyarginine, polyaspartic acid, polyglutamic acid, polyethylene imine, alginic acid, sodium alginate, propylene glycol alginate, and sodium polyethyleneglycolalginate, sodium hexametaphosphate and its salts, and other cationic polymers and anionic polymers.

The polymer is present in the composition in an amount effective to provide a concentration from about 30 ppm to about 2,000 ppm when present in a consumable, such as, for example, a beverage.

Suitable protein or protein hydrolysate additives include, but are not limited to, bovine serum albumin (BSA), whey protein (including fractions or concentrates thereof such as 90% instant whey protein isolate, 34% whey protein, 50% hydrolyzed whey protein, and 80% whey protein concentrate), soluble rice protein, soy protein, protein isolates, protein hydrolysates, reaction products of protein hydrolysates, glycoproteins, and/or proteoglycans containing amino acids (e.g., glycine, alanine, serine, threonine, asparagine, glutamine, arginine, valine, isoleucine, leucine, norvaline, methionine, proline, tyrosine, hydroxyproline, and the like), collagen (e.g., gelatin), partially hydrolyzed collagen (e.g., hydrolyzed fish collagen), and collagen hydrolysates (e.g., porcine collagen hydrolysate).

The protein hydrolysate is present in the composition in an amount effective to provide a concentration from about 200 ppm to about 50,000 ppm when present in a consumable, such as, for example, a beverage.

Suitable surfactant additives include, but are not limited to, polysorbates (e.g., polyoxyethylene sorbitan monooleate (polysorbate 80), polysorbate 20, polysorbate 60), sodium dodecylbenzenesulfonate, dioctyl sulfosuccinate or dioctyl sulfosuccinate sodium, sodium dodecyl sulfate, cetylpyridinium chloride (hexadecylpyridinium chloride), hexadecyltrimethylammonium bromide, sodium cholate, carbamoyl, choline chloride, sodium glycocholate, sodium taurodeoxycholate, lauric arginate, sodium stearoyl lactylate, sodium taurocholate, lecithins, sucrose oleate esters, sucrose stearate esters, sucrose palmitate esters, sucrose laurate esters, and other emulsifiers, and the like.

The surfactant additive is present in the composition in an amount effective to provide a concentration from about 30 ppm to about 2,000 ppm when present in a consumable, such as, for example, a beverage.

Suitable flavonoid additives are classified as flavonols, flavones, flavanones, flavan-3-ols, isoflavones, or anthocyanidins. Non-limiting examples of flavonoid additives include, but are not limited to, catechins (e.g., green tea extracts such as Polyphenon™ 60, Polyphenon™ 30, and Polyphenon™ 25 (Mitsui Norin Co., Ltd., Japan), polyphenols, rutins (e.g., enzyme modified rutin Sanmelin™ AO (San-fi Gen F.F.I., Inc., Osaka, Japan)), neohesperidin, naringin, neohesperidin dihydrochalcone, and the like.

The flavonoid additive is present in the composition in an amount effective to provide a concentration from about 0.1 ppm to about 1,000 ppm when present in a consumable, such as, for example, a beverage.

Suitable alcohol additives include, but are not limited to, ethanol. In particular embodiments, the alcohol additive is present in the composition in an amount effective to provide a concentration from about 625 ppm to about 10,000 ppm when present in a consumable, such as, for example, a beverage.

Suitable astringent compound additives include, but are not limited to, tannic acid, europium chloride ($EuCl_3$), gadolinium chloride ($GdCl_3$), terbium chloride ($TbCl_3$), alum, tannic acid, and polyphenols (e.g., tea polyphenols). The astringent additive is present in the composition in an amount effective to provide a concentration from about 10 ppm to about 5,000 ppm when present in a consumable, such as, for example, a beverage.

Functional Ingredients

The compositions provided herein can also contain one or more functional ingredients, which provide a real or perceived heath benefit to the composition. Functional ingredients include, but are not limited to, saponins, antioxidants, dietary fiber sources, fatty acids, vitamins, glucosamine, minerals, preservatives, hydration agents, probiotics, prebiotics, weight management agents, osteoporosis management agents, phytoestrogens, long chain primary aliphatic saturated alcohols, phytosterols and combinations thereof.

Saponin

In certain embodiments, the functional ingredient is at least one saponin. As used herein, the at least one saponin may comprise a single saponin or a plurality of saponins as a functional ingredient for the composition provided herein. Generally, according to particular embodiments of this invention, the at least one saponin is present in the composition in an amount sufficient to promote health and wellness.

Saponins are glycosidic natural plant products comprising an aglycone ring structure and one or more sugar moieties. The combination of the nonpolar aglycone and the water soluble sugar moiety gives saponins surfactant properties, which allow them to form a foam when shaken in an aqueous solution.

The saponins are grouped together based on several common properties. In particular, saponins are surfactants which display hemolytic activity and form complexes with cholesterol. Although saponins share these properties, they are structurally diverse. The types of aglycone ring structures forming the ring structure in saponins can vary greatly. Non-limiting examples of the types of aglycone ring structures in saponin for use in particular embodiments of the invention include steroids, triterpenoids, and steroidal alkaloids. Non-limiting examples of specific aglycone ring structures for use in particular embodiments of the invention include soyasapogenol A, soyasapogenol B and soyasapogenol E. The number and type of sugar moieties attached to the aglycone ring structure can also vary greatly. Non-limiting examples of sugar moieties for use in particular embodiments of the invention include glucose, galactose, glucuronic acid, xylose, rhamnose, and methylpentose moieties. Non-limiting examples of specific saponins for use in particular embodiments of the invention include group A acetyl saponin, group B acetyl saponin, and group E acetyl saponin.

Saponins can be found in a large variety of plants and plant products, and are especially prevalent in plant skins and barks where they form a waxy protective coating. Several common sources of saponins include soybeans, which have approximately 5% saponin content by dry weight, soapwort plants (Saponaria), the root of which was used historically as soap, as well as alfalfa, aloe, asparagus, grapes, chickpeas, yucca, and various other beans and weeds. Saponins may be obtained from these sources by using extraction techniques well known to those of ordinary skill in the art. A description of conventional extraction techniques can be found in U.S. Pat. Appl. No. 2005/0123662, the disclosure of which is expressly incorporated by reference.

Antioxidant

In certain embodiments, the functional ingredient is at least one antioxidant. As used herein, the at least one antioxidant may comprise a single antioxidant or a plurality of antioxidants as a functional ingredient for the compositions provided herein. Generally, according to particular embodiments of this invention, the at least one antioxidant is present in the composition in an amount sufficient to promote health and wellness.

As used herein "antioxidant" refers to any substance which inhibits, suppresses, or reduces oxidative damage to cells and biomolecules. Without being bound by theory, it is believed that antioxidants inhibit, suppress, or reduce oxidative damage to cells or biomolecules by stabilizing free radicals before they can cause harmful reactions. As such, antioxidants may prevent or postpone the onset of some degenerative diseases.

Examples of suitable antioxidants for embodiments of this invention include, but are not limited to, vitamins, vitamin cofactors, minerals, hormones, carotenoids, carotenoid terpenoids, non-carotenoid terpenoids, flavonoids, flavonoid polyphenolics (e.g., bioflavonoids), flavonols, flavones, phenols, polyphenols, esters of phenols, esters of polyphenols, nonflavonoid phenolics, isothiocyanates, and combinations thereof. In some embodiments, the antioxidant is vitamin A, vitamin C, vitamin E, ubiquinone, mineral selenium, manganese, melatonin, α-carotene, β-carotene, lycopene, lutein, zeanthin, crypoxanthin, reservatol, eugenol, quercetin, catechin, gossypol, hesperetin, curcumin, ferulic acid, thymol, hydroxytyrosol, tumeric, thyme, olive oil, lipoic acid, glutathinone, gutamine, oxalic acid, tocopherol-derived compounds, butylated hydroxyanisole (BHA), butylated hydroxytoluene (BHT), ethylenediaminetetraacetic acid (EDTA), tert-butylhydroquinone, acetic acid, pectin, tocotrienol, tocopherol, coenzyme Q10, zeaxanthin, astaxanthin, canthaxantin, saponins, limonoids, kaempfedrol, myricetin, isorhamnetin, proanthocyanidins, quercetin, rutin, luteolin, apigenin, tangeritin, hesperetin, naringenin, erodictyol, flavan-3-ols (e.g., anthocyanidins), gallocatechins, epicatechin and its gallate forms, epigallocatechin and its gallate forms (ECGC) theaflavin and its gallate forms, thearubigins, isoflavone, phytoestrogens, genistein, daidzein, glycitein, anythocyanins, cyaniding, delphinidin, malvidin, pelargonidin, peonidin, petunidin, ellagic acid, gallic acid, salicylic acid, rosmarinic acid, cinnamic acid and its derivatives (e.g., ferulic acid), chlorogenic acid, chicoric acid, gallotannins, ellagitannins, anthoxanthins, betacyanins and other plant pigments, silymarin, citric acid, lignan, antinutrients, bilirubin, uric acid, R-α-lipoic acid, N-acetylcysteine, emblicanin, apple extract, apple skin extract (applephenon), rooibos extract red, rooibos extract, green, hawthorn berry extract, red raspberry extract, green coffee antioxidant (GCA), aronia extract 20%, grape seed extract (VinOseed), cocoa extract, hops extract, mangosteen extract, mangosteen hull extract, cranberry extract, pomegranate extract, pomegranate hull extract, pomegranate seed extract, hawthorn berry extract, pomella pomegranate extract, cinnamon bark extract, grape skin extract, bilberry extract, pine bark extract, pycnogenol, elderberry extract, mulberry root extract, wolfberry (gogi) extract, blackberry extract, blueberry extract, blueberry leaf extract, raspberry extract, turmeric extract, citrus bioflavonoids, black currant, ginger, acai powder, green coffee bean extract, green tea extract, and phytic acid, or combinations thereof. In alternate embodiments, the antioxidant is a synthetic antioxidant such as butylated hydroxytolune or butylated hydroxyanisole, for example. Other sources of suitable antioxidants for embodiments of this invention include, but are not limited to, fruits, vegetables, tea, cocoa, chocolate, spices, herbs, rice, organ meats from livestock, yeast, whole grains, or cereal grains.

Particular antioxidants belong to the class of phytonutrients called polyphenols (also known as "polyphenolics"), which are a group of chemical substances found in plants, characterized by the presence of more than one phenol group per molecule. A variety of health benefits may be derived from polyphenols, including prevention of cancer, heart disease, and chronic inflammatory disease and improved mental strength and physical strength, for example. Suitable polyphenols for embodiments of this invention include catechins, proanthocyanidins, procyanidins, anthocyanins, quercerin, rutin, reservatrol, isoflavones, curcumin, punicalagin, ellagitannin, hesperidin, naringin, citrus flavonoids, chlorogenic acid, other similar materials, and combinations thereof.

In particular embodiments, the antioxidant is a catechin such as, for example, epigallocatechin gallate (EGCG). Suitable sources of catechins for embodiments of this invention include, but are not limited to, green tea, white tea, black tea, oolong tea, chocolate, cocoa, red wine, grape seed, red grape skin, purple grape skin, red grape juice, purple grape juice, berries, pycnogenol, and red apple peel.

In some embodiments, the antioxidant is chosen from proanthocyanidins, procyanidins or combinations thereof. Suitable sources of proanthocyanidins and procyanidins for embodiments of this invention include, but are not limited to, red grapes, purple grapes, cocoa, chocolate, grape seeds, red wine, cacao beans, cranberry, apple peel, plum, blueberry, black currants, choke berry, green tea, sorghum, cinnamon, barley, red kidney bean, pinto bean, hops, almonds, hazelnuts, pecans, pistachio, pycnogenol, and colorful berries.

In particular embodiments, the antioxidant is an anthocyanin. Suitable sources of anthocyanins for embodiments of this invention include, but are not limited to, red berries, blueberries, bilberry, cranberry, raspberry, cherry, pomegranate, strawberry, elderberry, choke berry, red grape skin, purple grape skin, grape seed, red wine, black currant, red currant, cocoa, plum, apple peel, peach, red pear, red cabbage, red onion, red orange, and blackberries.

In some embodiments, the antioxidant is chosen from quercetin, rutin or combinations thereof. Suitable sources of quercetin and rutin for embodiments of this invention include, but are not limited to, red apples, onions, kale, bog whortleberry, lingonberrys, chokeberry, cranberry, blackberry, blueberry, strawberry, raspberry, black currant, green tea, black tea, plum, apricot, parsley, leek, broccoli, chili pepper, berry wine, and ginkgo.

In some embodiments, the antioxidant is reservatrol. Suitable sources of reservatrol for embodiments of this invention include, but are not limited to, red grapes, peanuts, cranberry, blueberry, bilberry, mulberry, Japanese Itadori tea, and red wine.

In particular embodiments, the antioxidant is an isoflavone. Suitable sources of isoflavones for embodiments of this invention include, but are not limited to, soy beans, soy products, legumes, alfalfa spouts, chickpeas, peanuts, and red clover.

In some embodiments, the antioxidant is curcumin. Suitable sources of curcumin for embodiments of this invention include, but are not limited to, turmeric and mustard.

In particular embodiments, the antioxidant is chosen from punicalagin, ellagitannin or combinations thereof. Suitable sources of punicalagin and ellagitannin for embodiments of this invention include, but are not limited to, pomegranate, raspberry, strawberry, walnut, and oak-aged red wine.

In some embodiments, the antioxidant is a citrus flavonoid, such as hesperidin or naringin. Suitable sources of citrus flavonoids, such as hesperidin or naringin, for embodiments of this invention include, but are not limited to, oranges, grapefruits, and citrus juices.

In particular embodiments, the antioxidant is chlorogenic acid. Suitable sources of chlorogenic acid for embodiments of this invention include, but are not limited to, green coffee, yerba mate, red wine, grape seed, red grape skin, purple grape skin, red grape juice, purple grape juice, apple juice, cranberry, pomegranate, blueberry, strawberry, sunflower, Echinacea, pycnogenol, and apple peel.

Dietary Fiber

In certain embodiments, the functional ingredient is at least one dietary fiber source. As used herein, the at least one dietary fiber source may comprise a single dietary fiber source or a plurality of dietary fiber sources as a functional ingredient for the compositions provided herein. Generally, according to particular embodiments of this invention, the at least one dietary fiber source is present in the composition in an amount sufficient to promote health and wellness.

Numerous polymeric carbohydrates having significantly different structures in both composition and linkages fall within the definition of dietary fiber. Such compounds are well known to those skilled in the art, non-limiting examples of which include non-starch polysaccharides, lignin, cellulose, methylcellulose, the hemicelluloses, β-glucans, pectins, gums, mucilage, waxes, inulins, oligosaccharides, fructooligosaccharides, cyclodextrins, chitins, and combinations thereof.

Polysaccharides are complex carbohydrates composed of monosaccharides joined by glycosidic linkages. Non-starch polysaccharides are bonded with β-linkages, which humans are unable to digest due to a lack of an enzyme to break the β-linkages. Conversely, digestible starch polysaccharides generally comprise α(1-4) linkages.

Lignin is a large, highly branched and cross-linked polymer based on oxygenated phenylpropane units. Cellulose is a linear polymer of glucose molecules joined by a β(1-4) linkage, which mammalian amylases are unable to hydrolyze. Methylcellulose is a methyl ester of cellulose that is often used in foodstuffs as a thickener, and emulsifier. It is commercially available (e.g., Citrucel by GlaxoSmithKline, Celevac by Shire Pharmaceuticals). Hemicelluloses are highly branched polymers consisting mainly of glucurono- and 4-O-methylglucuroxylans. β-Glucans are mixed-linkage (1-3), (1-4) β-D-glucose polymers found primarily in cereals, such as oats and barley. Pectins, such as beta pectin, are a group of polysaccharides composed primarily of D-galacturonic acid, which is methoxylated to variable degrees.

Gums and mucilages represent a broad array of different branched structures. Guar gum, derived from the ground endosperm of the guar seed, is a galactomannan. Guar gum is commercially available (e.g., Benefiber by Novartis AG). Other gums, such as gum arabic and pectins, have still different structures. Still other gums include xanthan gum, gellan gum, tara gum, psyllium seed husk gum, and locust been gum.

Waxes are esters of ethylene glycol and two fatty acids, generally occurring as a hydrophobic liquid that is insoluble in water.

Inulins comprise naturally occurring oligosaccharides belonging to a class of carbohydrates known as fructans. They generally are comprised of fructose units joined by β(2-1) glycosidic linkages with a terminal glucose unit. Oligosaccharides are saccharide polymers containing typically three to six component sugars. They are generally found either O- or N-linked to compatible amino acid side chains in proteins or to lipid molecules. Fructooligosaccharides are oligosaccharides consisting of short chains of fructose molecules.

Food sources of dietary fiber include, but are not limited to, grains, legumes, fruits, and vegetables. Grains providing dietary fiber include, but are not limited to, oats, rye, barley, wheat. Legumes providing fiber include, but are not limited to, peas and beans such as soybeans. Fruits and vegetables providing a source of fiber include, but are not limited to, apples, oranges, pears, bananas, berries, tomatoes, green beans, broccoli, cauliflower, carrots, potatoes, celery. Plant foods such as bran, nuts, and seeds (such as flax seeds) are also sources of dietary fiber. Parts of plants providing dietary fiber include, but are not limited to, the stems, roots, leaves, seeds, pulp, and skin.

Although dietary fiber generally is derived from plant sources, indigestible animal products such as chitins are also classified as dietary fiber. Chitin is a polysaccharide composed of units of acetylglucosamine joined by β(1-4) linkages, similar to the linkages of cellulose.

Sources of dietary fiber often are divided into categories of soluble and insoluble fiber based on their solubility in water. Both soluble and insoluble fibers are found in plant foods to varying degrees depending upon the characteristics of the plant. Although insoluble in water, insoluble fiber has passive hydrophilic properties that help increase bulk, soften stools, and shorten transit time of fecal solids through the intestinal tract.

Unlike insoluble fiber, soluble fiber readily dissolves in water. Soluble fiber undergoes active metabolic processing via fermentation in the colon, increasing the colonic microflora and thereby increasing the mass of fecal solids. Fermentation of fibers by colonic bacteria also yields endproducts with significant health benefits. For example, fermentation of the food masses produces gases and shortchain fatty acids. Acids produced during fermentation include butyric, acetic, propionic, and valeric acids that have various beneficial properties such as stabilizing blood glucose levels by acting on pancreatic insulin release and providing liver control by glycogen breakdown. In addition, fiber fermentation may reduce atherosclerosis by lowering cholesterol synthesis by the liver and reducing blood levels of LDL and triglycerides. The acids produced during fermentation lower colonic pH, thereby protecting the colon lining from cancer polyp formation. The lower colonic pH also increases mineral absorption, improves the barrier properties of the colonic mucosal layer, and inhibits inflammatory and adhesion irritants. Fermentation of fibers also may benefit the immune system by stimulating production of T-helper cells, antibodies, leukocytes, splenocytes, cytokinins and lymphocytes.

Fatty Acid

In certain embodiments, the functional ingredient is at least one fatty acid. As used herein, the at least one fatty acid may be single fatty acid or a plurality of fatty acids as a functional ingredient for the compositions provided herein. Generally, according to particular embodiments of this invention, the at least one fatty acid is present in the composition in an amount sufficient to promote health and wellness.

As used herein, "fatty acid" refers to any straight chain monocarboxylic acid and includes saturated fatty acids, unsaturated fatty acids, long chain fatty acids, medium chain fatty acids, short chain fatty acids, fatty acid precursors (including omega-9 fatty acid precursors), and esterified fatty acids. As used herein, "long chain polyunsaturated fatty acid" refers to any polyunsaturated carboxylic acid or organic acid with a long aliphatic tail. As used herein, "omega-3 fatty acid" refers to any polyunsaturated fatty acid having a first double bond as the third carbon-carbon bond from the terminal methyl end of its carbon chain. In particular embodiments, the omega-3 fatty acid may comprise a long chain omega-3 fatty acid. As used herein, "omega-6 fatty acid" any polyunsaturated fatty acid having a first double bond as the sixth carbon-carbon bond from the terminal methyl end of its carbon chain.

Suitable omega-3 fatty acids for use in embodiments of the present invention can be derived from algae, fish, animals, plants, or combinations thereof, for example. Examples of suitable omega-3 fatty acids include, but are not limited to, linolenic acid, alpha-linolenic acid, eicosapentaenoic acid, docosahexaenoic acid, stearidonic acid, eicosatetraenoic acid and combinations thereof. In some embodiments, suitable omega-3 fatty acids can be provided in fish oils, (e.g., menhaden oil, tuna oil, salmon oil, bonito oil, and cod oil), microalgae omega-3 oils or combinations thereof. In particular embodiments, suitable omega-3 fatty acids may be derived from commercially available omega-3 fatty acid oils such as Microalgae DHA oil (from Martek, Columbia, Md.), OmegaPure (from Omega Protein, Houston, Tex.), Marinol C-38 (from Lipid Nutrition, Channahon, Ill.), Bonito oil and MEG-3 (from Ocean Nutrition, Dartmouth, NS), Evogel (from Symrise, Holzminden, Germany), Marine Oil, from tuna or salmon (from Arista Wilton, Conn.), OmegaSource 2000, Marine Oil, from menhaden and Marine Oil, from cod (from OmegaSource, RTP, NC).

Suitable omega-6 fatty acids include, but are not limited to, linoleic acid, gamma-linolenic acid, dihommo-gamma-linolenic acid, arachidonic acid, eicosadienoic acid, docosadienoic acid, adrenic acid, docosapentaenoic acid and combinations thereof.

Suitable esterified fatty acids for embodiments of the present invention may include, but are not limited to, monoacylglycerols containing omega-3 and/or omega-6 fatty acids, diacylglycerols containing omega-3 and/or omega-6 fatty acids, or triacylglycerols containing omega-3 and/or omega-6 fatty acids and combinations thereof.

Vitamin

In certain embodiments, the functional ingredient is at least one vitamin.

As used herein, the at least one vitamin may be single vitamin or a plurality of vitamins as a functional ingredient for the compositions provided herein. Generally, according to particular embodiments of this invention, the at least one vitamin is present in the composition in an amount sufficient to promote health and wellness.

Vitamins are organic compounds that the human body needs in small quantities for normal functioning. The body uses vitamins without breaking them down, unlike other nutrients such as carbohydrates and proteins. To date, thirteen vitamins have been recognized, and one or more can be used in the compositions herein. Suitable vitamins include, vitamin A, vitamin D, vitamin E, vitamin K, vitamin B1, vitamin B2, vitamin B3, vitamin B5, vitamin B6, vitamin B7, vitamin B9, vitamin B12, and vitamin C. Many of vitamins also have alternative chemical names, non-limiting examples of which are provided below.

| Vitamin | Alternative names |
| --- | --- |
| Vitamin A | Retinol |
|  | Retinaldehyde |
|  | Retinoic acid |
|  | Retinoids |
|  | Retinal |
|  | Retinoic ester |
| Vitamin D (vitamins D1-D5) | Calciferol |
|  | Cholecalciferol |
|  | Lumisterol |
|  | Ergocalciferol |
|  | Dihydrotachysterol |
|  | 7-dehydrocholesterol |
| Vitamin E | Tocopherol |
|  | Tocotrienol |
| Vitamin K | Phylloquinone |
|  | Naphthoquinone |
| Vitamin B1 | Thiamin |
| Vitamin B2 | Riboflavin |
|  | Vitamin G |
| Vitamin B3 | Niacin |
|  | Nicotinic acid |
|  | Vitamin PP |
| Vitamin B5 | Pantothenic acid |
| Vitamin B6 | Pyridoxine |
|  | Pyridoxal |
|  | Pyridoxamine |
| Vitamin B7 | Biotin |
|  | Vitamin H |
| Vitamin B9 | Folic acid |
|  | Folate |
|  | Folacin |
|  | Vitamin M |
|  | Pteroyl-L-glutamic acid |
| Vitamin B12 | Cobalamin |
|  | Cyanocobalamin |
| Vitamin C | Ascorbic acid |

Various other compounds have been classified as vitamins by some authorities. These compounds may be termed pseudo-vitamins and include, but are not limited to, compounds such as ubiquinone (coenzyme Q10), pangamic acid, dimethylglycine, taestrile, amygdaline, flavanoids, para-aminobenzoic acid, adenine, adenylic acid, and s-methylmethionine. As used herein, the term vitamin includes pseudo-vitamins.

In some embodiments, the vitamin is a fat-soluble vitamin chosen from vitamin A, D, E, K and combinations thereof.

In other embodiments, the vitamin is a water-soluble vitamin chosen from vitamin B1, vitamin B2, vitamin B3, vitamin B6, vitamin B12, folic acid, biotin, pantothenic acid, vitamin C and combinations thereof.

Glucosamine

In certain embodiments, the functional ingredient is glucosamine.

Generally, according to particular embodiments of this invention, glucosamine is present in the compositions in an amount sufficient to promote health and wellness.

Glucosamine, also called chitosamine, is an amino sugar that is believed to be an important precursor in the biochemical synthesis of glycosylated proteins and lipids. D-glucosamine occurs naturally in the cartilage in the form of glucosamine-6-phosphate, which is synthesized from fructose-6-phosphate and glutamine. However, glucosamine also is available in other forms, non-limiting examples of which include glucosamine hydrochloride, glucosamine sulfate, N-acetyl-glucosamine, or any other salt forms or combinations thereof. Glucosamine may be obtained by acid hydrolysis of the shells of lobsters, crabs, shrimps, or prawns using methods well known to those of ordinary skill in the art. In a particular embodiment, glucosamine may be derived from fungal biomass containing chitin, as described in U.S. Patent Publication No. 2006/0172392.

The compositions can further comprise chondroitin sulfate.

Mineral

In certain embodiments, the functional ingredient is at least one mineral.

As used herein, the at least one mineral may be single mineral or a plurality of minerals as a functional ingredient for the compositions provided herein. Generally, according to particular embodiments of this invention, the at least one mineral is present in the composition in an amount sufficient to promote health and wellness.

Minerals, in accordance with the teachings of this invention, comprise inorganic chemical elements required by living organisms. Minerals are comprised of a broad range of compositions (e.g., elements, simple salts, and complex silicates) and also vary broadly in crystalline structure. They may naturally occur in foods and beverages, may be added as a supplement, or may be consumed or administered separately from foods or beverages.

Minerals may be categorized as either bulk minerals, which are required in relatively large amounts, or trace minerals, which are required in relatively small amounts. Bulk minerals generally are required in amounts greater than or equal to about 100 mg per day and trace minerals are those that are required in amounts less than about 100 mg per day.

In particular embodiments of this invention, the mineral is chosen from bulk minerals, trace minerals or combinations thereof. Non-limiting examples of bulk minerals include calcium, chlorine, magnesium, phosphorous, potassium, sodium, and sulfur. Non-limiting examples of trace minerals include chromium, cobalt, copper, fluorine, iron, manganese, molybdenum, selenium, zinc, and iodine. Although iodine generally is classified as a trace mineral, it is required in larger quantities than other trace minerals and often is categorized as a bulk mineral.

In other particular embodiments of this invention, the mineral is a trace mineral, believed to be necessary for human nutrition, non-limiting examples of which include bismuth, boron, lithium, nickel, rubidium, silicon, strontium, tellurium, tin, titanium, tungsten, and vanadium.

The minerals embodied herein may be in any form known to those of ordinary skill in the art. For example, in a particular embodiment the minerals may be in their ionic form, having either a positive or negative charge. In another particular embodiment the minerals may be in their molecular form. For example, sulfur and phosphorous often are found naturally as sulfates, sulfides, and phosphates.

Preservative

In certain embodiments, the functional ingredient is at least one preservative.

As used herein, the at least one preservative may be single preservative or a plurality of preservatives as a functional ingredient for the compositions provided herein. Generally, according to particular embodiments of this invention, the at least one preservative is present in the composition in an amount sufficient to promote health and wellness.

In particular embodiments of this invention, the preservative is chosen from antimicrobials, antioxidants, antienzymatics or combinations thereof. Non-limiting examples of antimicrobials include sulfites, propionates, benzoates, sorbates, nitrates, nitrites, bacteriocins, salts, sugars, acetic acid, dimethyl dicarbonate (DMDC), ethanol, and ozone.

According to a particular embodiment, the preservative is a sulfite. Sulfites include, but are not limited to, sulfur dioxide, sodium bisulfite, and potassium hydrogen sulfite.

According to another particular embodiment, the preservative is a propionate. Propionates include, but are not limited to, propionic acid, calcium propionate, and sodium propionate.

According to yet another particular embodiment, the preservative is a benzoate. Benzoates include, but are not limited to, sodium benzoate and benzoic acid.

In another particular embodiment, the preservative is a sorbate. Sorbates include, but are not limited to, potassium sorbate, sodium sorbate, calcium sorbate, and sorbic acid.

In still another particular embodiment, the preservative is a nitrate and/or a nitrite. Nitrates and nitrites include, but are not limited to, sodium nitrate and sodium nitrite.

In yet another particular embodiment, the at least one preservative is a bacteriocin, such as, for example, nisin.

In another particular embodiment, the preservative is ethanol.

In still another particular embodiment, the preservative is ozone.

Non-limiting examples of antienzymatics suitable for use as preservatives in particular embodiments of the invention include ascorbic acid, citric acid, and metal chelating agents such as ethylenediaminetetraacetic acid (EDTA).

Hydration Agent

In certain embodiments, the functional ingredient is at least one hydration agent.

As used herein, the at least one hydration agent may be single hydration agent or a plurality of hydration agents as a functional ingredient for the compositions provided herein. Generally, according to particular embodiments of this invention, the at least one hydration agent is present in the composition in an amount sufficient to promote health and wellness.

Hydration products help the body to replace fluids that are lost through excretion. For example, fluid is lost as sweat in order to regulate body temperature, as urine in order to excrete waste substances, and as water vapor in order to exchange gases in the lungs. Fluid loss can also occur due to a wide range of external causes, non-limiting examples of which include physical activity, exposure to dry air, diarrhea, vomiting, hyperthermia, shock, blood loss, and hypotension. Diseases causing fluid loss include diabetes, cholera, gastroenteritis, shigellosis, and yellow fever. Forms of malnutrition that cause fluid loss include the excessive consumption of alcohol, electrolyte imbalance, fasting, and rapid weight loss.

In a particular embodiment, the hydration product is a composition that helps the body replace fluids that are lost during exercise. Accordingly, in a particular embodiment, the hydration product is an electrolyte, non-limiting examples of which include sodium, potassium, calcium, magnesium, chloride, phosphate, bicarbonate, and combinations thereof. Suitable electrolytes for use in particular embodiments of this invention are also described in U.S. Pat. No. 5,681,569, the disclosure of which is expressly incorporated herein by reference. In particular embodiments, the electrolytes are obtained from their corresponding water-soluble salts. Non-limiting examples of salts for use in particular embodiments include chlorides, carbonates, sulfates, acetates, bicarbonates, citrates, phosphates, hydrogen phosphates, tartrates, sorbates, citrates, benzoates, or combinations thereof. In other embodiments, the electrolytes are provided by juice, fruit extracts, vegetable extracts, tea, or teas extracts.

In particular embodiments of this invention, the hydration product is a carbohydrate to supplement energy stores burned by muscles. Suitable carbohydrates for use in particular embodiments of this invention are described in U.S. Pat. Nos. 4,312,856, 4,853,237, 5,681,569, and 6,989,171, the disclosures of which are expressly incorporated herein by reference. Non-limiting examples of suitable carbohydrates include monosaccharides, disaccharides, oligosaccharides, complex polysaccharides or combinations thereof. Non-limiting examples of suitable types of monosaccharides for use in particular embodiments include trioses, tetroses, pentoses, hexoses, heptoses, octoses, and nonoses. Non-limiting examples of specific types of suitable monosaccharides include glyceraldehyde, dihydroxyacetone, erythrose, threose, erythrulose, arabinose, lyxose, ribose, xylose, ribulose, xylulose, allose, altrose, galactose, glucose, gulose, idose, mannose, talose, fructose, psicose, sorbose, tagatose, mannoheptulose, sedoheltulose, octolose, and sialose. Non-limiting examples of suitable disaccharides include sucrose, lactose, and maltose. Non-limiting examples of suitable oligosaccharides include saccharose, maltotriose, and maltodextrin. In other particular embodiments, the carbohydrates are provided by a corn syrup, a beet sugar, a cane sugar, a juice, or a tea.

In another particular embodiment, the hydration is a flavanol that provides cellular rehydration. Flavanols are a class of natural substances present in plants, and generally comprise a 2-phenylbenzopyrone molecular skeleton attached to one or more chemical moieties. Non-limiting examples of suitable flavanols for use in particular embodiments of this invention include catechin, epicatechin, gallocatechin, epigallocatechin, epicatechin gallate, epigallocatechin 3-gallate, theaflavin, theaflavin 3-gallate, theaflavin 3'-gallate, theaflavin 3,3' gallate, thearubigin or combinations thereof. Several common sources of flavanols include tea plants, fruits, vegetables, and flowers. In preferred embodiments, the flavanol is extracted from green tea.

In a particular embodiment, the hydration product is a glycerol solution to enhance exercise endurance. The ingestion of a glycerol containing solution has been shown to provide beneficial physiological effects, such as expanded blood volume, lower heart rate, and lower rectal temperature.

Probiotics/Prebiotics

In certain embodiments, the functional ingredient is chosen from at least one probiotic, prebiotic and combination thereof.

As used herein, the at least one probiotic or prebiotic may be single probiotic or prebiotic or a plurality of probiotics or prebiotics as a functional ingredient for the compositions provided herein. Generally, according to particular embodiments of this invention, the at least one probiotic, prebiotic or combination thereof is present in the composition in an amount sufficient to promote health and wellness.

Probiotics, in accordance with the teachings of this invention, comprise microorganisms that benefit health when consumed in an effective amount. Desirably, probiotics beneficially affect the human body's naturally-occurring gastrointestinal microflora and impart health benefits apart from nutrition. Probiotics may include, without limitation, bacteria, yeasts, and fungi.

Prebiotics, in accordance with the teachings of this invention, are compositions that promote the growth of beneficial bacteria in the intestines. Prebiotic substances can be consumed by a relevant probiotic, or otherwise assist in keeping the relevant probiotic alive or stimulate its growth. When consumed in an effective amount, prebiotics also beneficially affect the human body's naturally-occurring gastrointestinal microflora and thereby impart health benefits apart from just nutrition. Prebiotic foods enter the colon and serve as substrate for the endogenous bacteria, thereby indirectly providing the host with energy, metabolic substrates, and essential micronutrients. The body's digestion and absorption of prebiotic foods is dependent upon bacterial metabolic activity, which salvages energy for the host from nutrients that escaped digestion and absorption in the small intestine.

According to particular embodiments, the probiotic is a beneficial microorganisms that beneficially affects the human body's naturally-occurring gastrointestinal microflora and imparts health benefits apart from nutrition. Examples of probiotics include, but are not limited to, bacteria of the genus *Lactobacilli, Bifidobacteria, Streptococci*, or combinations thereof, that confer beneficial effects to humans.

In particular embodiments of the invention, the at least one probiotic is chosen from the genus *Lactobacilli. Lactobacilli* (i.e., bacteria of the genus *Lactobacillus*, hereinafter "*L.*") have been used for several hundred years as a food preservative and for promoting human health. Non-limiting examples of species of *Lactobacilli* found in the human intestinal tract include *L. acidophilus, L. casei, L. fermentum, L. saliva roes, L. brevis, L. leichmannii, L. plantarum, L. cellobiosus, L. reuteri, L. rhamnosus, L. GG, L. bulgaricus*, and *L. thermophilus*.

According to other particular embodiments of this invention, the probiotic is chosen from the genus *Bifidobacteria*. *Bifidobacteria* also are known to exert a beneficial influence on human health by producing short chain fatty acids (e.g., acetic, propionic, and butyric acids), lactic, and formic acids as a result of carbohydrate metabolism. Non-limiting species of *Bifidobacteria* found in the human gastrointestinal tract include *B. angulatum, B. animalis, B. asteroides, B. bifidum, B. bourn, B. breve, B. catenulatum, B. choerinum, B. coryneforme, B. cuniculi, B. dentium, B. gallicum, B. gallinarum, B indicum, B. longum, B. magnum, B. merycicum, B. minimum, B. pseudocatenulatum, B. pseudolongum, B. psychraerophilum, B. pullorum, B. ruminantium, B. saeculare, B. scardovii, B. simiae, B. subtile, B. thermacidophilum, B. thermophilum, B. urinalis*, and *B.* sp.

According to other particular embodiments of this invention, the probiotic is chosen from the genus *Streptococcus*. *Streptococcus thermophilus* is a gram-positive facultative anaerobe. It is classified as a lactic acid bacteria and commonly is found in milk and milk products, and is used in the production of yogurt. Other non-limiting probiotic species of this bacteria include *Streptococcus salivarus* and *Streptococcus cremoris*.

Probiotics that may be used in accordance with this invention are well-known to those of skill in the art. Non-limiting examples of foodstuffs comprising probiotics include yogurt, sauerkraut, kefir, kimchi, fermented vegetables, and other foodstuffs containing a microbial element that beneficially affects the host animal by improving the intestinal microbalance.

Prebiotics, in accordance with the embodiments of this invention, include, without limitation, mucopolysaccharides, oligosaccharides, polysaccharides, amino acids, vitamins, nutrient precursors, proteins and combinations thereof.

According to a particular embodiment of this invention, the prebiotic is chosen from dietary fibers, including, without limitation, polysaccharides and oligosaccharides. These compounds have the ability to increase the number of probiotics, which leads to the benefits conferred by the probiotics. Non-limiting examples of oligosaccharides that are categorized as prebiotics in accordance with particular embodiments of this invention include fructooligosaccharides, inulins, isomalto-oligosaccharides, lactitol, lactosucrose, lactulose, pyrodextrins, soy oligosaccharides, transgalacto-oligosaccharides, and xylo-oligosaccharides.

According to other particular embodiments of the invention, the prebiotic is an amino acid. Although a number of known prebiotics break down to provide carbohydrates for probiotics, some probiotics also require amino acids for nourishment.

Prebiotics are found naturally in a variety of foods including, without limitation, bananas, berries, asparagus, garlic, wheat, oats, barley (and other whole grains), flaxseed, tomatoes, Jerusalem artichoke, onions and chicory, greens (e.g., dandelion greens, spinach, collard greens, chard, kale, mustard greens, turnip greens), and legumes (e.g., lentils, kidney beans, chickpeas, navy beans, white beans, black beans).

Weight Management Agent

In certain embodiments, the functional ingredient is at least one weight management agent.

As used herein, the at least one weight management agent may be single weight management agent or a plurality of weight management agents as a functional ingredient for the compositions provided herein. Generally, according to particular embodiments of this invention, the at least one weight management agent is present in the composition in an amount sufficient to promote health and wellness.

As used herein, "a weight management agent" includes an appetite suppressant and/or a thermogenesis agent. As used herein, the phrases "appetite suppressant", "appetite satiation compositions", "satiety agents", and "satiety ingredients" are synonymous. The phrase "appetite suppressant" describes macronutrients, herbal extracts, exogenous hormones, anorectics, anorexigenics, pharmaceutical drugs, and combinations thereof, that when delivered in an effective amount, suppress, inhibit, reduce, or otherwise curtail a person's appetite. The phrase "thermogenesis agent" describes macronutrients, herbal extracts, exogenous hormones, anorectics, anorexigenics, pharmaceutical drugs, and combinations thereof, that when delivered in an effective amount, activate or otherwise enhance a person's thermogenesis or metabolism.

Suitable weight management agents include macronutrient selected from the group consisting of proteins, carbohydrates, dietary fats, and combinations thereof. Consumption of proteins, carbohydrates, and dietary fats stimulates the release of peptides with appetite-suppressing effects. For example, consumption of proteins and dietary fats stimulates the release of the gut hormone cholecytokinin (CCK), while consumption of carbohydrates and dietary fats stimulates release of Glucagon-like peptide 1 (GLP-1).

Suitable macronutrient weight management agents also include carbohydrates. Carbohydrates generally comprise sugars, starches, cellulose and gums that the body converts into glucose for energy. Carbohydrates often are classified into two categories, digestible carbohydrates (e.g., monosaccharides, disaccharides, and starch) and non-digestible carbohydrates (e.g., dietary fiber). Studies have shown that non-digestible carbohydrates and complex polymeric carbohydrates having reduced absorption and digestibility in the small intestine stimulate physiologic responses that inhibit food intake. Accordingly, the carbohydrates embodied herein desirably comprise non-digestible carbohydrates or carbohydrates with reduced digestibility. Non-limiting examples of such carbohydrates include polydextrose; inulin; monosaccharide-derived polyols such as erythritol, mannitol, xylitol, and sorbitol; disaccharide-derived alcohols such as isomalt, lactitol, and maltitol; and hydrogenated starch hydrolysates. Carbohydrates are described in more detail herein below.

In another particular embodiment weight management agent is a dietary fat. Dietary fats are lipids comprising combinations of saturated and unsaturated fatty acids. Polyunsaturated fatty acids have been shown to have a greater satiating power than mono-unsaturated fatty acids. Accordingly, the dietary fats embodied herein desirably comprise poly-unsaturated fatty acids, non-limiting examples of which include triacylglycerols.

In a particular embodiment, the weight management agents is an herbal extract. Extracts from numerous types of plants have been identified as possessing appetite suppressant properties. Non-limiting examples of plants whose extracts have appetite suppressant properties include plants of the genus *Hoodia, Trichocaulon, Caralluma, Stapelia, Orbea, Asclepias*, and *Camelia*. Other embodiments include extracts derived from Gymnema Sylvestre, Kola Nut, Citrus Auran tium, Yerba Mate, Griffonia Simplicifolia, Guarana, myrrh, guggul Lipid, and black current seed oil.

The herbal extracts may be prepared from any type of plant material or plant biomass. Non-limiting examples of plant material and biomass include the stems, roots, leaves, dried powder obtained from the plant material, and sap or dried sap. The herbal extracts generally are prepared by extracting sap from the plant and then spray-drying the sap. Alternatively, solvent extraction procedures may be employed. Following the initial extraction, it may be desirable to further fractionate the initial extract (e.g., by column chromatography) in order to obtain an herbal extract with enhanced activity. Such techniques are well known to those of ordinary skill in the art.

In a particular embodiment, the herbal extract is derived from a plant of the genus *Hoodia*, species of which include *H. alstonii, H. currorii, H. dregei, H. flava, H. gordonii, H. jutatae, H. mossamedensis, H. officinalis, H. parviflorai, H. pedicellata, H. pilifera, H. ruschii*, and *H. triebneri*. *Hoodia* plants are stem succulents native to southern Africa. A sterol glycoside of *Hoodia*, known as P57, is believed to be responsible for the appetite-suppressant effect of the *Hoodia* species.

In another particular embodiment, the herbal extract is derived from a plant of the genus *Caralluma*, species of which include *C. indica, C. fimbriata, C. attenuate, C. tuberculate, C. edulis, C. adscendens, C. stalagmifera, C. umbellate, C. penicillata, C. russeliana, C. retrospicens, C. Arabica*, and *C. lasiantha*. *Carralluma* plants belong to the same Subfamily as *Hoodia*, Asclepiadaceae. *Caralluma* are small, erect and fleshy plants native to India having medicinal properties, such as appetite suppression, that generally are attributed to glycosides belonging to the pregnane group of glycosides, non-limiting examples of which include caratuberside A, caratuberside B, bouceroside I, bouceroside II, bouceroside III, bouceroside IV, bouceroside V, bouceroside VI, bouceroside VII, bouceroside VIII, bouceroside IX, and bouceroside X.

In another particular embodiment, the at least one herbal extract is derived from a plant of the genus *Trichocaulon*. *Trichocaulon* plants are succulents that generally are native to southern Africa, similar to *Hoodia*, and include the species *T. piliferum* and *T. officinale*.

In another particular embodiment, the herbal extract is derived from a plant of the genus *Stapelia* or *Orbea*, species of which include *S. gigantean* and *O. variegate*, respectively. Both *Stapelia* and *Orbea* plants belong to the same Subfamily as *Hoodia*, Asclepiadaceae. Not wishing to be bound by any theory, it is believed that the compounds exhibiting appetite suppressant activity are saponins, such as pregnane glycosides, which include stavarosides A, B, C, D, E, F, G, H, I, J, and K.

In another particular embodiment, the herbal extract is derived from a plant of the genus *Asclepias*. *Asclepias* plants also belong to the Asclepiadaceae family of plants. Non-limiting examples of *Asclepias* plants include *A. incarnate, A. curassayica, A. syriaca*, and *A. tuberose*. Not wishing to be bound by any theory, it is believed that the extracts comprise steroidal compounds, such as pregnane glycosides and pregnane aglycone, having appetite suppressant effects.

In a particular embodiment, the weight management agent is an exogenous hormone having a weight management effect. Non-limiting examples of such hormones include CCK, peptide YY, ghrelin, bombesin and gastrin-releasing peptide (GRP), enterostatin, apolipoprotein A-IV, GLP-1, amylin, somastatin, and leptin.

In another embodiment, the weight management agent is a pharmaceutical drug. Non-limiting examples include phentenime, diethylpropion, phendimetrazine, sibutramine, rimonabant, oxyntomodulin, floxetine hydrochloride, ephedrine, phenethylamine, or other stimulants.

Osteoporosis Management Agent

In certain embodiments, the functional ingredient is at least one osteoporosis management agent.

As used herein, the at least one osteoporosis management agent may be single osteoporosis management agent or a plurality of osteoporosis management agent as a functional ingredient for the compositions provided herein. Generally, according to particular embodiments of this invention, the at least one osteoporosis management agent is present in the composition in an amount sufficient to promote health and wellness.

Osteoporosis is a skeletal disorder of compromised bone strength, resulting in an increased risk of bone fracture. Generally, osteoporosis is characterized by reduction of the bone mineral density (BMD), disruption of bone micro-architecture, and changes to the amount and variety of non-collagenous proteins in the bone.

In certain embodiments, the osteoporosis management agent is at least one calcium source. According to a particular embodiment, the calcium source is any compound containing calcium, including salt complexes, solubilized species, and other forms of calcium. Non-limiting examples of calcium sources include amino acid chelated calcium, calcium carbonate, calcium oxide, calcium hydroxide, calcium sulfate, calcium chloride, calcium phosphate, calcium hydrogen phosphate, calcium dihydrogen phosphate, calcium citrate, calcium malate, calcium citrate malate, calcium gluconate, calcium tartrate, calcium lactate, solubilized species thereof, and combinations thereof.

According to a particular embodiment, the osteoporosis management agent is a magnesium soucrce. The magnesium source is any compound containing magnesium, including salt complexes, solubilized species, and other forms of magnesium. Non-limiting examples of magnesium sources include magnesium chloride, magnesium citrate, magnesium gluceptate, magnesium gluconate, magnesium lactate, magnesium hydroxide, magnesium picolate, magnesium sulfate, solubilized species thereof, and mixtures thereof. In another particular embodiment, the magnesium source comprises an amino acid chelated or creatine chelated magnesium.

In other embodiments, the osteoporosis agent is chosen from vitamins D, C, K, their precursors and/or beta-carotene and combinations thereof.

Numerous plants and plant extracts also have been identified as being effective in the prevention and treatment of osteoporosis. Not wishing to be bound by any theory, it is believed that the plants and plant extracts stimulates bone morphogenic proteins and/or inhibits bone resorption, thereby stimulating bone regeneration and strength. Non-limiting examples of suitable plants and plant extracts as osteoporosis management agents include species of the genus *Taraxacum* and *Amelanchier*, as disclosed in U.S. Patent Publication No. 2005/0106215, and species of the genus *Lindera, Artemisia, Acorus, Carthamus, Carum, Cnidium, Curcuma, Cyperus, Juniperus, Prunus, Iris, Cichorium, Dodonaea, Epimedium, Erigonoum, Soya, Mentha, Ocimum, thymus, Tanacetum, Plantago, Spearmint, Bixa, Vitis, Rosemarinus, Rhus*, and *Anethum*, as disclosed in U.S. Patent Publication No. 2005/0079232.

Phytoestrogen

In certain embodiments, the functional ingredient is at least one phytoestrogen.

As used herein, the at least one phytoestrogen may be single phytoestrogen or a plurality of phytoestrogens as a functional ingredient for the compositions provided herein. Generally, according to particular embodiments of this invention, the at least one phytoestrogen is present in the composition in an amount sufficient to promote health and wellness.

Phytoestrogens are compounds found in plants which can typically be delivered into human bodies by ingestion of the plants or the plant parts having the phytoestrogens. As used herein, "phytoestrogen" refers to any substance which, when introduced into a body causes an estrogen-like effect of any degree. For example, a phytoestrogen may bind to estrogen receptors within the body and have a small estrogen-like effect.

Examples of suitable phytoestrogens for embodiments of this invention include, but are not limited to, isoflavones, stilbenes, lignans, resorcyclic acid lactones, coumestans, coumestrol, equol, and combinations thereof. Sources of suitable phytoestrogens include, but are not limited to, whole grains, cereals, fibers, fruits, vegetables, black cohosh, agave root, black currant, black haw, chasteberries, cramp bark, dong quai root, devil's club root, false unicorn root, ginseng root, groundsel herb, licorice, liferoot herb, motherwort herb, peony root, raspberry leaves, rose family plants, sage leaves, sarsaparilla root, saw palmetto berried, wild yam root, yarrow blossoms, legumes, soybeans, soy products (e.g., miso, soy flour, soymilk, soy nuts, soy protein isolate, tempen, or tofu) chick peas, nuts, lentils, seeds, clover, red clover, dandelion leaves, dandelion roots, fenugreek seeds, green tea, hops, red wine, flaxseed, garlic, onions, linseed, borage, butterfly weed, caraway, chaste tree, vitex, dates, dill, fennel seed, gotu kola, milk thistle, pennyroyal, pomegranates, southernwood, soya flour, tansy, and root of the kudzu vine (pueraria root) and the like, and combinations thereof.

Isoflavones belong to the group of phytonutrients called polyphenols. In general, polyphenols (also known as "polyphenolics"), are a group of chemical substances found in plants, characterized by the presence of more than one phenol group per molecule.

Suitable phytoestrogen isoflavones in accordance with embodiments of this invention include genistein, daidzein, glycitein, biochanin A, formononetin, their respective naturally occurring glycosides and glycoside conjugates, matairesinol, secoisolariciresinol, enterolactone, enterodiol, textured vegetable protein, and combinations thereof.

Suitable sources of isoflavones for embodiments of this invention include, but are not limited to, soy beans, soy products, legumes, alfalfa sprouts, chickpeas, peanuts, and red clover.

Long-Chain Primary Aliphatic Saturated Alcohol

In certain embodiments, the functional ingredient is at least one long chain primary aliphatic saturated alcohol.

As used herein, the at least one long chain primary aliphatic saturated alcohol may be single long chain primary aliphatic saturated alcohol or a plurality of long chain primary aliphatic saturated alcohols as a functional ingredient for the compositions provided herein. Generally, according to particular embodiments of this invention, the at least one long chain primary aliphatic saturated alcohol is present in the composition in an amount sufficient to promote health and wellness.

Long-chain primary aliphatic saturated alcohols are a diverse group of organic compounds. The term alcohol refers to the fact these compounds feature a hydroxyl group (—OH) bound to a carbon atom. The term primary refers to the fact that in these compounds the carbon atom which is bound to the hydroxyl group is bound to only one other carbon atom. The term saturated refers to the fact that these compounds feature no carbon to carbon pi bonds. The term aliphatic refers to the fact that the carbon atoms in these compounds are joined together in straight or branched chains rather than in rings. The term long-chain refers to the fact that the number of carbon atoms in these compounds is at least 8 carbons).

Non-limiting examples of particular long-chain primary aliphatic saturated alcohols for use in particular embodiments of the invention include the 8 carbon atom 1-octanol, the 9 carbon 1-nonanol, the 10 carbon atom 1-decanol, the 12 carbon atom 1-dodecanol, the 14 carbon atom 1-tetradecanol, the 16 carbon atom 1-hexadecanol, the 18 carbon atom 1-octadecanol, the 20 carbon atom 1-eicosanol, the 22 carbon 1-docosanol, the 24 carbon 1-tetracosanol, the 26 carbon 1-hexacosanol, the 27 carbon 1-heptacosanol, the 28 carbon 1-octanosol, the 29 carbon 1-nonacosanol, the 30 carbon 1-triacontanol, the 32 carbon 1-dotriacontanol, and the 34 carbon 1-tetracontanol.

In a particularly desirable embodiment of the invention, the long-chain primary aliphatic saturated alcohols are policosanol. Policosanol is the term for a mixture of long-chain primary aliphatic saturated alcohols composed primarily of 28 carbon 1-octanosol and 30 carbon 1-triacontanol, as well as other alcohols in lower concentrations such as 22 carbon 1-docosanol, 24 carbon 1-tetracosanol, 26 carbon 1-hexacosanol, 27 carbon 1-heptacosanol, 29 carbon 1-nonacosanol, 32 carbon 1-dotriacontanol, and 34 carbon 1-tetracontanol.

Long-chain primary aliphatic saturated alcohols are derived from natural fats and oils. They may be obtained from these sources by using extraction techniques well known to those of ordinary skill in the art. Policosanols can be isolated from a variety of plants and materials including sugar cane (*Saccharum officinarium*), yams (e.g. *Dioscorea opposite*), bran from rice (e.g. *Oryza sativa*), and beeswax. Policosanols may be obtained from these sources by using extraction techniques well known to those of ordinary skill in the art. A description of such extraction techniques can be found in U.S. Pat. Appl. No. 2005/0220868, the disclosure of which is expressly incorporated by reference.

Phytosterols

In certain embodiments, the functional ingredient is at least one phytosterol, phytostanol or combination thereof.

Generally, according to particular embodiments of this invention, the at least one phytosterol, phytostanol or combination thereof is present in the composition in an amount sufficient to promote health and wellness.

As used herein, the phrases "stanol", "plant stanol" and "phytostanol" are synonymous.

Plant sterols and stanols are present naturally in small quantities in many fruits, vegetables, nuts, seeds, cereals, legumes, vegetable oils, bark of the trees and other plant sources. Although people normally consume plant sterols and stanols every day, the amounts consumed are insufficient to have significant cholesterol-lowering effects or other health benefits. Accordingly, it would be desirable to supplement food and beverages with plant sterols and stanols.

Sterols are a subgroup of steroids with a hydroxyl group at C-3. Generally, phytosterols have a double bond within the steroid nucleus, like cholesterol; however, phytosterols also may comprise a substituted side chain (R) at C-24, such as an ethyl or methyl group, or an additional double bond. The structures of phytosterols are well known to those of skill in the art.

At least 44 naturally-occurring phytosterols have been discovered, and generally are derived from plants, such as corn, soy, wheat, and wood oils; however, they also may be produced synthetically to form compositions identical to those in nature or having properties similar to those of naturally-occurring phytosterols. According to particular embodiments of this invention, non-limiting examples of phytosterols well known to those or ordinary skill in the art include 4-desmethylsterols (e.g., β-sitosterol, campesterol, stigmasterol, brassicasterol, 22-dehydrobrassicasterol, and Δ5-avenasterol), 4-monomethyl sterols, and 4,4-dimethyl sterols (triterpene alcohols) (e.g., cycloartenol, 24-methylenecycloartanol, and cyclobranol).

As used herein, the phrases "stanol", "plant stanol" and "phytostanol" are synonymous. Phytostanols are saturated sterol alcohols present in only trace amounts in nature and also may be synthetically produced, such as by hydrogenation of phytosterols. According to particular embodiments of this invention, non-limiting examples of phytostanols include β-sitostanol, campestanol, cycloartanol, and saturated forms of other triterpene alcohols.

Both phytosterols and phytostanols, as used herein, include the various isomers such as the α and β isomers (e.g., α-sitosterol and β-sitostanol, which comprise one of the most effective phytosterols and phytostanols, respectively, for lowering serum cholesterol in mammals).

The phytosterols and phytostanols of the present invention also may be in their ester form. Suitable methods for deriving the esters of phytosterols and phytostanols are well known to those of ordinary skill in the art, and are disclosed in U.S. Pat. Nos. 6,589,588, 6,635,774, 6,800,317, and U.S. Patent Publication Number 2003/0045473, the disclosures of which are incorporated herein by reference in their entirety. Non-limiting examples of suitable phytosterol and phytostanol esters include sitosterol acetate, sitosterol oleate, stigmasterol oleate, and their corresponding phytostanol esters. The phytosterols and phytostanols of the present invention also may include their derivatives.

Generally, the amount of functional ingredient in the composition varies widely depending on the particular composition and the desired functional ingredient. Those of ordinary skill in the art will readily ascertain the appropriate amount of functional ingredient for each composition.

In one embodiment, a method for preparing a composition comprises combining at least one diterpene glycoside of the present invention and at least one sweetener and/or additive and/or functional ingredient.

Consumables

In one embodiment, the present invention is a consumable comprising at least one diterpene glycoside of the present invention, or a composition comprising at least one diterpene glycoside of the present invention.

The diterpene glycoside(s) of the present invention, or a composition comprising the same, can be admixed with any known edible or oral composition (referred to herein as a "consumable"), such as, for example, pharmaceutical compositions, edible gel mixes and compositions, dental compositions, foodstuffs (confections, condiments, chewing gum, cereal compositions baked goods dairy products, and tabletop sweetener compositions) beverages and beverage products.

Consumables, as used herein, mean substances which are contacted with the mouth of man or animal, including substances which are taken into and subsequently ejected from the mouth and substances which are drunk, eaten, swallowed or otherwise ingested, and are safe for human or animal consumption when used in a generally acceptable range.

For example, a beverage is a consumable. The beverage may be sweetened or unsweetened. The diterpene glycoside(s) of the present invention, or a composition comprising the same, may be added to a beverage or beverage matrix to sweeten the beverage or enhance its existing sweetness or flavor.

In one embodiment, the present invention is a consumable comprising at least one diterpene glycoside of the present invention. In particular embodiments, a diterpene glycoside of the present invention is present in the consumable in a concentration greater than about 1 ppm, such as, for example, from about 1 ppm to about 1,000 ppm, from about 25 ppm to about 1,000 ppm, from about 50 ppm to about 1,000 ppm, from about 75 ppm to about 1,000 ppm, from about 100 ppm to about 1,000 ppm, from about 200 ppm to about 1,000 ppm, from about 300 ppm to about 1,000 ppm, from about 400 ppm to about 1,000 ppm or from about 500 ppm to about 1,000 ppm. In other particular embodiments, a diterpene glycoside of the present invention is present in the consumable in a purity of at least about 5% with respect to a mixture of diterpene glycosides or *Stevia* extract, such as, for example, at least about 10%, at least about 20%, at least about 30%, at least about 40%, at least about 50%, at least about 60%, at least about 70%, at least about 80%, at least about 90%, at least about 95% or at least about 97%. In still other embodiments, a diterpene glycoside of the present invention is present in the consumable in >99% purity.

The consumable can optionally include additives, additional sweeteners, functional ingredients and combinations thereof, as described herein. Any of the additive, additional sweetener and functional ingredients described above can be present in the consumable.

Pharmaceutical Compositions

In one embodiment, the present invention is a pharmaceutical composition comprising a pharmaceutically active substance and at least one diterpene glycoside of the present invention.

In another embodiment, a pharmaceutical composition comprises a pharmaceutically active substance and a composition comprising at least one diterpene glycoside of the present invention.

The diterpene glycoside(s) of the present invention, or composition comprising the same, can be present as an excipient material in the pharmaceutical composition, which can mask a bitter or otherwise undesirable taste of a pharmaceutically active substance or another excipient material. The pharmaceutical composition may be in the form of a tablet, a capsule, a liquid, an aerosol, a powder, an effervescent tablet or powder, a syrup, an emulsion, a suspension, a solution, or any other form for providing the pharmaceutical composition to a patient. In particular embodiments, the pharmaceutical composition may be in a form for oral administration, buccal administration, sublingual administration, or any other route of administration as known in the art.

As referred to herein, "pharmaceutically active substance" means any drug, drug formulation, medication, prophylactic agent, therapeutic agent, or other substance having biological activity. As referred to herein, "excipient material" refers to any inactive substance used as a vehicle for an active ingredient, such as any material to facilitate handling, stability, dispersibility, wettability, and/or release kinetics of a pharmaceutically active substance.

Suitable pharmaceutically active substances include, but are not limited to, medications for the gastrointestinal tract or digestive system, for the cardiovascular system, for the central nervous system, for pain or consciousness, for musculo-skeletal disorders, for the eye, for the ear, nose and oropharynx, for the respiratory system, for endocrine problems, for the reproductive system or urinary system, for contraception, for obstetrics and gynecology, for the skin, for infections and infestations, for immunology, for allergic disorders, for nutrition, for neoplastic disorders, for diagnostics, for euthanasia, or other biological functions or disorders. Examples of suitable pharmaceutically active substances for embodiments of the present invention include, but are not limited to, antacids, reflux suppressants, antiflatulents, antidopaminergics, proton pump inhibitors, cytoprotectants, prostaglandin analogues, laxatives, antispasmodics, antidiarrhoeals, bile acid sequestrants, opioids, beta-receptor blockers, calcium channel blockers, diuretics, cardiac glycosides, antiarrhythmics, nitrates, antianginals, vasoconstrictors, vasodilators, peripheral activators, ACE inhibitors, angiotensin receptor blockers, alpha blockers, anticoagulants, heparin, antiplatelet drugs, fibrinolytics, anti-hemophilic factors, haemostatic drugs, hypolipidaemic agents, statins, hynoptics, anaesthetics, antipsychotics, antidepressants, anti-emetics, anticonvulsants, antiepileptics, anxiolytics, barbiturates, movement disorder drugs, stimulants, benzodiazepines, cyclopyrrolones, dopamine antagonists, antihistamines, cholinergics, anticholinergics, emetics, cannabinoids, analgesics, muscle relaxants, antibiotics, aminoglycosides, anti-virals, anti-fungals, anti-inflammatories, anti-glaucoma drugs, sympathomimetics, steroids, ceruminolytics, bronchodilators, NSAIDS, antitussive, mucolytics, decongestants, corticosteroids, androgens, antiandrogens, gonadotropins, growth hormones, insulin, antidiabetics, thyroid hormones, calcitonin, diphosponates, vasopressin analogues, alkalizing agents, quinolones, anticholinesterase, sildenafil, oral contraceptives, Hormone Replacement Therapies, bone regulators, follicle stimulating hormones, luteinizings hormones, gamolenic acid, progestogen, dopamine agonist, oestrogen, prostaglandin, gonadorelin, clomiphene, tamoxifen, diethylstilbestrol, antileprotics, antituberculous drugs, antimalarials, anthelmintics, antiprotozoal, antiserums, vaccines, interferons, tonics, vitamins, cytotoxic drugs, sex hormones, aromatase inhibitors, somatostatin inhibitors, or similar type substances, or combinations thereof. Such components generally are recognized as safe (GRAS) and/or are U.S. Food and Drug Administration (FDA)-approved.

The pharmaceutically active substance is present in the pharmaceutical composition in widely ranging amounts depending on the particular pharmaceutically active agent being used and its intended applications. An effective dose of any of the herein described pharmaceutically active substances can be readily determined by the use of conventional techniques and by observing results obtained under analogous circumstances. In determining the effective dose, a number of factors are considered including, but not limited to: the species of the patient; its size, age, and general health; the specific disease involved; the degree of involvement or the severity of the disease; the response of the individual patient; the particular pharmaceutically active agent administered; the mode of administration; the bioavailability characteristic of the preparation administered; the dose regimen selected; and the use of concomitant medication. The pharmaceutically active substance is included in the pharmaceutically acceptable carrier, diluent, or excipient in an amount sufficient to deliver to a patient a therapeutic amount of the pharmaceutically active substance in vivo in the absence of serious toxic effects when used in generally acceptable amounts. Thus, suitable amounts can be readily discerned by those skilled in the art.

According to particular embodiments of the present invention, the concentration of pharmaceutically active substance in the pharmaceutical composition will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimes should be adjusted over time according to the individual need and the professional judgment of the person administering or supervising the administration of the pharmaceutical compositions, and that the dosage ranges set forth herein are exemplary only and are not intended to limit the scope or practice of the claimed composition. The pharmaceutically active substance may be administered at once, or may be divided into a number of smaller doses to be administered at varying intervals of time.

The pharmaceutical composition also may comprise pharmaceutically acceptable excipient materials. Examples of suitable excipient materials for embodiments of this invention include, but are not limited to, antiadherents, binders (e.g., microcrystalline cellulose, gum tragacanth, or gelatin), coatings, disintegrants, fillers, diluents, softeners, emulsifiers, flavoring agents, coloring agents, adjuvants, lubricants, functional agents (e.g., nutrients), viscosity modifiers, bulking agents, glidiants (e.g., colloidal silicon dioxide) surface active agents, osmotic agents, diluents, or any other non-active ingredient, or combinations thereof. For example, the pharmaceutical compositions of the present invention may include excipient materials selected from the group consisting of calcium carbonate, coloring agents, whiteners, preservatives, and flavors, triacetin, magnesium stearate, sterotes, natural or artificial flavors, essential oils, plant extracts, fruit essences, gelatins, or combinations thereof.

The excipient material of the pharmaceutical composition may optionally include other artificial or natural sweeteners, bulk sweeteners, or combinations thereof. Bulk sweeteners include both caloric and non-caloric compounds. In a particular embodiment, the additive functions as the bulk sweetener. Non-limiting examples of bulk sweeteners include sucrose, dextrose, maltose, dextrin, dried invert sugar, fructose, high fructose corn syrup, levulose, galactose, corn syrup solids, tagatose, polyols (e.g., sorbitol, mannitol, xylitol, lactitol, erythritol, and maltitol), hydrogenated starch hydrolysates, isomalt, trehalose, and mixtures thereof. In particular embodiments, the bulk sweetener is present in the pharmaceutical composition in widely ranging amounts depending on the degree of sweetness desired. Suitable amounts of both sweeteners would be readily discernable to those skilled in the art.

Edible Gel Mixes and Edible Gel Compositions

In one embodiment, the present invention is an edible gel or edible gel mix comprising at least one diterpene glycoside of the present invention. In another embodiment, an edible gel or edible gel mix comprises a composition comprising at least one diterpene glycoside of the present invention.

Edible gels are gels that can be eaten. A gel is a colloidal system in which a network of particles spans the volume of a liquid medium. Although gels mainly are composed of liquids, and thus exhibit densities similar to liquids, gels have the structural coherence of solids due to the network of particles that spans the liquid medium. For this reason, gels generally appear to be solid, jelly-like materials. Gels can be used in a number of applications. For example, gels can be used in foods, paints, and adhesives.

Non-limiting examples of edible gel compositions for use in particular embodiments include gel desserts, puddings, jellies, pastes, trifles, aspics, marshmallows, gummy candies, or the like. Edible gel mixes generally are powdered or granular solids to which a fluid may be added to form an edible gel composition. Non-limiting examples of fluids for use in particular embodiments include water, dairy fluids, dairy analogue fluids, juices, alcohol, alcoholic beverages, and combinations thereof. Non-limiting examples of dairy fluids which may be used in particular embodiments include milk, cultured milk, cream, fluid whey, and mixtures thereof. Non-limiting examples of dairy analogue fluids which may be used in particular embodiments include, for example, soy milk and non-dairy coffee whitener. Because edible gel products found in the marketplace typically are sweetened with sucrose, it is desirable to sweeten edible gels with an alternative sweetener in order provide a low-calorie or non-calorie alternative.

As used herein, the term "gelling ingredient" denotes any material that can form a colloidal system within a liquid medium. Non-limiting examples of gelling ingredients for use in particular embodiments include gelatin, alginate, carageenan, gum, pectin, konjac, agar, food acid, rennet, starch, starch derivatives, and combinations thereof. It is well known to those having ordinary skill in the art that the amount of gelling ingredient used in an edible gel mix or an edible gel composition varies considerably depending on a number of factors, such as the particular gelling ingredient used, the particular fluid base used, and the desired properties of the gel.

It is well known to those having ordinary skill in the art that the edible gel mixes and edible gels may be prepared using other ingredients, including, but not limited to, a food acid, a salt of a food acid, a buffering system, a bulking agent, a sequestrant, a cross-linking agent, one or more flavors, one or more colors, and combinations thereof. Non-limiting examples of food acids for use in particular embodiments include citric acid, adipic acid, fumaric acid, lactic acid, malic acid, and combinations thereof. Non-limiting examples of salts of food acids for use in particular embodiments include sodium salts of food acids, potassium salts of food acids, and combinations thereof. Non-limiting examples of bulking agents for use in particular embodiments include raftilose, isomalt, sorbitol, polydextrose, maltodextrin, and combinations thereof. Non-limiting examples of sequestrants for use in particular embodiments include calcium disodium ethylene tetra-acetate, glucono delta-lactone, sodium gluconate, potassium gluconate, ethylenediaminetetraacetic acid (EDTA), and combinations thereof. Non-limiting examples of cross-linking agents for use in particular embodiments include calcium ions, magnesium ions, sodium ions, and combinations thereof.

Dental Compositions

In one embodiment, the present invention is a dental composition comprising at least one diterpene glycoside of the present invention. In another embodiment, a dental composition comprises at least one diterpene glycoside of the present invention. Dental compositions generally comprise an active dental substance and a base material. The diterpene glycoside(s) of the present invention, or a composition comprising the same, can be used as the base material to sweeten the dental composition. The dental composition may be in the form of any oral composition used in the oral cavity such as mouth freshening agents, gargling agents, mouth rinsing agents, toothpaste, tooth polish, dentifrices, mouth sprays, teeth-whitening agent, dental floss, and the like, for example.

As referred to herein, "active dental substance" means any composition which can be used to improve the aesthetic appearance and/or health of teeth or gums or prevent dental caries. As referred to herein, "base material" refers to any inactive substance used as a vehicle for an active dental substance, such as any material to facilitate handling, stability, dispersibility, wettability, foaming, and/or release kinetics of an active dental substance.

Suitable active dental substances for embodiments of this invention include, but are not limited to, substances which remove dental plaque, remove food from teeth, aid in the elimination and/or masking of halitosis, prevent tooth decay, and prevent gum disease (i.e., Gingiva). Examples of suitable active dental substances for embodiments of the present invention include, but are not limited to, anticaries drugs, fluoride, sodium fluoride, sodium monofluorophosphate, stannous fluoride, hydrogen peroxide, carbamide peroxide (i.e., urea peroxide), antibacterial agents, plaque removing agents, stain removers, anticalculus agents, abrasives, baking soda, percarbonates, perborates of alkali and alkaline earth metals, or similar type substances, or combinations thereof. Such components generally are recognized as safe (GRAS) and/or are U.S. Food and Drug Administration (FDA)-approved.

According to particular embodiments of the invention, the active dental substance is present in the dental composition in an amount ranging from about 50 ppm to about 3000 ppm of the dental composition. Generally, the active dental substance is present in the dental composition in an amount effective to at least improve the aesthetic appearance and/or health of teeth or gums marginally or prevent dental caries. For example, a dental composition comprising a toothpaste may include an active dental substance comprising fluoride in an amount of about 850 to 1,150 ppm.

The dental composition also may comprise other base materials including, but not limited to, water, sodium lauryl sulfate or other sulfates, humectants, enzymes, vitamins, herbs, calcium, flavorings (e.g., mint, bubblegum, cinnamon, lemon, or orange), surface-active agents, binders, preservatives, gelling agents, pH modifiers, peroxide activators, stabilizers, coloring agents, or similar type materials, and combinations thereof.

The base material of the dental composition may optionally include other artificial or natural sweeteners, bulk sweeteners, or combinations thereof. Bulk sweeteners include both caloric and non-caloric compounds. Non-limiting examples of bulk sweeteners include sucrose, dextrose, maltose, dextrin, dried invert sugar, fructose, high fructose corn syrup, levulose, galactose, corn syrup solids, tagatose, polyols (e.g., sorbitol, mannitol, xylitol, lactitol, erythritol, and maltitol), hydrogenated starch hydrolysates, isomalt, trehalose, and mixtures thereof. Generally, the amount of bulk sweetener present in the dental composition ranges widely depending on the particular embodiment of the dental composition and the desired degree of sweetness. Those of ordinary skill in the art will readily ascertain the appropriate amount of bulk sweetener. In particular embodiments, the bulk sweetener is present in the dental composition in an amount in the range of about 0.1 to about 5 weight percent of the dental composition.

According to particular embodiments of the invention, the base material is present in the dental composition in an amount ranging from about 20 to about 99 percent by weight of the dental composition. Generally, the base material is present in an amount effective to provide a vehicle for an active dental substance.

In a particular embodiment, a dental composition comprises at least one diterpene glycoside of the present invention and an active dental substance. In another particular embodiment, a dental composition comprises a composition comprising at least one diterpene glycoside of the present invention and an active dental substance. Generally, the amount of the sweetener varies widely depending on the nature of the particular dental composition and the desired degree of sweetness.

Foodstuffs include, but are not limited to, confections, condiments, chewing gum, cereal, baked goods, and dairy products.

Confections

In one embodiment, the present invention is a confection comprises at least one diterpene glycoside of the present invention. In another embodiment, a confection comprises a composition comprising at least one diterpene glycoside of the present invention As referred to herein, "confection" can mean a sweet, a lollie, a confectionery, or similar term. The confection generally contains a base composition component and a sweetener component. The diterpene glycoside(s) of the present invention, or a composition comprising the same, can serve as the sweetener component. The confection may be in the form of any food that is typically perceived to be rich in sugar or is typically sweet. According to particular embodiments of the present invention, the confections may be bakery products such as pastries; desserts such as yogurt, jellies, drinkable jellies, puddings, Bavarian cream, blancmange, cakes, brownies, mousse and the like, sweetened food products eaten at tea time or following meals; frozen foods; cold confections, e. g. types of ice cream such as ice cream, ice milk, lacto-ice and the like (food products in which sweeteners and various other types of raw materials are added to milk products, and the resulting mixture is agitated and frozen), and ice confections such as sherbets, dessert ices and the like (food products in which various other types of raw materials are added to a sugary liquid, and the resulting mixture is agitated and frozen); general confections, e. g., baked confections or steamed confections such as crackers, biscuits, buns with bean-jam filling, halvah, alfajor, and the like; rice cakes and snacks; table top products; general sugar confections such as chewing gum (e.g. including compositions which comprise a substantially water-insoluble, chewable gum base, such as chicle or substitutes thereof, including jetulong, guttakay rubber or certain comestible natural synthetic resins or waxes), hard candy, soft candy, mints, nougat candy, jelly beans, fudge, toffee, taffy, Swiss milk tablet, licorice candy, chocolates, gelatin candies, marshmallow, marzipan, divinity, cotton candy, and the like; sauces including fruit flavored sauces, chocolate sauces and the like; edible gels; crèmes including butter crèmes, flour pastes, whipped cream and the like; jams including strawberry jam, marmalade and the like; and breads including sweet breads and the like or other starch products, and combinations thereof.

As referred to herein, "base composition" means any composition which can be a food item and provides a matrix for carrying the sweetener component.

Suitable base compositions for embodiments of this invention may include flour, yeast, water, salt, butter, eggs, milk, milk powder, liquor, gelatin, nuts, chocolate, citric acid, tartaric acid, fumaric acid, natural flavors, artificial flavors, colorings, polyols, sorbitol, isomalt, maltitol, lactitol, malic acid, magnesium stearate, lecithin, hydrogenated glucose syrup, glycerine, natural or synthetic gum, starch, and the like, and combinations thereof. Such components generally are recognized as safe (GRAS) and/or are U.S. Food and Drug Administration (FDA)-approved. According to particular embodiments of the invention, the base composition is present in the confection in an amount ranging from about 0.1 to about 99 weight percent of the confection.

The base composition of the confection may optionally include other artificial or natural sweeteners, bulk sweeteners, or combinations thereof. Bulk sweeteners include both caloric and non-caloric compounds. Non-limiting examples of bulk sweeteners include sucrose, dextrose, maltose, dextrin, dried invert sugar, fructose, high fructose corn syrup, levulose, galactose, corn syrup solids, tagatose, polyols (e.g., sorbitol, mannitol, xylitol, lactitol, erythritol, and maltitol), hydrogenated starch hydrolysates, isomalt, trehalose, and mixtures thereof. Generally, the amount of bulk sweetener present in the confection ranges widely depending on the particular embodiment of the confection and the desired degree of sweetness. Those of ordinary skill in the art will readily ascertain the appropriate amount of bulk sweetener.

In a particular embodiment, a confection comprises at least one diterpene glycoside of the present invention, or a composition comprising the same, and a base composition. Generally, the amount of diterpene glycoside(s) of the present invention in the confection ranges widely depending on the particular embodiment of the confection and the desired degree of sweetness. Those of ordinary skill in the art will readily ascertain the appropriate amount. In a particular embodiment, a diterpene glycoside of the present invention is present in the confection in an amount in the range of about 30 ppm to about 6000 ppm of the confection. In another embodiment, a diterpene glycoside of the present invention is present in the confection in an amount in the range of about 1 ppm to about 10,000 ppm of the confection. In embodiments where the confection comprises hard candy, a diterpene glycoside of the present invention is present in an amount in the range of about 150 ppm to about 2250 ppm of the hard candy.

Condiment Compositions

In one embodiment, the present invention is a condiment comprising at least one diterpene glycoside of the present invention. In another embodiment, a condiment comprises a composition comprising at least one diterpene glycoside of the present invention. Condiments, as used herein, are compositions used to enhance or improve the flavor of a food or beverage. Non-limiting examples of condiments include ketchup (catsup); mustard; barbecue sauce; butter; chili sauce; chutney; cocktail sauce; curry; dips; fish sauce; horseradish; hot sauce; jellies, jams, marmalades, or preserves; mayonnaise; peanut butter; relish; remoulade; salad dressings (e.g., oil and vinegar, Caesar, French, ranch, bleu cheese, Russian, Thousand Island, Italian, and balsamic vinaigrette), salsa; sauerkraut; soy sauce; steak sauce; syrups; tartar sauce; and Worcestershire sauce.

Condiment bases generally comprise a mixture of different ingredients, non-limiting examples of which include vehicles (e.g., water and vinegar); spices or seasonings (e.g., salt, pepper, garlic, mustard seed, onion, paprika, turmeric, and combinations thereof); fruits, vegetables, or their products (e.g., tomatoes or tomato-based products (paste, puree), fruit juices, fruit juice peels, and combinations thereof); oils or oil emulsions, particularly vegetable oils; thickeners (e.g., xanthan gum, food starch, other hydrocolloids, and combinations thereof); and emulsifying agents (e.g., egg yolk solids, protein, gum arabic, carob bean gum, guar gum, gum karaya, gum tragacanth, carageenan, pectin, propylene glycol esters of alginic acid, sodium carboxymethyl-cellulose, polysorbates, and combinations thereof). Recipes for condiment bases and methods of making condiment bases are well known to those of ordinary skill in the art.

Generally, condiments also comprise caloric sweeteners, such as sucrose, high fructose corn syrup, molasses, honey, or brown sugar. In exemplary embodiments of the condiments provided herein, the diterpene glycoside(s) of the present invention, or a composition comprising the same, is used instead of traditional caloric sweeteners. Accordingly, a condiment composition desirably comprises at least one diterpene glycoside of the present invention, or a composition comprising the same, and a condiment base.

The condiment composition optionally may include other natural and/or synthetic high-potency sweeteners, bulk sweeteners, pH modifying agents (e.g., lactic acid, citric acid, phosphoric acid, hydrochloric acid, acetic acid, and combinations thereof), fillers, functional agents (e.g., pharmaceutical agents, nutrients, or components of a food or plant), flavorings, colorings, or combinations thereof.

Chewing Gum Compositions

In one embodiment, the present invention is a chewing gum composition comprising at least one diterpene glycoside of the present invention. In another embodiment, a chewing gum composition comprises at least one diterpene glycoside of the present invention. Chewing gum compositions generally comprise a water-soluble portion and a water-insoluble chewable gum base portion. The water soluble portion, which typically includes at least one diterpene glycoside of the present invention, dissipates with a portion of the flavoring agent over a period of time during chewing while the insoluble gum base portion is retained in the mouth. The insoluble gum base generally determines whether a gum is considered chewing gum, bubble gum, or a functional gum.

The insoluble gum base, which is generally present in the chewing gum composition in an amount in the range of about 15 to about 35 weight percent of the chewing gum composition, generally comprises combinations of elastomers, softeners (plasticizers), emulsifiers, resins, and fillers. Such components generally are considered food grade, recognized as safe (GRA), and/or are U.S. Food and Drug Administration (FDA)-approved.

Elastomers, the primary component of the gum base, provide the rubbery, cohesive nature to gums and can include one or more natural rubbers (e.g., smoked latex, liquid latex, or guayule); natural gums (e.g., jelutong, perillo, sorva, massaranduba balata, massaranduba chocolate, nispero, rosindinha, chicle, and gutta hang kang); or synthetic elastomers (e.g., butadiene-styrene copolymers, isobutylene-isoprene copolymers, polybutadiene, polyisobutylene, and vinyl polymeric elastomers). In a particular embodiment, the elastomer is present in the gum base in an amount in the range of about 3 to about 50 weight percent of the gum base.

Resins are used to vary the firmness of the gum base and aid in softening the elastomer component of the gum base. Non-limiting examples of suitable resins include a rosin ester, a terpene resin (e.g., a terpene resin from α-pinene, β-pinene and/or d-limonene), polyvinyl acetate, polyvinyl alcohol, ethylene vinyl acetate, and vinyl acetate-vinyl laurate copolymers. Non-limiting examples of rosin esters include a glycerol ester of a partially hydrogenated rosin, a glycerol ester of a polymerized rosin, a glycerol ester of a partially dimerized rosin, a glycerol ester of rosin, a pentaerythritol ester of a partially hydrogenated rosin, a methyl ester of rosin, or a methyl ester of a partially hydrogenated rosin. In a particular embodiment, the resin is present in the gum base in an amount in the range of about 5 to about 75 weight percent of the gum base.

Softeners, which also are known as plasticizers, are used to modify the ease of chewing and/or mouthfeel of the chewing gum composition. Generally, softeners comprise oils, fats, waxes, and emulsifiers. Non-limiting examples of oils and fats include tallow, hydrogenated tallow, large, hydrogenated or partially hydrogenated vegetable oils (e.g., soybean, canola, cottonseed, sunflower, palm, coconut, corn, safflower, or palm kernel oils), cocoa butter, glycerol monostearate, glycerol triacetate, glycerol abietate, leithin, monoglycerides, diglycerides, triglycerides acetylated monoglycerides, and free fatty acids. Non-limiting examples of waxes include polypropylene/polyethylene/Fisher-Tropsch waxes, paraffin, and microcrystalline and natural waxes (e.g., candelilla, beeswax and carnauba). Microcrystalline waxes, especially those with a high degree of crystallinity and a high melting point, also may be considered as bodying agents or textural modifiers. In a particular embodiment, the softeners are present in the gum base in an amount in the range of about 0.5 to about 25 weight percent of the gum base.

Emulsifiers are used to form a uniform dispersion of the insoluble and soluble phases of the chewing gum composition and also have plasticizing properties. Suitable emulsifiers include glycerol monostearate (GMS), lecithin (Phosphatidyl choline), polyglycerol polyricinoleic acid (PPGR), mono and diglycerides of fatty acids, glycerol distearate, tracetin, acetylated monoglyceride, glycerol triactetate, and magnesium stearate. In a particular embodiment, the emulsifiers are present in the gum base in an amount in the range of about 2 to about 30 weight percent of the gum base.

The chewing gum composition also may comprise adjuvants or fillers in either the gum base and/or the soluble portion of the chewing gum composition. Suitable adjuvants and fillers include lecithin, inulin, polydextrin, calcium carbonate, magnesium carbonate, magnesium silicate, ground limestone, aluminum hydroxide, aluminum silicate, talc, clay, alumina, titanium dioxide, and calcium phosphate. In particular embodiments, lecithin can be used as an inert filler to decrease the stickiness of the chewing gum composition. In other particular embodiments, lactic acid copolymers, proteins (e.g., gluten and/or zein) and/or guar can be used to create a gum that is more readily biodegradable. The adjuvants or fillers are generally present in the gum base in an amount up to about 20 weight percent of the gum base. Other optional ingredients include coloring agents, whiteners, preservatives, and flavors.

In particular embodiments of the chewing gum composition, the gum base comprises about 5 to about 95 weight percent of the chewing gum composition, more desirably about 15 to about 50 weight percent of the chewing gum composition, and even more desirably from about 20 to about 30 weight percent of the chewing gum composition.

The soluble portion of the chewing gum composition may optionally include other artificial or natural sweeteners, bulk sweeteners, softeners, emulsifiers, flavoring agents, coloring agents, adjuvants, fillers, functional agents (e.g., pharmaceutical agents or nutrients), or combinations thereof. Suitable examples of softeners and emulsifiers are described above.

Bulk sweeteners include both caloric and non-caloric compounds. Non-limiting examples of bulk sweeteners include sucrose, dextrose, maltose, dextrin, dried invert sugar, fructose, high fructose corn syrup, levulose, galactose, corn syrup solids, tagatose, polyols (e.g., sorbitol, mannitol, xylitol, lactitol, erythritol, and maltitol), hydrogenated starch hydrolysates, isomalt, trehalose, and mixtures thereof. In particular embodiments, the bulk sweetener is present in the chewing gum composition in an amount in the range of about 1 to about 75 weight percent of the chewing gum composition.

Flavoring agents may be used in either the insoluble gum base or soluble portion of the chewing gum composition. Such flavoring agents may be natural or artificial flavors. In a particular embodiment, the flavoring agent comprises an essential oil, such as an oil derived from a plant or a fruit, peppermint oil, spearmint oil, other mint oils, clove oil, cinnamon oil, oil of wintergreen, bay, thyme, cedar leaf, nutmeg, allspice, sage, mace, and almonds. In another particular embodiment, the flavoring agent comprises a plant extract or a fruit essence such as apple, banana, watermelon, pear, peach, grape, strawberry, raspberry, cherry, plum, pineapple, apricot, and mixtures thereof. In still another particular embodiment, the flavoring agent comprises a citrus flavor, such as an extract, essence, or oil of lemon, lime, orange, tangerine, grapefruit, citron, or kumquat.

In a particular embodiment, a chewing gum composition comprises at least one diterpene glycoside of the present invention, or a composition comprising the same, and a gum base. In a particular embodiment, a diterpene glycoside of the present invention is present in the chewing gum composition in an amount in the range of about 1 ppm to about 10,000 ppm of the chewing gum composition.

Cereal Compositions

In one embodiment, the present invention is a cereal composition comprising at least one diterpene glycoside of the present invention. In another embodiment, a cereal composition comprises a composition comprising at least one diterpene glycoside of the present invention. Cereal compositions typically are eaten either as staple foods or as snacks. Non-limiting examples of cereal compositions for use in particular embodiments include ready-to-eat cereals as well as hot cereals. Ready-to-eat cereals are cereals which may be eaten without further processing (i.e. cooking) by the consumer. Examples of ready-to-eat cereals include breakfast cereals and snack bars. Breakfast cereals typically are processed to produce a shredded, flaky, puffy, or extruded form. Breakfast cereals generally are eaten cold and are often mixed with milk and/or fruit. Snack bars include, for example, energy bars, rice cakes, granola bars, and nutritional bars. Hot cereals generally are cooked, usually in either milk or water, before being eaten. Non-limiting examples of hot cereals include grits, porridge, polenta, rice, and rolled oats.

Cereal compositions generally comprise at least one cereal ingredient. As used herein, the term "cereal ingredient" denotes materials such as whole or part grains, whole or part seeds, and whole or part grass. Non-limiting examples of cereal ingredients for use in particular embodiments include maize, wheat, rice, barley, bran, bran endosperm, bulgur, sorghums, millets, oats, rye, triticale, buckwheat, fonio, quinoa, bean, soybean, amaranth, teff, spelt, and kaniwa.

In a particular embodiment, the cereal composition comprises at least one diterpene glycoside of the present invention, or a composition comprising the same, and at least one cereal ingredient. The at least one diterpene glycoside of the present invention, or the composition comprising the same, may be added to the cereal composition in a variety of ways, such as, for example, as a coating, as a frosting, as a glaze, or as a matrix blend (i.e. added as an ingredient to the cereal formulation prior to the preparation of the final cereal product).

Accordingly, in a particular embodiment, at least one diterpene glycoside of the present invention, or a composition comprising the same, is added to the cereal composition as a matrix blend. In one embodiment, at least one diterpene glycoside of the present invention, or a composition comprising the same, is blended with a hot cereal prior to cooking to provide a sweetened hot cereal product. In another embodiment, at least one diterpene glycoside of the present invention, or a composition comprising the same, is blended with the cereal matrix before the cereal is extruded.

In another particular embodiment, at least one diterpene glycoside of the present invention, or a composition comprising the same, is added to the cereal composition as a coating, such as, for example, by combining at least one diterpene glycoside of the present invention, or a comprising the same, with a food grade oil and applying the mixture onto the cereal. In a different embodiment, at least one diterpene glycoside of the present invention, or a composition comprising the same, and the food grade oil may be applied to the cereal separately, by applying either the oil or the sweetener first. Non-limiting examples of food grade oils for use in particular embodiments include vegetable oils such as corn oil, soybean oil, cottonseed oil, peanut oil, coconut oil, canola oil, olive oil, sesame seed oil, palm oil, palm kernel oil, and mixtures thereof. In yet another embodiment, food grade fats may be used in place of the oils, provided that the fat is melted prior to applying the fat onto the cereal.

In another embodiment, at least one diterpene glycoside of the present invention, or a composition comprising the same, is added to the cereal composition as a glaze. Non-limiting examples of glazing agents for use in particular embodiments include corn syrup, honey syrups and honey syrup solids, maple syrups and maple syrup solids, sucrose, isomalt, polydextrose, polyols, hydrogenated starch hydrolysate, aqueous solutions thereof, and mixtures thereof. In another such embodiment, at least one diterpene glycoside of the present invention, or a composition comprising the same, is added as a glaze by combining with a glazing agent and a food grade oil or fat and applying the mixture to the cereal. In yet another embodiment, a gum system, such as, for example, gum acacia, carboxymethyl cellulose, or algin, may be added to the glaze to provide structural support. In addition, the glaze also may include a coloring agent, and also may include a flavor.

In another embodiment, at least one diterpene glycoside of the present invention, or a composition comprising the same, is added to the cereal composition as a frosting. In one such embodiment, at least one diterpene glycoside of the present invention, or a composition comprising the same, is combined with water and a frosting agent and then applied to the cereal. Non-limiting examples of frosting agents for use in particular embodiments include maltodextrin, sucrose, starch, polyols, and mixtures thereof. The frosting also may include a food grade oil, a food grade fat, a coloring agent, and/or a flavor.

Generally, the amount of the diterpene glycoside(s) of the present invention in a cereal composition varies widely depending on the particular type of cereal composition and its desired sweetness. Those of ordinary skill in the art can readily discern the appropriate amount of sweetener to put in the cereal composition. In a particular embodiment, a diterpene glycoside of the present invention is present in the cereal composition in an amount in the range of about 0.02 to about 1.5 weight percent of the cereal composition and the at least one additive is present in the cereal composition in an amount in the range of about 1 to about 5 weight percent of the cereal composition.

Baked Goods

In one embodiment, the present invention is a baked good comprising at least one diterpene glycoside of the present invention. In another embodiment, a baked good comprises a composition comprising at least one diterpene glycoside of the present invention. Baked goods, as used herein, include ready to eat and all ready to bake products, flours, and mixes requiring preparation before serving. Non-limiting examples of baked goods include cakes, crackers, cookies, brownies, muffins, rolls, bagels, donuts, strudels, pastries, croissants, biscuits, bread, bread products, and buns.

Preferred baked goods in accordance with embodiments of this invention can be classified into three groups: bread-type doughs (e.g., white breads, variety breads, soft buns, hard rolls, bagels, pizza dough, and flour tortillas), sweet doughs (e.g., danishes, croissants, crackers, puff pastry, pie crust, biscuits, and cookies), and batters (e.g., cakes such as sponge, pound, devil's food, cheesecake, and layer cake, donuts or other yeast raised cakes, brownies, and muffins). Doughs generally are characterized as being flour-based, whereas batters are more water-based.

Baked goods in accordance with particular embodiments of this invention generally comprise a combination of sweetener, water, and fat. Baked goods made in accordance with many embodiments of this invention also contain flour in order to make a dough or a batter. The term "dough" as used herein is a mixture of flour and other ingredients stiff enough to knead or roll. The term "batter" as used herein consists of flour, liquids such as milk or water, and other ingredients, and is thin enough to pour or drop from a spoon. Desirably, in accordance with particular embodiments of the invention, the flour is present in the baked goods in an amount in the range of about 15 to about 60% on a dry weight basis, more desirably from about 23 to about 48% on a dry weight basis.

The type of flour may be selected based on the desired product. Generally, the flour comprises an edible non-toxic flour that is conventionally utilized in baked goods. According to particular embodiments, the flour may be a bleached bake flour, general purpose flour, or unbleached flour. In other particular embodiments, flours also may be used that have been treated in other manners. For example, in particular embodiments flour may be enriched with additional vitamins, minerals, or proteins. Non-limiting examples of flours suitable for use in particular embodiments of the invention include wheat, corn meal, whole grain, fractions of whole grains (wheat, bran, and oatmeal), and combinations thereof. Starches or farinaceous material also may be used as the flour in particular embodiments. Common food starches generally are derived from potato, corn, wheat, barley, oat, tapioca, arrow root, and sago. Modified starches and pregelatinized starches also may be used in particular embodiments of the invention.

The type of fat or oil used in particular embodiments of the invention may comprise any edible fat, oil, or combination thereof that is suitable for baking. Non-limiting examples of fats suitable for use in particular embodiments of the invention include vegetable oils, tallow, lard, marine oils, and combinations thereof. According to particular embodiments, the fats may be fractionated, partially hydrogenated, and/or intensified. In another particular embodiment, the fat desirably comprises reduced, low calorie, or non-digestible fats, fat substitutes, or synthetic fats. In yet another particular embodiment, shortenings, fats, or mixtures of hard and soft fats also may be used. In particular embodiments, shortenings may be derived principally from triglycerides derived from vegetable sources (e.g., cotton seed oil, soybean oil, peanut oil, linseed oil, sesame oil, palm oil, palm kernel oil, rapeseed oil, safflower oil, coconut oil, corn oil, sunflower seed oil, and mixtures thereof). Synthetic or natural triglycerides of fatty acids having chain lengths from 8 to 24 carbon atoms also may be used in particular embodiments. Desirably, in accordance with particular embodiments of this invention, the fat is present in the baked good in an amount in the range of about 2 to about 35% by weight on a dry basis, more desirably from about 3 to about 29% by weight on a dry basis.

Baked goods in accordance with particular embodiments of this invention also comprise water in amounts sufficient to provide the desired consistency, enabling proper forming, machining and cutting of the baked good prior or subsequent to cooking. The total moisture content of the baked good includes any water added directly to the baked good as well as water present in separately added ingredients (e.g., flour, which generally includes about 12 to about 14% by weight moisture). Desirably, in accordance with particular embodiments of this invention, the water is present in the baked good in an amount up to about 25% by weight of the baked good.

Baked goods in accordance with particular embodiments of this invention also may comprise a number of additional conventional ingredients such as leavening agents, flavors, colors, milk, milk by-products, egg, egg by-products, cocoa, vanilla or other flavoring, as well as inclusions such as nuts, raisins, cherries, apples, apricots, peaches, other fruits, citrus peel, preservative, coconuts, flavored chips such a chocolate chips, butterscotch chips, and caramel chips, and combinations thereof. In particular embodiments, the baked goods may also comprise emulsifiers, such as lecithin and monoglycerides.

According to particular embodiments of this invention, leavening agents may comprise chemical leavening agents or yeast leavening agents. Non-limiting examples of chemical leavening agents suitable for use in particular embodiments of this invention include baking soda (e.g., sodium, potassium, or aluminum bicarbonate), baking acid (e.g., sodium aluminum phosphate, monocalcium phosphate, or dicalcium phosphate), and combinations thereof.

In accordance with another particular embodiment of this invention, cocoa may comprise natural or "Dutched" chocolate from which a substantial portion of the fat or cocoa butter has been expressed or removed by solvent extraction, pressing, or other means. In a particular embodiment, it may be necessary to reduce the amount of fat in a baked good comprising chocolate because of the additional fat present in cocoa butter. In particular embodiments, it may be necessary to add larger amounts of chocolate as compared to cocoa in order to provide an equivalent amount of flavoring and coloring.

Baked goods generally also comprise caloric sweeteners, such as sucrose, high fructose corn syrup, erythritol, molasses, honey, or brown sugar. In exemplary embodiments of the baked goods provided herein, the caloric sweetener is replaced partially or totally with the diterpene glycoside(s) of the present invention, or a composition comprising the same. Accordingly, in one embodiment a baked good comprises at least one diterpene glycoside of the present invention, or a composition comprising the same, in combination with a fat, water, and optionally flour. In a particular embodiment, the baked good optionally may include other natural and/or synthetic high-potency sweeteners and/or bulk sweeteners.

Dairy Products

In one embodiment, the present invention is a dairy product comprising at least one diterpene glycoside of the present invention. In another embodiment, a dairy product comprises a composition comprising at least one diterpene glycoside of the present invention. Dairy products and processes for making dairy products suitable for use in this invention are well known to those of ordinary skill in the art. Dairy products, as used herein, comprise milk or foodstuffs produced from milk. Non-limiting examples of dairy products suitable for use in embodiments of this invention include milk, milk cream, sour cream, crème fraiche, buttermilk, cultured buttermilk, milk powder, condensed milk, evaporated milk, butter, cheese, cottage cheese, cream cheese, yogurt, ice cream, frozen custard, frozen yogurt, gelato, vla, piima, filmjolk, kajmak, kephir, viili, kumiss, airag, ice milk, casein, ayran, lassi, khoa, or combinations thereof.

Milk is a fluid secreted by the mammary glands of female mammals for the nourishment of their young. The female ability to produce milk is one of the defining characteristics of mammals and provides the primary source of nutrition for newborns before they are able to digest more diverse foods. In particular embodiments of this invention, the dairy products are derived from the raw milk of cows, goats, sheep, horses, donkeys, camels, water buffalo, yaks, reindeer, moose, or humans.

In particular embodiments of this invention, the processing of the dairy product from raw milk generally comprises the steps of pasteurizing, creaming, and homogenizing. Although raw milk may be consumed without pasteurization, it usually is pasteurized to destroy harmful microorganisms such as bacteria, viruses, protozoa, molds, and yeasts. Pasteurizing generally comprises heating the milk to a high temperature for a short period of time to substantially reduce the number of microorganisms, thereby reducing the risk of disease.

Creaming traditionally follows pasteurization step, and involves the separation of milk into a higher-fat cream layer and a lower-fat milk layer. Milk will separate into milk and cream layers upon standing for twelve to twenty-four hours. The cream rises to the top of the milk layer and may be skimmed and used as a separate dairy product. Alternatively, centrifuges may be used to separate the cream from the milk. The remaining milk is classified according to the fat content of the milk, non-limiting examples of which include whole, 2%, 1%, and skim milk.

After removing the desired amount of fat from the milk by creaming, milk is often homogenized. Homogenization prevents cream from separating from the milk and generally involves pumping the milk at high pressures through narrow tubes in order to break up fat globules in the milk. Pasteurization, creaming, and homogenization of milk are common but are not required to produce consumable dairy products. Accordingly, suitable dairy products for use in embodiments of this invention may undergo no processing steps, a single processing step, or combinations of the processing steps described herein. Suitable dairy products for use in embodiments of this invention may also undergo processing steps in addition to or apart from the processing steps described herein.

Particular embodiments of this invention comprise dairy products produced from milk by additional processing steps. As described above, cream may be skimmed from the top of milk or separated from the milk using machine-centrifuges. In a particular embodiment, the dairy product comprises sour cream, a dairy product rich in fats that is obtained by fermenting cream using a bacterial culture. The bacteria produce lactic acid during fermentation, which sours and thickens the cream. In another particular embodiment, the dairy product comprises crème fraiche, a heavy cream slightly soured with bacterial culture in a similar manner to sour cream. Crème fraiche ordinarily is not as thick or as sour as sour cream. In yet another particular embodiment, the dairy product comprises cultured buttermilk. Cultured buttermilk is obtained by adding bacteria to milk. The resulting fermentation, in which the bacterial culture turns lactose into lactic acid, gives cultured buttermilk a sour taste. Although it is produced in a different manner, cultured buttermilk generally is similar to traditional buttermilk, which is a by-product of butter manufacture.

According to other particular embodiments of this invention, the dairy products comprise milk powder, condensed milk, evaporated milk, or combinations thereof. Milk powder, condensed milk, and evaporated milk generally are produced by removing water from milk. In a particular embodiment, the dairy product comprises a milk powder comprising dried milk solids with a low moisture content. In another particular embodiment, the dairy product comprises condensed milk. Condensed milk generally comprises milk with a reduced water content and added sweetener, yielding a thick, sweet product with a long shelf-life. In yet another particular embodiment, the dairy product comprises evaporated milk. Evaporated milk generally comprises fresh, homogenized milk from which about 60% of the water has been removed, that has been chilled, fortified with additives such as vitamins and stabilizers, packaged, and finally sterilized. According to another particular embodiment of this invention, the dairy product comprises a dry creamer and at least one diterpene glycoside of the present invention, or a composition comprising the same.

In another particular embodiment, the dairy product provided herein comprises butter. Butter generally is made by churning fresh or fermented cream or milk. Butter generally comprises butterfat surrounding small droplets comprising mostly water and milk proteins. The churning process damages the membranes surrounding the microscopic globules of butterfat, allowing the milk fats to conjoin and to separate from the other parts of the cream. In yet another particular embodiment, the dairy product comprises buttermilk, which is the sour-tasting liquid remaining after producing butter from full-cream milk by the churning process.

In still another particular embodiment, the dairy product comprises cheese, a solid foodstuff produced by curdling milk using a combination of rennet or rennet substitutes and acidification. Rennet, a natural complex of enzymes produced in mammalian stomachs to digest milk, is used in cheese-making to curdle the milk, causing it to separate into solids known as curds and liquids known as whey. Generally, rennet is obtained from the stomachs of young ruminants, such as calves; however, alternative sources of rennet include some plants, microbial organisms, and genetically modified bacteria, fungus, or yeast. In addition, milk may be coagulated by adding acid, such as citric acid. Generally, a combination of rennet and/or acidification is used to curdle the milk. After separating the milk into curds and whey, some cheeses are made by simply draining, salting, and packaging the curds. For most cheeses, however, more processing is needed. Many different methods may be used to produce the hundreds of available varieties of cheese. Processing methods include heating the cheese, cutting it into small cubes to drain, salting, stretching, cheddaring, washing, molding, aging, and ripening. Some cheeses, such as the blue cheeses, have additional bacteria or molds introduced to them before or during aging, imparting flavor and aroma to the finished product. Cottage cheese is a cheese curd product with a mild flavor that is drained but not pressed so that some whey remains. The curd is usually washed to remove acidity. Cream cheese is a soft, mild-tasting, white cheese with a high fat content that is produced by adding cream to milk and then curdling to form a rich curd. Alternatively, cream cheese can be made from skim milk with cream added to the curd. It should be understood that cheese, as used herein, comprises all solid foodstuff produced by the curdling milk.

In another particular embodiment of this invention, the dairy product comprises yogurt. Yogurt generally is produced by the bacterial fermentation of milk. The fermentation of lactose produces lactic acid, which acts on proteins in milk to give the yogurt a gel-like texture and tartness. In particularly desirable embodiments, the yogurt may be sweetened with a sweetener and/or flavored. Non-limiting examples of flavorings include, but are not limited to, fruits (e.g., peach, strawberry, banana), vanilla, and chocolate. Yogurt, as used herein, also includes yogurt varieties with different consistencies and viscosities, such as dahi, dadih or dadiah, labneh or labaneh, bulgarian, kefir, and matsoni. In another particular embodiment, the dairy product comprises a yogurt-based beverage, also known as drinkable yogurt or a yogurt smoothie. In particularly desirable embodiments, the yogurt-based beverage may comprise sweeteners, flavorings, other ingredients, or combinations thereof.

Other dairy products beyond those described herein may be used in particular embodiments of this invention. Such dairy products are well known to those of ordinary skill in the art, non-limiting examples of which include milk, milk and juice, coffee, tea, vla, piima, filmjolk, kajmak, kephir, viili, kumiss, airag, ice milk, casein, ayran, lassi, and khoa.

According to particular embodiments of this invention, the dairy compositions also may comprise other additives. Non-limiting examples of suitable additives include sweeteners and flavorants such as chocolate, strawberry, and banana. Particular embodiments of the dairy compositions provided herein also may comprise additional nutritional supplements such as vitamins (e.g., vitamin D) and minerals (e.g., calcium) to improve the nutritional composition of the milk.

In a particularly desirable embodiment, the dairy composition comprises at least one diterpene glycoside of the present invention, or a composition comprising the same, in combination with a dairy product. In a particular embodiment, a diterpene glycoside of the present invention is present in the dairy composition in an amount in the range of about 200 to about 20,000 weight percent of the dairy composition.

The diterpene glycosides of the present invention, or compositions comprising at least one diterpene glycoside of the present invention, are also suitable for use in processed agricultural products, livestock products or seafood; processed meat products such as sausage and the like; retort food products, pickles, preserves boiled in soy sauce, delicacies, side dishes; soups; snacks such as potato chips, cookies, or the like; as shredded filler, leaf, stem, stalk, homogenized leaf cured and animal feed.

Tabletop Sweetener Compositions

In one embodiment, the present invention is a tabletop sweetener comprising at least one diterpene glycoside of the present invention. The tabletop composition can further include at least one bulking agent, additive, anti-caking agent, functional ingredient or combination thereof.

Suitable "bulking agents" include, but are not limited to, allulose, maltodextrin (10 DE, 18 DE, or 5 DE), corn syrup solids (20 or 36 DE), sucrose, fructose, glucose, invert sugar, sorbitol, xylose, ribulose, mannose, xylitol, mannitol, galactitol, erythritol, maltitol, lactitol, isomalt, maltose, tagatose, lactose, inulin, glycerol, propylene glycol, polyols, polydextrose, fructooligosaccharides, cellulose and cellulose derivatives, and the like, and mixtures thereof. Particularly desirable bulking agents include erythritol, allulose, maltodextrin, maltose, isomalt, sucrose, glucose and fructose. Additionally, in accordance with still other embodiments of the invention, granulated sugar (sucrose) or other caloric sweeteners such as crystalline fructose, other carbohydrates, or sugar alcohol can be used as a bulking agent due to their provision of good content uniformity without the addition of significant calories.

As used herein, the phrase "anti-caking agent" and "flow agent" refer to any composition which assists in content uniformity and uniform dissolution. In accordance with particular embodiments, non-limiting examples of anti-caking agents include cream of tartar, calcium silicate, silicon dioxide, microcrystalline cellulose (Avicel, FMC BioPolymer, Philadelphia, Pa.), and tricalcium phosphate. In one embodiment, the anti-caking agents are present in the tabletop sweetener composition in an amount from about 0.001 to about 3% by weight of the tabletop sweetener composition.

The tabletop sweetener compositions can be packaged in any form known in the art. Non-limiting forms include, but are not limited to, powder form, granular form, packets, tablets, sachets, pellets, cubes, solids, and liquids.

In one embodiment, the tabletop sweetener composition is a single-serving (portion control) packet comprising a dry-blend. Dry-blend formulations generally may comprise powder or granules. Although the tabletop sweetener composition may be in a packet of any size, an illustrative non-limiting example of conventional portion control tabletop sweetener packets are approximately 2.5 by 1.5 inches and hold approximately 1 gram of a sweetener composition having a sweetness equivalent to 2 teaspoons of granulated sugar (~8 g). The amount of the diterpene glycoside(s) of the present invention in a dry-blend tabletop sweetener formulation can vary. In a particular embodiment, a dry-blend tabletop sweetener formulation may contain at least one diterpene glycoside of the present invention in an amount from about 1% (w/w) to about 10% (w/w) of the tabletop sweetener composition.

Solid tabletop sweetener embodiments include cubes and tablets. A non-limiting example of conventional cubes are equivalent in size to a standard cube of granulated sugar, which is approximately 2.2×2.2×2.2 cm$^3$ and weigh approximately 8 g. In one embodiment, a solid tabletop sweetener is in the form of a tablet or any other form known to those skilled in the art.

A tabletop sweetener composition also may be embodied in the form of a liquid, wherein at least one diterpene glycoside of the present invention is combined with a liquid carrier. Suitable non-limiting examples of carrier agents for liquid tabletop sweeteners include water, alcohol, polyol, glycerin base or citric acid base dissolved in water, and mixtures thereof. The sweetness equivalent of a tabletop sweetener composition for any of the forms described herein or known in the art may be varied to obtain a desired sweetness profile. For example, a tabletop sweetener composition may comprise a sweetness comparable to that of an equivalent amount of standard sugar. In another embodiment, the tabletop sweetener composition may comprise a sweetness of up to 100 times that of an equivalent amount of sugar. In another embodiment, the tabletop sweetener composition may comprise a sweetness of up to 90 times, 80 times, 70 times, 60 times, 50 times, 40 times, 30 times, 20 times, 10 times, 9 times, 8 times, 7 times, 6 times, 5 times, 4 times, 3 times, and 2 times that of an equivalent amount of sugar.

Beverage and Beverage Products

In one embodiment, the present invention is a beverage or beverage product comprising at least one diterpene glycoside of the present invention.

In another embodiment, the present invention is a beverage or beverage product comprising a composition that comprises at least one diterpene glycoside of the present invention.

As used herein a "beverage product" is a ready-to-drink beverage, a beverage concentrate, a beverage syrup, or a powdered beverage. Suitable ready-to-drink beverages include carbonated and non-carbonated beverages. Carbonated beverages include, but are not limited to, enhanced sparkling beverages, cola, lemon-lime flavored sparkling beverage, orange flavored sparkling beverage, grape flavored sparkling beverage, strawberry flavored sparkling beverage, pineapple flavored sparkling beverage, ginger-ale, soft drinks and root beer. Non-carbonated beverages include, but are not limited to fruit juice, fruit-flavored juice, juice drinks, nectars, vegetable juice, vegetable-flavored juice, sports drinks, energy drinks, enhanced water drinks, enhanced water with vitamins, near water drinks (e.g., water with natural or synthetic flavorants), coconut water, tea type drinks (e.g. black tea, green tea, red tea, oolong tea), coffee, cocoa drink, beverage containing milk components (e.g. milk beverages, coffee containing milk components, café au lait, milk tea, fruit milk beverages), beverages containing cereal extracts, smoothies and combinations thereof.

Beverage concentrates and beverage syrups are prepared with an initial volume of liquid matrix (e.g. water) and the desired beverage ingredients. Full strength beverages are then prepared by adding further volumes of water. Powdered beverages are prepared by dry-mixing all of the beverage ingredients in the absence of a liquid matrix. Full strength beverages are then prepared by adding the full volume of water.

Beverages comprise a matrix, i.e. the basic ingredient in which the ingredients—including the compositions of the present invention—are dissolved. In one embodiment, a beverage comprises water of beverage quality as the matrix, such as, for example deionized water, distilled water, reverse osmosis water, carbon-treated water, purified water, demineralized water and combinations thereof, can be used. Additional suitable matrices include, but are not limited to phosphoric acid, phosphate buffer, citric acid, citrate buffer and carbon-treated water.

In one embodiment, the present invention is a beverage comprising at least one diterpene glycoside of the present invention.

In another embodiment, the present invention is a beverage comprising a composition comprising at least one diterpene glycoside of the present invention.

In a further embodiment, the present invention is a beverage product comprising at least one diterpene glycoside of the present invention.

In another embodiment, the present invention is a beverage product comprising a composition comprising at least one diterpene glycoside of the present invention.

The concentration of the diterpene glycoside of the present invention in the beverage may be above, at or below the threshold sweetness or flavor recognition concentration of the diterpene glycoside of the present invention.

In a particular embodiment, the concentration of the diterpene glycoside of the present invention in the beverage is above its threshold sweetness or flavor recognition concentration. In one embodiment, the concentration of a diterpene glycoside of the present invention is at least about 1%, at least about 5%, at least about 10%, at least about 15%, at least about 20%, at least about 25%, at least about 30%, about least about 35%, at least about 40%, about least about 45%, at least about 50% or more above its threshold sweetness or flavor recognition.

In another particular embodiment, the concentration of a diterpene glycoside of the present invention in the beverage is at or approximately the threshold sweetness or flavor recognition concentration of the diterpene glycoside.

In yet another particular embodiment, the concentration of a diterpene glycoside of the present invention in the beverage is below the threshold sweetness or flavor recognition concentration of the diterpene glycoside of the present invention. In one embodiment, the concentration of a diterpene glycoside of the present invention is at least about 1%, at least about 5%, at least about 10%, at least about 15%, at least about 20%, at least about 25%, at least about 30%, about least about 35%, at least about 40%, about least about 45%, at least about 50% or more below the threshold sweetness or flavor recognition concentration of the diterpene glycoside.

In one embodiment, a diterpene glycoside of the present invention is present in the beverage in a concentration greater than about 1 ppm, such as, for example, from about 1 ppm to about 1,000 ppm, from about 25 ppm to about 1,000 ppm, from about 50 ppm to about 1,000 ppm, from about 75 ppm to about 1,000 ppm, from about 100 ppm to about 1,000 ppm, from about 200 ppm to about 1,000 ppm, from about 300 ppm to about 1,000 ppm, from about 400 ppm to about 1,000 ppm or from about 500 ppm to about 1,000 ppm.

In a more particular embodiment, a diterpene glycoside of the present invention is present in the beverage in a concentration from about 25 ppm to about 600 ppm, such as, for example, from about 25 ppm to about 500 ppm, from about 25 ppm to about 400 ppm, from about 25 ppm to about 300 ppm, from about 25 ppm to about 200 ppm, from about 25 ppm to about 100 ppm, from about 50 ppm to about 600 ppm, from about 50 ppm to about 500 ppm, from about 50 ppm to about 400 ppm, from about 50 ppm to about 300 ppm, from about 50 ppm to about 200 ppm, from about 50 ppm to about 100 ppm, from about 100 ppm to about 600 ppm, from about 100 ppm to about 500 ppm, from about 100 ppm to about 400 ppm, from about 100 ppm to about 300 ppm, from about 100 ppm to about 200 ppm, from about 200 ppm to about 600 ppm, from about 200 ppm to about 500 ppm, from about 200 ppm to about 400 ppm, from about 200 ppm to about 300 ppm, from about 300 ppm to about 600 ppm, from about 300 ppm to about 500 ppm, from about 300 ppm to about 400 ppm, from about 400 ppm to about 600 ppm, from about 400 ppm to about 500 ppm or from about 500 ppm to about 600 ppm.

In other particular embodiments, a diterpene glycoside of the present invention is present in the beverage in a purity of at least about 5% with respect to a mixture of diterpene glycosides or *Stevia* extract, such as, for example, at least about 10%, at least about 20%, at least about 30%, at least about 40%, at least about 50%, at least about 60%, at least about 70%, at least about 80%, at least about 90%, at least about 95% or at least about 97%. In still other embodiments, a diterpene glycoside of the present invention is present in the beverage in >99% purity.

The beverage can include one or more sweeteners. Any of the sweeteners detailed herein can be used, including natural, non-natural, or synthetic sweeteners. These may be added to the beverage either before, contemporaneously with or after the diterpene glycoside(s) of the present invention.

In one embodiment, the beverage contains a carbohydrate sweetener in a concentration from about 100 ppm to about 140,000 ppm. Synthetic sweeteners may be present in the beverage in a concentration from about 0.3 ppm to about 3,500 ppm. Natural high potency sweeteners may be present in the beverage in a concentration from about 0.1 ppm to about 3,000 ppm.

In another embodiment, a beverage comprises a diterpene glycoside of the present invention and a compound selected from the group consisting of rebaudioside A, rebaudioside B, rebaudioside D, rebaudioside M, rebaudioside E, glycosylated steviol glycosides, Luo Han Guo, Mogroside V, erythritol, allulose and combinations thereof.

The amount of compound selected from the group consisting of rebaudioside A, rebaudioside B, rebaudioside D, rebaudioside M, rebaudioside E, glycosylated steviol glycosides, Luo Han Guo, Mogroside V, erythritol, allulose present in the beverage can vary.

Typically, a compound selected from rebaudioside A, rebaudioside B, rebaudioside D, rebaudioside M, rebaudioside E, glycosylated steviol glycosides, Luo Han Guo, Mogroside V is present in an amount from about 25 ppm to about 600 ppm, such as, for example, from about 25 ppm to about 500 ppm, from about 25 ppm to about 400 ppm, from about 25 ppm to about 300 ppm, from about 25 ppm to about 200 ppm, from about 25 ppm to about 100 ppm, from about 50 ppm to about 600 ppm, from about 50 ppm to about 500 ppm, from about 50 ppm to about 400 ppm, from about 50 ppm to about 300 ppm, from about 50 ppm to about 200 ppm, from about 50 ppm to about 100 ppm, from about 100 ppm to about 600 ppm, from about 100 ppm to about 500 ppm, from about 100 ppm to about 400 ppm, from about 100 ppm to about 300 ppm, from about 100 ppm to about 200 ppm, from about 200 ppm to about 600 ppm, from about 200 ppm to about 500 ppm, from about 200 ppm to about 400 ppm, from about 200 ppm to about 300 ppm, from about 300 ppm to about 600 ppm, from about 300 ppm to about 500 ppm, from about 300 ppm to about 400 ppm, from about 400 ppm to about 600 ppm, from about 400 ppm to about 500 ppm or from about 500 ppm to about 600 ppm.

In some embodiments, the total amount of steviol glycosides in the beverage does not exceed about 600 ppm. Accordingly, in some embodiment, a beverage comprises at least one diterpene glycoside of the present invention and a compound selected from rebaudioside A, rebaudioside B, rebaudioside D, rebaudioside M, rebaudioside E, glycosylated steviol glycosides and a combination thereof, wherein the total concentration of steviol glycosides does not exceed about 600 ppm. In a particular embodiment, the total concentration of steviol of steviol glycosides is at least 25 ppm, at least 50 ppm or at least 100 ppm.

Typically, erythritol can comprise from about 0.1% to about 3.5% by weight of the sweetener component, i.e. the compounds that provide sweetness to the beverage. In one example, a sweetener component is erythritol and a diterpene glycoside of the present invention. In another example, a sweetener component is erythritol, a diterpene glycoside of the present invention and rebaudioside M.

The beverage can comprise additives including, but not limited to, carbohydrates, polyols, amino acids and their corresponding salts, poly-amino acids and their corresponding salts, sugar acids and their corresponding salts, nucleotides, organic acids, inorganic acids, organic salts including organic acid salts and organic base salts, inorganic salts, bitter compounds, caffeine, flavorants and flavoring ingredients, astringent compounds, proteins or protein hydrolysates, surfactants, emulsifiers, weighing agents, juice, dairy, cereal and other plant extracts, flavonoids, alcohols, polymers and combinations thereof. Any suitable additive described herein can be used.

In particular embodiments, a beverage comprises at least one diterpene glycoside of the present invention; a carbohydrate sweetener selected from sucrose, fructose, glucose, maltose, high fructose corn syrup and combinations thereof; and optionally at least one additional sweetener and/or functional ingredient. The carbohydrate sweetener, such as, for example, sucrose, is present in the beverage in a concentration from about 100 ppm to about 140,000 ppm, such as, for example, from about 1,000 ppm to about 100,000 ppm, from about 5,000 ppm to about 80,000 ppm.

In particular embodiments, a beverage comprises at least one diterpene glycoside of the present invention; an amino acid selected from glycine, alanine, proline, taurine and combinations thereof; and optionally at least one additional sweetener and/or functional ingredient. The amino acid, such as, for example, glycine, can be present in the beverage in a concentration from about 10 ppm to about 50,000 ppm, such as, for example, from about 1,000 ppm to about 10,000 ppm, from about 2,500 ppm to about 5,000 ppm In particular embodiments, a beverage comprises at least one diterpene glycoside of the present invention; a salt selected from sodium chloride, magnesium chloride, potassium chloride, calcium chloride, phosphate salts and combinations thereof; and optionally at least one additional sweetener and/or functional ingredient. The salt, such as, for example, magnesium chloride, is present in the beverage in a concentration from about 25 ppm to about 25,000 ppm, such as, for example, from about 100 ppm to about 4,000 ppm or from about 100 ppm to about 3,000 ppm.

In particular embodiments, a beverage comprises at least one diterpene glycoside of the present invention and at least one flavonoid, isoflavonoid or combination thereof. Any of the flavonoids and isoflavonoids described herein above can be included. Typically, the concentration of flavonoid and/or isoflavonoid is from about 5 ppm to about 50 ppm, such as, for example, from about 5 ppm to about 15 ppm, from about 15 ppm to about 50 ppm, from about 15 ppm to about 30 ppm and from about 30 ppm to about 50 ppm. In one embodiment, the flavonoid or isoflavonoid is selected from the group consisting of naringenin, hesperetin, hesperidin eriodictyol and a combination thereof.

In other particular embodiments, a beverage comprises at least one diterpene glycoside of the present invention at least one compound selected from the group consisting of phyllodulcin, taxifolin 3-O-acetate and phloretin. Typically, the concentration of at least one compound selected from the group consisting of phyllodulcin, taxifolin 3-O-acetate and phloretin is from about 5 ppm to about 50 ppm, such as, for example, from about 5 ppm to about 15 ppm, from about 15 ppm to about 50 ppm, from about 15 ppm to about 30 ppm and from about 30 ppm to about 50 ppm.

In one embodiment, the polyol can be present in the beverage in a concentration from about 100 ppm to about 250,000 ppm, such as, for example, from about 5,000 ppm to about 40,000 ppm.

In another embodiment, the amino acid can be present in the beverage in a concentration from about 10 ppm to about 50,000 ppm, such as, for example, from about 1,000 ppm to about 10,000 ppm, from about 2,500 ppm to about 5,000 ppm or from about 250 ppm to about 7,500 ppm.

In still another embodiment, the nucleotide can be present in the beverage in a concentration from about 5 ppm to about 1,000 ppm.

In yet another embodiment, the organic acid additive can be present in the beverage in a concentration from about 10 ppm to about 5,000 ppm.

In yet another embodiment, the inorganic acid additive can be present in the beverage in a concentration from about 25 ppm to about 25,000 ppm.

In still another embodiment, the bitter compound can be present in the beverage in a concentration from about 25 ppm to about 25,000 ppm.

In yet another embodiment, the flavorant can be present in the beverage a concentration from about 0.1 ppm to about 4,000 ppm.

In a still further embodiment, the polymer can be present in the beverage in a concentration from about 30 ppm to about 2,000 ppm.

In another embodiment, the protein hydrolysate can be present in the beverage in a concentration from about 200 ppm to about 50,000.

In yet another embodiment, the surfactant additive can be present in the beverage in a concentration from about 30 ppm to about 2,000 ppm.

In still another embodiment, the flavonoid additive can be present in the beverage a concentration from about 0.1 ppm to about 1,000 ppm.

In yet another embodiment, the alcohol additive can be present in the beverage in a concentration from about 625 ppm to about 10,000 ppm.

In a still further embodiment, the astringent additive can be present in the beverage in a concentration from about 10 ppm to about 5,000 ppm.

The beverage can contain one or more functional ingredients, detailed above. Functional ingredients include, but are not limited to, vitamins, minerals, antioxidants, preservatives, glucosamine, polyphenols and combinations thereof. Any suitable functional ingredient described herein can be used.

It is contemplated that the pH of the consumable, such as, for example, a beverage, does not materially or adversely affect the taste of the sweetener. A non-limiting example of the pH range of the beverage may be from about 1.8 to about 10. A further example includes a pH range from about 2 to about 5. In a particular embodiment, the pH of beverage can be from about 2.5 to about 4.2. On of skill in the art will understand that the pH of the beverage can vary based on the type of beverage. Dairy beverages, for example, can have pHs greater than 4.2.

The titratable acidity of a beverage may, for example, range from about 0.01 to about 1.0% by weight of beverage.

In one embodiment, the sparkling beverage product has an acidity from about 0.01 to about 1.0% by weight of the beverage, such as, for example, from about 0.05% to about 0.25% by weight of beverage.

The carbonation of a sparkling beverage product has 0 to about 2% (w/w) of carbon dioxide or its equivalent, for example, from about 0.1 to about 1.0% (w/w).

The temperature of a beverage may, for example, range from about 4° C. to about 100° C., such as, for example, from about 4° C. to about 25° C.

The beverage can be a full-calorie beverage that has up to about 120 calories per 8 oz serving.

The beverage can be a mid-calorie beverage that has up to about 60 calories per 8 oz serving.

The beverage can be a low-calorie beverage that has up to about 40 calories per 8 oz serving.

The beverage can be a zero-calorie that has less than about 5 calories per 8 oz. serving.

In one embodiment, the beverage comprises natural sweetener(s) only, i.e. the only type of sweetener(s) are naturally-occurring. In another embodiment, the beverage comprises naturally-occurring flavonoids and isoflavonoids and only natural sweetener(s). In still another embodiment, the beverage comprises naturally-occurring compounds selected from phyllodulcin, taxifolin 3-O-acetate, phloretin and combinations thereof and only natural sweetener(s).

II. Methods of Use

The compounds and compositions of the present invention can be used to impart sweetness or to enhance the flavor or sweetness of consumables or other compositions.

In one aspect, the present invention is a method of preparing a consumable comprising (i) providing a consumable matrix and (ii) adding at least one diterpene glycoside of the present invention to the consumable matrix to provide a consumable.

In a particular embodiment, the present invention is a method of preparing a beverage comprising (i) providing a beverage matrix and (ii) adding at least one diterpene glycoside of the present invention to the liquid or beverage matrix to provide a beverage.

In a particular embodiment, the present invention is a method of preparing a sweetened beverage comprising (i) providing a sweetenable beverage and (ii) adding at least one diterpene glycoside of the present invention to the sweetenable beverage to provide a sweetened beverage.

In the above methods, the diterpene glycoside(s) of the present invention may be provided as such, i.e., in the form of a compound, or in form of a composition. When provided as a composition, the amount of diterpene glycoside in the composition is effective to provide a concentration of the diterpene glycoside that is above, at or below its flavor or sweetness recognition threshold when the composition is added to the consumable (e.g., the beverage). When the diterpene glycoside(s) of the present invention is not provided as a composition, it may be added to the consumable at a concentration that is above, at or below its flavor or sweetness recognition threshold.

In one embodiment, the present invention is a method for enhancing the sweetness of a consumable comprising (i) providing a consumable comprising at least one sweet ingredient and (ii) adding at least one diterpene glycoside of the present invention to the consumable to provide a consumable with enhanced sweetness, wherein the diterpene glycoside of the present invention is added to the consumable at a concentration at or below its sweetness recognition threshold. In a particular embodiment, a diterpene glycoside of the present invention is added to the consumable at a concentration below its sweetness recognition threshold.

In another embodiment, the present invention is a method for enhancing the sweetness of a consumable comprising (i) providing a consumable comprising at least one sweet ingredient and (ii) adding a composition comprising at least one diterpene glycoside of the present invention to the consumable to provide a consumable with enhanced sweetness, wherein the diterpene glycoside is present in the composition in an amount effective to provide a concentration of the diterpene glycoside at or below its sweetness recognition threshold when the composition is added to the consumable. In a particular embodiment, a diterpene glycoside of the present invention is present in the composition in an amount effective to provide a concentration of the diterpene glycoside below its sweetness recognition threshold when the composition is added to the consumable.

In a particular embodiment, the present invention is a method for enhancing the sweetness of a beverage comprising (i) providing a beverage comprising at least one sweet ingredient and (ii) adding at least one diterpene glycoside of the present invention to the beverage to provide a beverage with enhanced sweetness, wherein the diterpene glycoside is added to the beverage at a concentration at or below its sweetness recognition threshold. In a particular embodiment, the diterpene glycoside of the present invention is added to the consumable at a concentration below its sweetness recognition concentration threshold.

In another particular embodiment, the present invention is a method for enhancing the sweetness of a beverage comprising (i) providing a beverage comprising at least one sweet ingredient and (ii) adding a composition comprising at least one diterpene glycoside of the present invention to the consumable to provide a beverage with enhanced sweetness, wherein the diterpene glycoside of is present in the composition in an amount effective to provide a concentration of the diterpene glycoside of the present invention at or below its sweetness recognition threshold when the composition is added to the beverage. In a particular embodiment, the diterpene glycoside of the present invention is present in the composition in an amount effective to provide a concentration of the diterpene glycoside below its sweetness recognition threshold when the composition is added to the beverage.

In another embodiment, the present invention is a method for enhancing the flavor of a consumable comprising (i) providing a consumable comprising at least one flavor ingredient and (ii) adding at least one diterpene glycoside of the present invention to the consumable to provide a consumable with enhanced flavor, wherein the diterpene glycoside of the present invention is added to the consumable at a concentration at or below its flavor recognition threshold. In a particular embodiment, the diterpene glycoside of the present invention is added to the consumable at a concentration below its flavor recognition threshold.

In another embodiment, the present invention is a method for enhancing the flavor of a consumable comprising (i) providing a consumable comprising at least one flavor ingredient and (ii) adding a composition comprising at least one diterpene glycoside of the present invention to the consumable to provide a consumable with enhanced flavor, wherein the diterpene glycoside of the present invention is present in the composition in an amount effective to provide a concentration of the diterpene glycoside of the present invention at or below its flavor recognition threshold when the composition is added to the consumable. In a particular embodiment, the diterpene glycoside of the present invention is present in the composition in an amount effective to provide a concentration of the diterpene glycoside of the present invention below its flavor recognition threshold when the composition is added to the consumable.

In a particular embodiment, a method for enhancing the flavor of a beverage is provided that comprises (i) providing a beverage comprising at least one flavor ingredient and (ii) adding at least one diterpene glycoside of the present invention to the beverage to provide a beverage with enhanced flavor, wherein the diterpene glycoside is added to the beverage at a concentration at or below the flavor recognition threshold of the diterpene glycoside. In a particular embodiment, the diterpene glycoside of the present invention is added to the consumable at a concentration below its flavor recognition threshold.

In a particular embodiment, a method for enhancing the flavor of a beverage is provided that comprises (i) providing a beverage comprising at least one flavor ingredient and (ii) adding a composition comprising at least one diterpene glycoside of the present invention to the beverage to provide a beverage with enhanced flavor, wherein the diterpene glycoside of the present invention is present in the composition in an amount effective to provide a concentration of the diterpene glycoside at or below its flavor recognition threshold when the composition is added to the beverage. In a particular embodiment, the diterpene glycoside of the present invention is present in the composition in an amount effective to provide a concentration of the diterpene glycoside below its flavor recognition threshold when the composition is added to the consumable.

The present invention also includes methods of preparing sweetened compositions (e.g., sweetened consumables) and flavor enhanced compositions (e.g., flavored enhanced consumables) by adding at least one diterpene glycoside of the present invention or a composition comprising the same to such compositions/consumables.

III. Method of Purification

The present invention also extends to methods of purifying a diterpene glycoside of the present invention.

In one embodiment, the present invention is a method for purifying a diterpene glycoside of the present invention comprising (i) passing a solution comprising a source material comprising a diterpene glycoside of the present invention through a HPLC column and (ii) eluting fractions comprising a diterpene glycoside of the present invention to provide purified diterpene glycoside of the present invention. The HPLC column can be any suitable HPLC preparative or semi-preparative scale column.

As used herein, the term "preparative HPLC" refers to an HPLC system capable of producing high (500 or more) microgram, milligram, or gram sized product fractions. The term "preparative" includes both preparative and semi-preparative columns, but is not intended to include analytical columns, which provide fractions in the nanogram to low microgram range.

As used herein, an "HPLC compatible detector" is a detector suitable for use in an HPLC system which is capable of providing a detectable signal upon elution of a compound peak. For example, a detector capable of generating a signal when a compound elutes from the compound is an HPLC compatible detector. Where component absorbance varies widely, it may be necessary to utilize more than one detector. A detector capable of detecting a desired component is not an "incompatible" detector due to its inability to detect a non-desired peak.

An HPLC device typically includes at least the following components: a column, packed with a suitable stationary phase, a mobile phase, a pump for forcing the mobile phase through the column under pressure, and a detector for detecting the presence of compounds eluting off of the column. The devices can optionally include a means for providing for gradient elution, although such is not necessary using the methods described herein. Routine methods and apparatus for carrying out HPLC separations are well known in the art.

Suitable stationary phases are those in which the compound of interest elutes. Preferred columns can be, and are not limited to, normal phase columns (neutral, acidic or basic), reverse phase columns (of any length alkyl chain), a synthetic crosslinked polymer columns (e.g., styrene and divinylbenzene), size exclusion columns, ion exchange columns, bioaffinity columns, and any combination thereof. The particle size of the stationary phase is within the range from a few µm to several 100 µm.

Suitable detection devices include, but are not limited to, mass spectrometers, UV detectors, IR detectors and light scattering detectors. The methods described herein use any combination of these detectors. The most preferable embodiment uses mass spectrometers and UV detectors.

"Source material", as used herein, refers to the material being purified by the present method. The source material contains a diterpene glycoside of the present invention in a purity less than the purity provided by the present purification method. The source material can be liquid or solid. Exemplary source materials include, but are not limited to, mixtures of diterpene glycosides, Stevia extract, Stevia plant leaves, by-products of other diterpene glycosides' isolation and purification processes, commercially available diterpene extracts or Stevia extracts, by-products of biotransformation reactions of other diterpene glycosides, or any combination thereof.

As understood by persons skilled in the art, any solid source materials must be brought into solution prior to carrying out the HPLC method.

In one embodiment, a representative analytical HPLC protocol is correlated to a preparative or semi-preparative HPLC protocol used to purify a compound.

In another embodiment, appropriate conditions for purifying a diterpene glycoside of the present invention can be worked out by route scouting a representative sample for a given analytical HPLC column, solvent system and flow rate. In yet another embodiment, a correlated preparative or semipreparative HPLC method can be applied to purify a diterpene glycoside of the present invention with modifications to the purification parameters or without having to change the purification parameters.

In some embodiments, the eluent (mobile phase) is selected from the group consisting of water, acetonitrile, methanol, 2-propanol, ethyl acetate, dimethylformamide, dimethylsulfide, pyridine, triethylamine, formic acid, trifluoroacetic acid, acetic acid, an aqueous solution containing ammonium acetate, heptafluorobutyric acid, and any combination thereof.

In one embodiment, the HPLC method is isocratic. In another embodiment, the HPLC method is a gradient. In still another embodiment, the HPLC method is step-wise.

In one embodiment, impurities are eluted off of the HPLC column after eluting one or more fractions containing a diterpene glycoside of the present invention. In another embodiment, impurities are eluted off of the HPLC column before eluting one or more fractions containing a diterpene glycoside of the present invention.

The method can further include removal of solvent from the eluted solution, i.e. drying. In one embodiment, the method further comprises partial removal of solvents from the eluted solution to provide a concentrate comprising a diterpene glycoside of the present invention. In another embodiment, the method further comprises removing substantially all the solvent from the eluted solutions to provide substantially dry material comprising a diterpene glycoside of the present invention.

Removal of solvent can be performed by any known means to one of skill in the art including, but not limited to, evaporation, distillation, vacuum drying and spray drying.

The resulting purified fractions comprising a diterpene glycoside of the present invention can be further purified by other methods to increase purity. Suitable methods include, but are not limited to, crystallization, chromatography, extraction and distillation. Such methods are well-known to persons skilled in the art.

The source material can be one fraction, or multiple fractions, containing a diterpene glycoside of the present invention collected from at least one previous method or HPLC protocol. In one embodiment, multiple fractions from the same, previous methods or HPLC protocols are pooled and optionally, solvents are removed, prior to re-subjecting the source material to another method. In other embodiments, fractions from different, previous methods or HPLC protocol are pooled, and optionally, solvents are removed, prior to re-subjecting the source material to another method.

In one embodiment, the source material re-subjected to additional method(s) comprises liquid fractions obtained from one or more previous (and optionally, different) methods mixed with substantially dry material obtained via drying of fractions obtained from one or more previous (and optionally, different) methods. In another embodiment, the source material re-subjected to additional method(s) comprises substantially dry material obtained via drying of fractions obtained from one or more previous (and optionally, different) methods, where said source material is brought into solution prior to passing the solution through the next HPLC column.

The second and subsequent methods may have different HPLC protocols (e.g. solvent systems, columns, methods) and different steps following elution (e.g. partial removal of solvent, complete removal of solvent, elution of impurities, use of crystallization or extraction).

The material isolated can be subjected to further methods 2, 3, 4 or more times, each time providing a higher level of purity of purified diterpene glycoside of the present invention.

In one embodiment, the method provides a purified diterpene glycoside of the present invention in a purity of about 50% by weight or greater on a dry basis, such as, for example, about 60% or greater, about 65% or greater, about 70% or greater, about 75% or greater, about 80% or greater, about 85% or greater, about 90% or greater, about 95% or greater and about 97% or greater. In a particular embodiment, the method provides a diterpene glycoside of the present invention in a purity greater of about 99% or greater by weight on a dry basis.

EXAMPLES

Example 1

Isolation and Characterization of 1

HPLC Analysis. Preliminary HPLC analyses of samples were performed using a Waters 2695 Alliance System with the following method: Phenomenex Synergi Hydro-RP, 4.6× 250 mm, 4 μm (p/n 00G-4375-E0); Column Temp: 55° C.; Mobile Phase A: 0.0284% $NH_4OAc$ and 0.0116% HOAc in water; Mobile Phase B: Acetonitrile (MeCN); Flow Rate: 1.0 mL/min; Injection volume: 10 μL. Detection was by UV (210 nm) and CAD.

Gradient

| Time (min) | % A | % B |
|---|---|---|
| 0.0-8.5 | 75 | 25 |
| 10.0 | 71 | 29 |
| 16.5 | 70 | 30 |
| 18.5-24.5 | 66 | 34 |
| 26.5-29.0 | 48 | 52 |
| 31-37 | 30 | 70 |
| 38 | 75 | 25 |

LC-MS. Preliminary analysis of the sample was carried out on an AB Sciex API 150EX MS. MS detection using—Turbo Spray with a mass window of 500-2000 Da. Gradient conditions were as listed below. LC-MS analysis of enhanced fractions were performed on a Phenomenex Synergi Hydro-RP, 4.6×250 mm, 4 μm (p/n 00G-4375-E0); Column Temp: Ambient; Mobile Phase A: 15% MeCN in water; Mobile Phase B: 30% MeCN in water; Flow Rate: 1.0 mL/min; Injection volume: 10 μL. Detection was by UV (210 nm) and CAD.

Gradient

| Time (min) | % A | % B |
|---|---|---|
| 0-5 | 100 | 0 |
| 5-25 | 0 | 100 |
| 25-30 | 0 | 100 |
| 32 | 100 | 0 |

Isolation by preparative LC. Both primary and secondary processes were completed on a Waters Symmetry Shield RP18 OBD (30×150 mm, 10 μm) column using the conditions described below. Fractions were isolated and analyzed by HPLC as described above.

| Separation Parameters | |
|---|---|
| Column | Waters Symmetry Shield RP18 (30 × 150 mm, 10 μm) |
| Flow Rate (mL/min) | 45 |
| Detection | UV at 210 nm |

-continued

| Primary Processing | |
|---|---|
| Mobile Phases | (A) 20:80 MeCN/water with 0.1% HOAC (v/v) |
| | (B) 30:70 MeCN/water with 0.1% HOAC (v/v) |
| Load (g) | 0.5-3 g |
| Sample preparation | 3 g dissolved in 20 mL of DMSO, then added 90 mL of MP-A |

| Gradient | | |
|---|---|---|
| Time (min) | % A | % B |
| 0-10 | 100 | 0 |
| 10-25 | 0 | 100 |
| 25-30 | 0 | 100 |
| 32 | 100 | 0 |

| Secondary Processing | |
|---|---|
| Mobile Phases | (A) 15:85 MeCN/water with 0.1% HOAC (v/v) |
| | (B) 30:70 MeCN/water with 0.1% HOAC (v/v) |
| Load (g) | 75 mL of concentrated SJB-O-192 (1) |

| Gradient | | |
|---|---|---|
| Time (min) | % A | % B |
| 0-5 | 100 | 0 |
| 5-25 | 0 | 100 |
| 25-30 | 0 | 100 |
| 32 | 100 | 0 |

Tertiary processing to improve sample purity was conducted on a Waters Symmetry Shield RP 18 OBD (30×140 mm, 10 μm) column using conditions described in the table below.

| Tertiary Processing | |
|---|---|
| Mobile Phases | 18:82 MeCN/water with 0.1% HOAC (v/v) |
| Load (g) | 10-20 mL of RAM-U-131(2) |
| Gradient: | 100% MP-A for 25 min |

Figure 2:
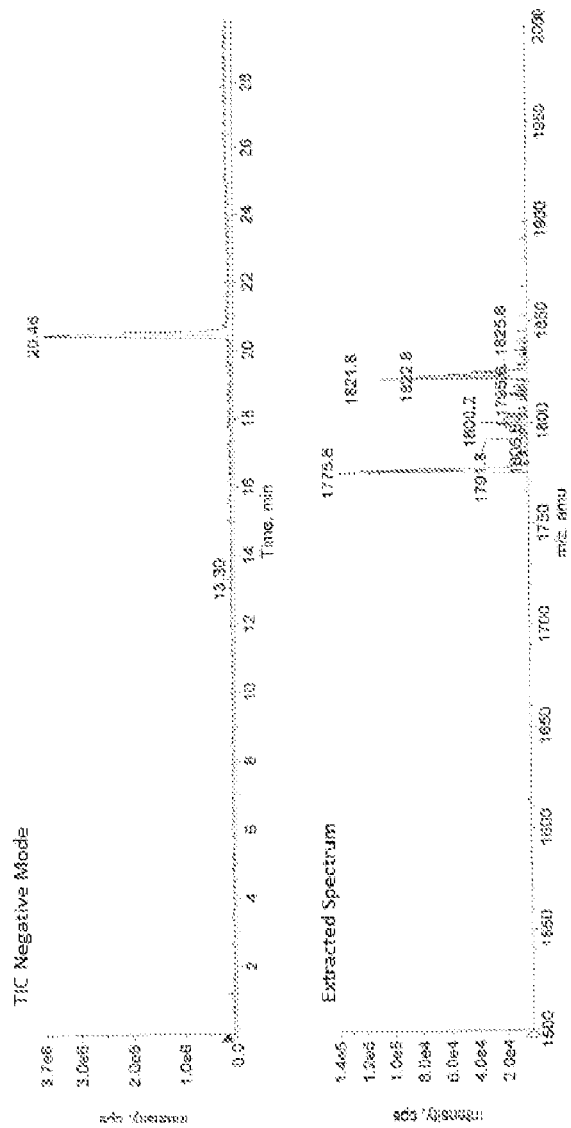
FIG. 2: Shows a representative HPLC-MS trace of diterpene glycoside 1 using the method described in Example 1.
Figure 3:
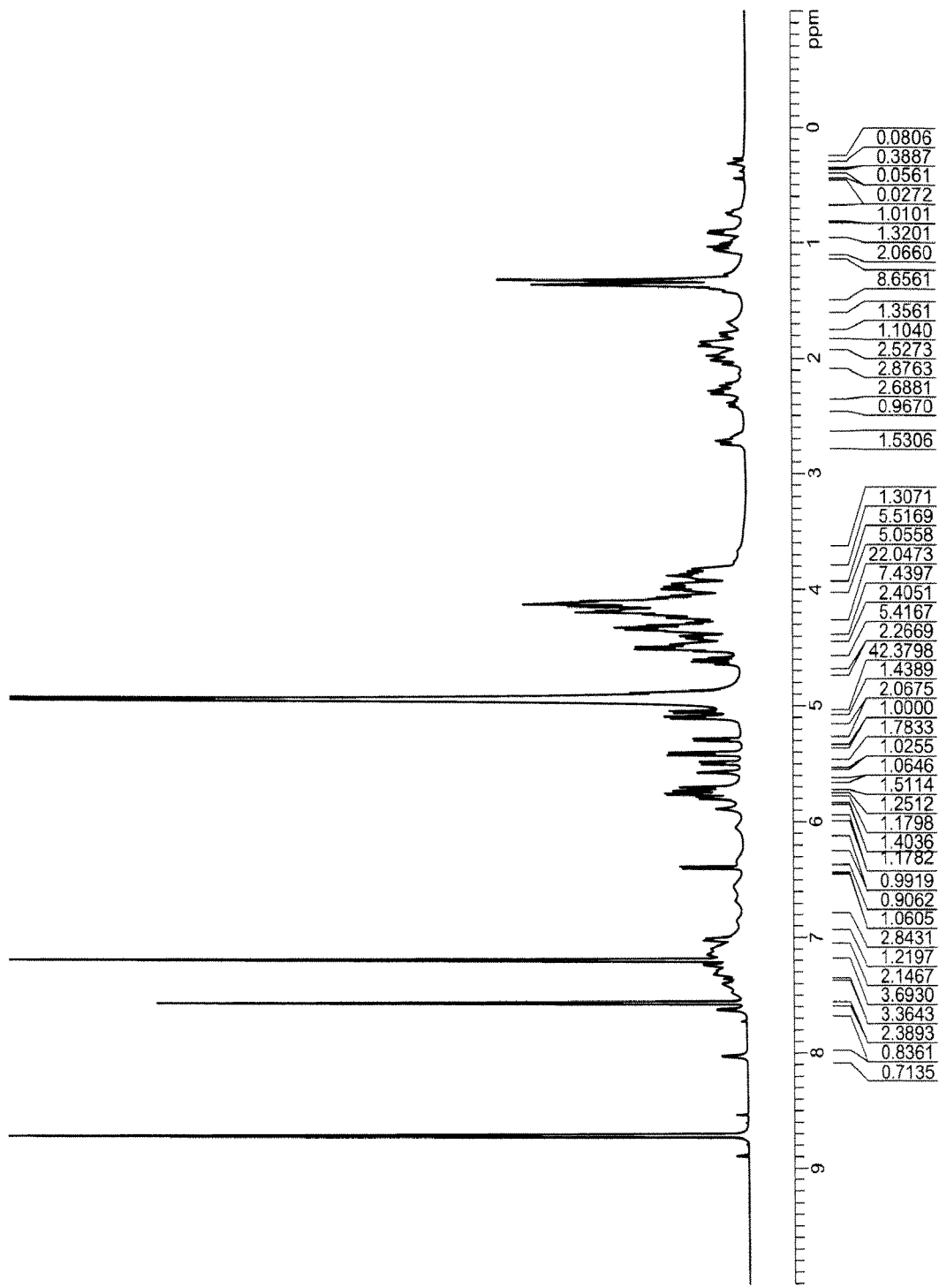
FIG. 3: Shows the $^1$H NMR spectrum (500 MHz, pyridine-$d_5$) of diterpene glycoside 1.
Figure 4:
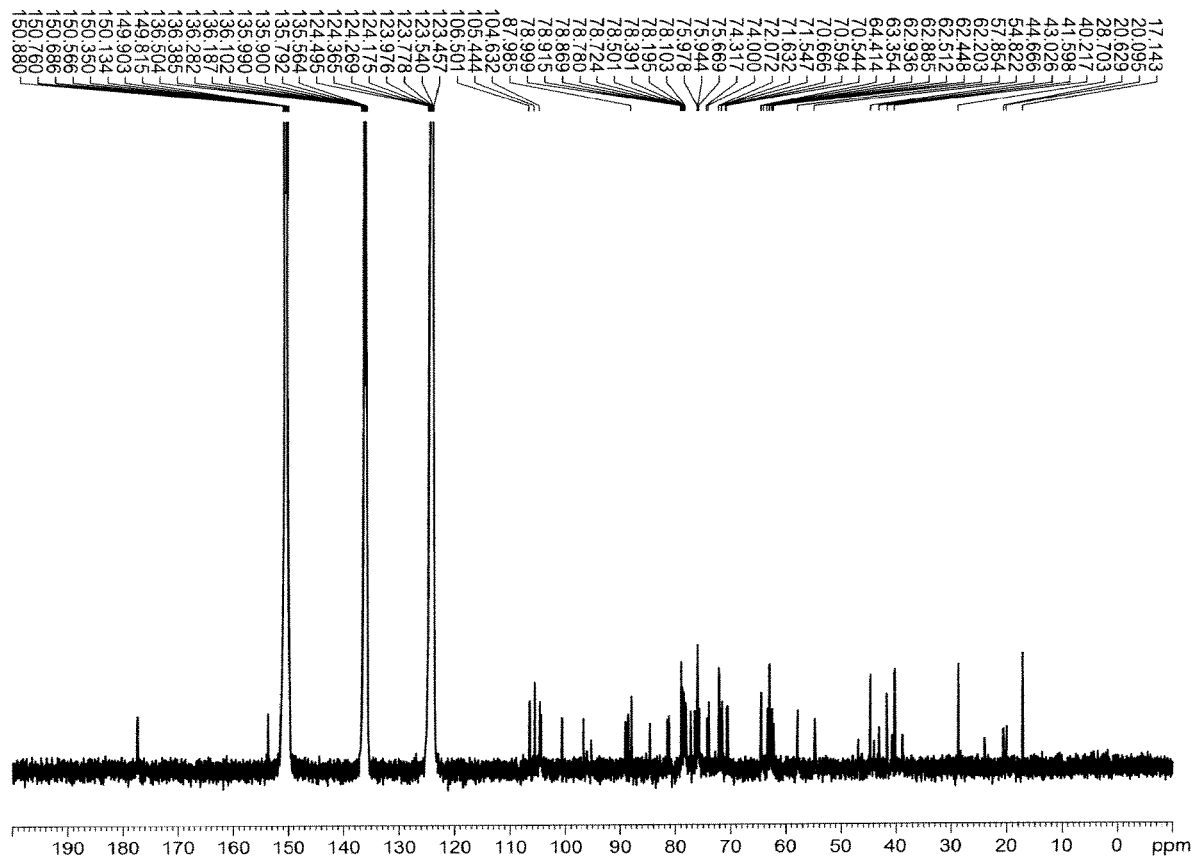
FIG. 4: Shows the $^{13}$C NMR spectrum (125 MHz, pyridine-$d_5$) of diterpene glycoside 1.
Figure 5:
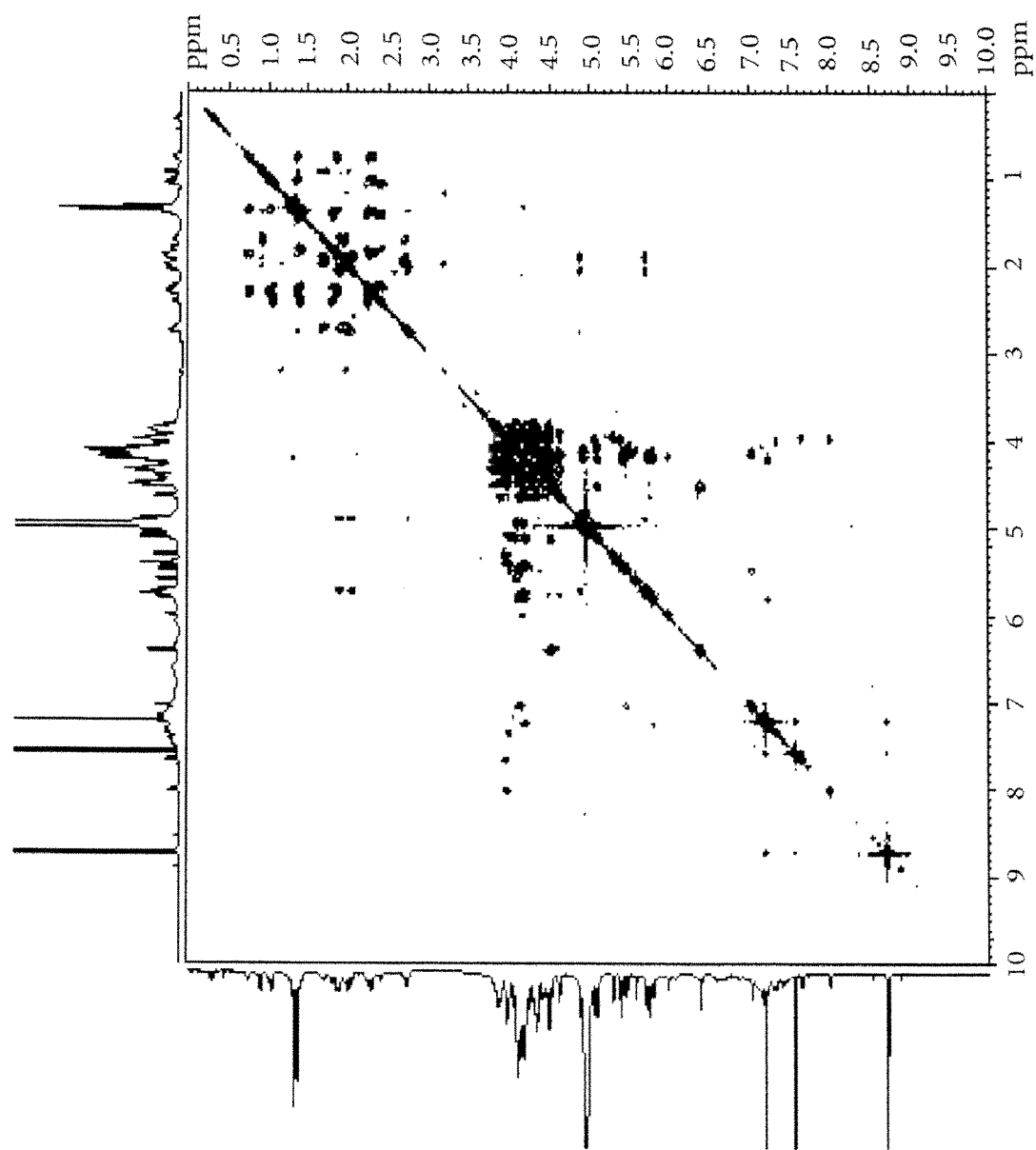
FIG. 5: Shows the $^1$H-$^1$H COSY spectrum (500 MHz, pyridine-$d_5$) of diterpene glycoside 1.
Figure 6:
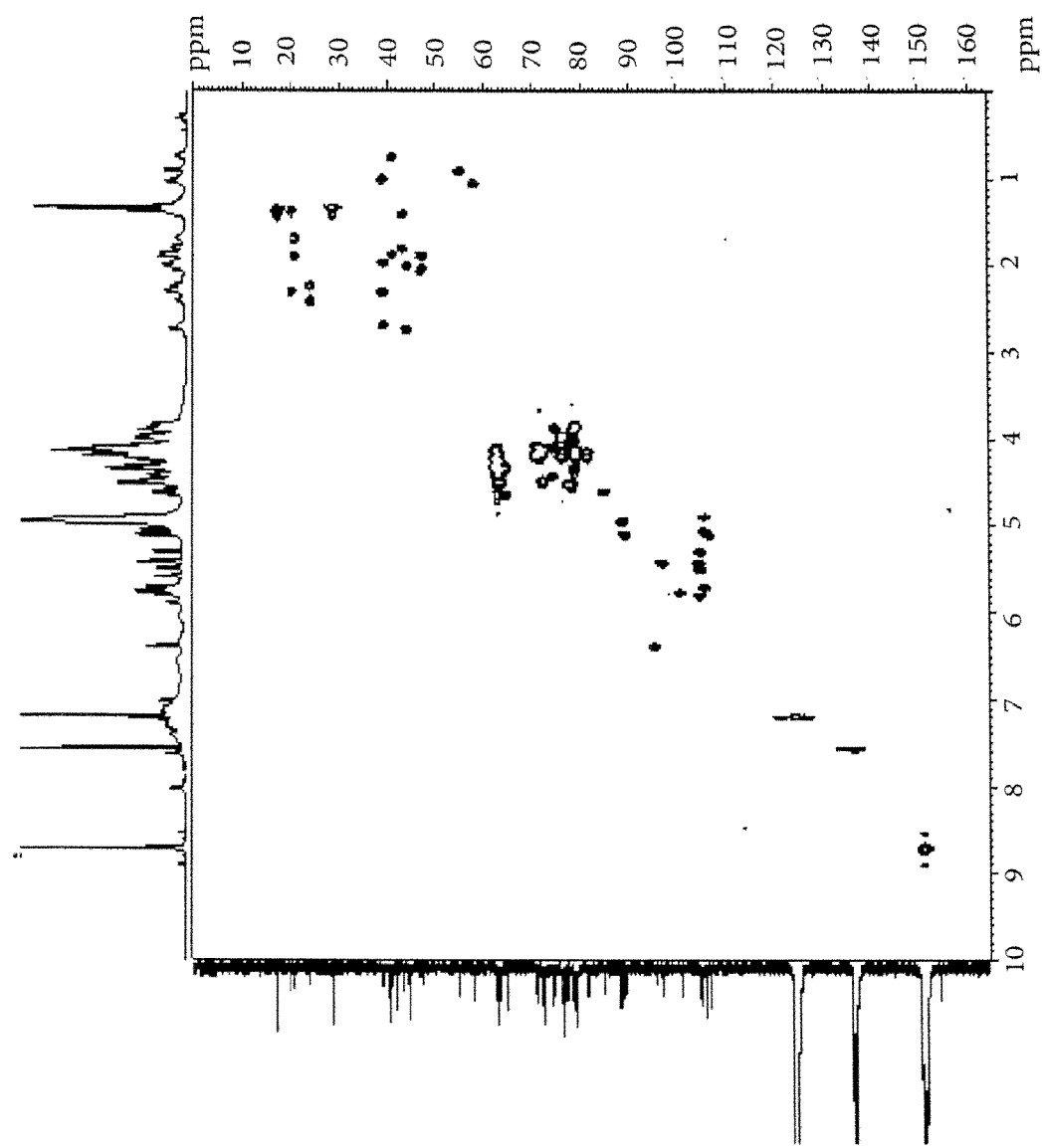
FIG. 6: Shows the HSQC-DEPT spectrum (500 MHz, pyridine-$d_5$) of diterpene glycoside 1.
Figure 7:
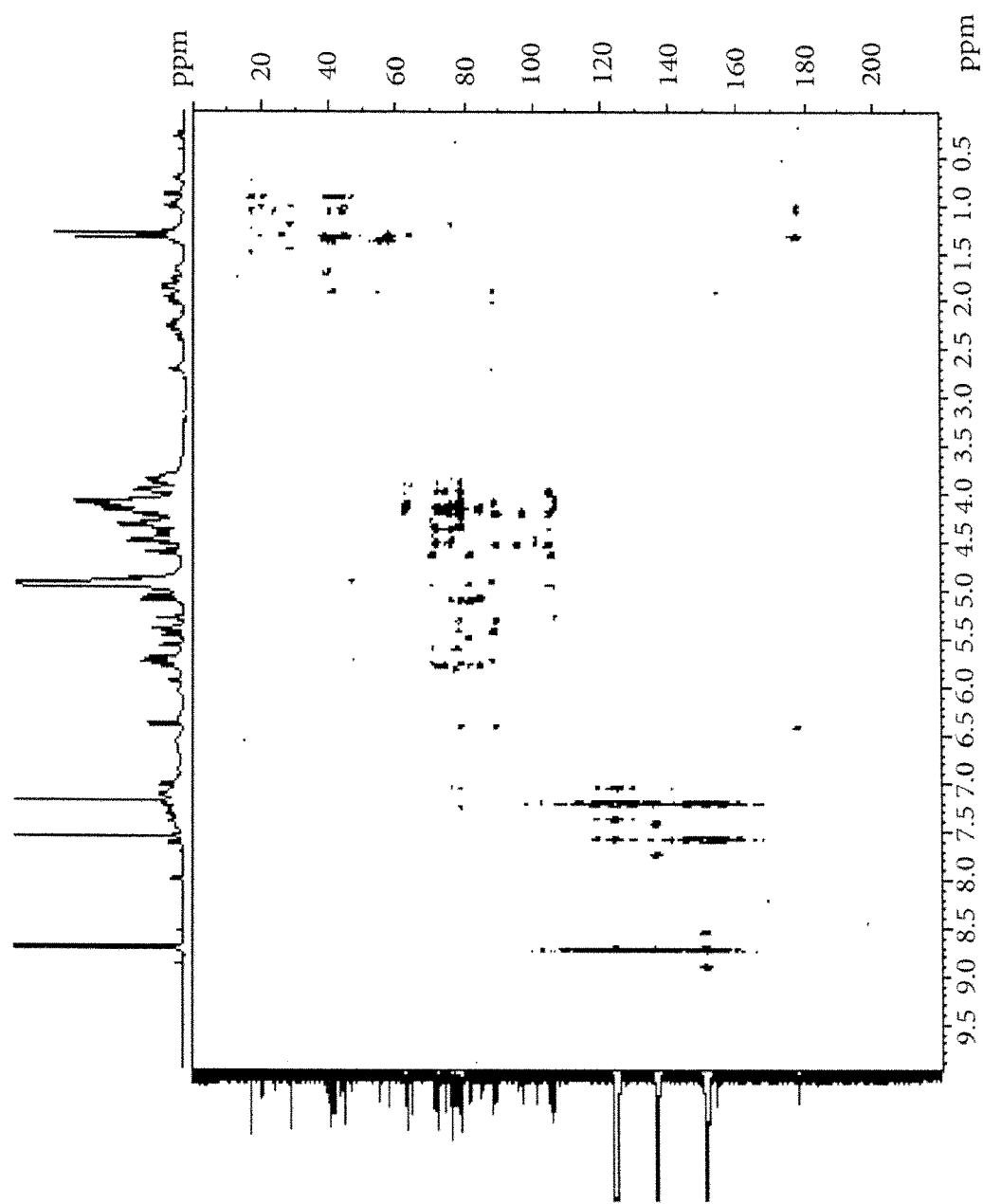
FIG. 7: Shows the HMBC spectrum (500 MHz, pyridine-$d_5$) of diterpene glycoside 1.
Figure 8:
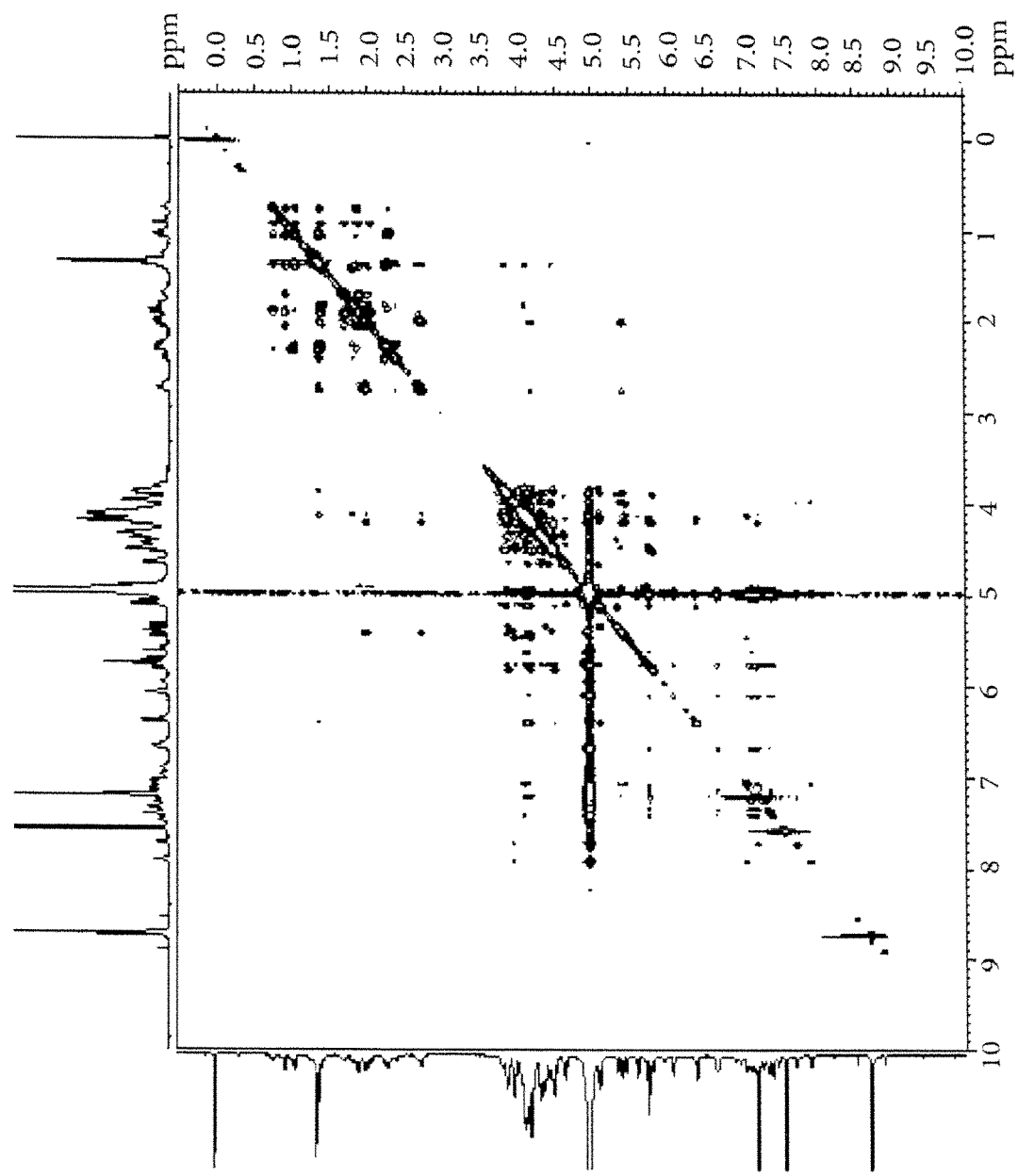
FIG. 8: Shows the NOESY spectrum (500 MHz, pyridine-$d_5$) of diterpene glycoside 1.

The target fractions were extracted into an organic phase by cartridge-based solid phase extraction (SPE), evaporated and lyophilized. The final sample had a weight of ~5 mg.
Results and Discussion
Isolation was performed using a crude glycoside mixture. The material was analyzed by HPLC. LCMS analysis following the primary processing indicated the presence of the target compound in fraction 1 (SJB-O-192-1). Secondary processing was completed. Fraction 4 was identified as having the target compound at m/z 1776 based on LC-CAD analysis. Final processing was completed to increase the purity of the sample. LCMS analysis of fraction 5 indicated the presence of the pure target with the mass m/z 1776 as shown in FIG. 2. Following the purification, the material was concentrated by rotary evaporation at 35° C. and lyophilized. Approximately 5 mg was provided for characterization.
MS and MS/MS. MS and MS/MS data were generated with a Waters QTof Premier mass spectrometer equipped with an electrospray ionization source. Samples were analyzed by negative ESI. Samples were diluted with $H_2O$:MeCN (1:1) by 50 fold and introduced via infusion using the onboard syringe pump. The samples were diluted to yield good s/n which occurred at an approximate concentration of 0.01 mg/mL.
The ESI-TOF mass spectrum showed a [M-H]⁻ ion at m/z 1775.7295. The mass of the [M-H]⁻ ion was in good agreement with the molecular formula $C_{74}H_{120}O_{48}$ (calcd for $C_{74}H_{119}O_{48}$: 1775.6871, error: −1.1 ppm) expected. The MS data confirmed a nominal mass of 1776 Daltons with the molecular formula, $C_{74}H_{120}O_{48}$.
The MS/MS spectrum, selecting the [M-H]⁻ ion at m/z 1775.8 for fragmentation, indicated the loss of one glucose unit at m/z 1613.6594, followed by the loss of two glucose units at m/z 1289.5540 and sequential loss of six glucose moieties at m/z 1127.4983, 965.4431, 803.3970, 641.3356, 479.2852 and 317.2128.
NMR Spectroscopy. A series of NMR experiments including $^1H$ NMR (FIG. 3), $^{13}C$ NMR (FIG. 4), $^1H$-$^1H$ COSY (FIG. 5), HSQC-DEPT (FIG. 6), HMBC (FIG. 7), NOESY (FIG. 8) and 1D TOCSY (not shown) were performed.
The sample was prepared by dissolving ~5 mg in ~700 μL of pyridine-$d_5$ and NMR data were acquired on Bruker Avance 500 MHz instruments with either a 5 mm broad band or 5 mm inverse probe. 2D NOESY data and some of the 1D TOCSY NMR experiments were conducted using ~1.8 mg sample dissolved in ~180 μL of pyridine-$d_5$ utilizing 2.5 mm inverse probe. The $^1H$ and $^{13}C$ NMR spectra were referenced to the residual solvent signal ($\delta_H$ 8.72 and $\delta_C$ 150.35 for pyridine-$d_5$).
The 1D and 2D NMR data indicated that the central core of the glycoside is a diterpene. An HMBC correlation from the methyl protons at $\delta_H$ 1.33 to the carbonyl at $\delta_C$ 177.3 allowed assignment of one of the tertiary methyl groups (C-18) as well as C-19 and provided a starting point for the assignment of the rest of the aglycone. Additional HMBC correlations from the methyl protons (H-18) to carbons at $\delta_C$ 38.9, 44.7, and 57.9 allowed assignment of C-3, C-4, and C-5. Analysis of the $^1H$-$^{13}C$ HSQC-DEPT data indicated that the carbon at $\delta_C$ 38.9 was a methylene group and the carbon at $\delta_C$ 57.9 was a methine which were assigned as C-3 and C-5, respectively. This left the carbon at $\delta_C$ 44.7, which did not show a correlation in the HSQC-DEPT spectrum, to be assigned as the quaternary carbon, C-4. The $^1H$ chemical shifts for C-3 ($\delta_H$ 1.01 and 2.30) and C-5 ($\delta_H$ 1.03) were assigned using the HSQC-DEPT data. A COSY correlation between one of the H-3 protons ($\delta_H$ 1.01) and a proton at $\delta_H$ 1.36 allowed assignment of one of the H-2 protons which in turn showed a correlation with a proton at $\delta_H$ 0.75 which was assigned to C-1. The remaining $^1H$ and $^{13}C$ chemical shifts for C-1 and C-2 were then assigned on the basis of additional COSY and HSQC-DEPT correlations.
The other tertiary methyl singlet, observed at $\delta_H$ 1.37, showed HMBC correlations to C-1 and C-5 and was assigned as H-20. The methyl protons showed additional HMBC correlations to a quaternary carbon ($\delta_C$ 40.2) and a methine carbon ($\delta_C$ 54.8) which were assigned as C-10 and C-9, respectively. COSY correlations between H-5 ($\delta_H$ 1.03) and protons at $\delta_H$ 2.23 and 2.39 then allowed assignment of the H-6 protons which in turn showed correlations to protons at $\delta_H$ 1.40 and 1.80 which were assigned to H-7. The $^{13}C$ chemical shifts for C-6 ($\delta_C$ 23.9) and C-7 ($\delta_C$ 43.0) were then determined from the HSQC-DEPT data. COSY correlations between H-9 ($\delta_H$ 0.91) and protons at $\delta_H$ 1.68 and 1.88 allowed assignment of the H-11 protons which in turn showed COSY correlations to protons at $\delta_H$ 1.95 and 2.69 which were assigned as the H-12 protons. The HSQC-DEPT data was then used to assign C-11 ($\delta_C$ 20.6) and C-12 ($\delta_C$ 39.0). HMBC correlations from the H-12 proton ($\delta_H$ 2.69) to a carbon at $\delta_C$ 88.0 allowed assignment of C-13. The olefinic protons observed at $\delta_H$ 4.89 and 5.71 showed HMBC correlations to C-13 and were assigned to C-17 ($\delta_C$ 105.4 via HSQC-DEPT). The methine proton H-9 showed HMBC correlations to carbons at $\delta_C$ 43.9 and 46.9 which were assigned as C-14 and C-15, respectively. Additionally, an HMBC correlation from H-17 to C-15 further confirmed the assignment made above. The $^1$H chemical shifts at C-14 ($\delta_H$ 1.99 and 2.74) and C-15 ($\delta_H$ 1.87 and 2.02) were assigned using the HSQC-DEPT data. An HMBC correlation from H-14 and H-15 to a quaternary carbon at $\delta_C$ 153.7 allowed assignment of C-16 to complete the assignment of the central core.

Figure 9:
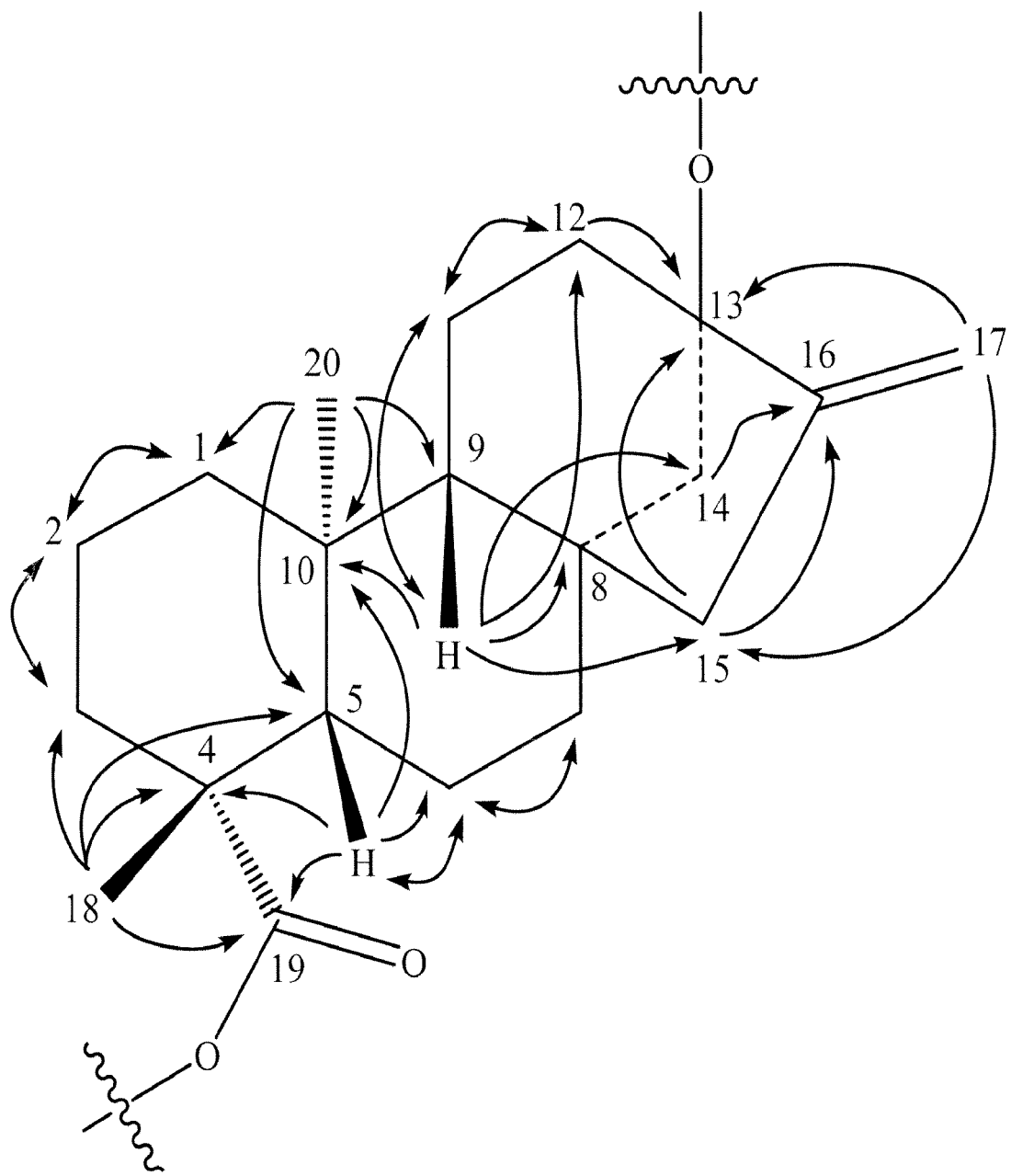
FIG. 9: Shows a summary of key HMBC and COSY correlations used to assign the aglycone region of diterpene glycoside 1.

Correlations observed in the NOESY spectrum were used to assign the relative stereochemistry of the central diterpene core. In the NOESY spectrum, NOE correlations were observed between H-14 and H-20 indicating that H-14 and H-20 are on the same face of the rings. Similarly, NOE correlations were observed between H-9 and H-5 as well as H-5 and H-18 but NOE correlations were not observed between H-9 and H-14 indicating that H-5, H-9 and H-18 were on the opposite face of the rings compared to H-14 and H-20 as presented in FIG. 9. These data thus indicated that the relative stereochemistry was retained during the glycosylation step.

Analysis of the $^1$H-$^{13}$C HSQC-DEPT data confirmed the presence of nine anomeric protons. Six of the anomeric protons were well resolved at $\delta_H$ 6.40 ($\delta_C$ 95.3), 5.80 ($\delta_C$ 104.6), 5.76 ($\delta_C$ 100.6), 5.48 ($\delta_C$ 104.8), 5.29 ($\delta_C$ 104.6), and 5.06 ($\delta_C$ 105.4) in the $^1$H NMR spectrum. The remaining three anomeric protons observed at $\delta_H$ 5.42 ($\delta_C$ 96.6), 5.40 ($\delta_C$ 104.3) and 5.10 ($\delta_C$ 106.5) which were overlapped in the $^1$H spectrum were identified by $^1$H-$^{13}$C HSQC-DEPT data. The proton at $\delta_H$ 5.76 had a small coupling (3.5 Hz) indicating that it had an α-configuration. The anomeric proton observed at $\delta_H$ 6.40 showed an HMBC correlation to C-19 which indicated that it corresponds to the anomeric proton of Glc$_I$. Similarly, the anomeric proton observed at $\delta_H$ 5.42 showed an HMBC correlation to C-13 allowing it to be assigned as the anomeric proton of Glu$_{II}$.

The Glc$_I$ anomeric proton ($\delta_H$ 6.40) showed a COSY correlation to a proton at $\delta_H$ 4.51 which was assigned as Glc$_I$ H-2 and in turn showed a COSY correlation to a proton at $\delta_H$ 5.11 (Glc$_I$ H-3) which showed a correlation with a proton at $\delta_H$ 4.20 (Glc$_I$ H-4). Due to overlap in the data the COSY spectrum did not allow assignment of H-5 or the H-6 protons. Therefore, a series of 1D TOCSY experiments were performed using selective irradiation of the Glc$_I$ anomeric proton with several different mixing times (not shown). In addition to confirming the assignments for Glc$_I$ H-2 through H-4, the TOCSY data showed a proton at $\delta_H$ 4.14 assigned as Glc$_I$ H-5 and a proton at $\delta_H$ 4.32 assigned as one of the Glc$_I$ H-6 protons. The $^{13}$C chemical shifts for Glc$_I$ C-2 ($\delta_C$ 77.2), C-3 ($\delta_C$ 89.0), and C-4 ($\delta_C$ 70.5) were assigned using the HSQC-DEPT data. An HMBC correlation from the anomeric proton to a carbon at $\delta_C$ 78.9 allowed assignment of Glc$_I$ C-5 and the HSQC-DEPT data was used to assign the remaining H-6 proton at $\delta_H$ 4.20 and C-6 ($\delta_C$ 62.2) to complete the assignment of Glc$_I$.

Of the eight remaining unassigned glucose moieties two were assigned as substituents at C-2 and C-3 of Glc$_I$ on the basis of HMBC correlations. The anomeric proton observed at $\delta_H$ 5.80 showed an HMBC correlation to Glc$_I$ C-2 and was assigned as the anomeric proton of Glc$_V$. The reciprocal HMBC correlations from Glc$_I$ H-2 to the anomeric carbon of Glc$_V$ was also observed. The anomeric proton observed at $\delta_H$ 5.29 showed an HMBC correlation to Glc$_I$ C-3 and was assigned as the anomeric proton of Glc$_{VI}$.

The anomeric proton of Glc$_V$ ($\delta_H$ 5.80) showed a COSY correlation with a proton at $\delta_H$ 4.19 which was assigned as Glc$_V$ H-2. Glc$_V$ C-2 ($\delta_C$ 75.8) was then assigned using the HSQC-DEPT data. Due to overlap in the data the COSY spectrum did not allow assignment of the remaining protons. Therefore, a series of 1D TOCSY experiments were performed using selective irradiation of the Glc$_V$ anomeric proton with several different mixing times (not shown). In addition to confirming the assignments for Glc$_V$ H-2, the TOCSY data allowed assignment of Glc$_V$ H-3 ($\delta_H$ 4.20), H-4 ($\delta_H$ 4.11), and H-5 ($\delta_H$ 3.90). In the TOCSY data the protons observed at $\delta_H$ 4.33 and $\delta_H$ 4.63 were assigned as the Glc$_V$ H-6 protons. The $^{13}$C chemical shifts for Glc$_V$ C-3 ($\delta_C$ 78.5), C-4 ($\delta_C$ 74.0), C-5 ($\delta_C$ 78.0) and C-6 ($\delta_C$ 64.4) were assigned using the HSQC-DEPT data. An HMBC correlation from H-5 to a carbon at $\delta_C$ 64.4 further confirmed the assignment of Glc$_V$ C-6 to complete the assignment of Glc$_V$.

Assignment of Glc$_{VI}$ was carried out in a similar manner. The anomeric proton of Glc$_{VI}$ ($\delta_H$ 5.29) showed a COSY correlation with a proton at $\delta_H$ 3.95 which was assigned as Glc$_{VI}$ H-2. Glc$_{VI}$ C-2 ($\delta_C$ 75.9) was then assigned using the HSQC-DEPT data. The remaining proton and carbon assignments were done on the basis of 1D TOCSY, HSQC-DEPT and HMBC data discussed below. A series of 1D TOCSY experiments were performed using selective irradiation of the Glc$_{VI}$ anomeric proton with several different mixing times (not shown). In addition to confirming the assignments for Glc$_{VI}$ H-2, the TOCSY data allowed assignment of Glc$_{VI}$ H-3 ($\delta_H$ 4.35), H-4 ($\delta_H$ 4.09), and H-5 ($\delta_H$ 3.86). In the TOCSY data the proton observed at $\delta_H$ 4.30 was assigned as one of the Glc$_V$ H-6 protons and HSQC-DEPT data allowed assignment of the other H-6 proton at $\delta_H$ 4.10 and C-6 ($\delta_C$ 62.5). The $^{13}$C chemical shifts for C-3 ($\delta_C$ 78.4), C-4 ($\delta_C$ 71.5 or 71.6) and C-5 ($\delta_C$ 78.4) were assigned using the HSQC-DEPT data. HMBC correlations from H-1 to C-3/C-5 and H-4 to C-6 further confirmed the assignments of Glc$_{VI}$ C-3/C-5 and C-6 to complete the assignment of Glc$_{VI}$.

Figure 10:
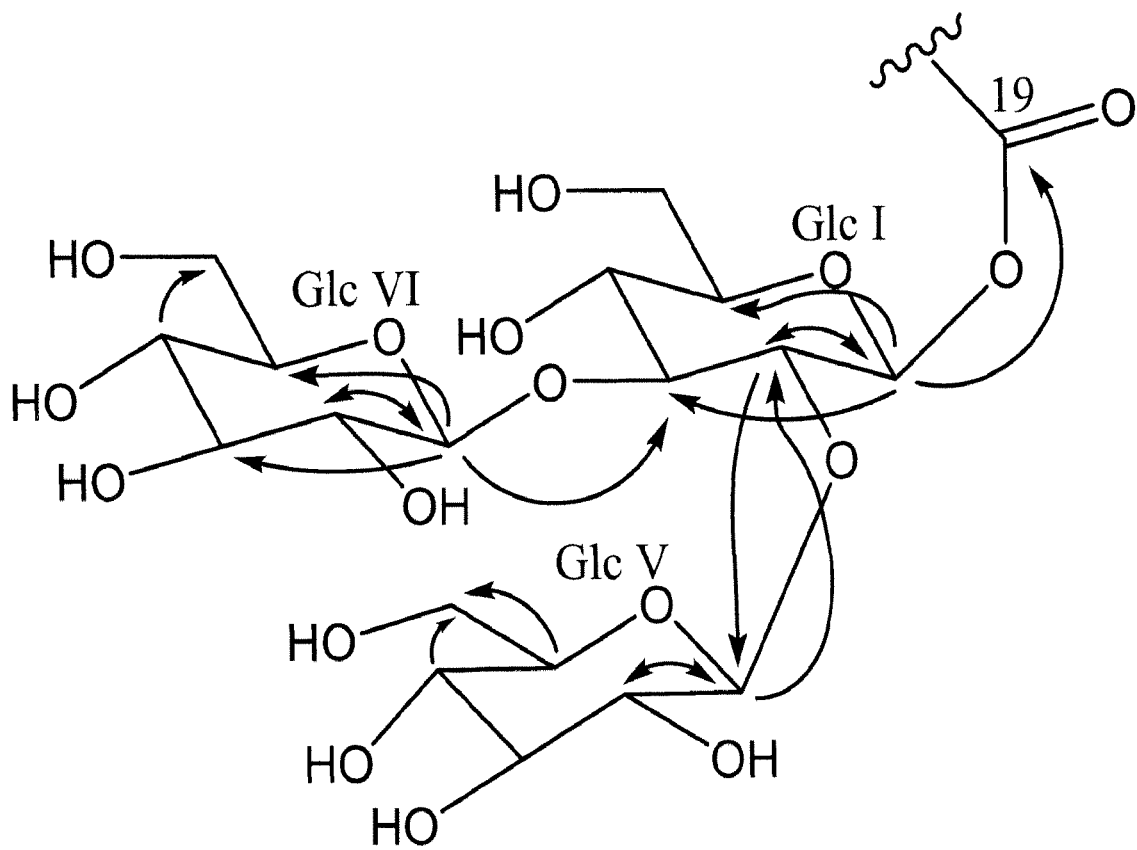
FIG. 10: Shows a summary of key HMBC and COSY correlations used to assign the C-19 glycoside region of diterpene glycoside 1.

A summary of the key HMBC and COSY correlations used to assign the C-19 glycoside region are provided in FIG. 10.

Assignment of Glc$_{II}$ was carried out in a similar manner. The Glc$_{II}$ anomeric proton ($\delta_H$ 5.42) showed a COSY correlation to a proton at $\delta_H$ 4.19 which was assigned as Glc$_{II}$ H-2 and in turn showed a COSY correlation to a proton at $\delta_H$ 4.93 (Glc$_{II}$ H-3) which showed an additional correlation with a proton at $\delta_H$ 4.09 (Glc$_{II}$ H-4) which also showed a COSY correlation to a proton at $\delta_H$ 3.88 (Glc$_{II}$ H-5). Assignment of the $^{13}$C chemical shifts for Glc$_{II}$ C-2 ($\delta_C$ 81.2), C-3 ($\delta_C$ 88.6), C-4 (6c 70.6), and C-5 ($\delta_C$ 78.1 or 78.2) was based on HSQC-DEPT data. HMBC correlations from Glc$_{II}$ H-3 to C-2 and C-4 and also from Glc$_{II}$ H-4 to C-3 and C-5 confirmed the assignments made above. An additional HMBC correlation from Glc$_{II}$ H-4 to carbon at $\delta_C$ 62.4 or 62.9 allowed assignment of Glc$_{II}$ C-6. The HSQC-DEPT data were then used to assign the Glc$_{II}$ H-6 protons ($\delta_H$ 4.19 and 4.33) to complete the assignment of Glc$_{II}$.

Two of the remaining unassigned glucose moieties were assigned as substituents at C-2 and C-3 of Glc$_{II}$ on the basis of HMBC correlations. The anomeric proton observed at $\delta_H$ 5.48 showed an HMBC correlation to Glc$_{II}$ C-2 and was assigned as the anomeric proton of Glc$_{II}$. The anomeric proton observed at $\delta_H$ 5.40 showed an HMBC correlation to Glc$_{II}$ C-3 and was assigned as the anomeric proton of Glc$_{II}$. The reciprocal HMBC correlations from Glc$_{II}$ H-2 to the anomeric carbon of Glc$_{III}$ and from Glc$_{II}$ H-3 to the anomeric carbon of Glc$_{IV}$ were also observed.

The anomeric proton of Glc$_{IV}$ ($\delta_H$ 5.40) showed a COSY correlation with a proton at $\delta_H$ 3.97 which was assigned as Glc$_{IV}$ H-2 and showed a COSY correlation with a proton at $\delta_H$ 4.47 which was assigned as Glc$_{IV}$ H-3. Glc$_{IV}$ C-2 ($\delta_C$ 75.9 or 76.0) was then assigned using the HSQC-DEPT data. Although specific assignment for C-3 could not be made HSQC-DEPT data indicated it to be in the range of $\delta_C$ ~78.7-79. A combination of 1D TOCSY and COSY data allowed the assignment of the remaining protons. Since the anomeric protons of $Glc_{IV}$ and $Glc_{II}$ were partially overlapped the 1D TOCSY data showed protons belonging to both sugars, however, the protons due to $Glc_{II}$ were differentiated on the basis of their HMBC correlations and hence allowed assignment of $Glc_{IV}$ H-4 ($\delta_H$ 4.13) and H-5 ($\delta_H$ 3.94). $Glc_{IV}$ C-4 ($\delta_C$ 71.5 or ~71.6) and C-5 ($\delta_C$ 78.1 or 78.2 or 78.4) were then assigned using the HSQC-DEPT data. A proton at $\delta_H$ 4.32, ($\delta_C$ 62.4 or 62.9) was assigned as one of the H-6 protons and HQSC-DEPT data indicated that the other methylene proton could be at ~4.22 ppm.

The anomeric proton of $Glc_{III}$ ($\delta_H$ 5.48) showed a COSY correlation with a proton at $\delta_H$ 4.11 which was assigned as $Glc_{III}$ H-2. $Glc_{III}$ C-2 ($\delta_C$ 75.9 or 76.0) was then assigned using the HSQC-DEPT data. Due to overlap in the data the COSY spectrum did not allow assignment of the remaining protons. Therefore, a series of 1D TOCSY experiments were performed using selective irradiation of the $Glc_{III}$ anomeric proton with several different mixing times (not shown). In addition to confirming the assignments for $Glc_{III}$ H-2, the TOCSY data allowed assignment of $Glc_{III}$ H-3 ($\delta_H$ 4.13), H-4 ($\delta_H$ 3.87) and H-5 ($\delta_H$ 3.97). In the TOCSY data the protons observed at $\delta_H$ 4.44 and $\delta_H$ 4.50 were assigned as the $Glc_{III}$ H-6 protons. The $^{13}$C chemical shifts for C-3 ($\delta_C$ 78.7-79.0), C-5 ($\delta_C$ 76.5) and C-6 ($\delta_C$ 72.1) were assigned using the HSQC-DEPT data, however, C-4 could not be unambiguously assigned. An HMBC correlation from H-4 and H-5 to a carbon at $\delta_C$ 72.1 further confirmed the assignment of $Glc_{III}$ C-6 to complete the assignment of $Glc_{III}$. The relatively downfield shift of the C-6 methylene carbon indicated a 1→6 glycoside linkage at $Glc_{III}$ C-6.

The anomeric proton of $Glc_{VII}$ at $\delta_H$ 5.76 ($\delta_C$ 100.6) showed HMBC correlations to the carbon at $\delta_C$ 72.1 ppm indicating that it was attached to $Glc_{III}$ via an 1→6 linkage. Reciprocal HMBC correlations were also observed from the methylene protons of $Glc_{III}$ to the anomeric carbon of $Glc_{VII}$ at $\delta_C$ 100.6 confirming the 1→6 linkage between $Glc_{VII}$ and $Glc_{III}$. Assignment of $Glc_{VII}$ was done using a combination of COSY, HSQC-DEPT, HMBC and 1D TOCSY data. The anomeric proton of $Glc_{VII}$ ($\delta_H$ 5.76) showed a COSY correlation with a proton at $\delta_H$ 4.13 which was assigned as $Glc_{VII}$ H-2 and showed a COSY correlation with a proton at $\delta_H$ 4.60 which was assigned as $Glc_{VII}$ H-3. $Glc_{VII}$ C-2 ($\delta_C$ 81.4) and C-3 ($\delta_C$ 84.7) were then assigned using the HSQC-DEPT data. Due to overlap in the data the COSY spectrum did not allow unambiguous assignment of the remaining protons. Therefore, a series of 1D TOCSY experiments were performed using selective irradiation of the $Glc_{VII}$ anomeric proton with several different mixing times (not shown). In addition to confirming the assignments for $Glc_{VII}$ H-2 and H-3, the TOCSY data allowed assignment of $Glc_{VII}$ H-4 ($\delta_H$ 4.16), H-5 ($\delta_H$ 4.41) and the proton at $\delta_H$ 4.36 as one of the $Glc_{VII}$ H-6 protons. Specific assignment of the other methylene proton could not be made but was deduced to be at $\delta_H$ ~4.5 based on HSQC-DEPT data. The $^{13}$C chemical shifts for $Glc_{VII}$ C-5 ($\delta_C$ 74.0) and C-6 ($\delta_C$ 62.9 or 63.4) were assigned using the HSQC-DEPT data, however, specific assignment of C-4 could not be made. HMBC correlations observed from the anomeric proton at $\delta_H$ 5.76 to carbons at $\delta_C$ 81.4 (C-2), $\delta_C$ 84.7 (C-3), and $\delta_C$ 74.0 (C-5) further confirmed the assignments made above.

The two remaining glucose moieties with anomeric protons at $\delta_H$ 5.10 ($\delta_C$ 106.5) and $\delta_H$ 5.06 ($\delta_C$ 105.4) were assigned as substituents at C-2 and C-3 of $Glc_{VII}$ on the basis of HMBC correlations. The anomeric proton observed at $\delta_H$ 5.10 showed an HMBC correlation to $Glc_{VII}$ C-2 and was assigned as the anomeric proton of $Glc_{VIII}$. The anomeric proton observed at $\delta_H$ 5.06 showed an HMBC correlation to $Glc_{VII}$ C-3 and was assigned as the anomeric proton of $Glc_{IX}$. The reciprocal HMBC correlations from $Glc_{VII}$ H-2 to the anomeric carbon of $Glc_{VIII}$ and from $Glc_{VII}$ H-3 to the anomeric carbon of $Glc_{IX}$ were also observed.

The anomeric proton of $Glc_{VIII}$ ($\delta_H$ 5.10) showed a COSY correlation with a proton at $\delta_H$ 4.06 which was assigned as $Glc_{VIII}$ H-2 and C-2 ($\delta_C$ 75.7) was then assigned based on HSQC-DEPT data. Due to overlap in the data, the COSY spectrum did not allow assignment of the remaining protons. Therefore, a series of 1D TOCSY experiments were performed using selective irradiation of the $Glc_{VIII}$ anomeric proton with several different mixing times (not shown). Since the anomeric protons of $Glc_{VIII}$ and $Glc_{IX}$ are very close in chemical shift the 1D TOCSY data showed protons belonging to both sugars. In addition, since the $Glc_{VIII}$ anomeric proton is overlapped with $Glc_I$ H-3, correlations due to $Glc_I$ H-3 were also observed, however, the protons due to $Glc_{VIII}$ were identified on the basis of HMBC correlations as well as by elimination of protons already assigned for $Glc_I$ and hence allowed assignment of $Glc_{VIII}$ H-3 ($\delta_H$ 4.17), H-4 ($\delta_H$ ~3.86) and H-5 ($\delta_H$ ~3.99). HSQC-DEPT data was then used to assign $Glc_{VIII}$ C-3 ($\delta_C$ 78.7-79.0) but specific assignment for C-4 and C-5 could not be made due to data overlap. Additionally, due to data overlap specific assignment for $Glc_{VIII}$ methylene group at position 6 could not be made but were deduced to be in the range of $\delta_H$ ~4.3-~4.5 ($\delta_C$ 62.9 or 63.4).

The anomeric proton of $Glc_{IX}$ ($\delta_H$ 5.06) showed a COSY correlation with a proton at $\delta_H$ 3.98 which was assigned as $Glc_{IX}$ H-2 and C-2 ($\delta_C$ 76.1) was then assigned based on HSQC-DEPT data. Due to overlap in the data the COSY spectrum did not allow assignment of the remaining protons. Therefore, a series of 1D TOCSY experiments were performed using selective irradiation of the $Glc_{IX}$ anomeric proton with several different mixing times (not shown). Since the anomeric protons of $Glc_{IX}$ and $Glc_{VIII}$ are very close in chemical shift the 1D TOCSY data showed protons belonging to both sugars as well as correlations from $Glc_I$ H-3 (since $Glc_{VIII}$ H-1 and $Glc_I$ H-3 are overlapped), however, the protons due to $Glc_{IX}$ were identified on the basis of HMBC correlations as well as by elimination of protons already assigned for $Glc_I$ and $Glc_{VIII}$ and hence allowed assignment of $Glc_{IX}$ H-3 ($\delta_H$ ~4.09), H-4 ($\delta_H$ ~4.16) and H-5 ($\delta_H$ 3.80). HSQC-DEPT data was then used to assign $Glc_{IX}$ C-3 ($\delta_C$ 78.7-79.0), but due to data overlap specific assignments for C-4 and C-5 could not be made. Additionally, due to data overlap specific assignment for the $Glc_{IX}$ methylene group at position 6 could not be made but were deduced to be in the range of $\delta_H$ ~4.3-~4.5 ($\delta_C$ 62.9 or 63.4).

Figure 11:
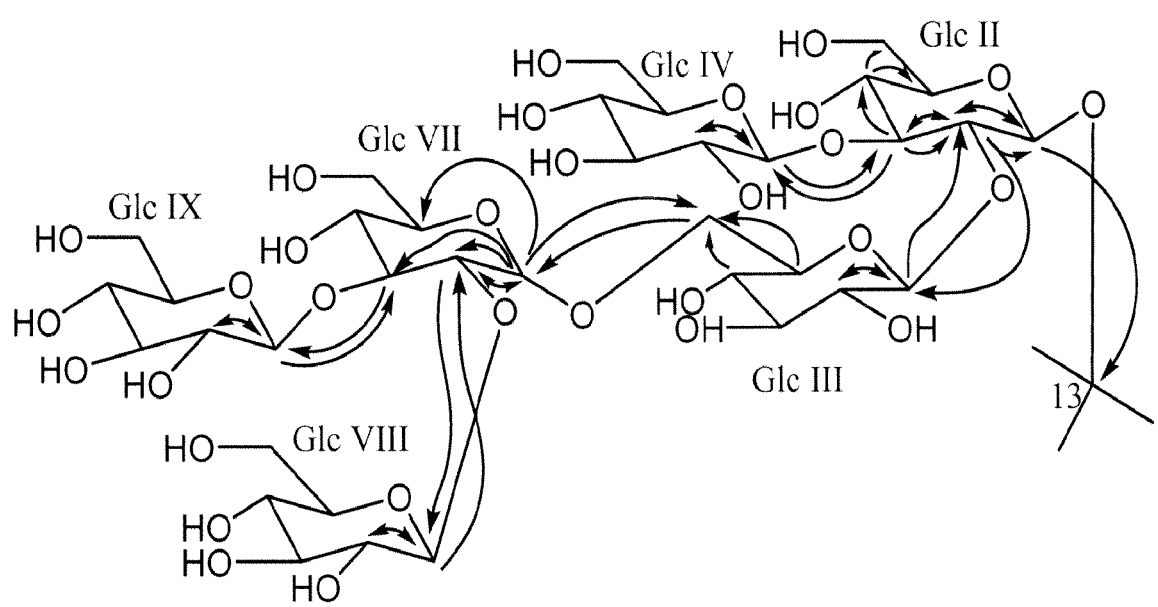
FIG. 11: Shows a summary of key HMBC and COSY correlations used to assign the C-13 glycoside region of the diterpene glycoside diterpene glycoside 1.

A summary of the key HMBC and COSY correlations used to assign the C-13 glycoside region are provided in FIG. 11.

The structure was determined to be (13-[(2-O-(6-O-α-D-glucopyranosyl-(2-O-β-D-glucopyranosyl-3-O-β-D-glucopyranosyl)-β-D-glucopyranosyl-3-O-β-D-glucopyranosyl)-β-D-glucopyranosyl-] ent-kaur-16-en-19-oic acid-[(2-O-β-D-glucopyranosyl-3-O-β-D-glucopyranosyl-β-D-glucopyranosyl) ester], as shown in FIG. 1.

Example 2

Isolation and Characterization of 2

Materials. The material used for isolation was *Stevia* extract, Lot #CB-2977-171, received from The Coca-Cola Company.

Analytical HPLC Method. HPLC analyses were performed on a Waters 2695 Alliance System coupled to a Waters 996 Photo Diode Array (PDA) detector. In addition, final sample purities were assessed using an ESA Corona Charged Aerosol Detector (CAD). Sample analyses were performed using the method conditions described in Tables 1-3.

TABLE 1

Analytical HPLC Conditions for fraction analysis.

| Column | Phenomenex Synergi Hydro RP (4.6 × 150 mm) |
|---|---|
| Column Temperature | 55° C. |
| Mobile Phases | 0.028% NH$_4$OAc, 0.012% HOAc in water (A) MeCN (B) |
| Flow Rate (mL/min) | 1.0 |
| Detection | CAD and UV at 210 nm |

| Gradient | | |
|---|---|---|
| Time (mm) | % A | % B |
| 0.0-5.1 | 85.0 | 15.0 |
| 15.0-30.0 | 75.0 | 25.0 |
| 31.0-36.0 | 25.0 | 75.0 |
| 36.1 | 85.0 | 15.0 |

TABLE 2

Analytical HPLC Conditions for fraction analysis.

| Column | Phenomenex Synergi Hydro RP (4.6 × 150 mm) |
|---|---|
| Column Temperature | 50° C. |
| Mobile Phases | 100% DI water (A) 100% MeCN (B) |
| Flow Rate (mL/min) | 1.0 |
| Detection | CAD and UV at 210 nm |

| Gradient | | |
|---|---|---|
| Time (mm) | % A | % B |
| 0.0-35.0 | 80.0 | 20.0 |
| 35.1-45.0 | 50.0 | 50.0 |
| 45.1 | 80.0 | 20.0 |

TABLE 3

Analytical HPLC Conditions for fraction analysis.

| Column | Waters XBridge Phenyl (4.6 × 150 mm, 5 μm) |
|---|---|
| Column Temperature | ambient |
| Mobile Phases | 100% DI water (A) 100% MeCN (B) |
| Flow Rate (mL/min) | 1.0 |
| Detection | CAD and UV at 210 nm |

| Gradient | | |
|---|---|---|
| Time (mm) | % A | % B |
| 0.0-60.0 | 84.0 | 16.0 |
| 60.1-65.0 | 0.0 | 100.0 |
| 65.1 | 84.0 | 16.0 |

Primary Preparative HPLC Method. Primary processing was performed using a pre-packed Waters Symmetry RP18 (50× 250 mm, 7 μm) column. The purification process was performed with a Waters Delta Prep LC Model 2000/4000 system coupled to a UV-Vis detector. Details of the preparative method are summarized in Table 4.

TABLE 4

Conditions for Primary Preparative HPLC Method.

| Column | Waters Symmetry Shield RP18 (50 × 250 mm, 7 μm) |
|---|---|
| Column Temperature | ambient |
| Flow Rate (mL/min) | 105 |
| Detection | UV at 210 nm |
| Mobile Phases | (C) 15% MeCN in water (D) 25% MeCN in water (E) 85% MeOH in water |
| Load | 12 g |
| Sample preparation | 12 g dissolved in 40 mL of DMSO, then added 80 mL of MP-A |

| Gradient | | | |
|---|---|---|---|
| Time (min) | % A | % B | % C |
| 0.0-11.0 | 100 | 0 | 0 |
| 30.0-40.0 | 0 | 100 | 0 |
| 41.0-51.0 | 0 | 0 | 100 |
| 52.0 | 100 | 0 | 0 |

Secondary Preparative HPLC Method. The secondary processing was performed using a Phenomenex Synergi Hydro RP 80 (50×250 mm, 10 μm) column. The purification process was performed with a Waters Delta Prep LC Model 2000/4000 system coupled to a UV-Vis detector. Details of the preparative method are summarized in Table 5.

TABLE 5

Conditions for Secondary Preparative HPLC Method.

| Column | Phenomenex Synergi Hydro RP 80 (50 × 250 mm, 10 μm) |
|---|---|
| Column Temperature | 50° C. |
| Flow Rate (mL/min) | 105 |
| Detection | UV at 210 nm |
| Mobile Phases | (A) 18% MeCN in water (B) 50% MeCN in water |
| Load | 0.5 g in 40 ml of water |
| Sample preparation | 500 mg of JAM-D-1-3, or JAM-D-10-3, or JAM-D-14-3 dissolved in 40 mL of water |

| Gradient | | |
|---|---|---|
| Time (min) | % A | % B |
| 0.0-75.0 | 100 | 0 |
| 75.1-85.1 | 0 | 100 |
| 86.0 | 100 | 0 |

Tertiary Preparative HPLC Method. The tertiary processing step was performed using a Phenomenex Gemini Nx C18 (21.2×250 mm, 10 μm) column. The purification process was performed with a Waters Delta Prep LC Model 2000/4000 system coupled to a UV-Vis detector. Details of the preparative method are summarized in Table 6. Analytical fractions processed with this method were analyzed using the same isocratic mobile phase with a flow rate of 1 mL/min in the corresponding analytical HPLC column: Phenomenex Gemini Nx C18 (4.6×100 mm, 5 μm).

TABLE 6

Conditions for Tertiary Preparative HPLC Method.

| Column | Phenomenex Gemini Nx C18 (21.2 × 250 mm, 10 μm) |
|---|---|
| Column Temperature | ambient |
| Flow Rate (mL/min) | 25 |
| Detection | UV at 210 nm |
| Mobile Phases | (A) 15% MeCN in water (B) 100% MeCN |
| Load | 0.04 g |

Gradient

| Time (min) | % A | % B |
|---|---|---|
| 0-130 | 100 | 0 |
| 130.1-135.0 | 0 | 100 |
| 135.1-145.0 | 100 | 0 |

Isolation Procedure. Fractions collected during the final pre-concentration step were filtered through a stainless steel sieve and concentrated in vacuo using a Buchi® Rotary Evaporator, Model R-114. The concentrated solution was dried for 48-72 h using the Kinetics Flexi-Dry Personal Freeze Dryer, followed by vacuum oven drying at 37° C. for 24 h to remove residual moisture.

MS and MS/MS. MS and MS/MS data were generated with a Waters QTof Micro mass spectrometer equipped with an electrospray ionization source. The sample was analyzed by negative ESI. The sample was diluted to a concentration of 0.25 mg/mL with $H_2O$:MeCN (1:1) and introduced via flow injection for MS data acquisition, tuned for MS/MS and acquired by direct infusion.

NMR. The sample was prepared by dissolving ~1.6 mg in 180 μL of $CD_3OD$+TMS and NMR data were acquired on a Bruker Avance 500 MHz instruments with either a 2.5 mm inverse probe or a 5 mm broad band probe. The $^1H$ and $^{13}C$ NMR spectra were referenced to the TMS resonance at $\delta_H$ 0.00 ppm and $CD_3OD$ resonance at 49.0 ppm, respectively.

Results and Discussion

Unless otherwise noted, all solvent ratios are listed as percent by volume (v/v).

Primary Purification. Approximately 300 g was processed using the primary preparative HPLC method described above. Collected fractions were analyzed by LC-MS using the analytical method summarized in Table 1. According to LC-MS analysis, Fraction 3 (Lot #JAM-D-10-3) contained the target of interest.

Secondary Purification. Equivalent fractions from primary processing were reprocessed with conditions summarized above. Fractions were analyzed using the analytical method summarized in Table 2. Fraction 4 contained the target of interest.

Tertiary Purification. Equivalent fractions from secondary processing were reprocessed with conditions summarized above. Fractions were analyzed using the analytical method summarized in Table 3. Fractions 12 and 13 (Lot #MAU-G-5-12 and Lot #MAU-G-5-13) were of interest as direct MS analysis indicated that these fractions had m/z values of 1776. Fractions were analyzed using the corresponding analytical HPLC method. The fractions were pooled, concentrated, and then re-purified using the same tertiary conditions (Table 6). For the final sample preparation, two fractions were collected and pooled.

Figure 13:
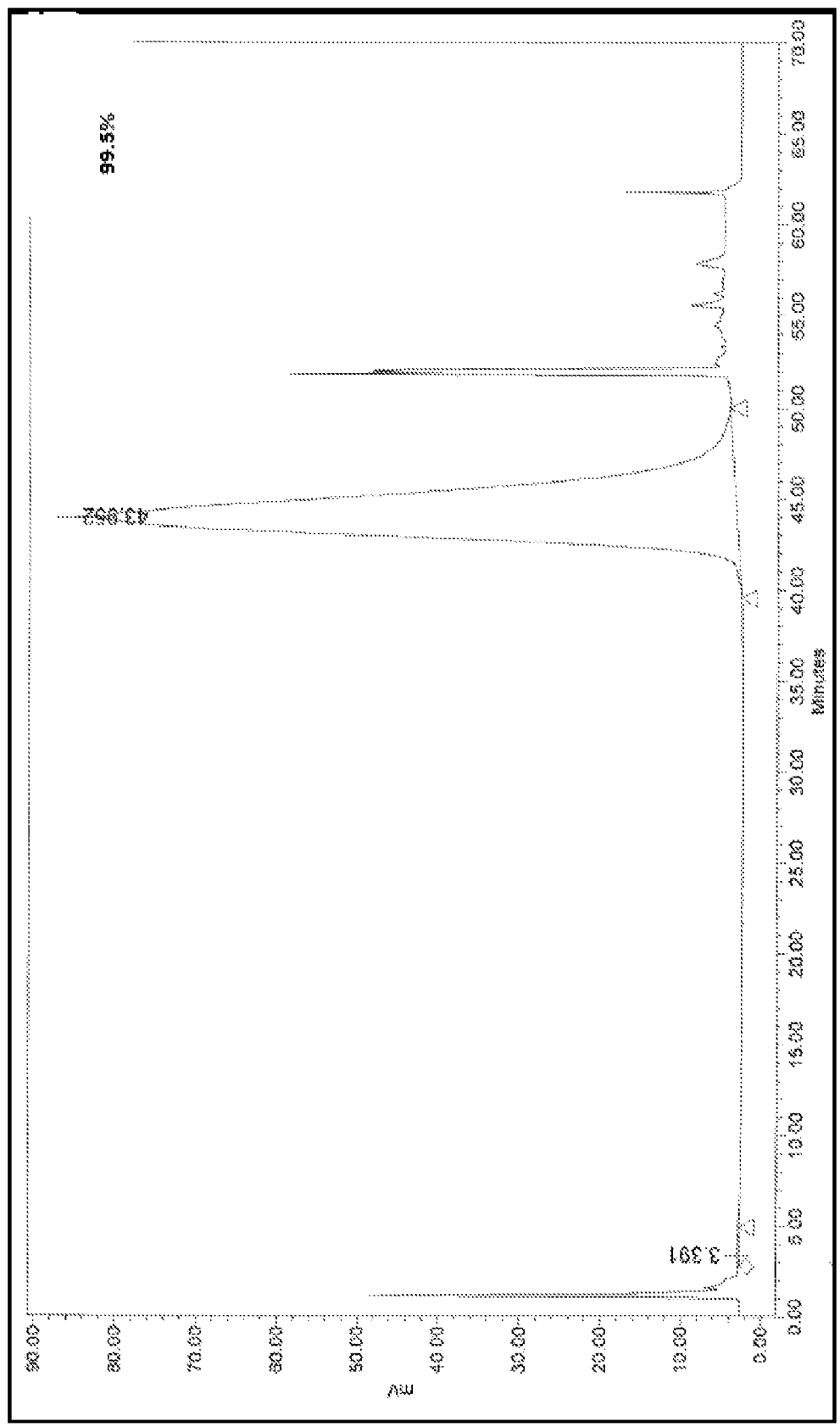
FIG. 13: Shows a representative HPLC trace of diterpene glycoside 2 using the final batch preparation described in Example 2.

Final Batch Preparation. The purified solution was filtered through a stainless steel sieve to remove particulates. The solution was then concentrated by rotary evaporation and lyophilized for about 72 h. The HPLC analysis was performed using the method corresponding to the tertiary process conditions, as this method provided a more accurate purity assessment of the final sample. The HPLC result is presented in FIG. 13. The final batch was >99% (AUC, CAD) pure.

Mass Spectrometry. The ESI-TOF mass spectrum showed a [M-H]$^-$ ion at m/z 1775.6874. The mass of the [M-H]$^-$ ion was in good agreement with the molecular formula $C_{74}H_{120}O_{48}$ (calcd for $C_{74}H_{119}O_{48}$: 1775.6871, error: 0.2 ppm) expected. The MS data confirmed a nominal mass of 1776 Daltons with the molecular formula, $C_{74}H_{120}O_{48}$.

The MS/MS spectrum, selecting the [M-H]$^-$ ion at m/z 1775.7 for fragmentation, indicated sequential loss of seven glucose units at m/z 1613.6685, 1451.5204, 1289.5427, 1127.4502, 965.4227, 803.3640, and 641.3337 followed by the loss of two glucose units at m/z 317.2014.

Figure 14:
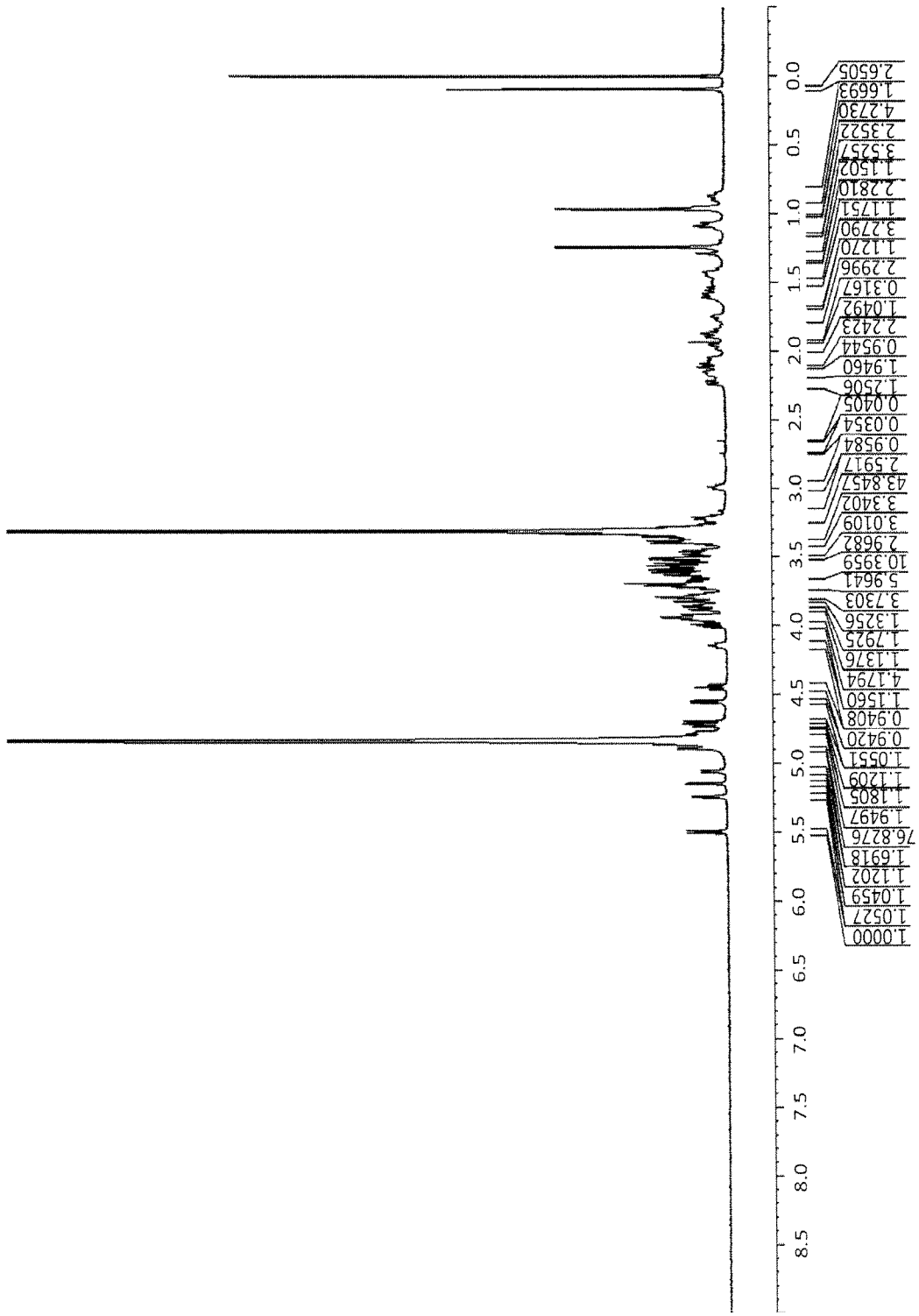
FIG. 14: Shows the $^1$H NMR spectrum (500 MHz, CD$_3$OD) of diterpene glycoside 2 at 300 K.
Figure 15:
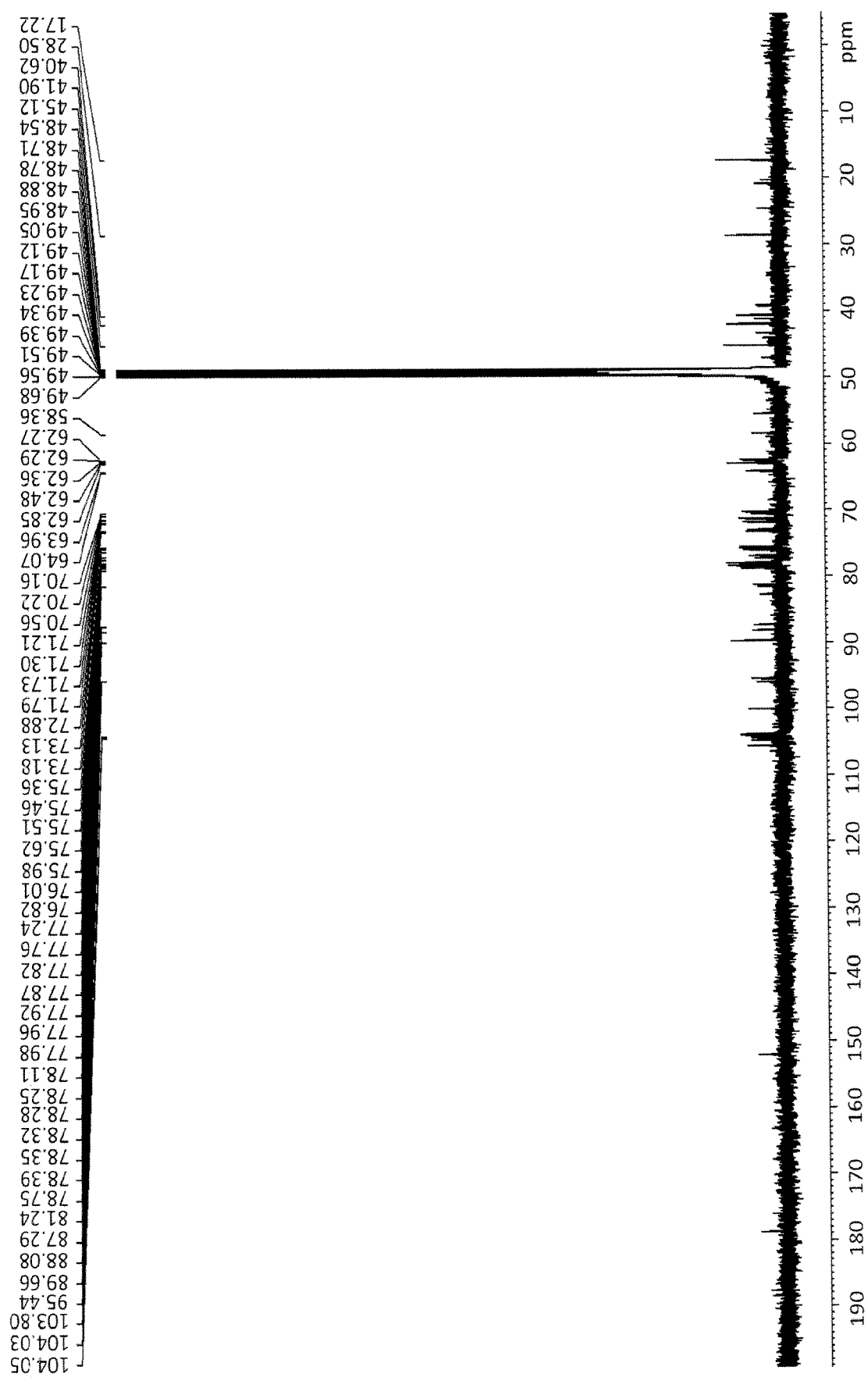
FIG. 15: Shows the $^{13}$C NMR spectrum (125 MHz, CD$_3$OD) of diterpene glycoside 2 at 300 K.
Figure 16:
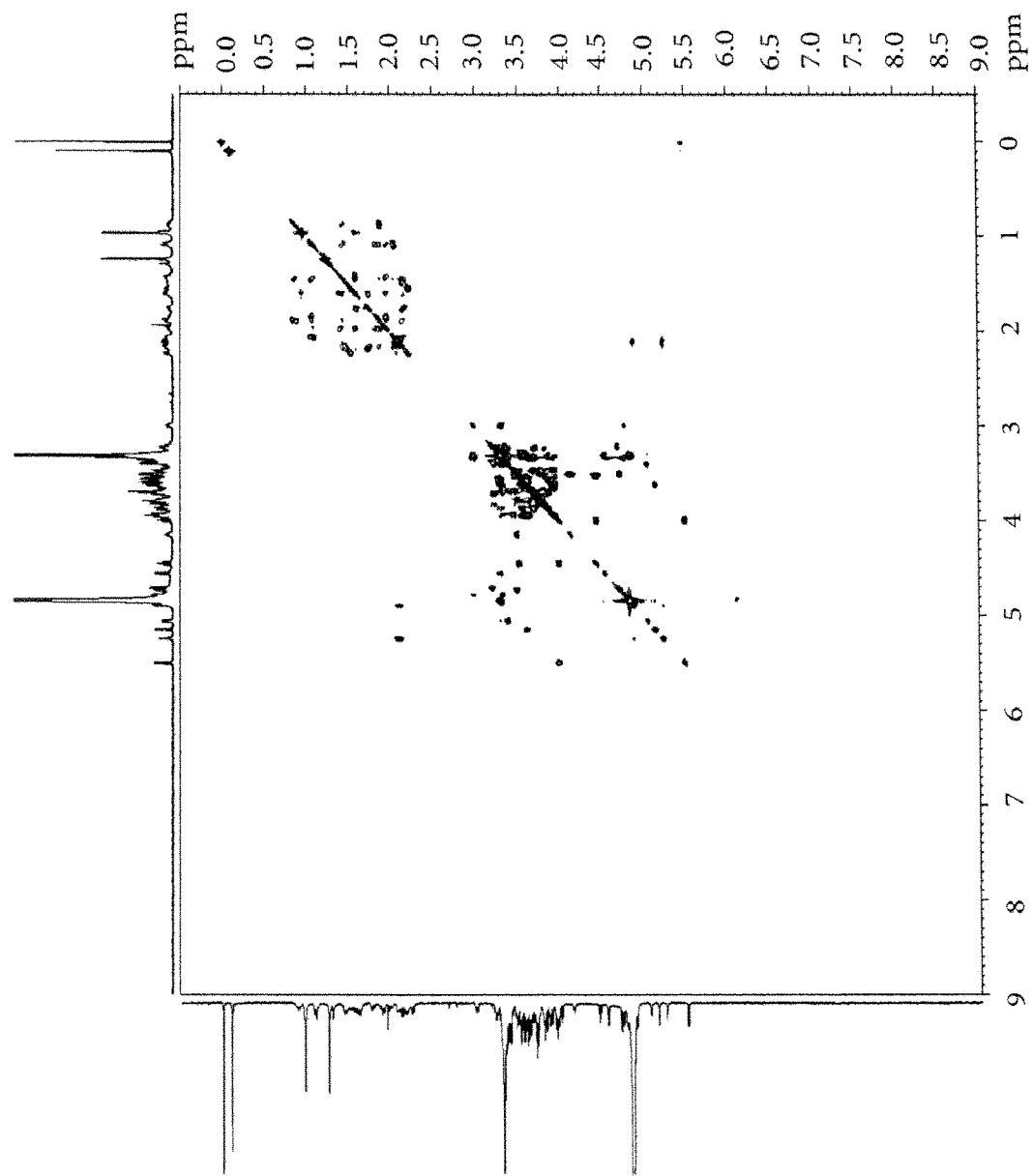
FIG. 16: Shows the $^1$H-$^1$H COSY spectrum (500 MHz, CD$_3$OD) of diterpene glycoside 2 at 300K.
Figure 17:
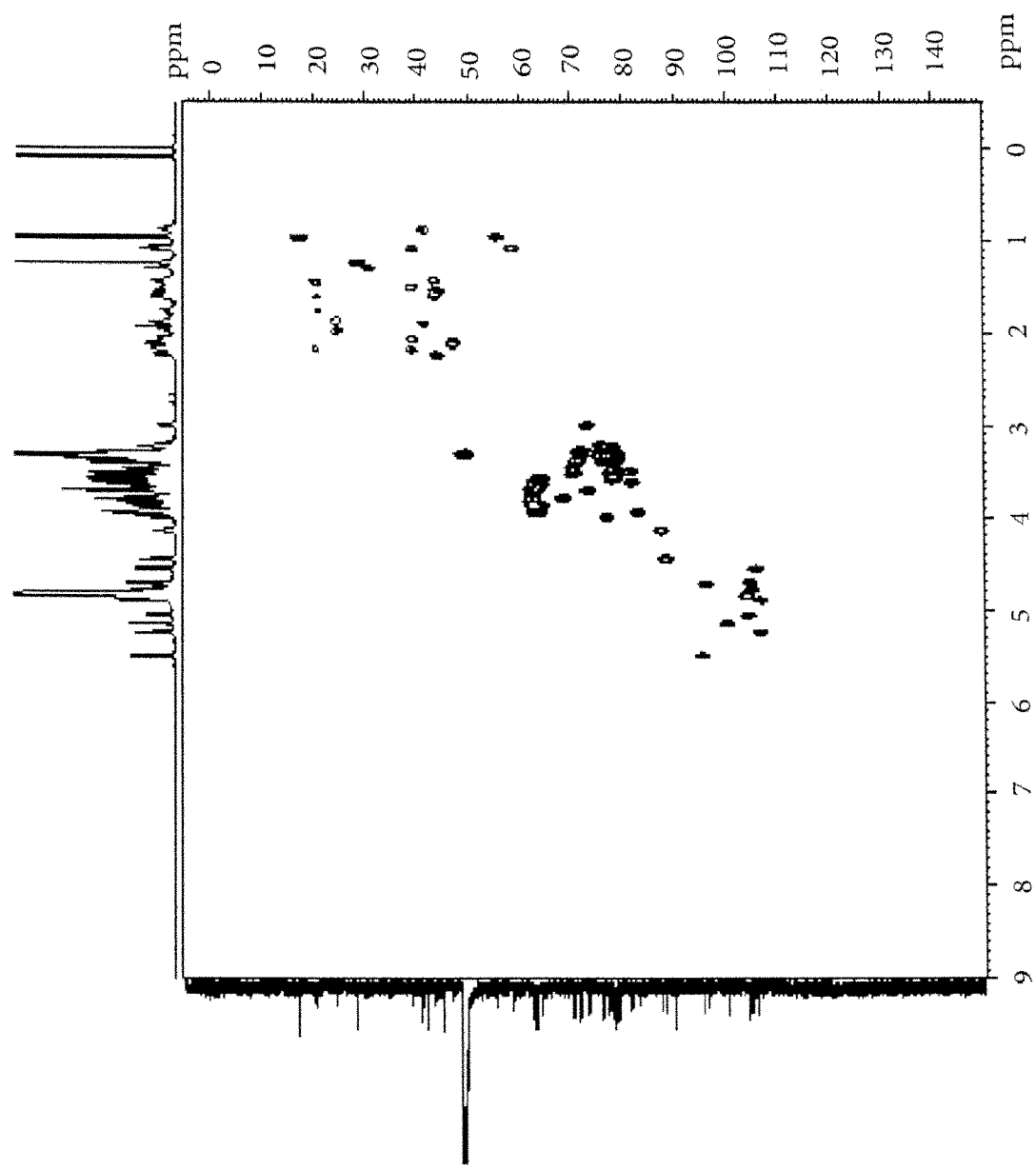
FIG. 17: Shows the HSQC-DEPT spectrum (500 MHz, CD$_3$OD) of diterpene glycoside 2 at 300K.
Figure 18:
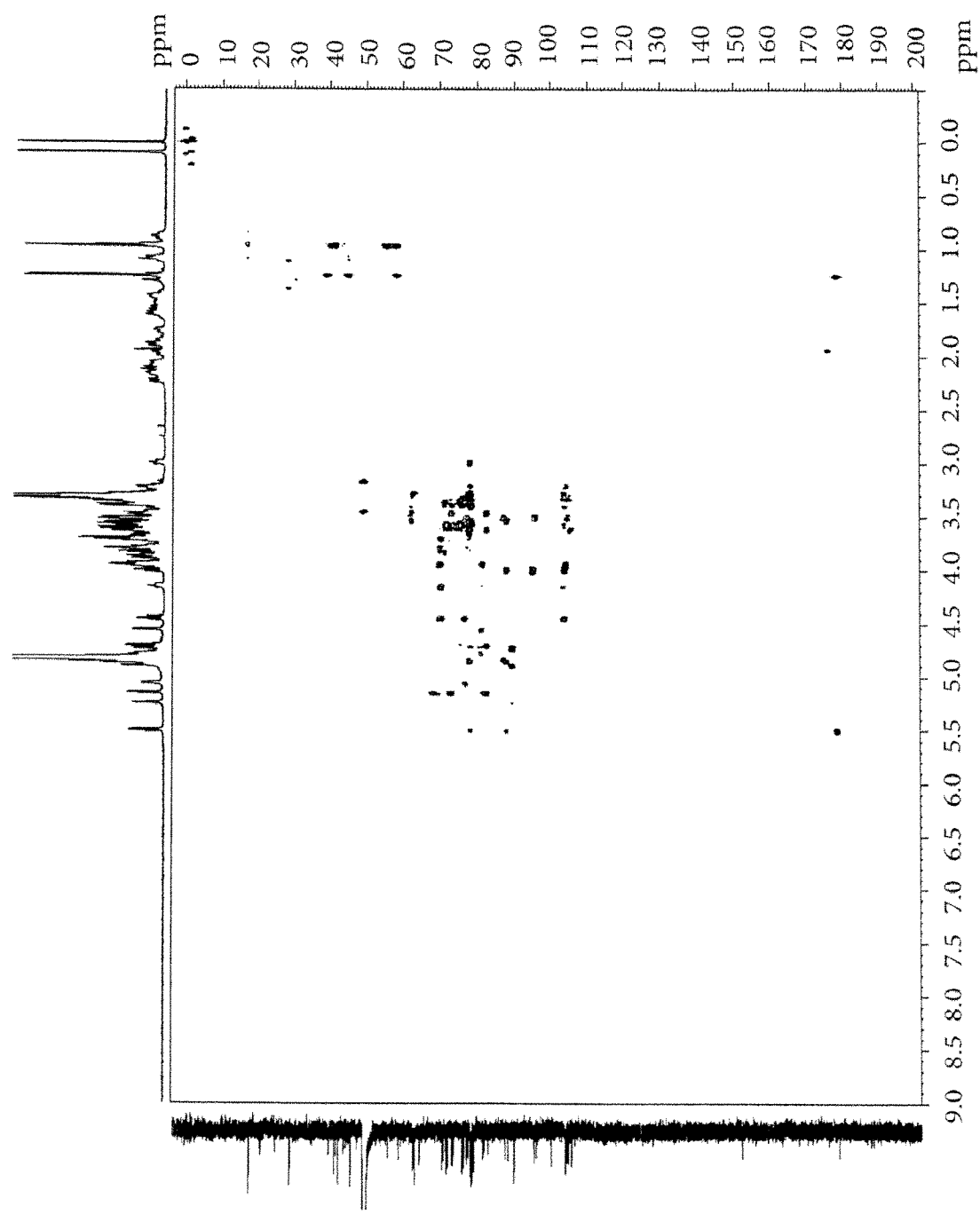
FIG. 18: Shows the HMBC spectrum (500 MHz, CD$_3$OD) of diterpene glycoside 2 at 300K.

NMR Spectroscopy. A series of NMR experiments including $^1H$ NMR (FIG. 14), $^{13}C$ NMR (FIG. 15), $^1H$-$^1H$ COSY (FIG. 16), HSQC-DEPT (FIG. 17), HMBC (FIG. 18), NOESY (FIG. 19), and 1D TOCSY (not shown) were performed.

The 1D and 2D NMR data indicated that the central core of the glycoside is a diterpene. An HMBC correlation from the methyl protons at $\delta_H$ 1.24 to the carbonyl at $\delta_C$ 178.8 allowed assignment of one of the tertiary methyl groups (C-18) as well as C-19 and provided a starting point for the assignment of the rest of the aglycone. Additional HMBC correlations from the methyl protons (H-18) to carbons at $\delta_C$ 39.2, 45.1, and 58.4 allowed assignment of C-3, C-4, and C-5. Analysis of the $^1H$-$^{13}C$ HSQC-DEPT data indicated that the carbon at $\delta_C$ 39.2 was a methylene group and the carbon at $\delta_C$ 58.4 was a methine which were assigned as C-3 and C-5, respectively. This left the carbon at $\delta_C$ 45.1, which did not show a correlation in the HSQC-DEPT spectrum, to be assigned as the quaternary carbon, C-4. The $^1H$ chemical shifts for C-3 ($\delta_H$ 1.09 and 2.06) and C-5 ($\delta_H$ 1.08) were assigned using the HSQC-DEPT data. A COSY correlation between one of the H-3 protons ($\delta_H$ 1.09) and a proton at $\delta_H$ 1.44 allowed assignment of one of the H-2 protons which in turn showed a correlation with a proton at $\delta_H$ 0.87 which was assigned to H-1. The remaining $^1H$ and $^{13}C$ chemical shifts for C-1 and C-2 were then assigned on the basis of additional COSY and HSQC-DEPT correlations.

The other tertiary methyl singlet, observed at $\delta_H$ 0.96, showed HMBC correlations to C-1 and C-5 and was assigned as H-20. The methyl protons showed additional HMBC correlations to a quaternary carbon ($\delta_C$ 40.6) and a methine carbon ($\delta_C$ 55.4) which were assigned as C-10 and C-9, respectively. COSY correlations between H-5 ($\delta_H$ 1.08) and protons at $\delta_H$ 1.86 and 1.97 then allowed assignment of the H-6 protons which in turn showed correlations to protons at $\delta_H$ 1.42 and 1.59 which were assigned to H-7. The $^{13}C$ chemical shifts for C-6 ($\delta_C$ 24.5) and C-7 ($\delta_C$ 43.3) were then determined from the HSQC-DEPT data. COSY correlations between H-9 ($\delta_H$ 0.95) and protons at $\delta_H$ 1.60 and 1.76 allowed assignment of the H-11 protons which in turn showed COSY correlations to protons at $\delta_H$ 1.50 and 2.17 which were assigned as the H-12 protons. The HSQC-DEPT data was then used to assign C-11 ($\delta_C$ 20.7) and C-12 ($\delta_C$ 39.1). The olefinic protons observed at $\delta_H$ 4.89 and 5.24 showed HMBC correlations to a carbon at $\delta_C$ 89.7 (C-13) and were assigned to H-17 ($\delta_C$ 106.5 via HSQC-DEPT). The methine proton H-9 showed HMBC correlations to carbons at $\delta_C$ 41.9 and 44.0 which were assigned as C-8 and C-14, respectively. An additional HMBC correlation from H-9 to a carbon at $\delta_C$ 47.0 allowed assignment of C-15. The $^1H$ chemical shifts at C-14 ($\delta_H$ 1.55 and 2.23) and C-15 ($\delta_H$ 2.09 and 2.12) were assigned using the HSQC-DEPT data. An HMBC correlation from H-14 ($\delta_H$ 2.23) to a quaternary carbon at $\delta_C$ 152.1 allowed assignment of C-16 to complete the assignment of the central core.

Figure 19:
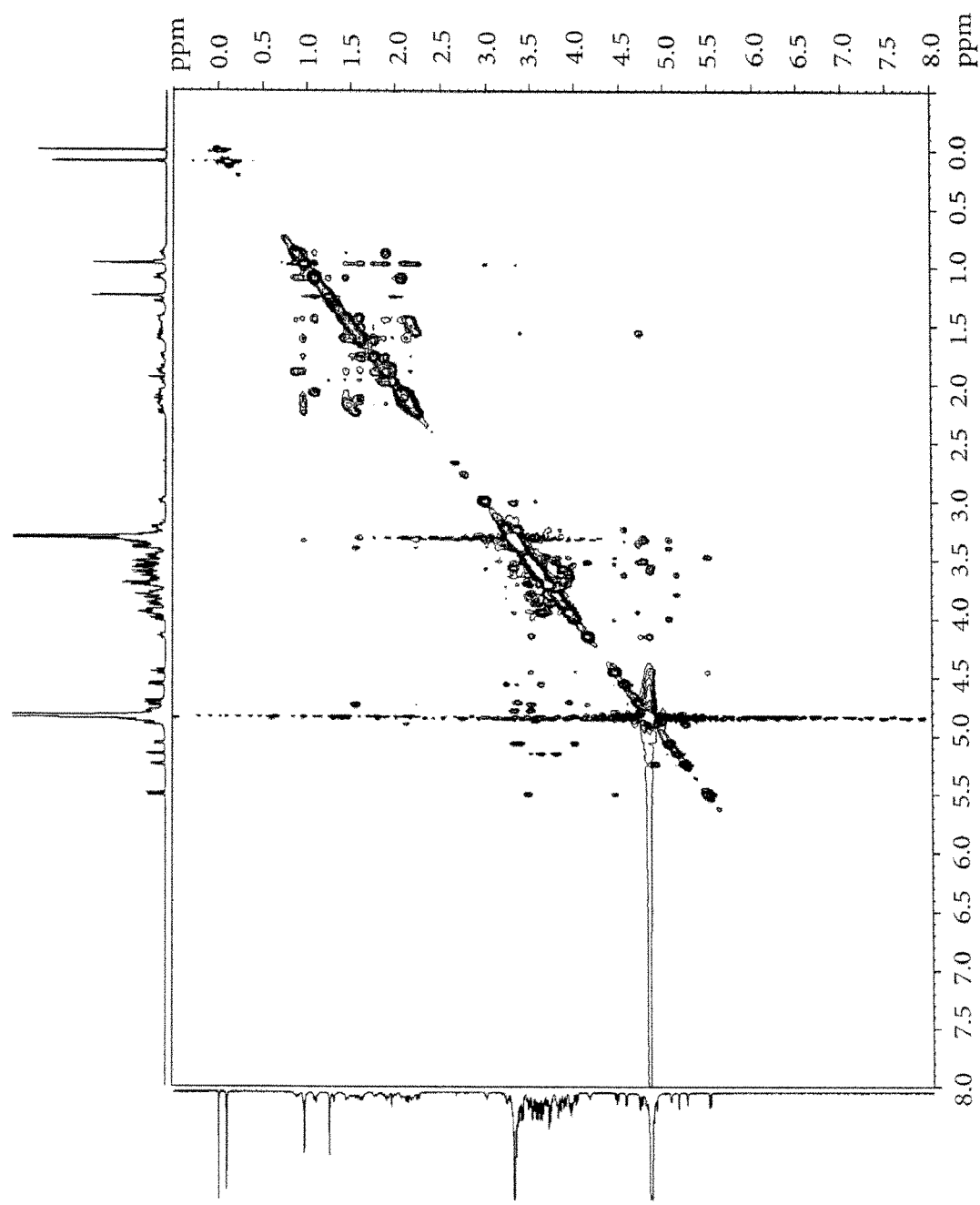
FIG. 19: Shows the NOESY spectrum (500 MHz, CD$_3$OD) of diterpene glycoside 2 at 300K.
Figure 20:
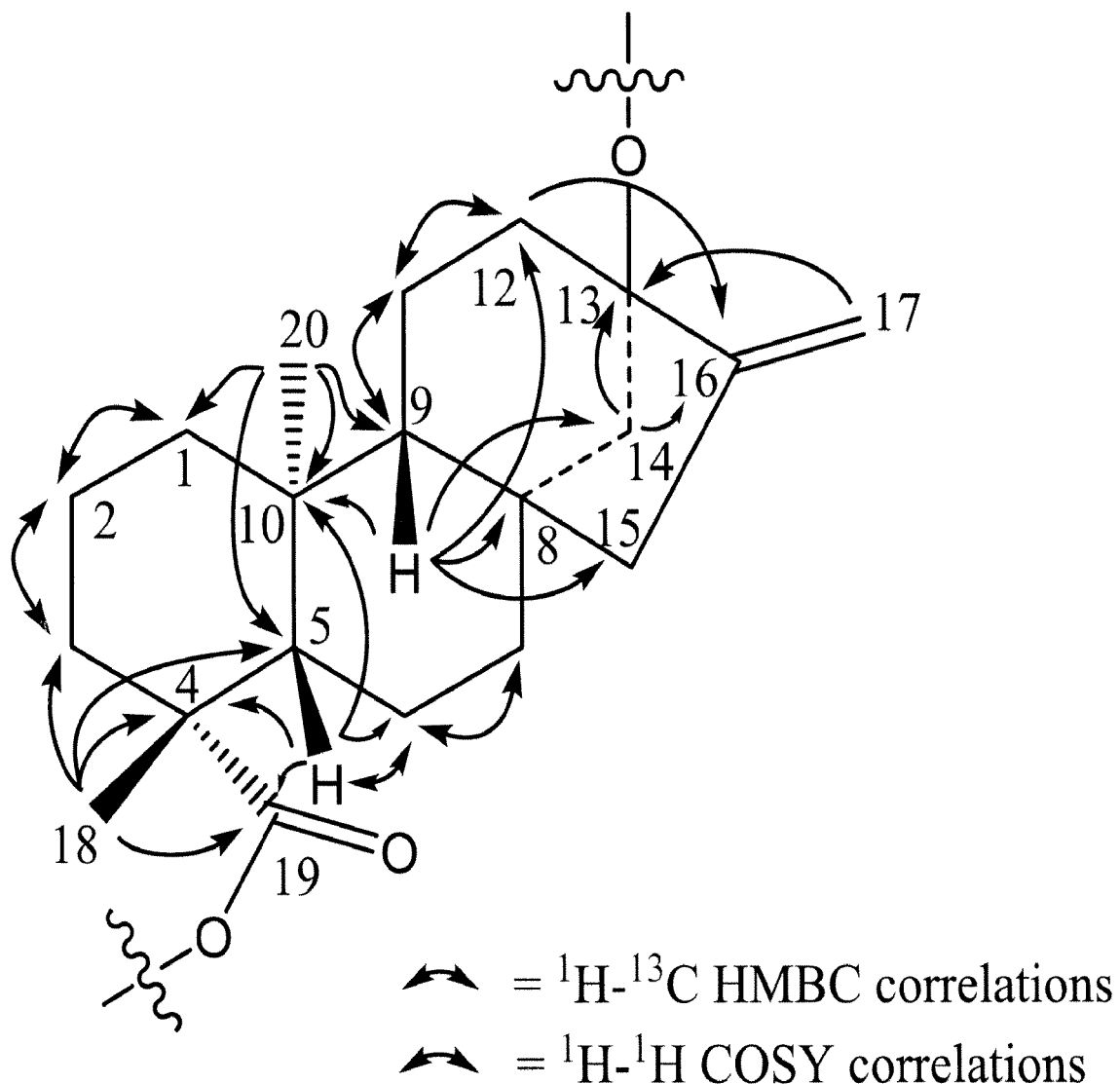
FIG. 20: Shows a summary of key HMBC and COSY correlations used to assign the aglycone region of diterpene glycoside 2.

Correlations observed in the NOESY spectrum were analyzed to assign the relative stereochemistry of the central diterpene core (FIG. 19). In the NOESY spectrum, NOE correlations were observed between H-5 and H-18 indicating that H-5 and H-18 are on the same face of the rings. Due to the very close chemical shifts of H-9 ($\delta_H$ 0.95) and H-20 ($\delta_H$ 0.96), it was not possible to unambiguously assign the relative stereochemistry of H-9, H-14 and H-20. However, based on the relative stereochemistry of the central diterpene core of reported *Stevia* glycosides and their $^1$H and $^{13}$C chemical shift comparisons, the relative stereochemistry of H-9, H-14 and H-20 is proposed as presented in FIG. 20.

Analysis of the $^1$H-$^{13}$C HSQC-DEPT data confirmed the presence of nine anomeric protons. Seven of the anomeric protons were well resolved at $\delta_H$ 5.50 ($\delta_C$ 95.4), 5.15 ($\delta_C$ 100.1), 5.06 ($\delta_C$ 104.0), 4.78 ($\delta_C$ 104.8), 4.73 ($\delta_C$ 96.0), 4.70 ($\delta_C$ 104.4), and 4.55 ($\delta_C$ 105.6) in the $^1$H NMR spectrum acquired at 300 K. Two anomeric protons that were obscured by the water resonance in the $^1$H NMR spectrum acquired at 300 K were observed in the $^1$H NMR spectrum acquired at 292 K at $\delta_H$ 4.85 ($\delta_C$ 104.0) and 4.83 ($\delta_C$ 103.8). The anomeric proton at $\delta_H$ 5.15 had a small coupling (3.5 Hz) indicating that it had an $\alpha$-configuration. The remaining eight anomeric protons had large couplings (7.4-8.3 Hz) indicating that they had $\beta$-configurations. The anomeric proton observed at $\delta_H$ 5.50 showed an HMBC correlation to C-19 which indicated that it corresponded to the anomeric proton of Glc$_I$. Similarly, the anomeric proton observed at $\delta_H$ 4.73 showed an HMBC correlation to C-13 allowing it to be assigned as the anomeric proton of Glc$_{II}$.

The Glc$_I$ anomeric proton ($\delta_H$ 5.50) showed a COSY correlation to a proton at $\delta_H$ 3.99 which was assigned as Glc$_I$ H-2 and in turn showed a COSY correlation to a proton at $\delta_H$ 4.45 (Glc$_I$ H-3) which showed a correlation with a proton at $\delta_H$ 3.52 (Glc$_I$ H-4). Due to data overlap the COSY spectrum did not allow assignment of the H-5 or H-6 protons. Therefore, a series of 1D TOCSY experiments were performed using selective irradiation of the Glc$_I$ anomeric proton with several different mixing times (not shown). In addition to confirming the assignments for Glc$_I$ H-2 through H-4, the TOCSY data showed a proton at $\delta_H$ 3.47 assigned as Glc$_I$ H-5 and protons at $\delta_H$ 3.69 and 3.82 assigned as Glc$_I$ H-6 protons. The $^{13}$C chemical shifts for Glc$_I$ C-2 ($\delta_C$ 76.8), C-3 ($\delta_C$ 88.1), C-4 ($\delta_C$ 70.2), C-5 ($\delta_C$ 78.3), and C-6 ($\delta_C$ 62.3-62.5) were assigned using the HSQC-DEPT data. HMBC correlations observed from Glc$_I$ H-1 to C-3 and C-5 and also from Glc$_I$ H-3 to C-2 and C-4 further confirmed the assignments made above to complete the assignment of Glc$_I$.

Of the eight remaining unassigned glucose moieties two were assigned as substituents at C-2 and C-3 of Glc$_I$ on the basis of HMBC correlations. The anomeric proton observed at $\delta_H$ 5.06 showed an HMBC correlation to Glc$_I$ C-2 and was assigned as the anomeric proton of Glc$_V$. The reciprocal HMBC correlation from Glc$_I$ H-2 to the anomeric carbon of Glc$_V$ was also observed. The anomeric proton observed at $\delta_H$ 4.85 showed an HMBC correlation to Glc$_I$ C-3 and was assigned as the anomeric proton of Glc$_{VI}$. The reciprocal HMBC correlation from Glc$_I$ H-3 to the anomeric carbon of Glc$_{VI}$ was also observed.

The anomeric proton of Glc$_V$ ($\delta_H$ 5.06) showed a COSY correlation with a proton at $\delta_H$ 3.39 which was assigned as Glc$_V$ H-2. Glc$_V$ C-2 ($\delta_C$ 76.0) was then assigned using the HSQC-DEPT data. Due to data overlap the COSY spectrum did not allow assignment of the remaining protons. Therefore, a series of 1D TOCSY experiments were performed using selective irradiation of the Glc$_V$ anomeric proton with several different mixing times (not shown). In addition to confirming the assignments for Glc$_V$ H-2, the TOCSY data allowed assignment of Glc$_V$ H-3 ($\delta_H$ 3.28), H-4 ($\delta_H$ 3.33), and H-5 ($\delta_H$ 3.31). The protons observed at $\delta_H$ 3.65 and $\delta_H$ 3.94 in the TOCSY spectrum were assigned as the Glc$_V$ H-6 protons. The $^{13}$C chemical shifts for Glc$_V$ C-3 ($\delta_C$ 78.3 or 78.4), C-4 ($\delta_C$ 75.4-75.6), C-5 ($\delta_C$ 77.8-78.8) and C-6 ($\delta_C$ 62.8 or 64.0 or 64.1) were assigned using the HSQC-DEPT data to complete the assignment of Glc$_V$.

Assignment of Glc$_{VI}$ was carried out in a similar manner. The anomeric proton of Glc$_{VI}$ ($\delta_H$ 4.85) showed a COSY correlation with a proton at $\delta_H$ 3.31 which was assigned as Glc$_{VI}$ H-2. Glc$_{VI}$ C-2 ($\delta_C$ 75.6) was then assigned using the HSQC-DEPT data. The remaining proton and carbon assignments were done on the basis of 1D TOCSY, HSQC-DEPT and HMBC data as discussed below. A series of 1D TOCSY experiments were performed using selective irradiation of the Glc$_{VI}$ anomeric proton with several different mixing times (not shown). In addition to confirming the assignments for Glc$_{VI}$ H-2, the TOCSY data allowed assignment of Glc$_{VI}$ H-3 ($\delta_H$ 3.56), H-4 ($\delta_H$ 3.29), and H-5 ($\delta_H$ 3.60). The TOCSY data also allowed assignment of one of the H-6 protons ($\delta_H$ 3.94). The H-6 proton at $\delta_H$ 3.94 showed a COSY correlation with a proton at $\delta_H$ 3.63 which was assigned as the other H-6 proton. The additional resonances at $\delta_H$ 4.89 and 5.24 ppm in the TOCSY spectra are due to H-17 since one of the H-17 protons at $\delta_H$ 4.89 being very close to Glc$_{VI}$ H-1 was also impacted by the TOCSY irradiation pulse. The $^{13}$C chemical shifts for C-3 ($\delta_C$ 77.8-78.8), C-4 ($\delta_C$ 71.7 or 71.8), C-5 ($\delta_C$ 77.8-78.8), and C-6 ($\delta_C$ 62.8 or 64.0 or 64.1) were assigned using the HSQC-DEPT data. HMBC correlation from H-4 to C-6 further confirmed the assignment of Glc$_{VI}$ C-6.

Figure 21:
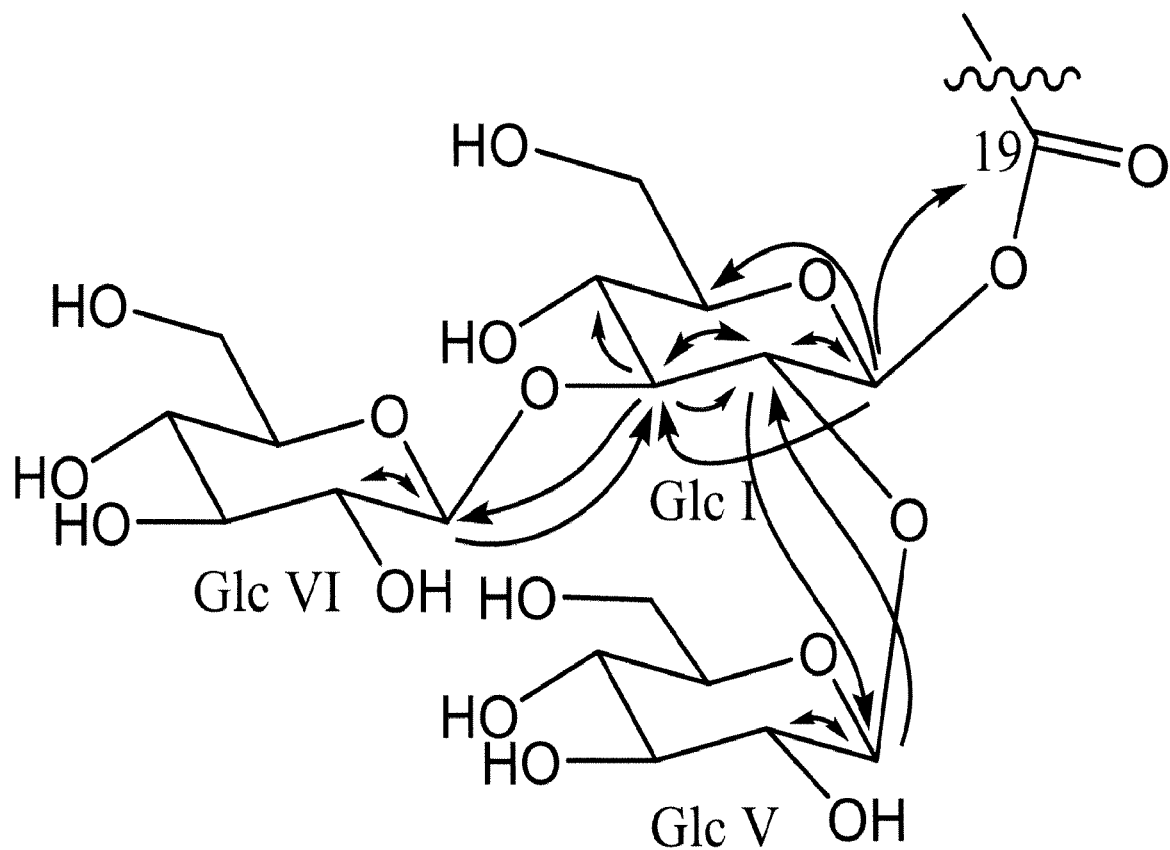
FIG. 21: Shows a summary of key HMBC and COSY correlations used to assign the C-19 glycoside region of diterpene glycoside 2.

A summary of the key HMBC and COSY correlations used to assign the C-19 glycoside region are provided in FIG. 21.

Assignment of Glc$_{II}$ was carried out in a similar manner. The Glc$_{II}$ anomeric proton ($\delta_H$ 4.73) showed a COSY correlation to a proton at $\delta_H$ 3.51 which was assigned as Glc$_{II}$ H-2 and in turn showed a COSY correlation to a proton at $\delta_H$ 4.14 (Glc$_{II}$ H-3). Due to data overlap the COSY spectrum did not allow assignment of the remaining protons. Therefore, a series of 1D TOCSY experiments were performed using selective irradiation of the Glc$_{II}$ anomeric proton with several different mixing times (not shown). However, since Glc$_{II}$ H-1 at $\delta_H$ 4.73 is close to the anomeric proton at $\delta_H$ 4.70 the irradiation also impacted the proton at $\delta_H$ 4.70 and TOCSY correlations from both anomeric protons were observed. Hence, H-4 to H-6 could not be unambiguously assigned. Therefore, the 1D-TOCSY experiments were performed using selective irradiation of the Glc$_{II}$ H-3 with several different mixing times (not shown). In addition to confirming the assignments for Glc$_V$ H-2, the TOCSY data allowed assignment of H-4 ($\delta_H$ 3.48), and H-5 ($\delta_H$ 3.50). The protons observed at $\delta_H$ 3.79 in the TOCSY spectrum were assigned as the Glc$_{II}$ H-6 protons. Assignment of the $^{13}$C chemical shifts for Glc$_{II}$ C-2 ($\delta_C$ 81.2), C-3 ($\delta_C$ 87.3), C-4 ($\delta_C$ 70.6), C-5 ($\delta_C$ 77.2) and C-6 ($\delta_C$ 68.4) was based on HSQC-DEPT data. A COSY correlation from H-6 to H-5 and HMBC correlations from Glc$_{II}$ H-1 to C-2; H-3 to C-2 and C-4 and also from H-4 to C-5 further confirmed the assignments of Glc$_{II}$. The relatively downfield shift of the C-6 methylene carbon indicated a 1→6 glycoside linkage at Glc$_{II}$ C-6.

Of the five remaining unassigned glucose moieties, two were assigned as substituents at C-2 and C-3 of $Glc_{II}$ on the basis of HMBC correlations. The anomeric proton observed at $\delta_H$ 4.78 showed an HMBC correlation to $Glc_{II}$ C-2 and was assigned as the anomeric proton of $Glc_{III}$. The anomeric proton observed at $\delta_H$ 4.83 showed an HMBC correlation to $Glc_{II}$ C-3 and was assigned as the anomeric proton of $Glc_{IV}$. The reciprocal HMBC correlations from $Glc_{II}$ H-2 to the anomeric carbon of $Glc_{III}$ and from $Glc_{II}$ H-3 to the anomeric carbon of $Glc_{IV}$ were also observed.

The anomeric proton of $Glc_{III}$ ($\delta_H$ 4.78) showed a COSY correlation with a proton at $\delta_H$ 3.33 which was assigned as $Glc_{III}$ H-2. $Glc_{III}$ C-2 ($\delta_C$ 77.8-78.8) was then assigned using the HSQC-DEPT data. Due to data overlap the COSY spectrum did not allow assignment of the remaining protons. Therefore, a series of 1D TOCSY experiments were performed using selective irradiation of the $Glc_{III}$ anomeric proton with several different mixing times (not shown). In addition to confirming the assignments for $Glc_{III}$ H-2, the TOCSY data allowed assignment of $Glc_{III}$ H-3 ($\delta_H$ 3.31), H-4 ($\delta_H$ 2.99) and H-5 ($\delta_H$ 3.33). The protons observed at $\delta_H$ 3.57 and $\delta_H$ 3.87 in the TOCSY spectrum were assigned as the $Glc_{III}$ H-6 protons. The additional resonances at ~3.51 and ~3.79 ppm in the TOCSY spectra are due to $Glc_{II}$ H-1 since $Glc_{II}$ H-1 at $\delta_H$ 4.73 is close to the $Glc_{III}$ H-1 at $\delta_H$ 4.78 and was also impacted by the TOCSY irradiation pulse. To confirm this, 1D-TOCSY experiments were performed using selective irradiation of the $Glc_{III}$ H-4 with several different mixing times (not shown) which did not show the resonances at ~3.51 and ~3.79 ppm confirming that they do not belong to $Glc_{III}$. The $^{13}C$ chemical shifts for C-3 ($\delta_C$ 75.4-75.6), C-4 ($\delta_C$ 72.9), C-5 ($\delta_C$ 77.8-78.8) and C-6 ($\delta_C$ 64.0 or 64.1) were assigned using the HSQC-DEPT data to complete the assignment of $Glc_{III}$.

The anomeric proton of $Glc_{IV}$ ($\delta_H$ 4.83) showed a COSY correlation with a proton at $\delta_H$ 3.29 which was assigned as $Glc_{IV}$ H-2 and showed a COSY correlation with a proton at $\delta_H$ 3.60 which was assigned as $Glc_{IV}$ H-3. $Glc_{IV}$ C-2 ($\delta_C$ 75.4-75.6) and C-3 ($\delta_C$ 77.8-78.4) were then assigned using the HSQC-DEPT data. Due to data overlap the COSY spectrum did not allow assignment of the remaining protons. In addition, the anomeric proton was completely obscured by the water resonance in the $^1H$ NMR acquired at 300 K. Therefore, a series of 1D TOCSY experiments were performed using selective irradiation of the $Glc_{IV}$ anomeric proton with several different mixing times at 292 K. In addition to confirming the assignments for $Glc_{IV}$ H-2 and H-3, the 1D TOCSY data allowed assignment of H-4 ($\delta_H$ 3.27), H-5 ($\delta_H$ 3.56) and one of the H-6 protons ($\delta_H$ 3.94). The remaining $Glc_{IV}$ H-6 proton was assigned at $\delta_H$ 3.63 based on COSY correlations with $\delta_H$ 3.94. The $^{13}C$ chemical shifts for C-4 ($\delta_C$ 71.7 or 71.8), C-5 ($\delta_C$ 77.8-78.8) and C-6 ($\delta_C$ 62.8 or 64.0 or 64.1) were assigned using the HSQC-DEPT data to complete the assignment of $Glc_{IV}$.

The anomeric proton of $Glc_{VII}$ at $\delta_H$ 5.15 ($\delta_C$ 100.1) showed an HMBC correlation to the carbon at $\delta_C$ 68.4 ppm ($Glc_{II}$ C-6) indicating that it was attached to $Glc_{II}$ via an 1→6 linkage. The reciprocal HMBC correlation was also observed from the methylene proton of $Glc_{II}$ ($\delta_H$ 3.79) to the anomeric carbon of $Glc_{VII}$ at $\delta_C$ 100.1 confirming the 1→6 linkage between $Glc_{VII}$ and $Glc_{II}$. Assignment of $Glc_{VII}$ was done using a combination of COSY, HSQC-DEPT, HMBC and 1D TOCSY data. The anomeric proton of $Glc_{VII}$ ($\delta_H$ 5.15) showed a COSY correlation with a proton at $\delta_H$ 3.62 which was assigned as $Glc_{VII}$ H-2 and in turn showed a COSY correlation with a proton at $\delta_H$ 3.94 which was assigned as $Glc_{VII}$ H-3. $Glc_{VII}$ C-2 ($\delta_C$ 81.4) and C-3 ($\delta_C$ 82.6) were then assigned using the HSQC-DEPT data. Due to data overlap the COSY spectrum did not allow unambiguous assignment of the remaining protons. Therefore, a series of 1D TOCSY experiments were performed using selective irradiation of the $Glc_{VII}$ anomeric proton with several different mixing times (not shown). In addition to confirming the assignments for $Glc_{VII}$ H-2 and H-3, the TOCSY data allowed assignment of $Glc_{VII}$ H-4 ($\delta_H$ 3.46), and H-5 ($\delta_H$ 3.71). The protons observed at $\delta_H$ 3.77 and $\delta_H$ 3.79 in the TOCSY spectrum were assigned as the $Glc_{III}$ H-6 protons. The $^{13}C$ chemical shifts for $Glc_{VII}$ C-4 ($\delta_C$ 70.2), C-5 ($\delta_C$ 73.1 or 73.2) and C-6 ($\delta_C$ 62.3-62.5) were assigned using the HSQC-DEPT data. HMBC correlations observed from $Glc_{VII}$ H-1 to C-2 and C-3; H-4 to C-3, and also from H-5 to C-1 and C-4 further confirmed the assignments of $Glc_{VII}$.

Two of the remaining glucose moieties with anomeric protons at $\delta_H$ 4.55 ($\delta_C$ 105.6) and $\delta_H$ 4.70 ($\delta_C$ 104.4) were assigned as substituents at C-2 and C-3 of $Glc_{VII}$ on the basis of HMBC correlations. The anomeric proton observed at $\delta_H$ 4.55 showed an HMBC correlation to $Glc_{VII}$ C-2 and was assigned as the anomeric proton of $Glc_{VIII}$. The anomeric proton observed at $\delta_H$ 4.70 showed an HMBC correlation to $Glc_{VII}$ C-3 and was assigned as the anomeric proton of $Glc_{IX}$. The reciprocal HMBC correlations from $Glc_{VII}$ H-2 to the anomeric carbon of $Glc_{VIII}$ and from $Glc_{VII}$ H-3 to the anomeric carbon of $Glc_{IX}$ were also observed.

The anomeric proton of $Glc_{VIII}$ ($\delta_H$ 4.55) showed a COSY correlation with a proton at $\delta_H$ 3.31 which was assigned as $Glc_{VIII}$ H-2. $Glc_{VIII}$ H-2 in turn showed a COSY correlation to $Glc_{VIII}$ H-3 ($\delta_H$ 3.35). Due to data overlap the COSY spectrum did not allow assignment of the remaining protons. Therefore, a series of 1D TOCSY experiments were performed using selective irradiation of the $Glc_{VIII}$ anomeric proton with several different mixing times (not shown). In addition to confirming the assignments for $Glc_{VIII}$ H-2 and H-3, the TOCSY data allowed assignment of $Glc_{VIII}$ H-4 ($\delta_H$ 3.39) and H-5 ($\delta_H$ 3.23). The protons observed at $\delta_H$ 3.71 and $\delta_H$ 3.83 in the TOCSY spectrum were assigned as the $Glc_{VIII}$ H-6 protons. Assignment of the $^{13}C$ chemical shifts for $Glc_{VIII}$ C-2 ($\delta_C$ 75.4-75.6), C-3 ($\delta_C$ 77.8-78.8), C-4 ($\delta_C$ 71.2 or 71.3), C-5 ($\delta_C$ 77.8-78.8), and C-6 ($\delta_C$ 62.3-62.5) was determined using the HSQC-DEPT data to complete the assignment of $Glc_{VIII}$.

The anomeric proton of $Glc_{IX}$ ($\delta_H$ 4.70) showed a COSY correlation with a proton at $\delta_H$ 3.21 which was assigned as $Glc_{IX}$ H-2. $Glc_{IX}$ H-2 in turn showed a COSY correlation to $Glc_{IX}$ H-3 ($\delta_H$ 3.37). Due to data overlap the COSY spectrum did not allow assignment of the remaining protons. Therefore, a series of 1D TOCSY experiments were performed using selective irradiation of the $Glc_{IX}$ anomeric proton with several different mixing times (not shows). In addition to confirming the assignments for $Glc_{IX}$ H-2 and H-3, the TOCSY data allowed assignment of $Glc_{IX}$ H-4 ($\delta_H$ 3.35), H-5 ($\delta_H$ 3.32) and H-6 ($\delta_H$ 3.70 and 3.87). In the TOCSY spectrum additional resonances at ~4.73, ~4.14, ~3.79, ~3.51, ~3.50, and ~3.48 ppm corresponding to $Glc_{II}$ protons were also observed. Since $Glc_{IX}$ H-1 at $\delta_H$ 4.70 is close to the $Glc_{II}$ H-1 at $\delta_H$ 4.73 the irradiation also impacted the proton at $\delta_H$ 4.73 and TOCSY correlations from both anomeric protons were observed. Assignment of the $^{13}C$ chemical shifts for $Glc_{IX}$ C-2 ($\delta_C$ 75.4-75.6), C-3 ($\delta_C$ 76.0), C-4 ($\delta_C$ 71.2 or 71.3), C-5 ($\delta_C$ 77.8-78.8), and C-6 ($\delta_C$ 62.3-62.5) was determined using the HSQC-DEPT data to complete the assignment of $Glc_{IX}$.

Figure 22:
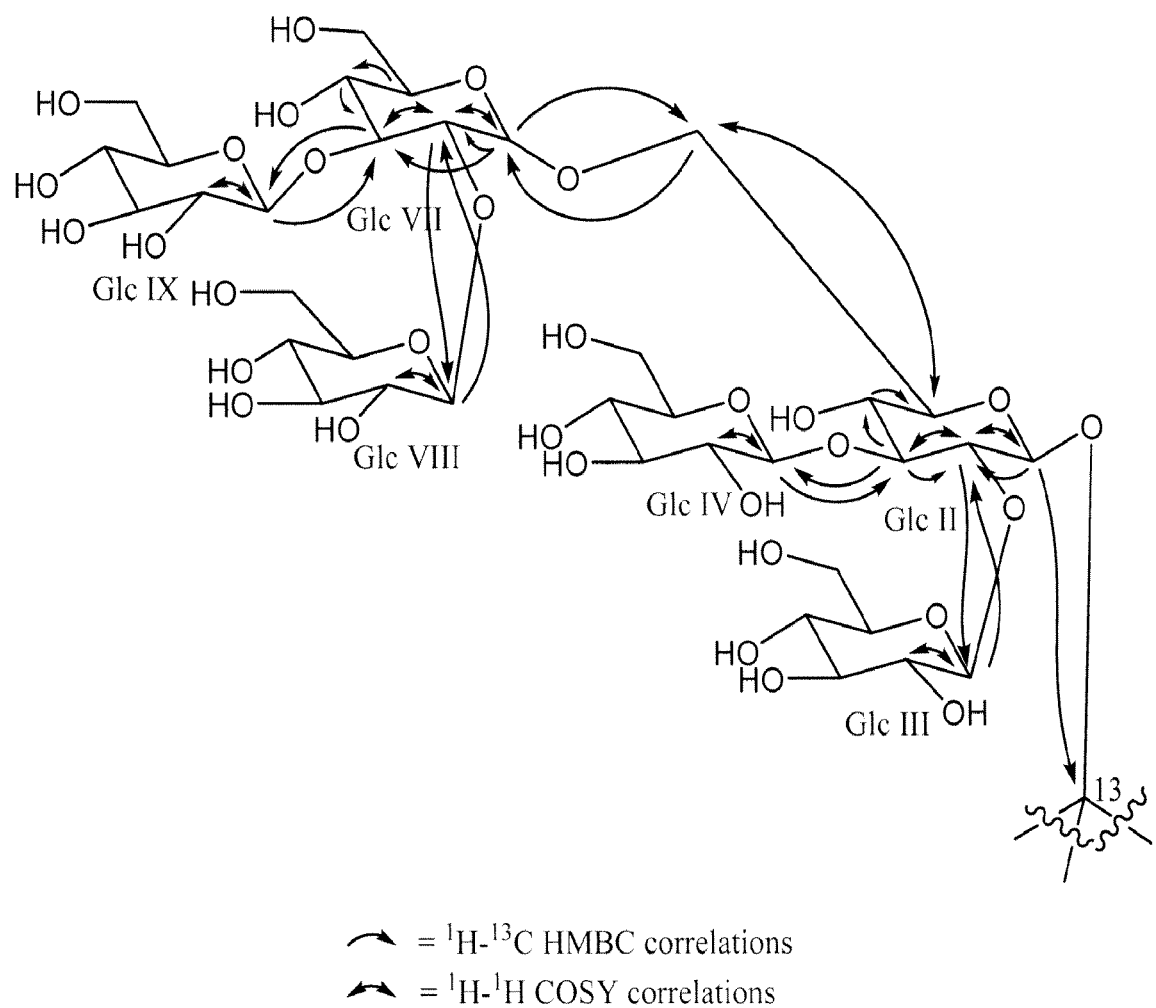
FIG. 22: Shows a summary of key HMBC and COSY correlations used to assign the C-13 glycoside region of diterpene glycoside 2.

A summary of the key HMBC and COSY correlations used to assign the C-13 glycoside region are provided in FIG. 22.

Figure 12:
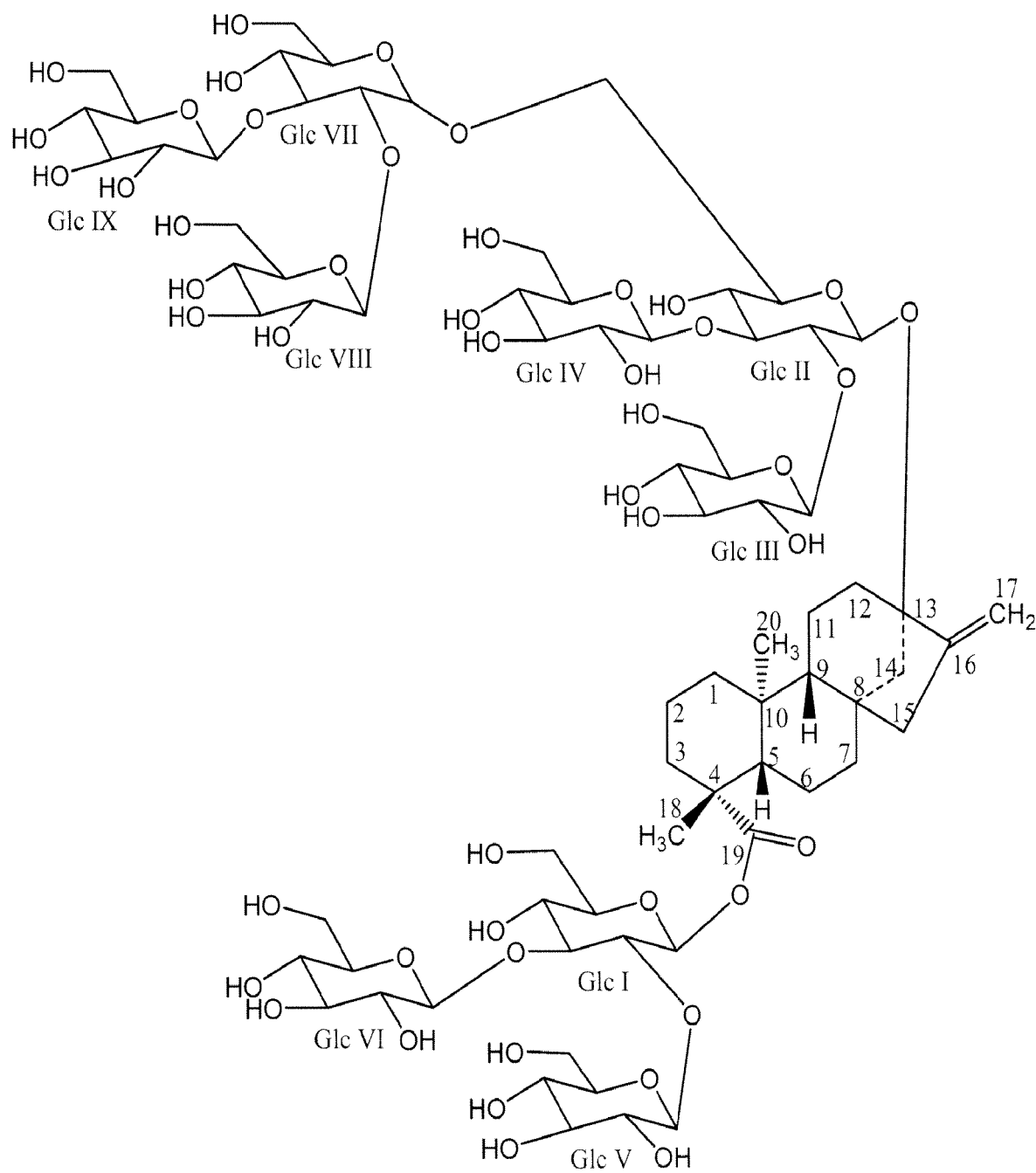
FIG. 12: Shows the structure of diterpene glycoside 2, i.e. 13-[(2-O-β-D-glucopyranosyl-3-O-β-D-glucopyranosyl-6-O-α-D-glucopyranosyl-(2-O-β-D-glucopyranosyl-3-O-β-D-glucopyranosyl)-β-D-glucopyranosyl)oxy] ent-kaur-16-en-19-oic acid-[(2-O-β-D-glucopyranosyl-3-O-β-D-glucopyranosyl-β-D-glucopyranosyl) ester].

The structure was determined to be (13-[(2-O-β-D-glucopyranosyl-3-O-β-D-glucopyranosyl-6-O-α-D-glucopyranosyl-(2-O-β-D-glucopyranosyl-3-O-β-D-glucopyranosyl)-β-D-glucopyranosyl)oxy] ent-kaur-16-en-19-oic acid-[(2-O-β-D-glucopyranosyl-3-O-β-D-glucopyranosyl-β-D-glucopyranosyl) ester], as shown in FIG. 12.

Example 3

Isolation and Characterization of 3

Reb M (80% purity), isolated from a *Stevia* extract, was used for the isolation of 3.

HPLC Analysis. Preliminary HPLC analyses of samples were performed using a Waters 2695 Alliance System with the following method: Phenomenex Synergi Hydro-RP 80 A, 4.6×250 mm, 4 μm (s/n 695639-21); Column Temp: 55° C.; Mobile Phase A: 0.00284% NH$_4$OAc and 0.0116% HOAc in water; Mobile Phase B: Acetonitrile (MeCN); Flow Rate: 1.0 mL/min; Injection volume: 10 μL. Detection was by UV (210 nm) and CAD.

Gradient

| Time (min) | % A | % B |
|---|---|---|
| 0.0-5 | 85 | 15 |
| 5.1 | 85 | 15 |
| 15.0 | 75 | 25 |
| 30.0 | 75 | 25 |
| 31.0 | 25 | 75 |
| 36 | 25 | 75 |
| 36.1 | 85 | 15 |

HPLC Analysis—Secondary Process. HPLC analyses of samples were performed using a Waters 2695 Alliance System with the following method: Phenomenex Synergi Hydro-RP 80A, 4.6×250 mm, 4 μm (s/n 695639-21); Column Temp: 50° C.; Mobile Phase A: Water; Mobile Phase B: Acetonitrile (MeCN); Flow Rate: 1.0 mL/min; Injection volume: 10 μL. Detection was by UV (210 nm) and CAD.

Gradient

| Time (min) | % A | % B |
|---|---|---|
| 0.0 | 80 | 20 |
| 35 | 80 | 20 |
| 35.1 | 50 | 50 |
| 45 | 50 | 50 |
| 45.1 | 80 | 20 |

HPLC Analysis—Tertiary and Quaternary Processes. HPLC analyses of samples were performed using a Waters 2695 Alliance System with the following method: Waters Symmetry Shield RP18 4.6×150, 5 μm (s/n 015835223116); Column Temp: 50° C.; Mobile Phase A: 0.00284% NH$_4$OAc and 0.0116% HOAc in water; Mobile Phase B: Methanol (MeOH); Flow Rate: 1.0 mL/min; Injection volume: 20 μL. Detection was by UV (210 nm) and CAD.

Gradient

| Time (min) | % A | % B |
|---|---|---|
| 0.0 | 65 | 35 |
| 35 | 65 | 35 |
| 36 | 50 | 50 |
| 46 | 50 | 50 |
| 47 | 65 | 35 |

Primary Processing. Primary processing was completed on a Waters Symmetry Shield RP18 OBD (50×250 mm, 7 μm) column using the conditions described below. Fractions were isolated and analyzed by HPLC as described above.

| Column | Waters Symmetry Shield RP18 (50 × 250 mm, 7 μm) |
|---|---|
| Flow Rate (mL/min) | 105 |
| Detection | UV at 210 nm |

Primary Processing

| Mobile Phases | (F) 15% MeCN in water |
|---|---|
| | (G) 25% MeCN in water |
| | (H) 85% MeOH in water |
| Load (g) | 12 g |
| Sample preparation | 12 g dissolved in 40 mL of DMSO, then added 80 mL of MP-A |

Gradient

| Time (min) | % A | % B | % C |
|---|---|---|---|
| 0-11 | 100 | 0 | 0 |
| 30-40 | 0 | 100 | 0 |
| 41-51 | 0 | 0 | 100 |
| 52 | 100 | 0 | 0 |

Secondary Processing. Secondary processing was conducted on a Phenomenex Synergi Hydro RP 80 (4.6×250, 10 μm) column using conditions described in the table below.

| Column | Phenomenex Synergi Hydro RP 80 (50 × 250 mm, 10 μm) |
|---|---|
| Temperature | 50° C. |
| Flow Rate (mL/min) | 105 |
| Detection | UV at 210 nm |

Secondary Processing

| Mobile Phases | (C) 18% MeCN in water |
|---|---|
| | (D) 50% MeCN in water |
| Load (g) | 0.5 g in 40 mL of water |
| Sample preparation | 500 mg of JAM-D-1-3, or JAM-D-10-3, or JAM-D-14-3 dissolved in 40 mL of water |

Gradient

| Time (min) | % A | % B |
|---|---|---|
| 0-75 | 100 | 0 |
| 75.1-85.1 | 0 | 100 |
| 86 | 100 | 0 |

Tertiary Processing. Tertiary processing was conducted on a Waters Symmetry Shield RP18 OBD (50×250 mm, 7 μm) column using conditions described in the table below.

| Column | Waters Symmetry Shield RP18 80Å (50 × 250 mm, 7 μm) |
|---|---|
| Temperature | 50° C. |
| Flow Rate (mL/min) | 105 |
| Detection | UV at 210 nm |
| Tertiary Processing | |
| Mobile Phases | (A) 40% MeOH in water with 0.0028% NH4OAc/0.012% HOAc (B) 50% MeCN in water |
| Load (g) | 0.050 g |
| Sample preparation | 50 mg in 20 mL of water |

| Gradient | | |
|---|---|---|
| Time (min) | % A | % B |
| 0-45 | 100 | 0 |
| 45.1-55.1 | 0 | 100 |
| 56 | 100 | 0 |

Quaternary processing. Quaternary processing was conducted on a Phenomenex Luna C18(2) 100A (50×250 mm, 15 μm) column using conditions described in the table below.

| Column | Phenomenex Luna C18(2) 100A (50 × 250 mm, 15 μm) |
|---|---|
| Flow Rate (mL/min) | 105 |
| Detection | UV at 210 nm |
| Quaternary Processing | |
| Mobile Phases | (C) 5% MeCN in water (D) 21% MeCN in water (E) 50% MeCN in water |
| Load (g) | 25 mL of partially lyophilized sample |

| Gradient | | | |
|---|---|---|---|
| Time (min) | % A | % B | % C |
| 0-10 | 100 | 0 | 0 |
| 10.1-30.1 | 0 | 100 | 0 |
| 30.2-40.2 | 0 | 0 | 100 |
| 41 | 100 | 0 | 0 |

MS and MS/MS. MS and MS/MS data were generated with a Waters QTof Micro mass spectrometer equipped with an electrospray ionization source. The sample was analyzed by negative ESI. The sample was diluted with $H_2O$:MeCN (1:1) 50 fold and introduced via flow injection. The sample was diluted to yield good s/n which occurred at an approximate concentration of 0.01 mg/mL.

NMR. The sample was prepared by dissolving ~3.7 mg in 175 μL of pyridine-$d_5$/TMS+$D_2O$ (~10:1) and NMR data were acquired on a Bruker Avance 500 MHz instruments with either a 2.5 mm inverse probe or a 5 mm broad band probe. The $^1H$ and $^{13}C$ NMR spectra were referenced to the TMS signal ($\delta_H$ 0.00 ppm and $\delta_C$ 0.0 ppm).

Results and Discussion

Isolation and Purification. 3 was isolated from a crude Reb M 80% mixture. Primary processing was performed as outlined above, and the material was first analyzed by HPLC. Direct mass spectral analysis (flow Injection) was also performed to verify the presence of a compound with the target mass of 1776 Da. Secondary processing was carried out on Fraction #3 (primary), using the method described above. HPLC comparison with a retention time marker and LC/MS analysis confirmed the presence of the target compound. Fraction #8 (secondary) was further processed as outlined in above upon which the tail fractions were pooled. This pool was further reprocessed, yielding pure 3 in Fraction #4.

Figure 24:
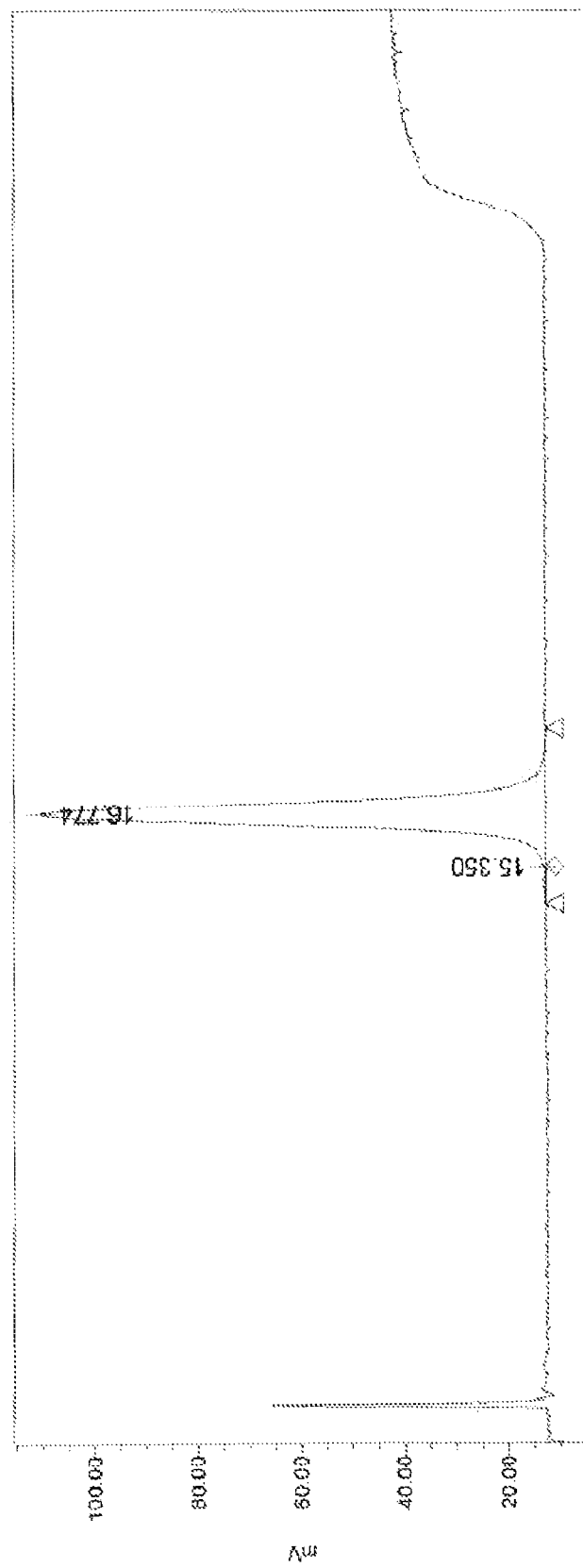
FIG. 24: Shows a HPLC trace of diterpene glycoside 3, final analysis, as described in Example 3.

Final Batch Preparation. Fraction #4 was concentrated by rotary evaporation for final isolation. The concentrated solution was further dried via lyophilization for 48 h. The final yield of the batch, JAM-D-88-4, was 4.4 mg (FIG. 24). The purity was >99% (AUC, CAD).

Mass Spectrometry. The ESI-TOF mass spectrum showed a [M-H]$^-$ ion at m/z 1775.6869. The mass of the [M-H]$^-$ ion was in good agreement with the molecular formula $C_{74}H_{120}O_{48}$ (calcd for $C_{74}H_{119}O_{48}$: 1775.6871, error: −0.1 ppm) expected. The MS data confirmed a nominal mass of 1776 Daltons with the molecular formula, $C_{74}H_{120}O_{48}$.

The MS/MS spectrum, selecting the [M-H]$^-$ ion at m/z 1775.7 for fragmentation, indicated sequential loss of four glucose units at m/z 1613.7109, 1451.6315, 1289.5242, 1127.4644 followed by the loss of two glucose units at m/z 803.3741 and sequential loss of three glucose units at 641.3300, 479.2630, and 317.2186. The ion at m/z 971.3421 likely corresponds to cleavage of the ester linkage and subsequent loss of water from one of the six sugar units.

Figure 25:
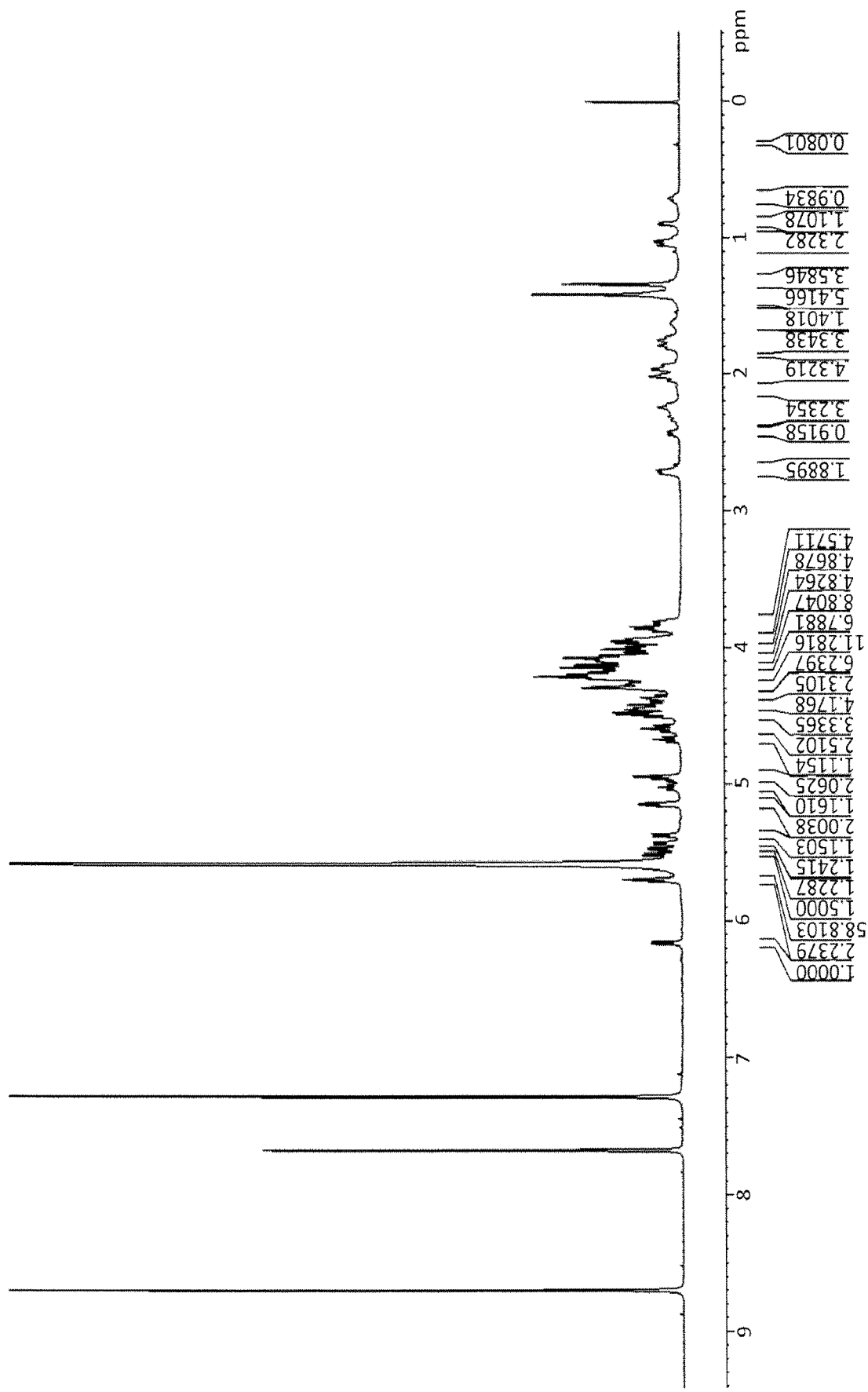
FIG. 25: Shows the $^1$H NMR spectrum (500 MHz, pyridine-d5+D$_2$O) of diterpene glycoside 3.
Figure 26:
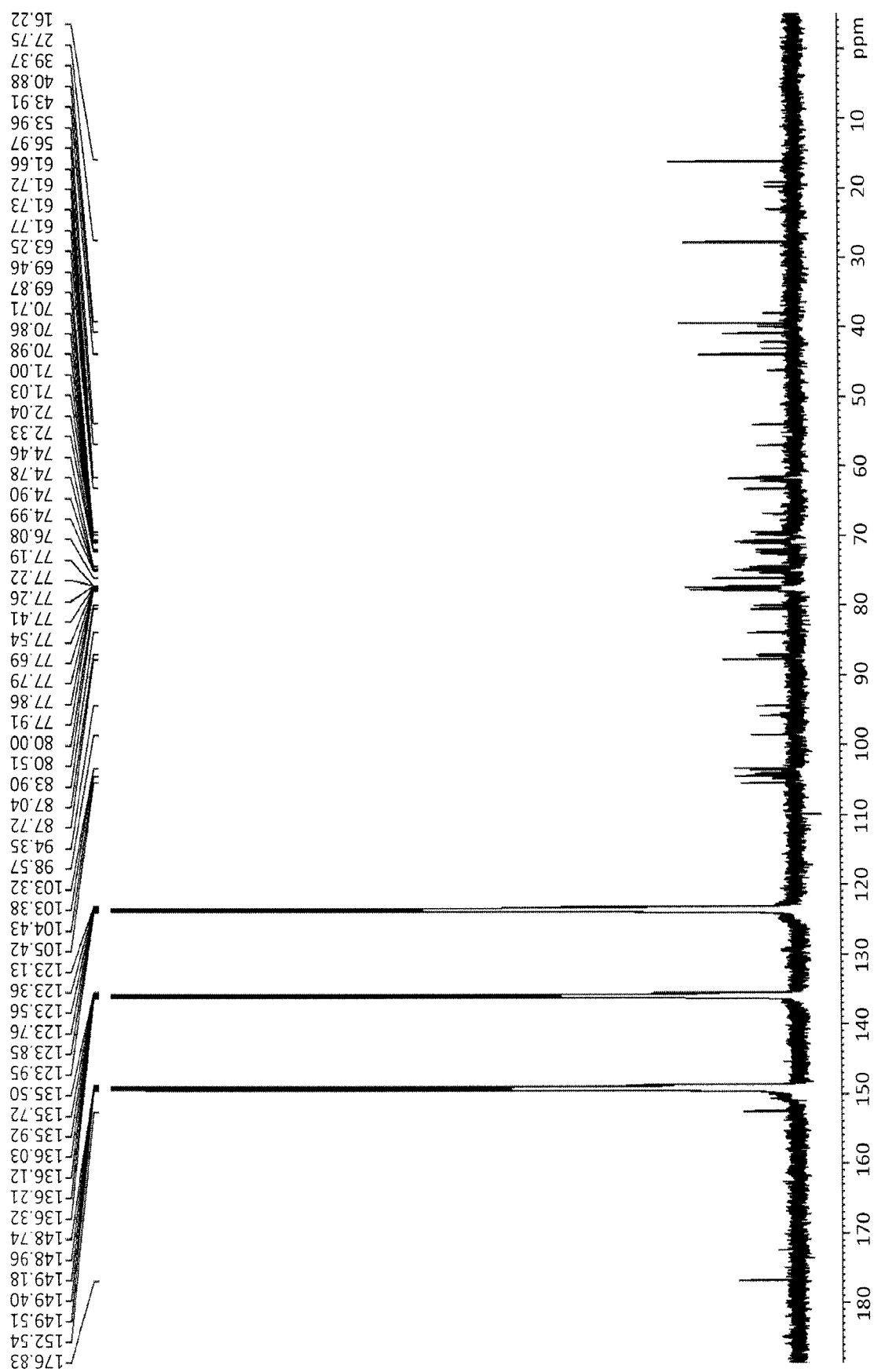
FIG. 26: Shows the $^{13}$C NMR spectrum (125 MHz, pyridine-d5+D$_2$O) of diterpene glycoside 3.
Figure 27:
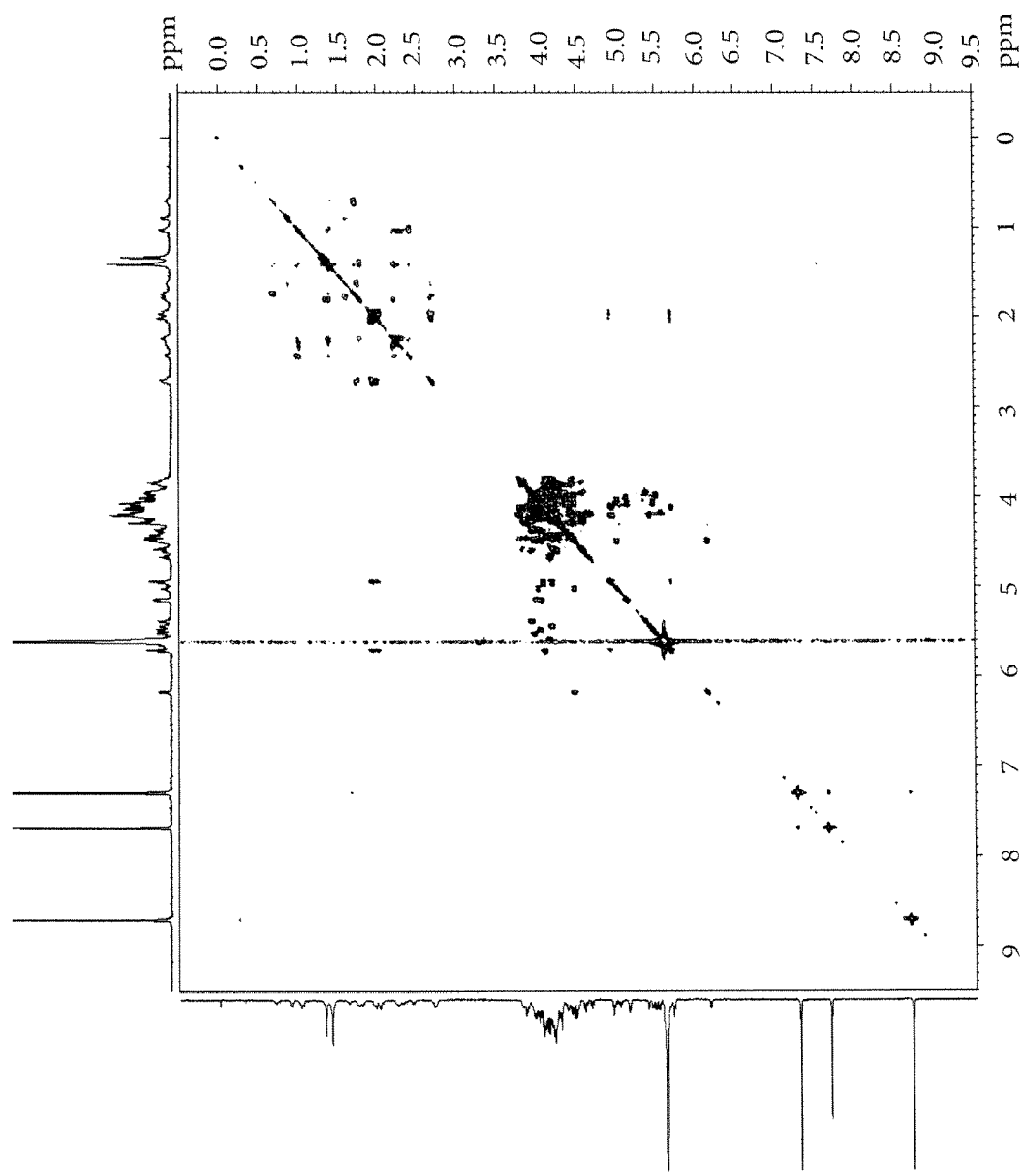
FIG. 27: Shows the $^1$H-$^1$H COSY spectrum (500 MHz, pyridine-d5+D$_2$O) of diterpene glycoside 3.
Figure 28:
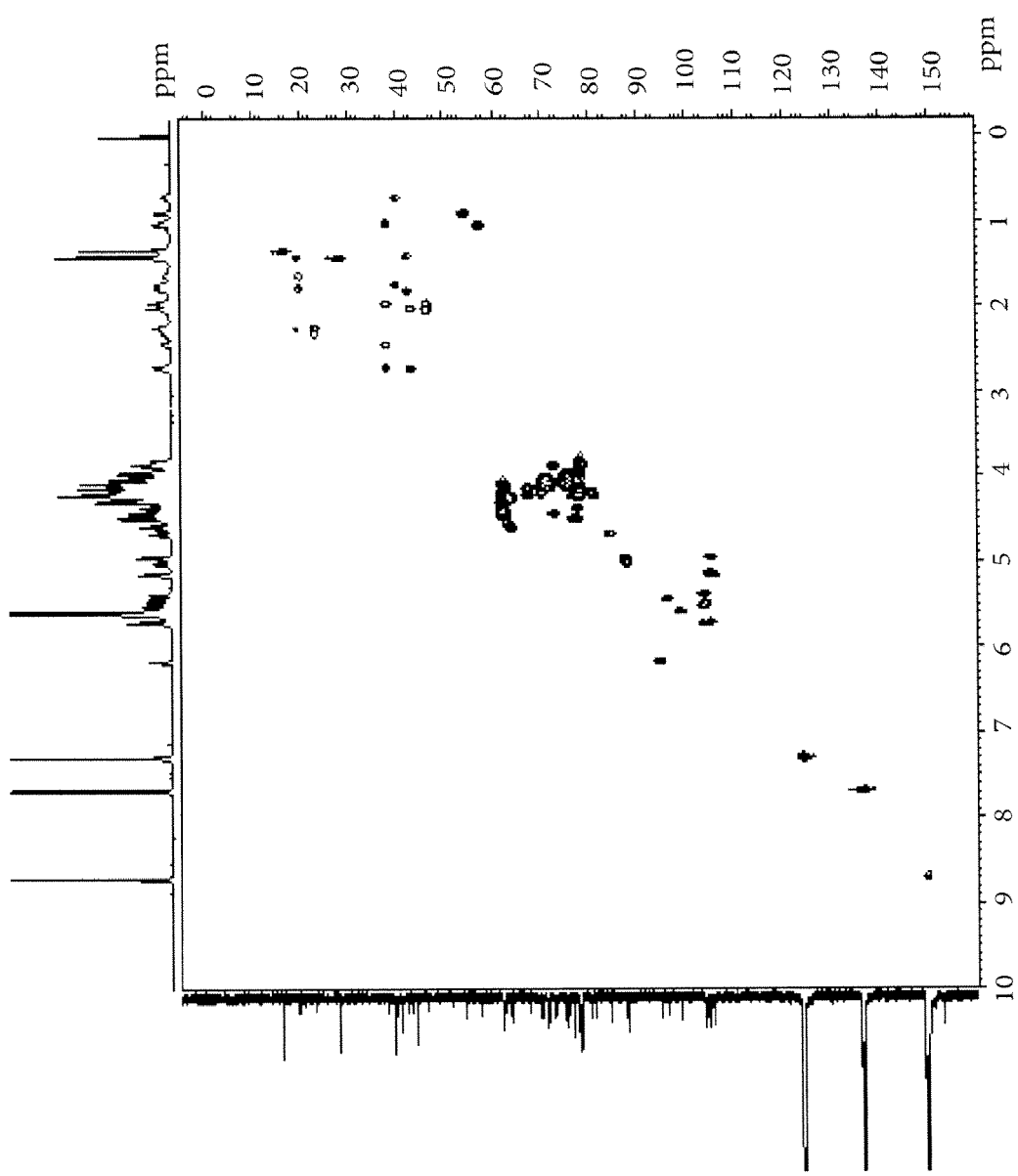
FIG. 28: Shows the HSQC-DEPT spectrum (500 MHz, pyridine-d5+D$_2$O) of diterpene glycoside 3.
Figure 29:
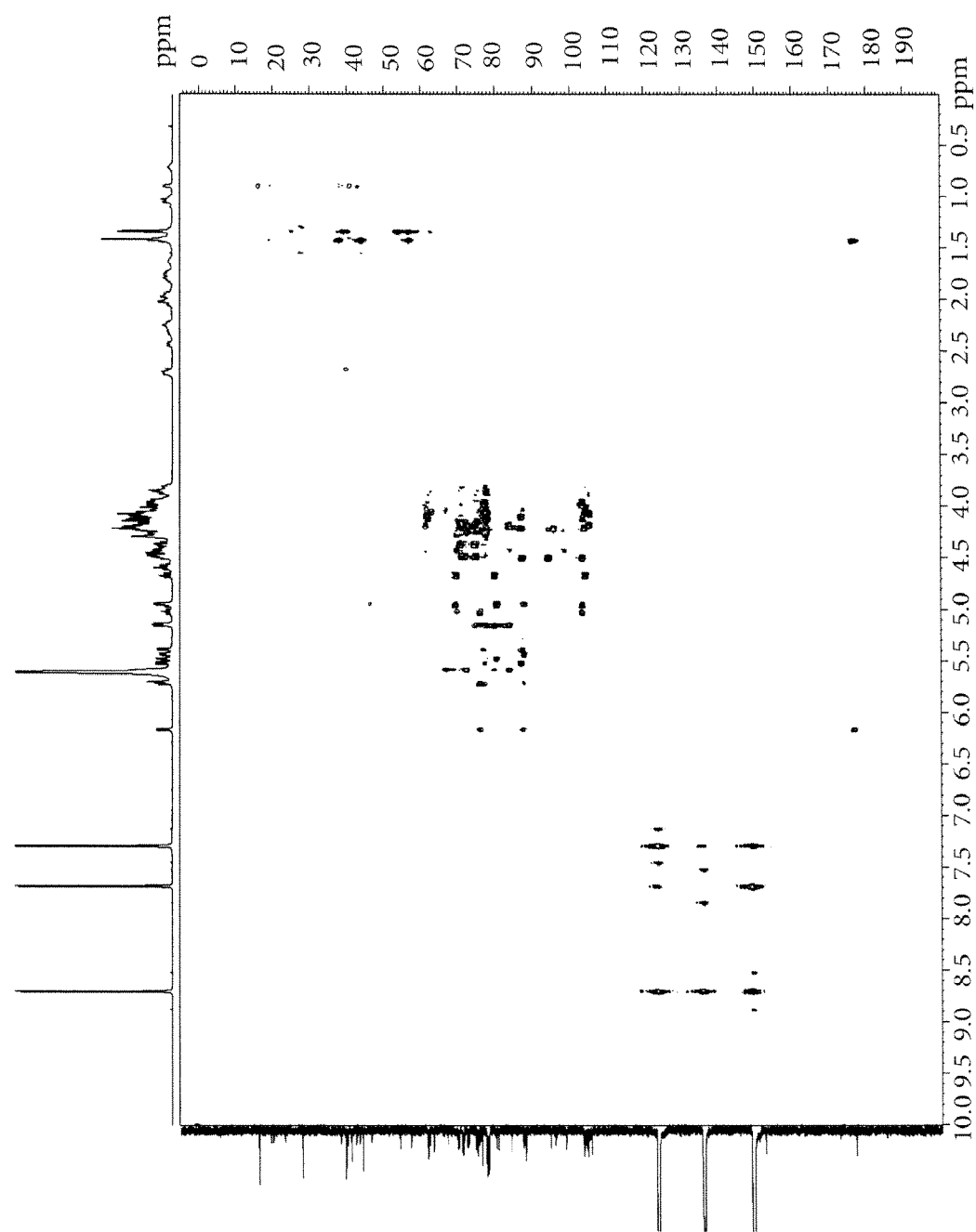
FIG. 29: Shows the HMBC spectrum (500 MHz, pyridine-d5+D$_2$O) of diterpene glycoside 3.
Figure 30:
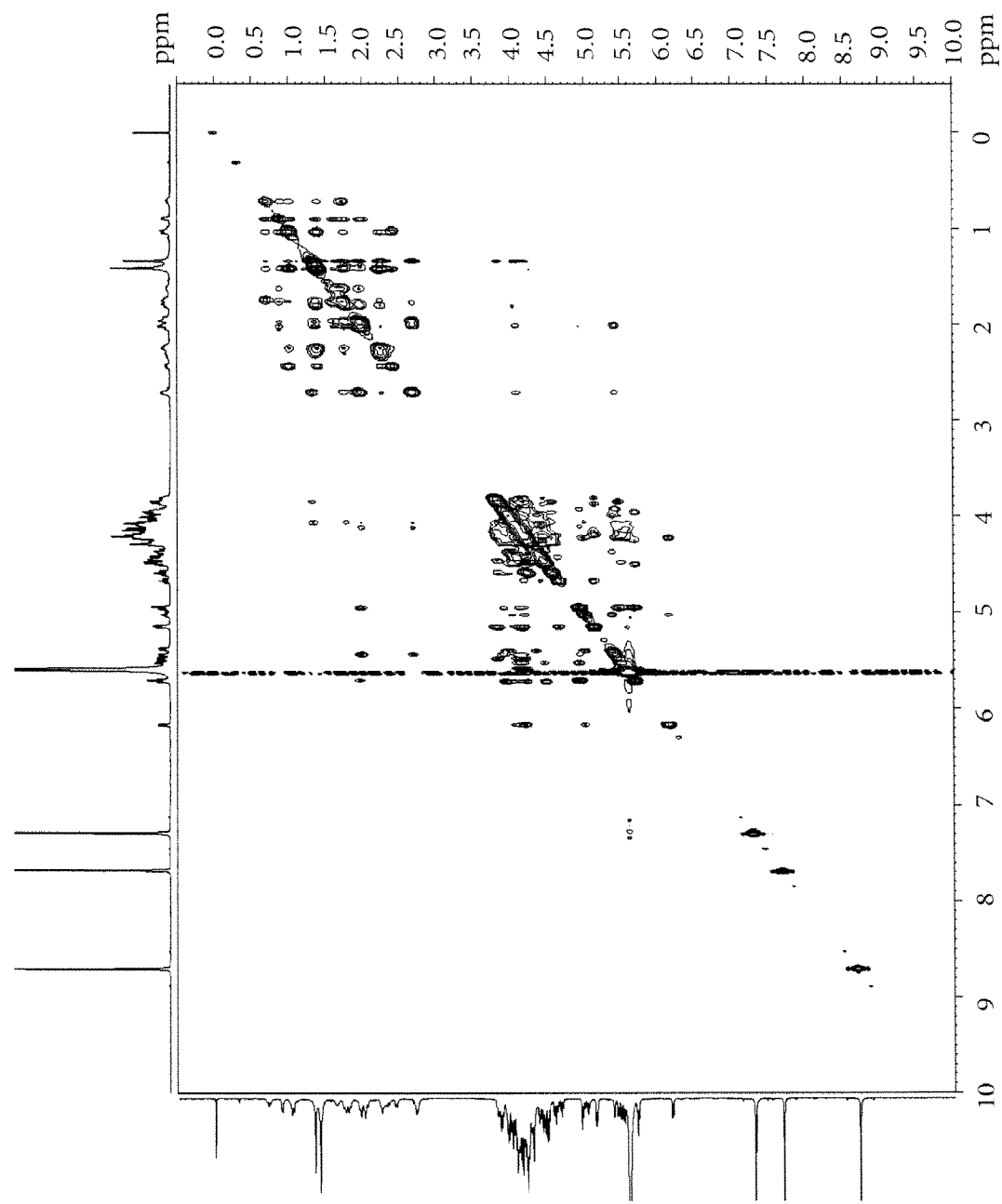
FIG. 30: Shows the NOESY spectrum (500 MHz, pyridine-d5+D$_2$O) of diterpene glycoside 3.

NMR Spectroscopy. A series of NMR experiments including $^1H$ NMR (FIG. 25), $^{13}C$ NMR (FIG. 26), $^1H$-$^1H$ COSY (FIG. 27), HSQC-DEPT (FIG. 28), HMBC (FIG. 29), NOESY (FIG. 30), and 1D TOCSY (not shown) were performed.

The 1D and 2D NMR data indicated that the central core of the glycoside is a diterpene. An HMBC correlation from the methyl protons at $\delta_H$ 1.41 to the carbonyl at $\delta_C$ 176.8 allowed assignment of one of the tertiary methyl groups (C-18) as well as C-19 and provided a starting point for the assignment of the rest of the aglycone. Additional HMBC correlations from the methyl protons (H-18) to carbons at $\delta_C$ 37.9, 43.9, and 57.0 allowed assignment of C-3, C-4, and C-5. Analysis of the $^1H$-$^{13}C$ HSQC-DEPT data indicated that the carbon at $\delta_C$ 37.9 was a methylene group and the carbon at $\delta_C$ 57.0 was a methine which were assigned as C-3 and C-5, respectively. This left the carbon at $\delta_C$ 43.9, which did not show a correlation in the HSQC-DEPT spectrum, to be assigned as the quaternary carbon, C-4. The $^1H$ chemical shifts for C-3 ($\delta_H$ 1.02 and 2.43) and C-5 ($\delta_H$ 1.03) were assigned using the HSQC-DEPT data. A COSY correlation between one of the H-3 protons ($\delta_H$ 1.02) and a proton at $\delta_H$ 1.41 allowed assignment of one of the H-2 protons which in turn showed a correlation with a proton at $\delta_H$ 0.71 which was assigned to H-1. The remaining $^1H$ and $^{13}C$ chemical shifts for C-1 and C-2 were then assigned on the basis of additional COSY and HSQC-DEPT correlations.

The other tertiary methyl singlet, observed at $\delta_H$ 1.33, showed HMBC correlations to C-1 and C-5 and was assigned as H-20. The methyl protons showed additional HMBC correlations to a quaternary carbon ($\delta_C$ 39.4) and a methine carbon ($\delta_C$ 54.0) which were assigned as C-10 and C-9, respectively. COSY correlations between H-5 ($\delta_H$ 1.03) and protons at $\delta_H$ 2.24 and 2.31 then allowed assignment of the H-6 protons which in turn showed correlations to protons at $\delta_H$ 1.40 and 1.80 which were assigned to H-7. The $^{13}C$ chemical shifts for C-6 ($\delta_C$ 23.1) and C-7 ($\delta_C$ 42.1) were then determined from the HSQC-DEPT data. COSY correlations between H-9 ($\delta_H$ 0.89) and protons at $\delta_H$ 1.62 and 1.77 allowed assignment of the H-11 protons which in turn showed COSY correlations to protons at $\delta_H$ 1.95 and 2.70 which were assigned as the H-12 protons. The HSQC-DEPT data was then used to assign C-11 ($\delta_C$ 19.8) and C-12 ($\delta_C$ 38.0). The olefinic protons observed at $\delta_H$ 4.94 and 5.70 showed HMBC correlations to a carbon at $\delta_C$ 87.7 assigned to C-13 and the olefinic protons were assigned to H-17 ($\delta_C$ 104.8 via HSQC-DEPT). The methine proton H-9 showed HMBC correlations to carbons at $\delta_C$ 40.9 and 43.0 which were assigned as C-8 and C-14, respectively. An additional HMBC correlation from H-17 ($\delta_H$ 4.94) to a carbon at $\delta_C$ 46.2 allowed assignment of C-15. The $^1$H chemical shifts at C-14 ($\delta_H$ 2.00 and 2.71) and C-15 ($\delta_H$ 1.95 and 2.03) were assigned using the HSQC-DEPT data. HMBC correlations expected from H-14 and H-15 to a quaternary carbon at $\delta_C$ 152.5 were not observed, however, based on the chemical shift observed in a similar exomethylene diterpene skeleton, $\delta_C$ 152.5 was assigned to C-16 to complete the assignment of the central core.

Correlations observed in the NOESY spectrum were used to assign the relative stereochemistry of the central diterpene core. In the NOESY spectrum, NOE correlations were observed between H-14 and H-20 indicating that H-14 and H-20 are on the same face of the rings. Similarly, NOE correlations were observed between H-9 and H-5; H-9 and H-18 as well as H-5 and H-18 but NOE correlations were not observed between H-9 and H-14 indicating that H-5, H-9 and H-18 were on the opposite face of the rings compared to H-14 and H-20 as presented in FIG. 30. These data thus indicated that the relative stereochemistry in the central core was retained during the glycosylation step.

Figure 31:
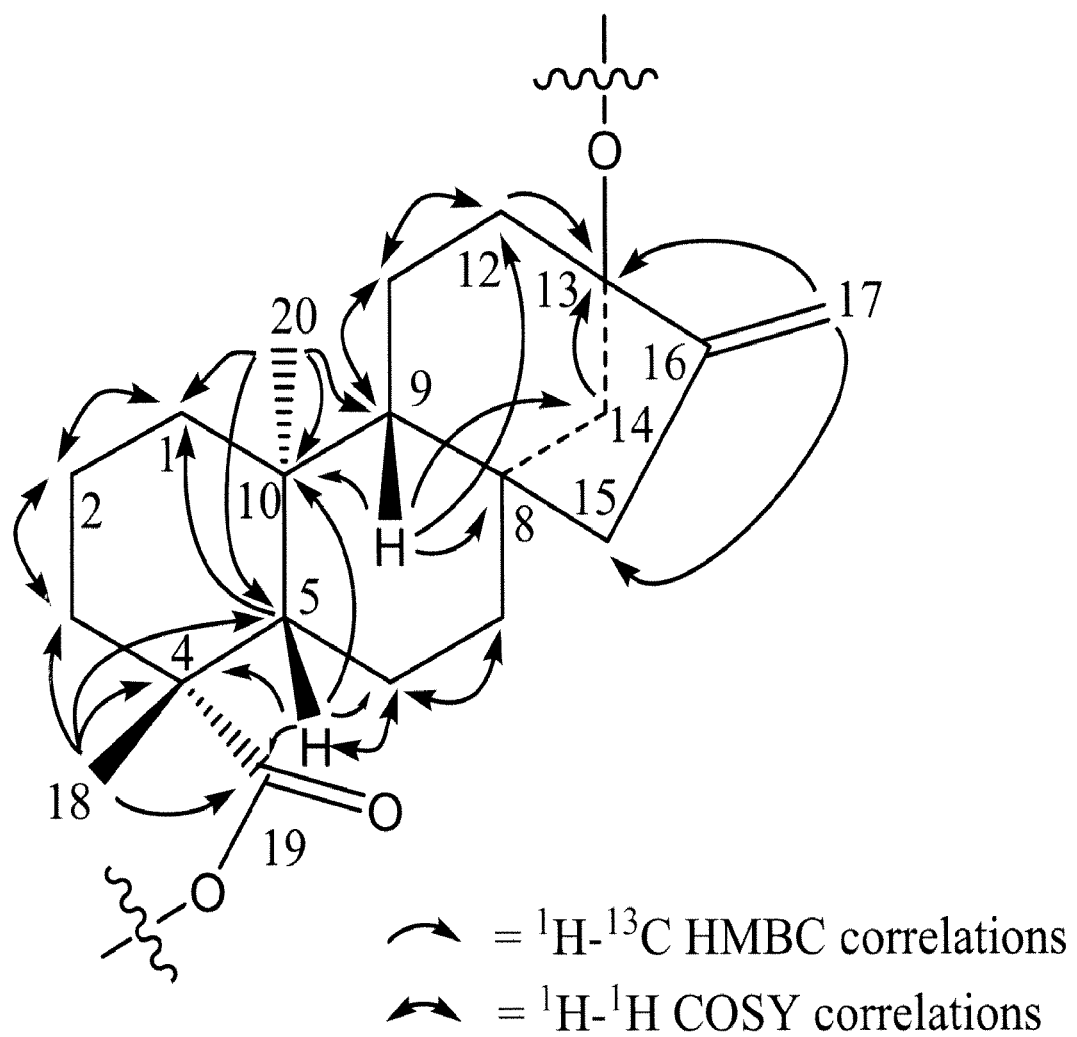
FIG. 31: Shows a summary of key HMBC and COSY correlations used to assign the aglycone region of diterpene glycoside 3.

A summary of the key HMBC and COSY correlations used to assign the aglycone region is provided in FIG. 31.

Analysis of the $^1$H-$^{13}$C HSQC-DEPT data confirmed the presence of nine anomeric protons. Five of the anomeric protons were well resolved at $\delta_H$ 6.16 ($\delta_C$ 94.4), 5.51 ($\delta_C$ 103.5), 5.47 ($\delta_C$ 104.0), 5.43 ($\delta_C$ 95.8), and 5.37 ($\delta_C$ 103.4) in the $^1$H NMR spectrum acquired immediately after sample preparation. One anomeric proton that was obscured by the water resonance was observed in the $^1$H NMR spectrum acquired after ~15 days of sample preparation at $\delta_H$ 5.58 ($\delta_C$ 98.6). The remaining three anomeric protons, one observed at $\delta_H$ 5.71 ($\delta_C$ 103.3) was overlapped by H-17, and two observed at 5.15 ($\delta_C$ 105.4) and 5.14 ($\delta_C$ 104.4) which were partially overlapped in the $^1$H spectrum were identified by $^1$H-$^{13}$C HSQC-DEPT data. An anomeric proton at $\delta_H$ 5.58 had a small coupling (3.2 Hz) indicating that it had an α-configuration. The remaining eight anomeric protons had large couplings (7.5 Hz-8.3 Hz) indicating that they had β-configurations. The anomeric proton observed at $\delta_H$ 6.16 showed an HMBC correlation to C-19 which indicated that it corresponds to the anomeric proton of Glc$_I$. Similarly, the anomeric proton observed at $\delta_H$ 5.43 showed an HMBC correlation to C-13 allowing it to be assigned as the anomeric proton of Glc$_{II}$.

The Glc$_I$ anomeric proton ($\delta_H$ 6.16) showed a COSY correlation to a proton at $\delta_H$ 4.49 which was assigned as Glc$_I$ H-2 and in turn showed a COSY correlation to a proton at $\delta_H$ 5.02 (Glc$_I$ H-3) which showed a correlation with a proton at $\delta_H$ 4.03 (Glc$_I$ H-4). Due to overlap in the data the COSY spectrum did not allow assignment of the H-5 or H-6 protons. Therefore, a series of 1D TOCSY experiments were performed using selective irradiation of the Glc$_I$ anomeric proton with several different mixing times (not shown). In addition to confirming the assignments for Glc$_I$ H-2 through H-4, the TOCSY data showed a proton at $\delta_H$ 4.22 assigned as Glc$_I$ H-5 and a proton at $\delta_H$ 4.12 assigned as one of the Glc$_I$ H-6 protons. The $^{13}$C chemical shifts for Glc$_I$ C-2 ($\delta_C$ 76.1), C-3 ($\delta_C$ 87.3), C-4 ($\delta_C$ 70.7-71.2), and C-5 ($\delta_C$ 77.4) were assigned using the HSQC-DEPT data. The HSQC-DEPT data was also used to assign the remaining H-6 proton at $\delta_H$ 4.22 and C-6 ($\delta_C$ 66.9) to complete the assignment of Glc$_I$. The proton assignment of Glc$_I$ was further supported by the 1D TOCSY experiment performed using Glc$_I$ H-3 (not shown). The relatively downfield shift of the C-6 methylene carbon indicated a 1→6 glycoside linkage at Glc$_I$ C-6.

Of the eight remaining unassigned glucose moieties two were assigned as substituents at C-2 and C-3 of Glc$_I$ on the basis of HMBC correlations. The anomeric proton observed at $\delta_H$ 5.71 showed an HMBC correlation to Glc$_I$ C-2 and was assigned as the anomeric proton of Glc$_V$. The reciprocal HMBC correlation from Glc$_I$ H-2 to the anomeric carbon of Glc$_V$ was also observed. The anomeric proton observed at $\delta_H$ 5.37 showed an HMBC correlation to Glc$_I$ C-3 and was assigned as the anomeric proton of Glc$_{VI}$. The reciprocal HMBC correlation from Glc$_I$ H-3 to the anomeric carbon of Glc$_{VI}$ was also observed.

The anomeric proton of Glc$_V$ ($\delta_H$ 5.71) showed a COSY correlation with a proton at $\delta_H$ 4.12 which was assigned as Glc$_V$ H-2. Glc$_V$ C-2 ($\delta_C$ 75.4) was then assigned using the HSQC-DEPT data. Due to overlap in the data the COSY spectrum did not allow assignment of the remaining protons. Therefore, a series of 1D TOCSY experiments were performed using selective irradiation of the Glc$_V$ anomeric proton with several different mixing times (not shown). In addition to confirming the assignments for Glc$_V$ H-2, the TOCSY data allowed assignment of Glc$_V$ H-3 ($\delta_H$ 4.23), H-4 ($\delta_H$ 4.05), and H-5 ($\delta_H$ 3.95). In the TOCSY data the protons observed at $\delta_H$ 4.27 and $\delta_H$ 4.58 were assigned as the Glc$_V$ H-6 protons. The $^{13}$C chemical shifts for Glc$_V$ C-3 ($\delta_C$ 76.1), C-4 ($\delta_C$ 72.6), C-5 ($\delta_C$ 77.5) and C-6 ($\delta_C$ 63.2) were assigned using the HSQC-DEPT data to complete the assignment of Glc$_V$.

Assignment of Glc$_{VI}$ was carried out in a similar manner. The anomeric proton of Glc$_{VI}$ ($\delta_H$ 5.37) showed a COSY correlation with a proton at $\delta_H$ 3.95 which was assigned as Glc$_{VI}$ H-2. Glc$_{VI}$ C-2 ($\delta_C$ 74.5) was then assigned using the HSQC-DEPT data. The remaining proton and carbon assignments were done on the basis of 1D TOCSY, HSQC-DEPT and HMBC data discussed below. A series of 1D TOCSY experiments were performed using selective irradiation of the Glc$_{VI}$ anomeric proton with several different mixing times (not shown). In addition to confirming the assignments for Glc$_{VI}$ H-2, the TOCSY data allowed assignment of Glc$_{VI}$ H-3 ($\delta_H$ 4.36), H-4 ($\delta_H$ 4.01), H-5 ($\delta_H$ 3.96), and H-6 ($\delta_H$ 4.07 and 4.38). The $^{13}$C chemical shifts for C-3 ($\delta_C$ 77.3), C-4 ($\delta_C$ 69.9), C-5 ($\delta_C$ 77.3), and C-6 ($\delta_C$ 61.8) were assigned using the HSQC-DEPT data. HMBC correlations from H-1 to C-5 and H-4 to C-6 further confirmed the assignments of Glc$_{VI}$ C-5 and C-6.

The anomeric proton of Glc$_{VII}$ at $\delta_H$ 5.58 ($\delta_C$ 98.6) showed HMBC correlations to the carbon at $\delta_C$ 66.9 ppm (Glc$_I$ C-6) indicating that it was attached to Glc$_I$ via an 1→6 linkage. The reciprocal HMBC correlation was also observed from the methylene proton of Glc$_I$ ($\delta_H$ 4.22) to the anomeric carbon of Glc$_{VII}$ at $\delta_C$ 98.6 confirming the 1→6 linkage between Glc$_{VII}$ and Glc$_I$. Assignment of Glc$_{VII}$ was done using a combination of COSY, HSQC-DEPT, HMBC and 1D TOCSY data. The anomeric proton of Glc$_{VII}$ ($\delta_H$ 5.58) showed a COSY correlation with a proton at $\delta_H$ 4.18 which was assigned as Glc$_{VII}$ H-2 and showed a COSY correlation with a proton at $\delta_H$ 4.66 which was assigned as Glc$_{VII}$ H-3. Glc$_{VII}$ C-2 ($\delta_C$ 80.0) and C-3 ($\delta_C$ 83.9) were then assigned using the HSQC-DEPT data. Due to overlap in the data the COSY spectrum did not allow unambiguous assignment of the remaining protons. Therefore, a series of 1D TOCSY experiments were performed using selective irradiation of the Glc$_{VII}$ anomeric proton and Glc$_{VII}$ H-3 with several different mixing times (not shown). In addition to confirming the assignments for Glc$_{VII}$ H-2 and H-3, the TOCSY data allowed assignment of Glc$_{VII}$ H-4 ($\delta_H$ 4.19), H-5 ($\delta_H$ 4.42) and the proton at $\delta_H$ 4.29 as one of the Glc$_{VII}$ H-6 protons. Specific assignment of the other methylene proton could not be made by the TOCSY experiment, but was deduced to be at $\delta_H$ ~4.2 based on COSY data. The $^{13}$C chemical shifts for Glc$_{VII}$ C-4 ($\delta_C$ 69.7), C-5 ($\delta_C$ 72.3) and C-6 ($\delta_C$ 61.5-62.2) were assigned using the HSQC-DEPT data. HMBC correlations observed from the anomeric proton at $\delta_H$ 5.58 to carbons at $\delta_C$ 80.0 (C-2), $\delta_C$ 83.9 (C-3), and $\delta_C$ 72.3 (C-5) further confirmed the assignments made above.

Two of the glucose moieties with anomeric protons at $\delta_H$ 5.15 ($\delta_C$ 105.4) and $\delta_H$ 5.14 ($\delta_C$ 104.4) were assigned as substituents at C-2 and C-3 of Glc$_{VII}$ on the basis of HMBC correlations. The anomeric proton observed at $\delta_H$ 5.15 showed an HMBC correlation to Glc$_{VII}$ C-2 and was assigned as the anomeric proton of Glc$_{VIII}$. The anomeric proton observed at $\delta_H$ 5.14 showed an HMBC correlation to Glc$_{VII}$ C-3 and was assigned as the anomeric proton of Glc$_{IX}$. The reciprocal HMBC correlations from Glc$_{VII}$ H-2 to the anomeric carbon of Glc$_{VIII}$ and from Glc$_{VII}$ H-3 to the anomeric carbon of Glc$_{IX}$ were also observed.

The anomeric proton of Glc$_{VIII}$ ($\delta_H$ 5.15) showed a COSY correlation with a proton at $\delta_H$ 4.07 which was assigned as Glc$_{VIII}$ H-2. The Glc$_{VIII}$ H-2 in turn showed a COSY correlation to Glc$_{VIII}$ H-3 ($\delta_H$ 4.19). This latter proton showed an additional correlation with Glc$_{VIII}$ H-4 ($\delta_H$ 4.13). H-4 also showed a COSY correlation to Glc$_{VIII}$ H-5 ($\delta_H$ 3.86) and H-5 in turn showed a COSY correlation to Glc$_{VIII}$ H-6 protons ($\delta_H$ 4.28 and 4.45). Assignment of the $^{13}$C chemical shifts for Glc$_{VIII}$ C-2 ($\delta_C$ 74.8), C-3 ($\delta_C$ 77.2-77.9), C-4 ($\delta_C$ 70.7-71.2), C-5 ($\delta_C$ 77.2-77.9), and C-6 ($\delta_C$ 61.5-62.2) was determined using the HSQC-DEPT data, but due to data overlap C-3 to C-6 could not be unequivocally assigned.

The anomeric proton of Glc$_{IX}$ ($\delta_H$ 5.14) showed a COSY correlation with a proton at $\delta_H$ 4.00 which was assigned as Glc$_{IX}$ H-2. The Glc$_{IX}$ H-2 in turn showed a COSY correlation to Glc$_{IX}$ H-3 ($\delta_H$ 4.14). This latter proton showed an additional correlation with Glc$_{IX}$ H-4 ($\delta_H$ 4.10). H-4 also showed a COSY correlation to Glc$_{IX}$ H-5 ($\delta_H$ 3.80) and H-5 in turn showed a COSY correlation to Glc$_{IX}$ H-6 protons ($\delta_H$ 4.21 and 4.45). Assignment of the $^{13}$C chemical shifts for Glc$_{IX}$ C-2 ($\delta_C$ 74.9), C-3 ($\delta_C$ 77.2-77.9), C-4 ($\delta_C$ 70.7-71.2), C-5 ($\delta_C$ 77.2-77.9), and C-6 ($\delta_C$ 61.5-62.2) was determined using the HSQC-DEPT data, but due to data overlap C-3 to C-6 could not be unequivocally assigned.

Figure 32:
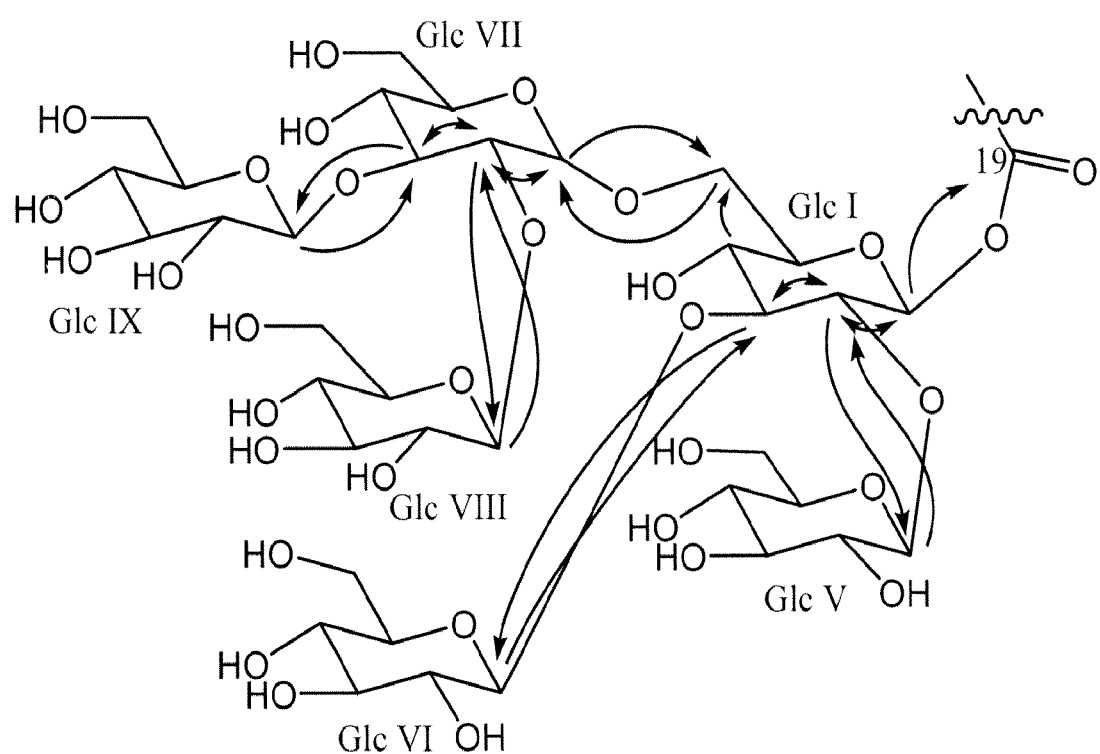
FIG. 32: Shows a summary of key HMBC and COSY correlations used to assign the C-19 glycoside region of diterpene glycoside 3.

A summary of the key HMBC and COSY correlations used to assign the C-19 glycoside region is provided in FIG. 32.

Assignment of Glc$_{II}$ was carried out in a similar manner. The Glc$_{II}$ anomeric proton ($\delta_H$ 5.43) showed a COSY correlation to a proton at $\delta_H$ 4.20 which was assigned as Glc$_{II}$ H-2 and in turn showed a COSY correlation to a proton at $\delta_H$ 4.96 (Glc$_{II}$ H-3) which showed an additional correlation with a proton at $\delta_H$ 4.10 (Glc$_{II}$ H-4) which also showed a COSY correlation to a proton at $\delta_H$ 3.94 (Glc$_{II}$ H-5). Assignment of the $^{13}$C chemical shifts for Glc$_{II}$ C-2 ($\delta_C$ 80.5), C-3 ($\delta_C$ 87.0), C-4 ($\delta_C$ 69.5), and C-5 ($\delta_C$ 77.2) was based on HSQC-DEPT data. HMBC correlations from Glc$_{II}$ H-3 to C-2 and C-4 and also from Glc$_{II}$ H-4 to C-3 and C-5 confirmed the assignments made above. A series of 1D TOCSY experiments were performed using selective irradiation of the Glc$_{II}$ anomeric proton with several different mixing times (not shown). In addition to confirming the assignments for Glc$_{VI}$ H-2 to H-5, the TOCSY data allowed assignment of one of the Glc$_{II}$ H-6 ($\delta_H$ 4.27). The HSQC-DEPT data were then used to assign the remaining Glc$_{II}$ H-6 proton ($\delta_H$ 4.20) and Glc$_{II}$ C-6 ($\delta_C$ 61.7) to complete the assignment of Glc$_{II}$.

The remaining two unassigned glucose moieties were assigned as substituents at C-2 and C-3 of Glc$_{II}$ on the basis of HMBC correlations. The anomeric proton observed at $\delta_H$ 5.47 showed an HMBC correlation to Glc$_{II}$ C-2 and was assigned as the anomeric proton of Glc$_{III}$. The anomeric proton observed at $\delta_H$ 5.51 showed an HMBC correlation to Glc$_{II}$ C-3 and was assigned as the anomeric proton of Glc$_{IV}$. The reciprocal HMBC correlations from Glc$_{II}$ H-2 to the anomeric carbon of Glc$_{III}$ and from Glc$_{II}$ H-3 to the anomeric carbon of Glc$_{IV}$ were also observed.

The anomeric proton of Glc$_{III}$ ($\delta_H$ 5.47) showed a COSY correlation with a proton at $\delta_H$ 4.07 which was assigned as Glc$_{III}$ H-2. Glc$_{III}$ C-2 ($\delta_C$ 75.0) was then assigned using the HSQC-DEPT data. Due to overlap in the data the COSY spectrum did not allow assignment of the remaining protons. Therefore, a series of 1D TOCSY experiments were performed using selective irradiation of the Glc$_{III}$ anomeric proton with several different mixing times (not shown). In addition to confirming the assignments for Glc$_{III}$ H-2, the TOCSY data allowed assignment of Glc$_{III}$ H-3 ($\delta_H$ 4.15), H-4 ($\delta_H$ 3.84) and H-5 ($\delta_H$ 3.87). In the TOCSY data the protons observed at $\delta_H$ 4.22 and $\delta_H$ 4.58 were assigned as the Glc$_{III}$ H-6 protons. The $^{13}$C chemical shifts for C-3 ($\delta_C$ 77.8), C-4 ($\delta_C$ 72.0), C-5 ($\delta_C$ 74.9) and C-6 ($\delta_C$ 63.2) were assigned using the HSQC-DEPT data. HMBC correlations from H-4 and H-5 to a carbon at $\delta_C$ 63.2 further confirmed the assignment of Glc$_{III}$ C-6.

The anomeric proton of Glc$_{IV}$ ($\delta_H$ 5.51) showed a COSY correlation with a proton at $\delta_H$ 3.98 which was assigned as Glc$_{IV}$ H-2 and showed a COSY correlation with a proton at $\delta_H$ 4.48 which was assigned as Glc$_{IV}$ H-3. Glc$_{IV}$ C-2 ($\delta_C$ 75.1) and C-3 ($\delta_C$ 77.2) were then assigned using the HSQC-DEPT data. A series of 1D TOCSY experiments were performed using selective irradiation of the Glc$_{IV}$ anomeric proton with several different mixing times (not shown). In addition to confirming the assignments for Glc$_{IV}$ H-2 and H-3, the 1D TOCSY data allowed assignment of H-4 ($\delta_H$ 4.07), H-5 ($\delta_H$ 4.15) and one of the H-6 ($\delta_H$ 4.43). The remaining Glc$_{IV}$ H-6 proton was assigned at $\delta_H$ 4.09 based upon its COSY correlations with $\delta_H$ 4.43. The $^{13}$C chemical shifts for C-4 ($\delta_C$ 70.7-71.2), C-5 ($\delta_C$ 77.7) and C-6 ($\delta_C$ 61.5-62.2) were assigned using the HSQC-DEPT data to complete the assignment of Glc$_{IV}$.

Figure 33:
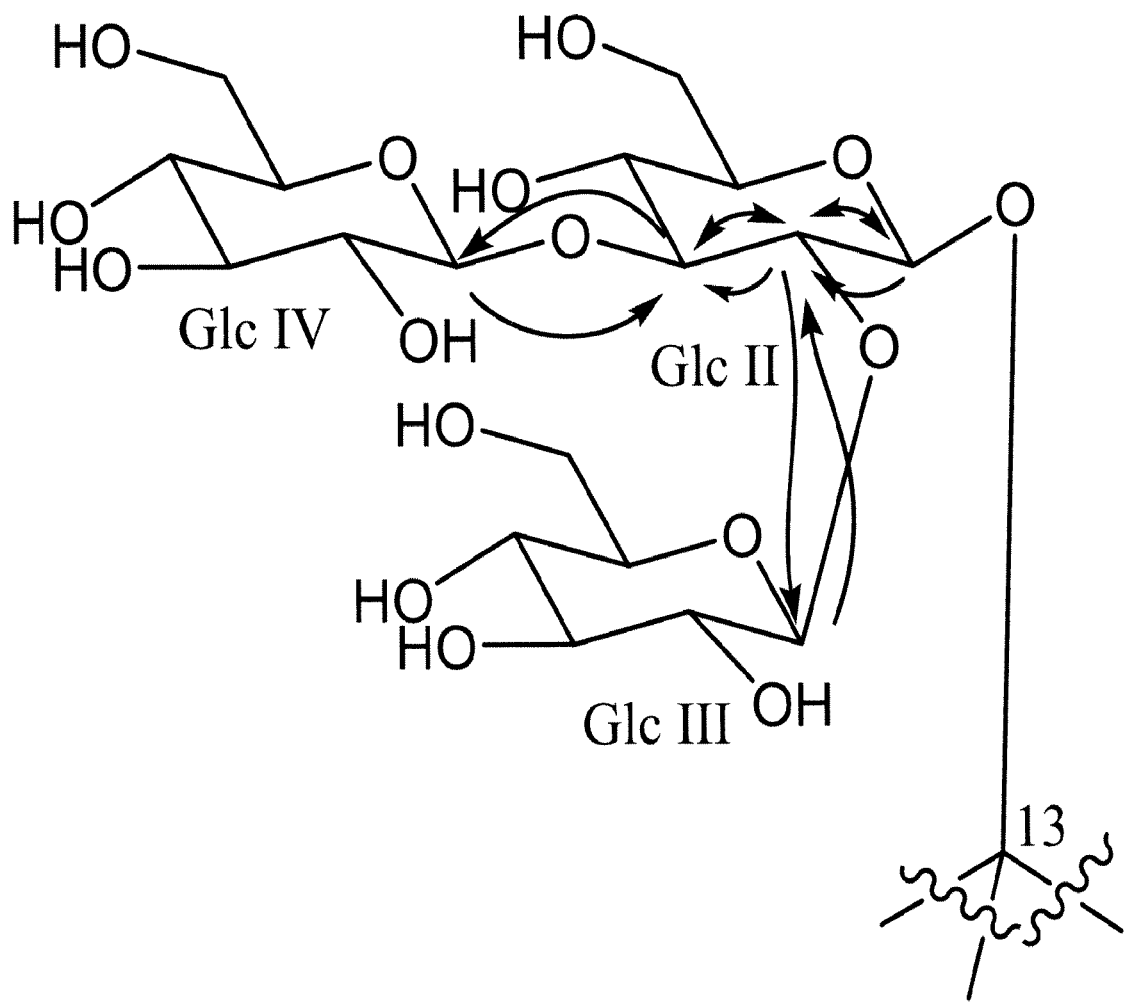
FIG. 33: Shows a summary of key HMBC and COSY correlations used to assign the C-13 glycoside region of diterpene glycoside 3.

A summary of the key HMBC and COSY correlations used to assign the C-13 glycoside region is provided in FIG. 33.

Figure 23:
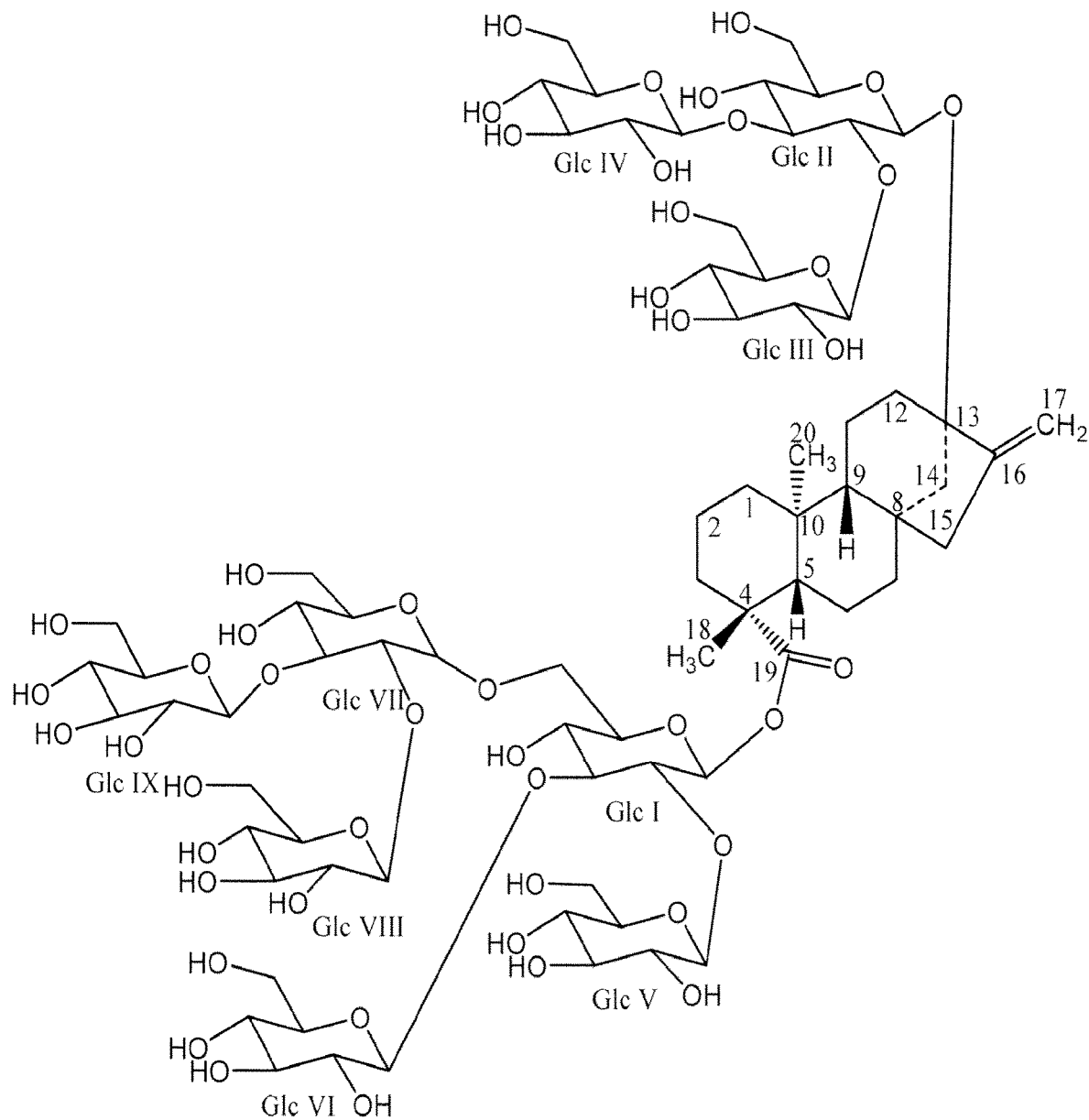
FIG. 23: Shows the structure of diterpene glycoside 3, i.e. (13-[(2-O-β-D-glucopyranosyl-3-O-β-D-glucopyranosyl)-β-D-glucopyranosyl)oxy] ent-kaur-16-en-19-oic acid-[(2-O-β-D-glucopyranosyl-3-O-β-D-glucopyranosyl-6-O-α-D-glucopyranosyl-(2-O-β-D-glucopyranosyl-3-O-β-D-glucopyranosyl)-β-D-glucopyranosyl) ester].

The structure was determined to be (13-[(2-O-β-D-glucopyranosyl-3-O-β-D-glucopyranosyl)-β-D-glucopyranosyl)oxy] ent-kaur-16-en-19-oic acid-[(2-O-β-D-glucopyranosyl-3-O-β-D-glucopyranosyl-6-O-α-D-glucopyranosyl-(2-O-β-D-glucopyranosyl-3-O-β-D-glucopyranosyl)-β-D-glucopyranosyl) ester] as shown in FIG. 23.

Example 4

Isolation and Characterization of 4

Materials. The material used for isolation was a *Stevia* extract, Lot #CB-2977-171, received from The Coca-Cola Company.

Analytical HPLC Method. HPLC analyses were performed on a Waters 2695 Alliance System coupled to a Waters 996 Photo Diode Array (PDA) detector. In addition, final sample purities were assessed using an ESA Corona Charged Aerosol Detector (CAD). Sample analyses were performed using the method conditions described in Tables 1-3.

TABLE 1

Analytical HPLC conditions for fraction analysis in primary process.

| Parameter | Description |
|---|---|
| Column | Phenomenex Synergi Hydro RP 80 Å (4.6 × 150 mm, 4 μm) @ 55° C. |
| Mobile Phases | 0.0028% $NH_4OAc$, 0.012% HOAc in water (A) |
| | Acetonitrile (B) |
| Flow Rate (mL/min) | 1.0 |
| Detection | CAD and UV at 210 nm |

| Gradient | | |
|---|---|---|
| Time (min) | % A | % B |
| 0.0-5.1 | 85.0 | 15.0 |
| 15.0-30.0 | 75.0 | 25.0 |
| 31.0-36.0 | 25.0 | 75.0 |
| 36.1 | 85.0 | 15.0 |

TABLE 2

Analytical HPLC conditions for fraction analysis in secondary process.

| Parameter | Description |
|---|---|
| Column | Phenomenex Synergi Hydro RP 80 Å (4.6 × 150 mm, 4 μm) @ 50° C. |
| Mobile Phases | 100% water (A) |
| | 100% Acetonitrile (B) |
| Flow Rate (mL/min) | 1.0 |
| Detection | CAD and UV at 210 nm |

| Gradient | | |
|---|---|---|
| Time (min) | % A | % B |
| 0.0-35.0 | 80.0 | 20.0 |
| 35.1-45.0 | 50.0 | 50.0 |
| 45.1 | 80.0 | 20.0 |

TABLE 3

Analytical HPLC conditions for analysis of final sample.

| Parameter | Description |
|---|---|
| Column | Waters Xbridge Phenyl (4.6 × 150 mm, 5 μm) @ ambient |
| Mobile Phases | 100% water (A) |
| | 100% Acetonitrile (B) |
| Flow Rate (mL/min) | 1.0 |
| Detection | CAD |

TABLE 3-continued

Analytical HPLC conditions for analysis of final sample.

| Gradient | | |
|---|---|---|
| Time (min) | % A | % B |
| 0.0-45 | 83 | 17 |
| 45.01-54 | 50 | 50 |
| 55 | 83 | 17 |

Primary Preparative HPLC Method. The primary processing was performed using a pre-packed Waters Symmetry RP18 column (50×250 mm, 7 μm). The purification process was performed with a Waters Delta Prep LC Model 2000/4000 system coupled to a UV-Vis detector. Details of the preparative method are summarized in Table 4.

TABLE 4

Conditions for primary preparative HPLC method.

| Column | Waters Symmetry Shield RP18 (50 × 250 mm, 7 μm) @ ambient |
|---|---|
| Flow Rate (mL/min) | 105 |
| Detection | UV at 210 nm |
| Mobile Phases | 15% Acetonitrile in water (A) |
| | 25% Acetonitrile in water (B) |
| | 85% Acetonitrile in water (C) |
| Load (g) | 12 |
| Sample preparation | 12 g dissolved in 40 mL of Dimethylsulfoxide, then added 80 mL of A |

| Gradient | | | |
|---|---|---|---|
| Time (min) | % A | % B | % C |
| 0.0-11.0 | 100 | 0 | 0 |
| 30.0-40.0 | 0 | 100 | 0 |
| 41.0-51.0 | 0 | 0 | 100 |
| 52.0 | 100 | 0 | 0 |

Secondary Preparative HPLC Method. The secondary processing was performed using a Phenomenex Synergi Hydro RP 80 (50×250 mm, 10 μm) column. The purification process was performed with a Waters Delta Prep LC Model 2000/4000 system coupled to a UV-Vis detector. Details of the preparative method are summarized in Table 5.

TABLE 5

Conditions for secondary preparative HPLC method.

| Column | Phenomenex Synergi Hydro RP 80 Å (50 × 250 mm, 10 μm) @ 50° C. |
|---|---|
| Flow Rate (mL/min) | 105 |
| Detection | UV at 210 nm |
| Mobile Phases | 18% Acetonitrile in water (A) |
| | 50% Acetonitrile in water (B) |
| Load | 0.5 g in 40 mL of water |
| Sample preparation | 500 mg of JAM-D-1-3, or JAM-D-10-3, or JAM-D-14-3 dissolved in 40 mL of water |

| Gradient | | |
|---|---|---|
| Time (min) | % A | % B |
| 0.0-75.0 | 100 | 0 |
| 75.1-85.1 | 0 | 100 |
| 86.0 | 100 | 0 |

Tertiary Processing Method. The tertiary processing for isolation was conducted on a Waters 2767 Auto-purification system using mass triggering for fraction collection as described in Table 6.

TABLE 6

Conditions for tertiary HPLC process.

| | |
|---|---|
| Column | Phenomenex Gemini-NX (10 × 250 mm) @ ambient |
| Mobile Phases | Water (A) Acetonitrile (B) |
| Gradient | 78% A Isocratic for 25 min followed by column flush |
| Flow Rate (mL/min) | 5 |
| Injection volume (μL) | 950 |
| Detection | Mass Range: 500-2000 m/z, ES(+/−) |

Quaternary Processing Method. The quaternary processing for isolation was conducted on a Waters 2767 Auto-purification system using mass triggering for fraction collection as described in Table 7.

TABLE 7

Conditions for quaternary HPLC process.

| | |
|---|---|
| Column | Phenomenex Gemini-NX (10 × 250 mm) @ ambient |
| Mobile Phases | Water (A) Methanol (B) |
| Gradient | 40% B to 65% B over 26 min followed by column flush |
| Flow Rate (mL/min) | 5 |
| Injection volume (μL) | 950 |
| Detection | Mass Range: 500-2000 m/z, ES(+/−) |

Quinary Processing Method. The quinary processing for isolation was conducted on a Waters 2767 Auto-purification system using mass triggering for fraction collection as described in Table 8.

TABLE 8

Conditions for quinary HPLC process.

| | |
|---|---|
| Column | Phenomenex Gemini-NX (10 × 250 mm) @ 50° C. |
| Mobile Phases | Water (A) Acetonitrile (B) |
| Gradient | 18% B isocratic for 45 min followed by column flush |
| Flow Rate (mL/min) | 5 |
| Injection volume (μL) | 950 |
| Detection | Mass Range: 500-2000 m/z, ES(+/−) |

Senary Preparative HPLC Method. The senary processing was performed using a Waters Xbridge Phenyl (19×250 mm) column. The purification process was performed with a Waters Delta Prep LC Model 2000/4000 system coupled to a UV-Vis detector. Details of the semi-preparative method are summarized in Table 9.

TABLE 9

Conditions for senary HPLC process.

| | |
|---|---|
| Column | Waters Xbridge Phenyl (19 × 250 mm, 5 μm) @ ambient |
| Flow Rate (mL/min) | 30 |
| Detection | 210 nm |
| Gradient | 16% Acetonitrile in water isocratic for 45 min |
| Load (mL) | 10 |

Isolation Procedure. Fractions collected during the final pre-concentration step were filtered through a stainless steel sieve and concentrated in vacuo using a Buchi® Rotary Evaporator, Model R-114. The concentrated solution was dried for 48-72 h using the Kinetics Flexi-Dry Personal Freeze Dryer, followed by vacuum oven drying at 37° C. for 24 h to remove residual moisture.

MS and MS/MS. MS and MS/MS data were generated with a Waters QTof Micro mass spectrometer equipped with an electrospray ionization source. The sample was analyzed by negative ESI. The sample was diluted to a concentration of 0.1 mg/mL with $H_2O$:MeCN (1:1) and introduced via flow injection for MS data acquisition, tuned for MS/MS and acquired by direct infusion.

NMR. An attempt was made to dissolve ~4.3 mg of the sample in 250 μL of $CD_3OD$+TMS, but the sample did not dissolve readily in the solvent. The undissolved solid material was observed at the bottom of the NMR tube; however, the soluble portion of the sample (~1.5 mg/250 μL) was sufficient to acquire the necessary NMR data. The $^1H$, COSY, HSQC-DEPT and NOESY NMR data were acquired on Bruker Avance 500 MHz instruments with either a 2.5 mm inverse probe or a 5 mm broad band probe. The $^{13}C$ and HMBC NMR data were acquired at the Rensselaer Polytechnic Institute using their Bruker Avance 600 MHz instrument with a 5 mm cryo-probe. The $^1H$ and $^{13}C$ NMR spectra were referenced to the TMS resonance at $\delta_H$ 0.00 ppm and $CD_3OD$ resonance at 49.0 ppm, respectively. [The NMR data was acquired in $CD_3OD$+TMS as mentioned above after a solvent screen in pyridine-$d_5$+TMS (~4 mg/170 μL), $D_2O$+TSP (~4 mg/170 μL), and DMSO-$d_6$+TMS (~4 mg/−500 μL) showed very poor solubility. The sample was recovered and blown dry under nitrogen or lyophilized between each solvent screen].

Results and Discussion

Unless otherwise noted, all solvent ratios are listed as percent by volume (v/v).

Primary Purification. Approximately 300 g of Lot #CB-2977-171 was processed using the primary preparative HPLC method described above. Collected fractions were analyzed by LC-MS using the analytical method summarized in Table 1. According to MS analysis, the presence of the [2M-H]⁻ ion at m/z 887 suggested the presence of a target with molecular weight of 1776 Daltons. Fraction 3 (Lot #JAM-D-10-3) contained the target of interest.

Secondary Purification. Lot #JAM-D-10-3 (and equivalent lots) was reprocessed with conditions summarized above. Fractions were analyzed using the analytical method summarized in Table 2. Direct injection MS (not shown) indicated that Fraction 2 (Lot #JAM-D-40-2) was of interest due to the detection of a target with molecular weight of 1776 Daltons.

Tertiary Purification. Fraction Lot #JAM-D-40-2 was reprocessed with conditions summarized above. Fractions with low level m/z 1776 targets were collected as CJP-C-128 (3, 4, 5, 7). These fractions were subsequently pooled to enhance signal strength for additional processing.

Quaternary Purification. Fraction Lot #CJP-C-128 (3, 4, 5, 7) (and equivalent lots) were reprocessed with conditions summarized above. Fraction 1, Lot #CJP-C-130(1), was isolated for additional processing.

Quinary Purification. Fraction Lot #CJP-C-130(1) (and equivalent lots) were reprocessed with conditions summarized above. Fraction 9, Lot #CJP-C-133(9), was isolated. The sample did not meet purity standards and required additional processing.

Secondary Purification. Fraction Lot #CJP-C-133(9) was reprocessed with conditions summarized above. Fraction 1, Lot #JMP-A-158(1), was isolated and analyzed using the analytical method summarized in Table 3.

Figure 35:
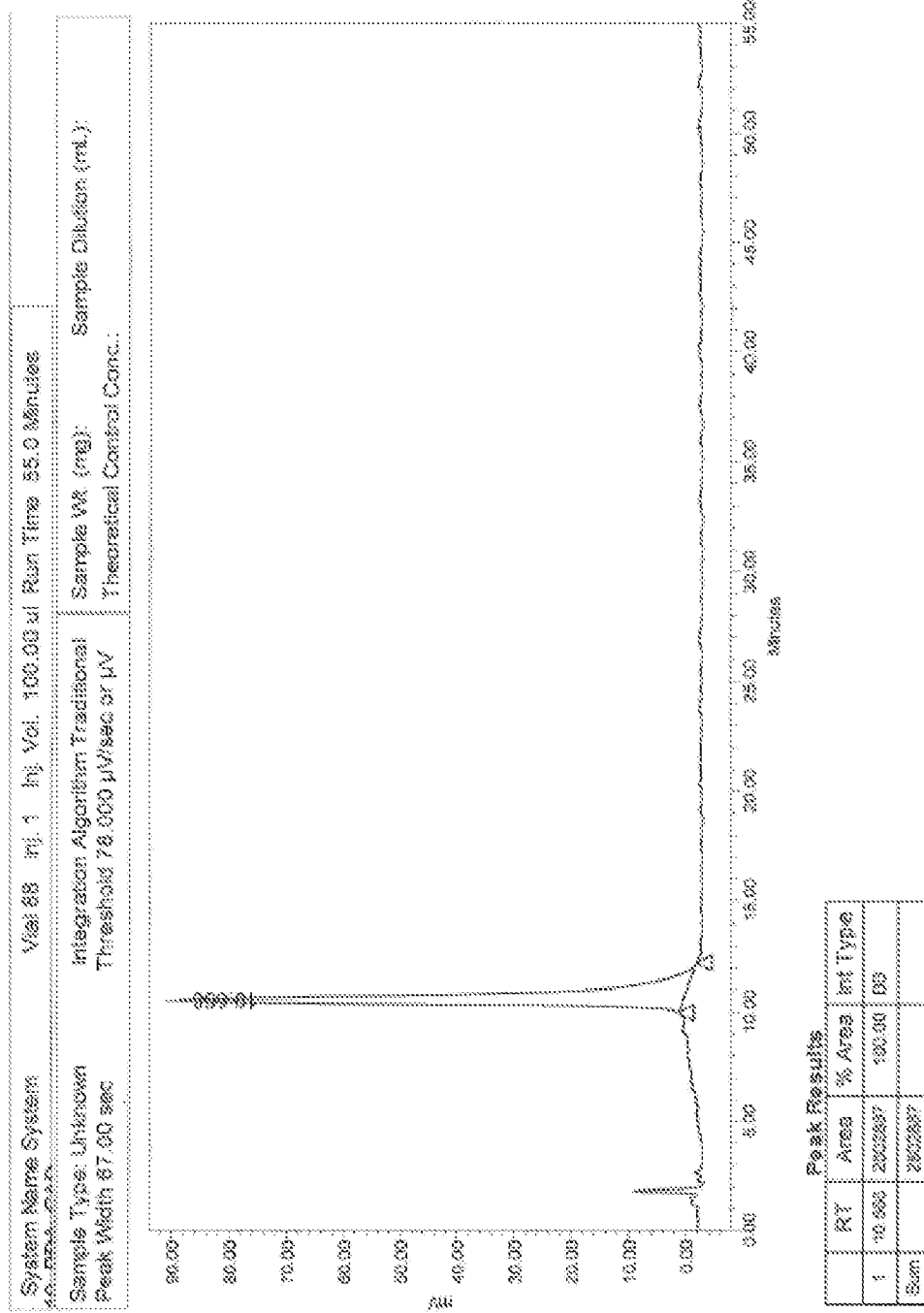
FIG. 35: Shows a HPLC trace of diterpene glycoside 4, final batch preparation, as described in Example 4, Table 3.

Final Batch Preparation. The purified solution was filtered through a stainless steel sieve to remove particulates. The solution was then concentrated by rotary evaporation and lyophilized for about 72 h. The HPLC analysis was performed using the method summarized in Table 3 and the trace is presented in FIG. 35. The final batch (4.3 mg), was isolated with >99% (AUC, CAD) purity.

Mass Spectrometry. The ESI-TOF mass spectrum showed a [M-H]$^-$ ion at m/z 1775.6680. The mass of the [M-H]$^-$ ion was in good agreement with the molecular formula $C_{74}H_{120}O_{48}$ (calcd for $C_{74}H_{119}O_{48}$: 1775.6871, error: 0.5 ppm) expected. The MS data confirmed a nominal mass of 1776 Daltons with the molecular formula, $C_{74}H_{120}O_{48}$.

The MS/MS spectrum, selecting the [M-H]$^-$ ion at m/z 1775.7 for fragmentation, indicated sequential loss of four glucose units at m/z 1613.6804, 1451.6212, 1289.5317, and 1127.4700 followed by the loss of two glucose units at m/z 803.3998 and sequential loss of three glucose units at m/z 641.3245, 479.2652, and 317.2070. The ion at m/z 971.2843 likely corresponds to cleavage of the ester linkage and subsequent loss of water from one of the six sugar units.

Figure 36:
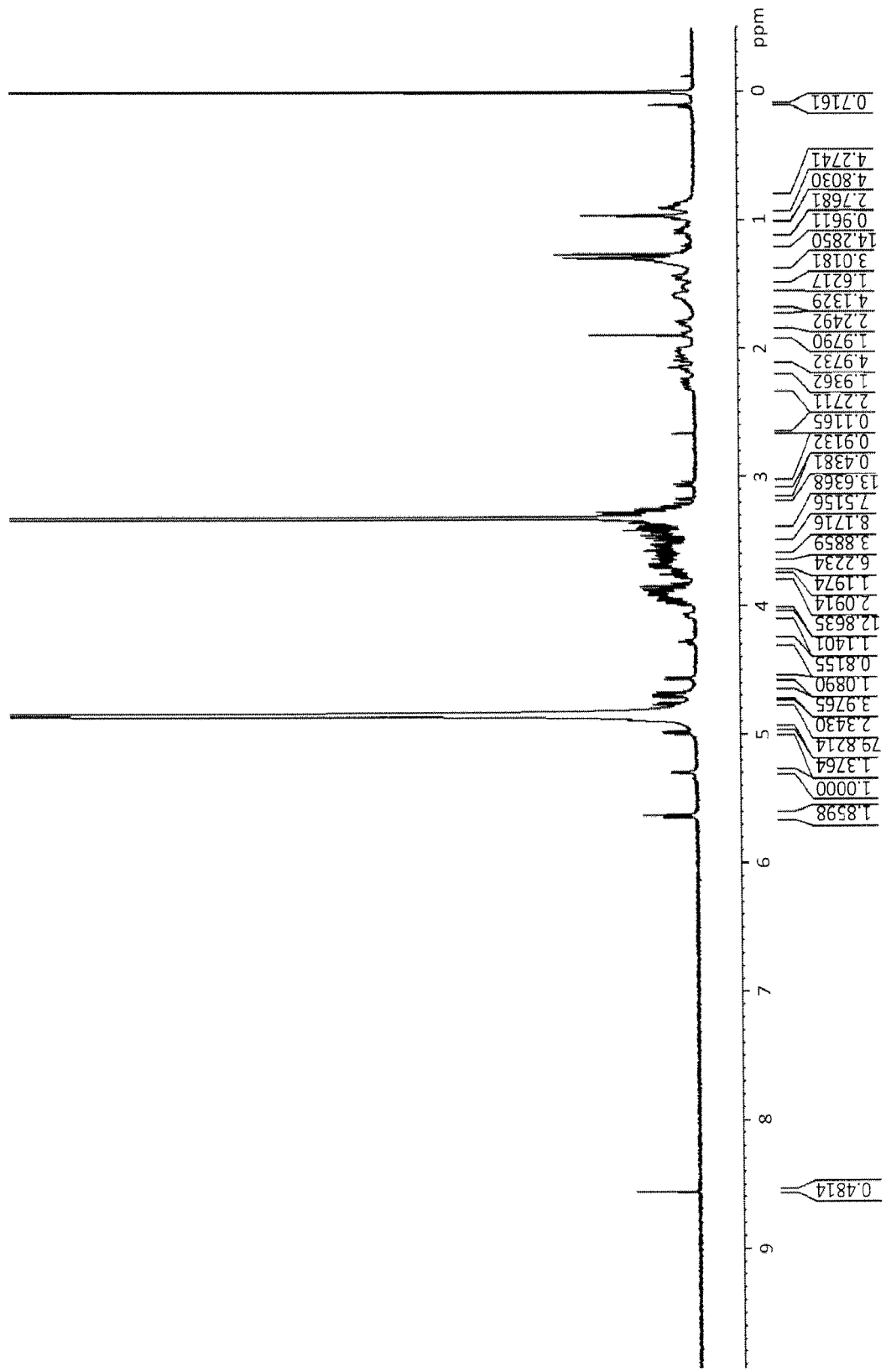
FIG. 36: Shows the $^1$H NMR spectrum (500 MHz, CD$_3$OD) of diterpene glycoside 4 at 300K.
Figure 37:
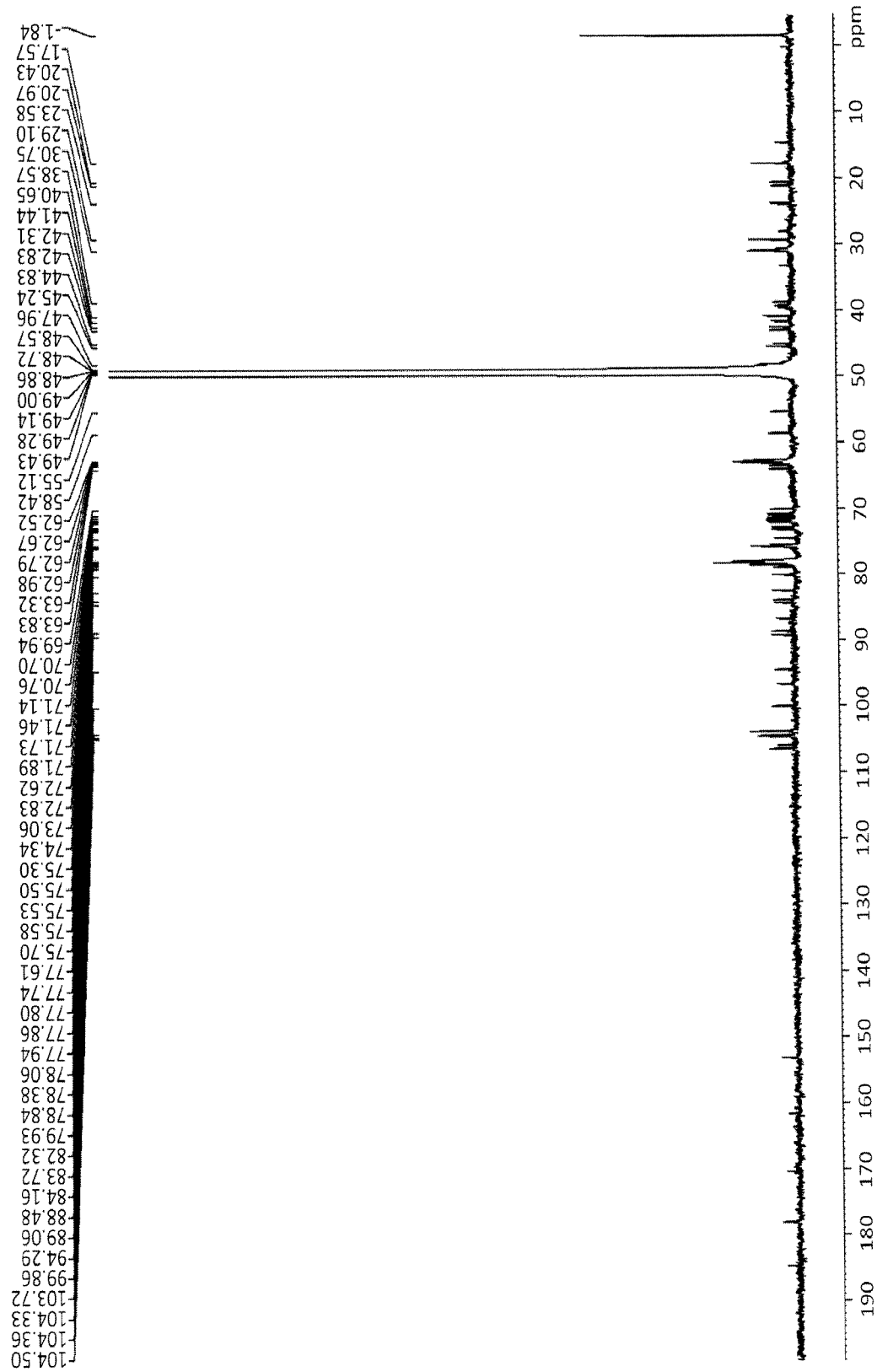
FIG. 37: Shows the $^{13}$C NMR spectrum (150 MHz, CD$_3$OD) of diterpene glycoside 4 at 300K.
Figure 38:
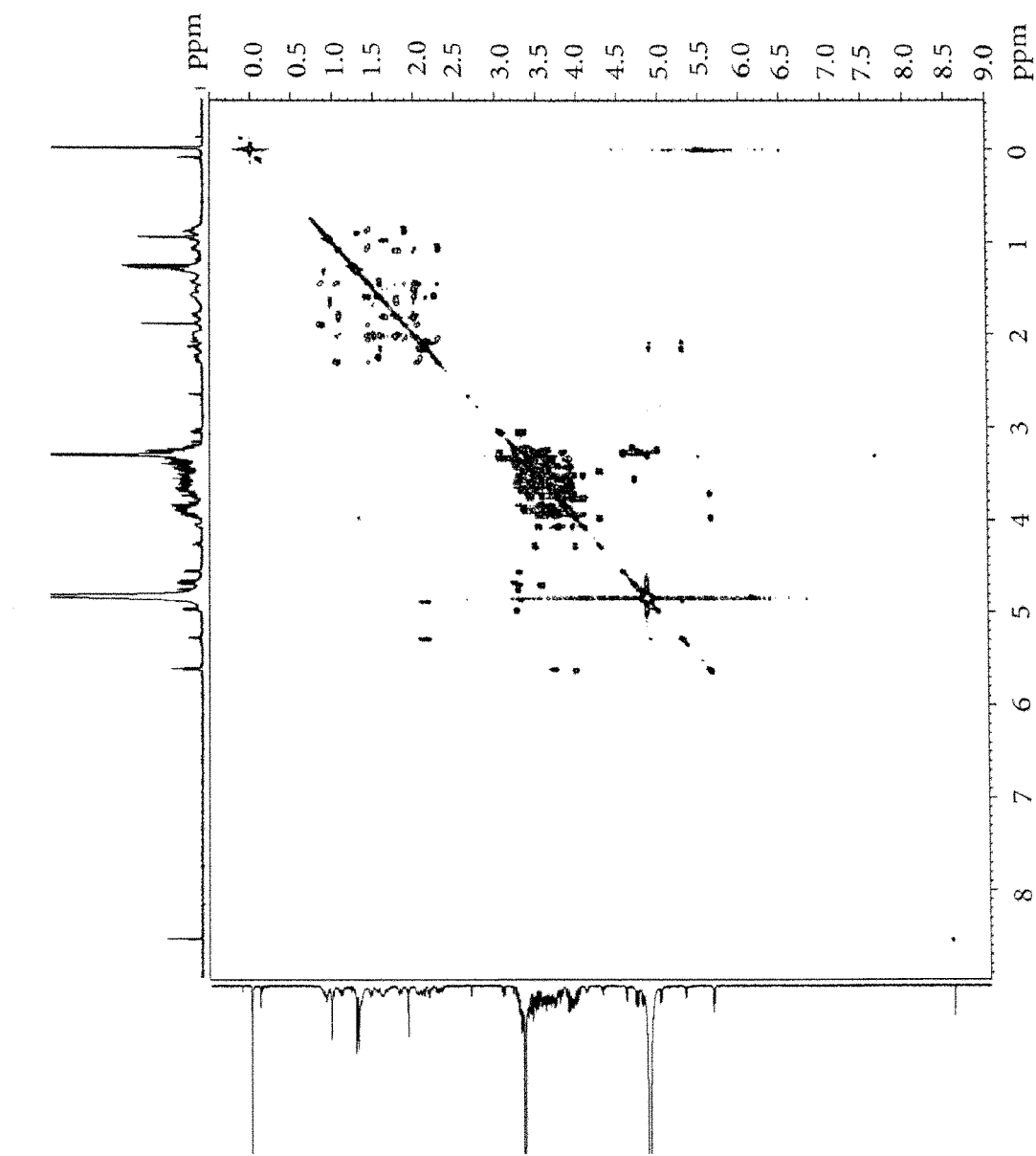
FIG. 38: Shows the $^1$H-$^1$H COSY spectrum (500 MHz, CD$_3$OD) of diterpene glycoside 4 at 300K.
Figure 39:
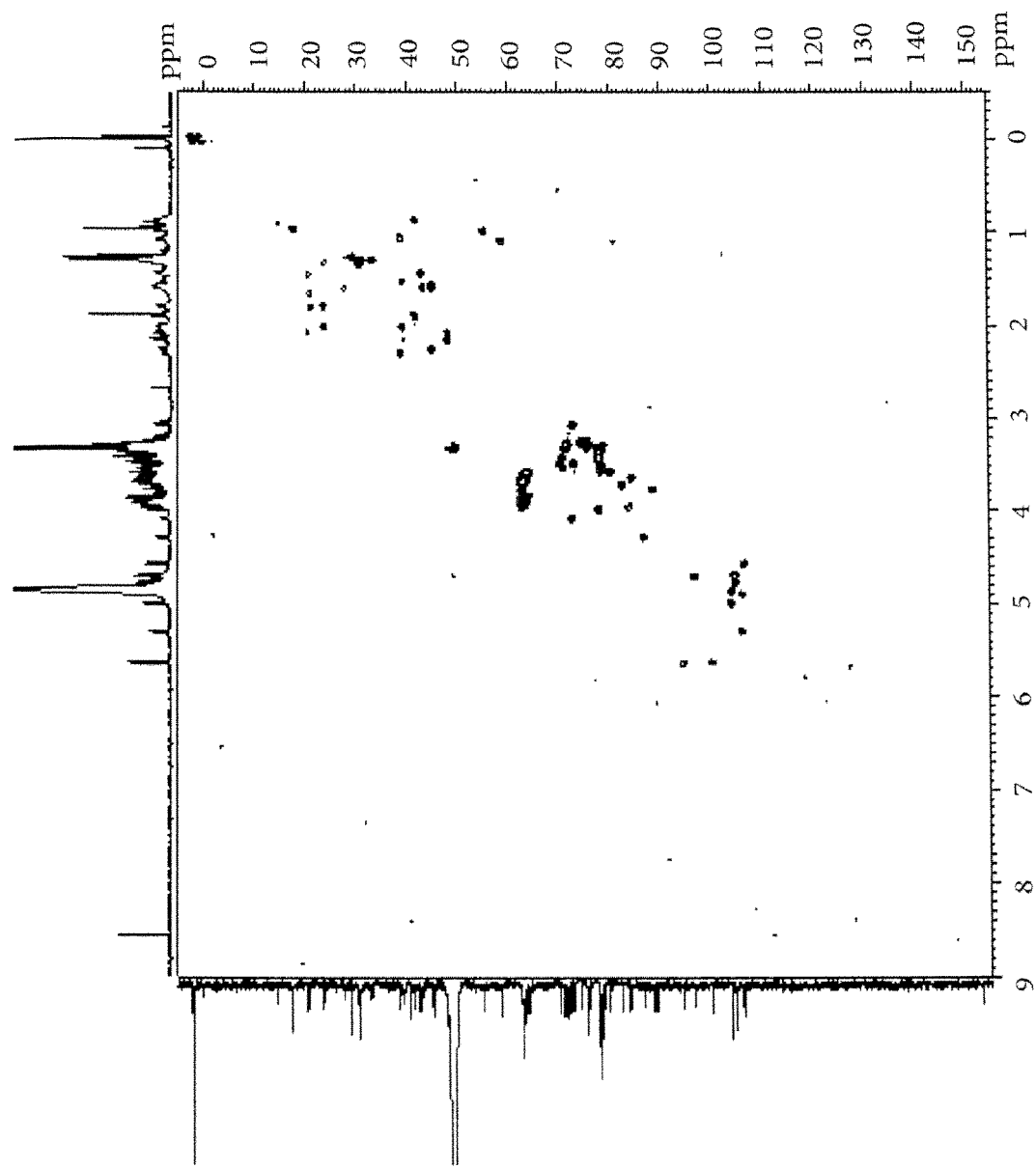
FIG. 39: Shows the HSQC-DEPT spectrum (500 MHz, CD$_3$OD) of diterpene glycoside 4 at 300K.
Figure 40:
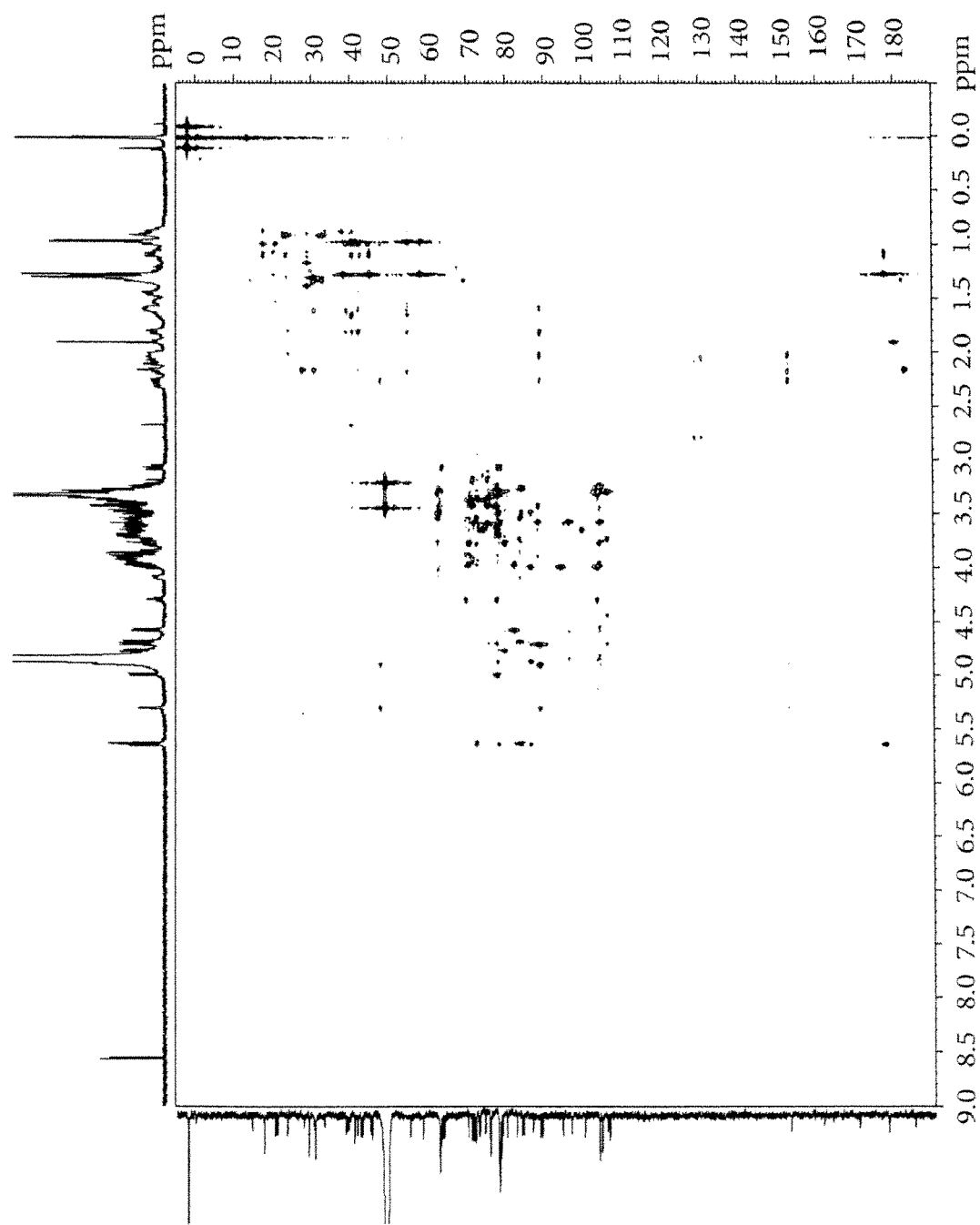
FIG. 40: Shows the HMBC spectrum (600 MHz, CD$_3$OD) of diterpene glycoside 4 at 300 K.
Figure 41:
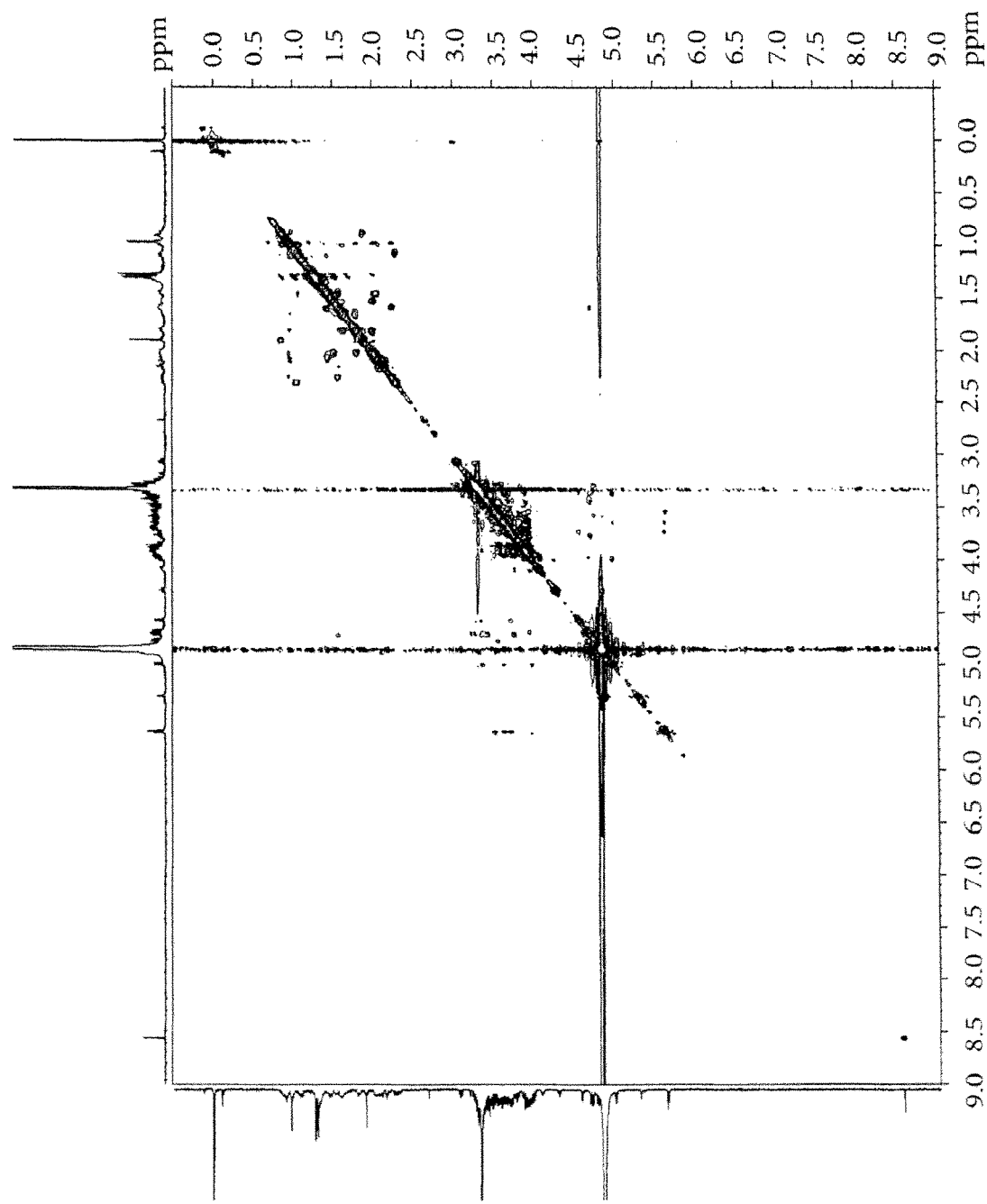
FIG. 41: Shows the NOESY spectrum (500 MHz, CD$_3$OD) of diterpene glycoside 4 at 300K.

NMR Spectroscopy. A series of NMR experiments including $^1$H NMR (FIG. 36), $^{13}$C NMR (FIG. 37), $^1$H-$^1$H COSY (FIG. 38), HSQC-DEPT (FIG. 39), HMBC (FIG. 40), NOESY (FIG. 21), and 1D TOCSY (not shown) were performed.

The 1D and 2D NMR data indicated that the central core of the glycoside is a diterpene. A HMBC correlation from the methyl protons at $\delta_H$ 1.26 to the carbonyl at $\delta_C$ 177.9 allowed assignment of one of the tertiary methyl groups (C-18) as well as C-19 and provided a starting point for the assignment of the rest of the aglycone. Additional HMBC correlations from the methyl protons (H-18) to carbons at $\delta_C$ 38.6, 45.2, and 58.4 allowed assignment of C-3, C-4, and C-5. Analysis of the $^1$H-$^{13}$C HSQC-DEPT data indicated that the carbon at $\delta_C$ 38.6 was a methylene and the carbon at $\delta_C$ 58.4 was a methine which were assigned as C-3 and C-5, respectively. This left the carbon at $\delta_C$ 45.2, which did not show a correlation in the HSQC-DEPT spectrum, to be assigned as the quaternary carbon, C-4. The $^1$H chemical shifts for C-3 ($\delta_H$ 1.06 and 2.29) and C-5 ($\delta_H$ 1.09) were assigned using the HSQC-DEPT data. A COSY correlation between one of the H-3 protons ($\delta_H$ 1.06) and a proton at $\delta_H$ 1.45 allowed assignment of one of the H-2 protons which in turn showed a correlation with a proton at $\delta_H$ 0.86 which was assigned to H-1. The remaining $^1$H and $^{13}$C chemical shifts for C-1 and C-2 were then assigned on the basis of additional COSY and HSQC-DEPT correlations.

The other tertiary methyl singlet, observed at $\delta_H$ 0.96 ($\delta_C$ 17.6), showed HMBC correlations to C-1 and C-5 and was assigned as H-20. The methyl protons showed additional HMBC correlations to a quaternary carbon ($\delta_C$ 40.6) and a methine carbon ($\delta_C$ 55.1) which were assigned as C-10 and C-9, respectively. COSY correlations between H-5 ($\delta_H$ 1.09) and protons at $\delta_H$ 1.80 and 2.00 then allowed assignment of the H-6 protons which in turn showed correlations to protons at $\delta_H$ 1.43 and 1.58 which were assigned to H-7. The $^{13}$C chemical shifts for C-6 ($\delta_C$ 23.6) and C-7 ($\delta_C$ 42.8) were then determined from the HSQC-DEPT data. COSY correlations between H-9 ($\delta_H$ 0.99) and protons at $\delta_H$ 1.65 and 1.80 allowed assignment of the H-11 protons which in turn showed COSY correlations to protons at $\delta_H$ 1.52 and 2.01 which were assigned as the H-12 protons. The HSQC-DEPT data was then used to assign C-11 ($\delta_C$ 21.0) and C-12 ($\delta_C$ 39.1). The olefinic protons observed at $\delta_H$ 4.89 and 5.29 showed HMBC correlations to a carbon at $\delta_C$ 89.1 (C-13) and were assigned to H-17 ($\delta_C$ 105.8 via HSQC-DEPT). The methine proton H-9 showed HMBC correlations to carbons at $\delta_C$ 42.3 and 44.8 which were assigned as C-8 and C-14, respectively. Additional HMBC correlations from H-9 and H-17 to a carbon at $\delta_C$ 48.0 allowed assignment of C-15. The $^1$H chemical shifts at C-14 ($\delta_H$ 1.58 and 2.25) and C-15 ($\delta_H$ 2.08 and 2.15) were assigned using the HSQC-DEPT data. HMBC correlations from H-14 ($\delta_H$ 2.25) and H-15 ($\delta_H$ 2.08) to a quaternary carbon at $\delta_C$ 153.0 allowed assignment of C-16 to complete the assignment of the central core.

Figure 42:
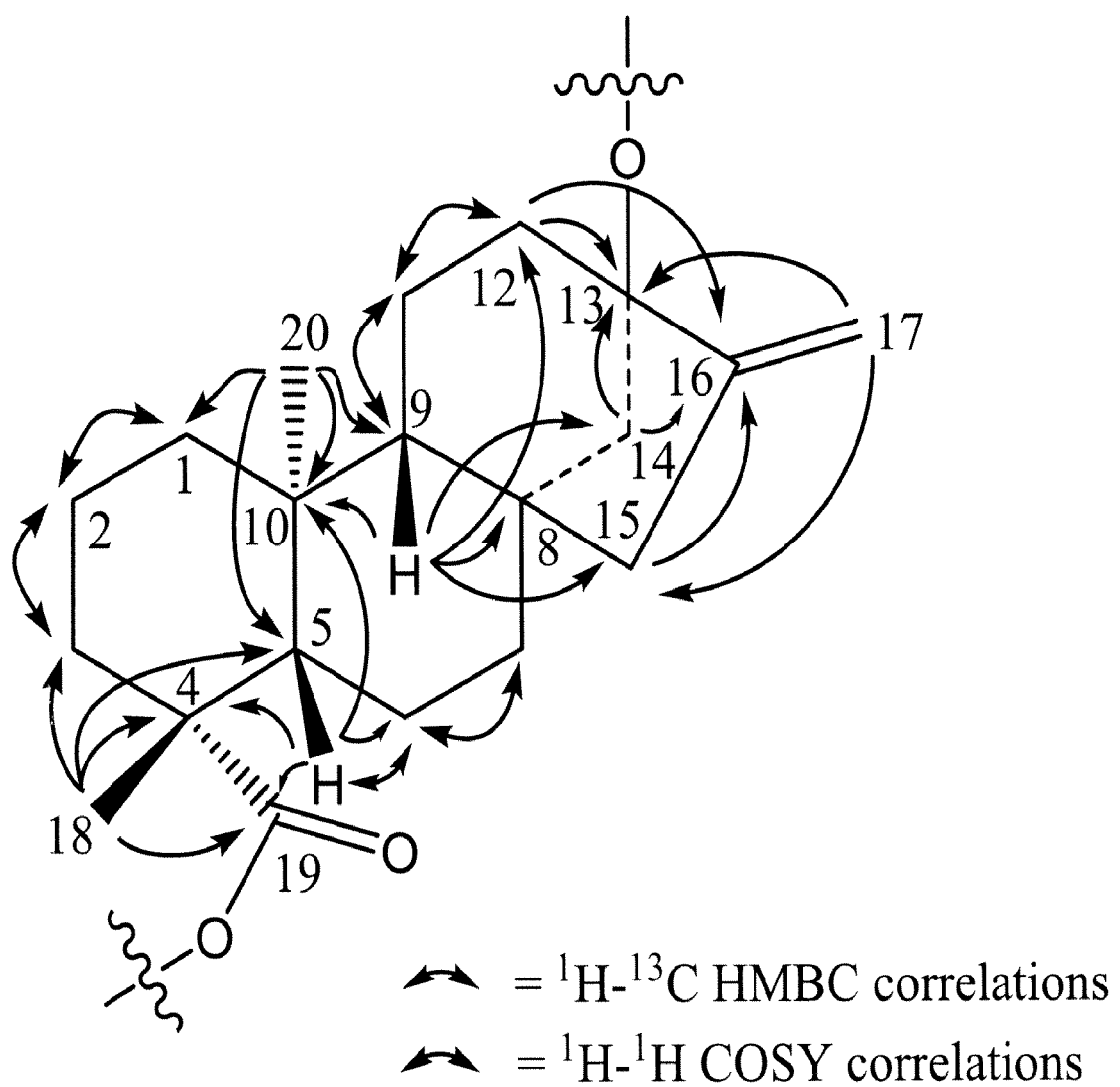
FIG. 42: Shows a summary of key HMBC and COSY correlations used to assign the aglycone region of diterpene glycoside 4.

Correlations observed in the NOESY spectrum were used to assign the relative stereochemistry of the central diterpene core. In the NOESY spectrum, NOE correlations were observed between H-14 and H-20 indicating that H-14 and H-20 are on the same face of the rings. Similarly, NOE correlations were observed between H-9 and H-5 as well as H-5 and H-18 but NOE correlations were not observed between H-9 and H-14 indicating that H-5, H-9 and H-18 were on the opposite face of the rings compared to H-14 and H-20 as presented in FIG. 42. These data thus indicated that the relative stereochemistry in the central core was retained during the glycosylation step.

Analysis of the $^1$H-$^{13}$C HSQC-DEPT data confirmed the presence of nine anomeric protons. Five of the anomeric protons were well resolved at $\delta_H$ 5.63 ($\delta_C$ 94.3), 4.98 ($\delta_C$ 103.7), 4.76 ($\delta_C$ 104.5), 4.67 ($\delta_C$ 104.3 or 104.4), and 4.56 ($\delta_C$ 106.3), one was partially overlapped with $\delta_H$ 5.63 and observed at $\delta_H$ 5.62 ($\delta_C$ 99.9) and two were overlapped at $\delta_H$ 4.70 ($\delta_C$ 104.3 or 104.4 and $\delta_C$ 96.5) in the $^1$H NMR spectrum acquired at 300 K. The remaining anomeric proton obscured by the water resonance in the $^1$H NMR spectrum acquired at 300 K was observed in the $^1$H NMR spectrum acquired at 290 K at $\delta_H$ 4.87 ($\delta_C$ 103.7). The anomeric proton at $\delta_H$ 5.62 had a small coupling (3.3 Hz) indicating that it had an α-configuration. The remaining eight anomeric protons had large couplings (7.7-8.5 Hz) indicating that they had β-configurations. The anomeric proton observed at $\delta_H$ 5.63 showed an HMBC correlation to C-19 which indicated that it corresponded to the anomeric proton of Glc$_I$. Similarly, the anomeric proton observed at $\delta_H$ 4.70 showed an HMBC correlation to C-13 allowing it to be assigned as the anomeric proton of Glc$_{II}$.

The Glc$_I$ anomeric proton ($\delta_H$ 5.63) showed a COSY correlation to a proton at $\delta_H$ 3.98 which was assigned as Glc$_I$ H-2 and in turn showed a COSY correlation to a proton at $\delta_H$ 4.28 (Glc$_I$ H-3) which showed a correlation with a proton at $\delta_H$ 3.48 (Glc$_I$ H-4). Due to data overlap the COSY spectrum did not allow assignment of the H-5 or H-6 protons. Therefore, a series of 1D TOCSY experiments were performed using selective irradiation of the Glc$_I$ anomeric proton with several different mixing times (not shown). In addition to confirming the assignments for Glc$_I$ H-2 through H-4, the TOCSY data showed a proton at $\delta_H$ 3.52 assigned as Glc$_I$ H-5 and protons at $\delta_H$ 3.69 and 3.86 assigned as the Glc$_I$ H-6 protons. The additional resonances at 3.72, 3.77, 3.94, 4.08, and 5.62 ppm in the TOCSY spectra are due to Glc$_{VII}$ H-1 since Glc$_{VII}$ H-1 at $\delta_H$ 5.62 is very close to the Glc$_I$ H-1 at $\delta_H$ 5.63 and hence was also impacted by the TOCSY irradiation pulse. The proton assignment of Glc$_I$ was further supported by the 1D TOCSY experiment performed using Glc$_I$ H-3 (not shown). The $^{13}$C chemical shifts for Glc$_I$ C-2 ($\delta_C$ 77.9), C-3 (6c 86.6), C-4 (6c 69.9), C-5 ($\delta_C$ 77.6-78.4), and C-6 (6c 62.5-63.3) were assigned using the HSQC-DEPT data to complete the assignment of Glc$_I$.

Of the eight remaining unassigned glucose moieties two were assigned as substituents at C-2 and C-3 of $Glc_I$ on the basis of HMBC correlations. The anomeric proton observed at $\delta_H$ 4.98 showed an HMBC correlation to $Glc_I$ C-2 and was assigned as the anomeric proton of $Glc_V$. The reciprocal HMBC correlation from $Glc_I$ H-2 to the anomeric carbon of $Glc_V$ was also observed. The anomeric proton observed at $\delta_H$ 4.87 showed an HMBC correlation to $Glc_I$ C-3 and was assigned as the anomeric proton of $Glc_{VI}$. The reciprocal HMBC correlation from $Glc_I$ H-3 to the anomeric carbon of $Glc_{VI}$ was also observed.

Assignment of $Glc_{VI}$ was carried out in a similar manner. The anomeric proton of $Glc_{VI}$ ($\delta_H$ 4.87) showed a COSY correlation with a proton at $\delta_H$ 3.30 which was assigned as $Glc_{VI}$ H-2. $Glc_{VI}$ C-2 ($\delta_C$ 75.3-75.7) was then assigned using the HSQC-DEPT data. Due to data overlap the COSY spectrum did not allow assignment of the remaining protons. Therefore, a series of 1D TOCSY experiments were performed using selective irradiation of the $Glc_{VI}$ anomeric proton with several different mixing times (not shown). In addition to confirming the assignments for $Glc_{VI}$ H-2, the TOCSY data allowed assignment of $Glc_{VI}$ H-3 ($\delta_H$ 3.57), H-4 ($\delta_H$ 3.28), and H-5 ($\delta_H$ 3.51). The protons observed at $\delta_H$ 3.63 and $\delta_H$ 3.93 in the TOCSY spectrum were assigned as the $Glc_{VI}$ H-6 protons. The additional resonances at $\delta_H$ 4.89 and 5.29 ppm in the TOCSY spectra are due to H-17 since one of the H-17 protons at $\delta_H$ 4.89 being very close to $Glc_{VI}$ H-1 was also impacted by the TOCSY irradiation pulse. In the TOCSY spectra, the resonance at 4.83 ppm is due to water. The $^{13}C$ chemical shifts for C-3 ($\delta_C$ 77.6-78.4), C-4 ($\delta_C$ 71.5 or 71.7 or 71.9), C-5 ($\delta_C$ 77.6-78.4), and C-6 ($\delta_C$ 62.5-63.3) were assigned using the HSQC-DEPT data to complete the assignment of $Glc_{VI}$.

The anomeric proton of $Glc_V$ ($\delta_H$ 4.98) showed a COSY correlation with a proton at $\delta_H$ 3.25 which was assigned as $Glc_V$ H-2. $Glc_V$ C-2 ($\delta_C$ 74.3) was then assigned using the HSQC-DEPT data. Due to data overlap the COSY spectrum did not allow assignment of the remaining protons. Therefore, a series of 1D TOCSY experiments were performed using selective irradiation of the $Glc_V$ anomeric proton with several different mixing times (not shown). In addition to confirming the assignments for $Glc_V$ H-2, the TOCSY data allowed assignment of $Glc_V$ H-3 ($\delta_H$ 3.63), H-4 ($\delta_H$ 3.47), and H-5 ($\delta_H$ 3.36). The protons observed at $\delta_H$ 3.67 and $\delta_H$ 3.91 in the TOCSY spectrum were assigned as the $Glc_V$ H-6 protons. The $^{13}C$ chemical shifts for $Glc_V$ C-3 ($\delta_C$ 84.2), C-4 ($\delta_C$ 73.1), C-5 ($\delta_C$ 77.6-78.4) and C-6 ($\delta_C$ 62.5-63.3) were assigned using the HSQC-DEPT data to complete the assignment of $Glc_V$. The downfield chemical shift of C-3 indicated that the hydroxyl group at C-3 is replaced by a sugar linkage. This was confirmed by HMBC correlations discussed below.

The anomeric proton of $Glc_{VII}$ at $\delta_H$ 5.62 ($\delta_C$ 99.9) showed an HMBC correlation to the carbon at $\delta_C$ 84.2 ppm ($Glc_V$ C-3) indicating that it was attached to $Glc_V$ via an 1→3 linkage. The reciprocal HMBC correlation was also observed from the methine proton of $Glc_V$ ($\delta_H$ 3.63) to the anomeric carbon of $Glc_{VII}$ at $\delta_C$ 99.9 confirming the 1→3 linkage between $Glc_{VII}$ and $Glc_V$. The anomeric proton of $Glc_{VII}$ ($\delta_H$ 5.62) showed a COSY correlation with a proton at $\delta_H$ 3.72 which was assigned as $Glc_{VII}$ H-2 and in turn showed a COSY correlation with a proton at $\delta_H$ 3.96 which was assigned as $Glc_{VII}$ H-3. $Glc_{VII}$ C-2 ($\delta_C$ 82.3) and C-3 ($\delta_C$ 83.7) were then assigned using the HSQC-DEPT data. Due to data overlap the COSY spectrum did not allow unambiguous assignment of the remaining protons. Therefore, a series of 1D TOCSY experiments were performed using selective irradiation of the $Glc_{VII}$ anomeric proton with several different mixing times (not shown). In addition to confirming the assignments for $Glc_{VII}$ H-2 and H-3, the TOCSY data allowed assignment of $Glc_{VII}$ H-4 ($\delta_H$ 3.52), and H-5 ($\delta_H$ 4.08). The proton observed at $\delta_H$ 3.77 in the TOCSY spectrum was assigned as one of the $Glc_{VII}$ H-6 protons. The other H-6 proton at $\delta_H$ 3.94 was assigned based on its COSY correlations with H-5 ($\delta_H$ 4.08) and H-6 ($\delta_H$ 3.77). The additional resonances at 3.48, 3.52, 3.69, 3.86, 3.98, 4.28, and 5.63 ppm in the TOCSY spectra are TOCSY correlations of $Glc_I$ H-1 since $Glc_I$ H-1 at $\delta_H$ 5.63 is very close to the $Glc_{VII}$ H-1 at $\delta_H$ 5.62 and was also was impacted by the TOCSY irradiation pulse. The proton assignment of $Glc_{VII}$ was further supported by the 1D TOCSY experiment performed using $Glc_{VII}$ H-5 ($\delta_H$ 4.08). The $^{13}C$ chemical shifts for $Glc_{VII}$ C-4 ($\delta_C$ 70.7 or 70.8), C-5 ($\delta_C$ 72.6) and C-6 ($\delta_C$ 62.7) were assigned using the HSQC-DEPT data to complete the assignments of $Glc_{VII}$. The HMBC correlations observed from the $Glc_{VII}$ anomeric proton ($\delta_H$ 5.62) to C-3 ($\delta_C$ 83.7) and C-5 ($\delta_C$ 72.6) further confirmed the assignments made above.

Of the five remaining unassigned glucose moieties, two glucose moieties with anomeric protons at $\delta_H$ 4.56 ($\delta_C$ 106.3) and $\delta_H$ 4.67 ($\delta_C$ 104.3 or 104.4) were assigned as substituents at C-2 and C-3 of $Glc_{VII}$ on the basis of HMBC correlations. The anomeric proton observed at $\delta_H$ 4.56 showed an HMBC correlation to $Glc_{VII}$ C-2 and was assigned as the anomeric proton of $Glc_{VIII}$. The anomeric proton observed at $\delta_H$ 4.67 showed an HMBC correlation to $Glc_{VII}$ C-3 and was assigned as the anomeric proton of $Glc_{IX}$. The reciprocal HMBC correlations from $Glc_{VII}$ H-2 to the anomeric carbon of $Glc_{VIII}$ and from $Glc_{VII}$ H-3 to the anomeric carbon of $Glc_{IX}$ were also observed.

The anomeric proton of $Glc_{VIII}$ ($\delta_H$ 4.56) showed a COSY correlation with a proton at $\delta_H$ 3.28 which was assigned as $Glc_{VIII}$ H-2. The $Glc_{VIII}$ H-2 in turn showed a COSY correlation to $Glc_{VIII}$ H-3 ($\delta_H$ 3.36). Due to data overlap the COSY spectrum did not allow assignment of the remaining protons. Therefore, a series of 1D TOCSY experiments were performed using selective irradiation of the $Glc_{VIII}$ anomeric proton with several different mixing times (not shown). In addition to confirming the assignments for $Glc_{VIII}$ H-2 and H-3, the TOCSY data allowed assignment of $Glc_{VIII}$ H-4 ($\delta_H$ 3.31) and H-5 ($\delta_H$ 3.35). The protons observed at $\delta_H$ 3.67 and $\delta_H$ 3.88 in the TOCSY spectrum were assigned as the $Glc_{VIII}$ H-6 protons. In the COSY spectrum, correlations from $Glc_{VIII}$ H-6 ($\delta_H$ 3.67 and 3.88) to $Glc_{VIII}$ H-5 ($\delta_H$ 3.35) further confirmed the assignments made above. Assignment of the $^{13}C$ chemical shifts for $Glc_{VIII}$ C-2 ($\delta_C$ 75.3-75.7), C-3 ($\delta_C$ 77.6-78.4), C-4 ($\delta_C$ 71.1), C-5 ($\delta_C$ 77.6-78.4), and C-6 ($\delta_C$ 62.5-63.3) was determined using the HSQC-DEPT data to complete the assignment of $Glc_{VIII}$.

The anomeric proton of $Glc_{IX}$ ($\delta_H$ 4.67) showed a COSY correlation with a proton at $\delta_H$ 3.23 which was assigned as $Glc_{IX}$ H-2. The $Glc_{IX}$ H-2 in turn showed a COSY correlation to $Glc_{IX}$ H-3 ($\delta_H$ 3.38). Due to data overlap the COSY spectrum did not allow assignment of the remaining protons. Therefore, a series of 1D TOCSY experiments were performed using selective irradiation of the $Glc_{IX}$ anomeric proton with several different mixing times (not shown). In addition to confirming the assignments for $Glc_{IX}$ H-2 and H-3, the TOCSY data allowed assignment of $Glc_{IX}$ H-4 ($\delta_H$ 3.27), H-5 ($\delta_H$ 3.43) and H-6 ($\delta_H$ 3.61 and 3.90). In the TOCSY spectrum additional resonances at 3.56, 3.68, 3.75, 3.87, and 4.70 ppm corresponding to $Glc_{II}$ and $Glc_{IV}$ protons were also observed since $Glc_{IX}$ H-1 at $\delta_H$ 4.67 is close to $Glc_{II}$ H-1 and $Glc_{IV}$ H-1 at $\delta_H$ 4.70. The irradiation also impacted the proton at $\delta_H$ 4.70 and thus TOCSY correlations from these anomeric protons were also observed. In the COSY spectrum, correlations from Glc$_{IX}$ H-6 ($\delta_H$ 3.61 and 3.90) to Glc$_{IX}$ H-5 ($\delta_H$ 3.43) further confirmed the assignments made above. Assignment of the $^{13}$C chemical shifts for Glc$_{IX}$ C-2 ($\delta_C$ 75.3-75.7), C-3 ($\delta_C$ 77.6-78.4), C-4 ($\delta_C$ 71.5 or 71.7 or 71.9), C-5 ($\delta_C$ 77.6-78.4), and C-6 ($\delta_C$ 62.5-63.3) was determined using the HSQC-DEPT data to complete the assignment of Glc$_{IX}$.

Figure 43:
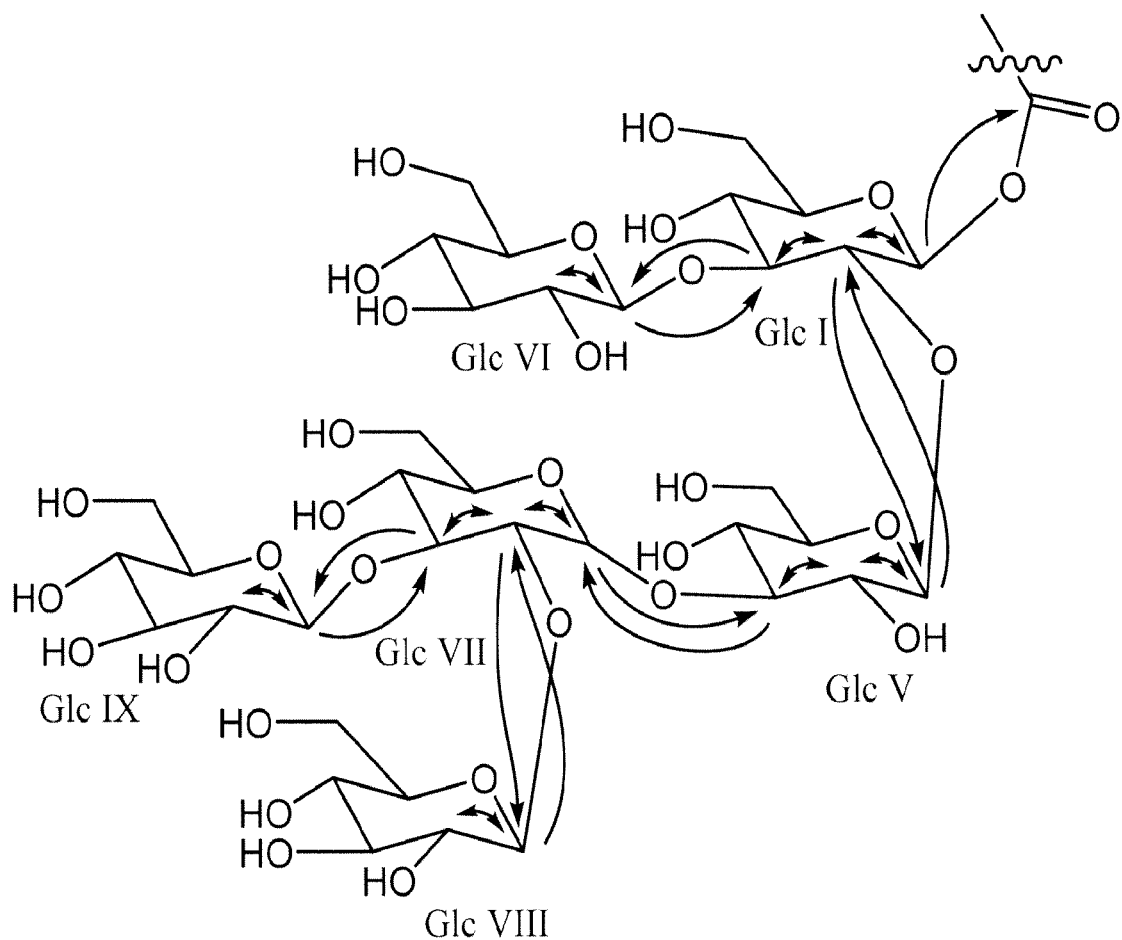
FIG. 43: Shows a summary of key HMBC and COSY correlations used to assign the C-19 glycoside region of diterpene glycoside 4.

A summary of the HMBC and COSY correlations used to assign the C-19 glycoside region is provided in FIG. 43.

Assignment of Glc$_{II}$ was carried out in a similar manner. The Glc$_{II}$ anomeric proton ($\delta_H$ 4.70) showed a COSY correlation to a proton at $\delta_H$ 3.56 which was assigned as Glc$_{II}$ H-2 and in turn showed a COSY correlation to a proton at $\delta_H$ 3.75 (Glc$_{II}$ H-3). This latter proton showed an additional correlation with a proton at $\delta_H$ 3.41 (Glc$_{II}$ H-4). H-4 also showed a COSY correlation to a proton at $\delta_H$ 3.34 (Glc$_{II}$ H-5). Glc$_{II}$ H-5 in turn showed COSY correlations to the Glc$_{II}$ H-6 protons ($\delta_H$ 3.68 and 3.87). To further confirm the above assignments, a series of 1D TOCSY experiments were performed using selective irradiation of the Glc$_{II}$ anomeric proton with several different mixing times (not shown). Since Glc$_{II}$ H-1 and Glc$_{IV}$ H-1 both have the same chemical shift ($\delta_H$ 4.70) the irradiation of the proton at $\delta_H$ 4.70 impacted the protons of both glucose moieties and TOCSY correlations for both glucose moieties were observed. However, the TOCSY experiments were helpful to confirm the proton assignments made from the COSY correlations. HMBC correlations from Glc$_{II}$ H-3 to C-2 and C-4 and also from Glc$_{II}$ H-4 to C-3 confirmed the assignments made above. Assignment of the $^{13}$C chemical shifts for Glc$_{II}$ C-2 ($\delta_C$ 79.9), C-3 ($\delta_C$ 88.5), C-4 ($\delta_C$ 70.7 or 70.8), C-5 ($\delta_C$ 77.6-78.4) and C-6 ($\delta_C$ 62.5-63.3) was based on HSQC-DEPT data to complete the assignment of Glc$_{II}$.

The remaining two unassigned glucose moieties were assigned as substituents at C-2 and C-3 of Glc$_{II}$ on the basis of HMBC correlations. The anomeric proton observed at $\delta_H$ 4.76 showed an HMBC correlation to Glc$_{II}$ C-2 and was assigned as the anomeric proton of Glc$_{III}$. The anomeric proton observed at $\delta_H$ 4.70 showed an HMBC correlation to Glc$_{II}$ C-3 and was assigned as the anomeric proton of Glc$_{IV}$. The reciprocal HMBC correlations from Glc$_{II}$ H-2 to the anomeric carbon of Glc$_{III}$ and from Glc$_{II}$ H-3 to the anomeric carbon of Glc$_{IV}$ were also observed.

The anomeric proton of Glc$_{III}$ ($\delta_H$ 4.76) showed a COSY correlation with a proton at $\delta_H$ 3.27 which was assigned as Glc$_{III}$ H-2. Glc$_{III}$ C-2 ($\delta_C$ 75.3-75.7) was then assigned using the HSQC-DEPT data. Due to data overlap the COSY spectrum did not allow assignment of the remaining protons. Therefore, a series of 1D TOCSY experiments were performed using selective irradiation of the Glc$_{III}$ anomeric proton with several different mixing times (not shown). In addition to confirming the assignments for Glc$_{III}$ H-2, the TOCSY data allowed assignment of Glc$_{III}$ H-3 ($\delta_H$ 3.34), H-4 ($\delta_H$ 3.05) and H-5 ($\delta_H$ 3.27). The protons observed at $\delta_H$ 3.57 and $\delta_H$ 3.84 in the TOCSY spectrum were assigned as the Glc$_{III}$ H-6 protons. The additional resonance at 4.83 ppm was due to water. The chemical shift of H-5 ($\delta_H$ 3.27) was further confirmed by COSY correlations between H-5 and H-6 ($\delta_H$ 3.57 and $\delta_H$ 3.84). The proton assignment of Glc$_{III}$ was further supported by the 1D TOCSY experiment performed using Glc$_I$ H-4 (not shown). The $^{13}$C chemical shifts for C-3 ($\delta_C$ 77.6-78.4), C-4 ($\delta_C$ 72.8), C-5 ($\delta_C$ 78.8) and C-6 ($\delta_C$ 63.8) were assigned using the HSQC-DEPT data to complete the assignment of Glc$_{IV}$.

The anomeric proton of Glc$_{IV}$ ($\delta_H$ 4.70) showed a COSY correlation with a proton at $\delta_H$ 3.27 which was assigned as Glc$_{IV}$ H-2 and showed a COSY correlation with a proton at $\delta_H$ 3.41 which was assigned as Glc$_{IV}$ H-3. This latter proton showed an additional correlation with a proton at $\delta_H$ 3.27 (Glc$_{IV}$ H-4). H-4 also showed a COSY correlation to a proton at $\delta_H$ 3.44 (Glc$_{IV}$ H-5). Glc$_{IV}$ H-5 in turn showed COSY correlations to the Glc$_{IV}$ H-6 protons ($\delta_H$ 3.60 and 3.92). To confirm the above assignments, a series of 1D TOCSY experiments that were performed using selective irradiation of the anomeric proton at $\delta_H$ 4.70 with several different mixing times (not shown) was utilized. Since the anomeric protons of Glc$_{IV}$ and Glc$_{II}$ were overlapped the 1D TOCSY data showed protons belonging to both sugars, however, the protons due to Glc$_{II}$ were differentiated on the basis of their COSY and HMBC correlations. Also, the TOCSY experiments were helpful to confirm the proton assignments made from the COSY correlations. Assignment of the $^{13}$C chemical shifts for Glc$_{IV}$ C-2 ($\delta_C$ 75.3-75.7), C-3 ($\delta_C$ 77.6-78.4), C-4 ($\delta_C$ 71.5 or 71.7 or 71.9), C-5 ($\delta_C$ 77.6-78.4) and C-6 ($\delta_C$ 62.5-63.3) was based on HSQC-DEPT data to complete the assignment of Glc$_{IV}$.

Figure 44:
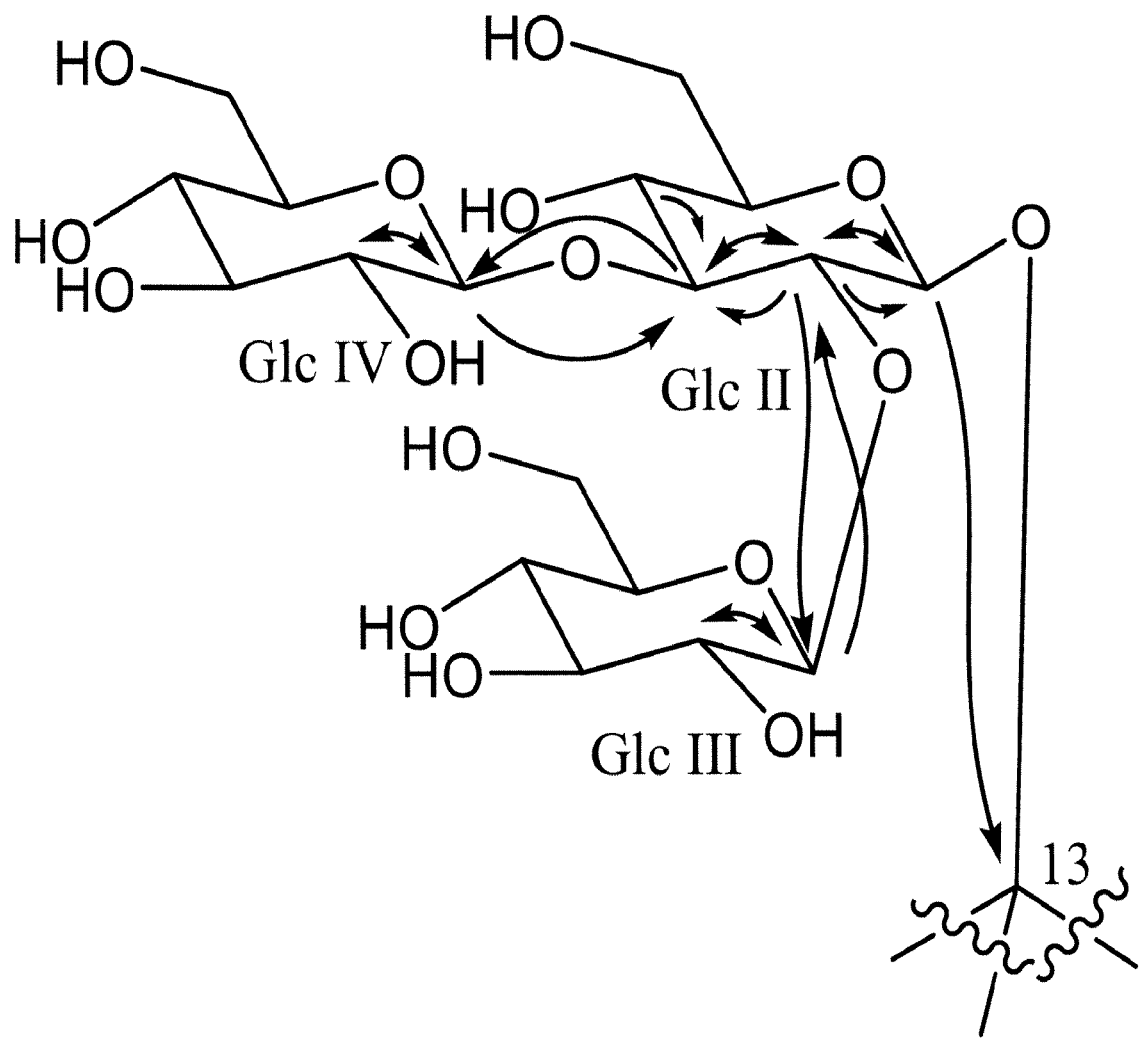
FIG. 44: Shows a summary of key HMBC and COSY correlations used to assign the C-13 glycoside region of diterpene glycoside 4.

A summary of the key HMBC and COSY correlations used to assign the C-13 glycoside region is provided in FIG. 44.

Figure 34:
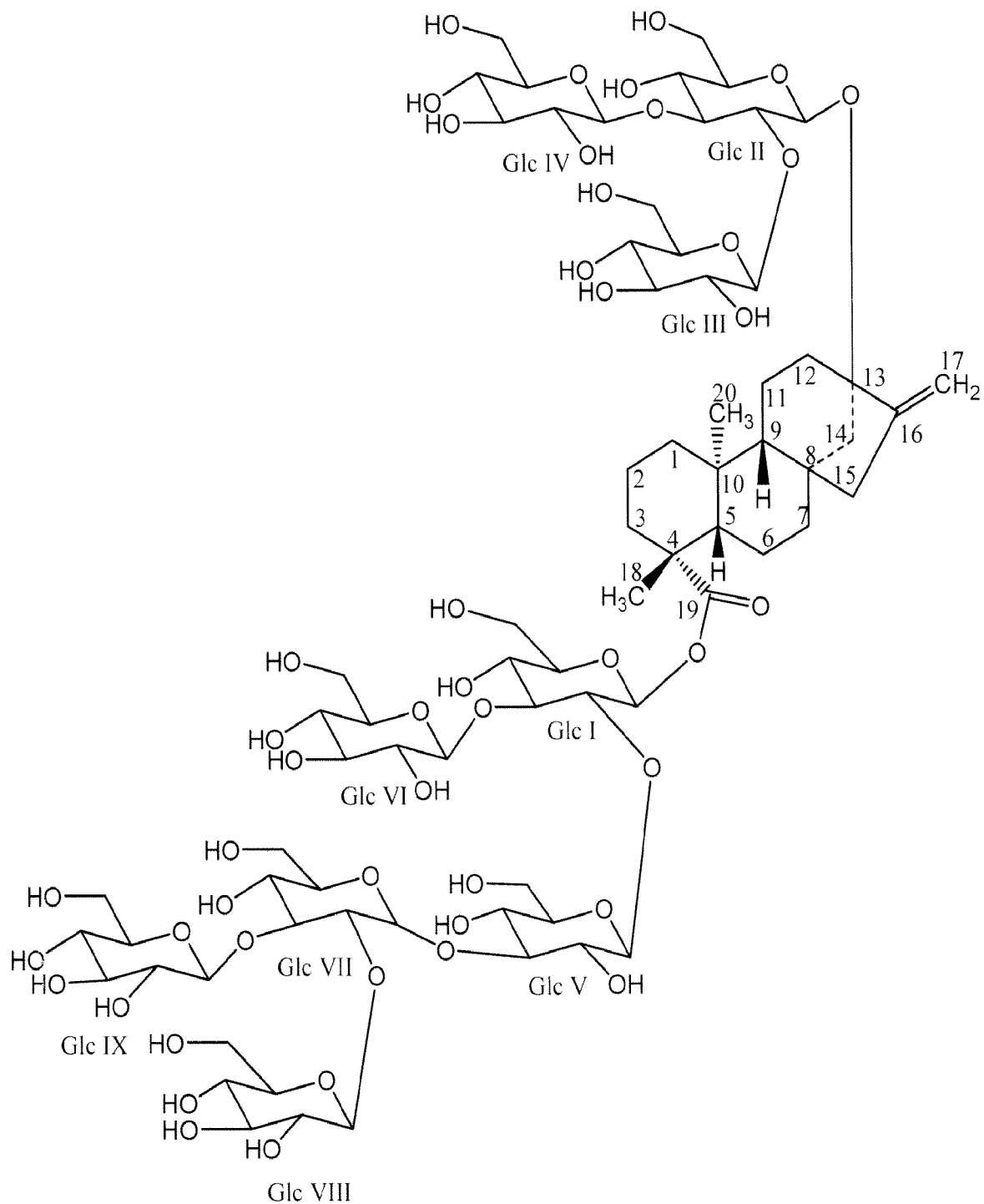
FIG. 34: Shows the structure of diterpene glycoside 4, i.e, (13-[(2-O-β-D-glucopyranosyl-3-O-β-D-glucopyranosyl)-β-D-glucopyranosyl)oxy] ent-kaur-16-en-19-oic acid-[(2-O-β-D-glucopyranosyl-β-O-α-D-glucopyranosyl-(2-O-β-D-glucopyranosyl-3-O-β-D-glucopyranosyl)-3-O-β-D-glucopyranosyl)-β-D-glucopyranosyl) ester].

The structure was determined to be (13-[(2-O-β-D-glucopyranosyl-3-O-β-D-glucopyranosyl)-β-D-glucopyranosyl)oxy] ent-kaur-16-en-19-oic acid-[(2-O-β-D-glucopyranosyl-β-O-α-D-glucopyranosyl-(2-O-β-D-glucopyranosyl-3-O-β-D-glucopyranosyl)-3-O-β-D-glucopyranosyl)-β-D-glucopyranosyl) ester] as shown in FIG. 34.

Example 5

Isolation and Characterization of 5

Materials. The material used for the isolation was a *Stevia* extract, Lot #CB-2977-171, received from The Coca-Cola Company.

Analytical HPLC Method. HPLC analyses were performed on a Waters 2695 Alliance System coupled to a Waters 996 Photo Diode Array (PDA) detector. In addition, final sample purities were assessed using an ESA Corona Charged Aerosol Detector (CAD). Sample analyses were performed using the method conditions described in Tables 1-3.

TABLE 1

Analytical HPLC conditions for fraction analysis in primary process.

| Parameter | Description |
|---|---|
| Column | Phenomenex Synergi Hydro RP 80 Å (4.6 × 150 mm, 4 µm) @ 55° C. |
| Mobile Phases | 0.0028% NH$_4$OAc, 0.012% HOAc in water (A) Acetonitrile (B) |
| Flow Rate (mL/min) | 1.0 |
| Detection | CAD and UV at 210 nm |

| Gradient | | |
|---|---|---|
| Time (min) | % A | % B |
| 0.0-5.1 | 85.0 | 15.0 |
| 15.0-30.0 | 75.0 | 25.0 |
| 31.0-36.0 | 25.0 | 75.0 |
| 36.1 | 85.0 | 15.0 |

TABLE 2

Analytical HPLC conditions for fraction analysis in secondary process.

| Parameter | Description |
|---|---|
| Column | Phenomenex Synergi Hydro RP80 Å (4.6 × 150 mm, 4 μm) @ 50° C. |
| Mobile Phases | 100% water (A) |
| | 100% Acetonitrile (B) |
| Flow Rate (mL/min) | 1.0 |
| Detection | CAD and UV at 210 nm |

| Gradient | | |
|---|---|---|
| Time (min) | % A | % B |
| 0.0-35.0 | 80.0 | 20.0 |
| 35.1-45.0 | 50.0 | 50.0 |
| 45.1 | 80.0 | 20.0 |

TABLE 3

Analytical HPLC conditions for analysis of final sample.

| Parameter | Description |
|---|---|
| Column | Waters Xbridge Phenyl (4.6 × 150 mm, 5 μm) @ ambient |
| Mobile Phases | 100% water (A) |
| | 100% Acetonitrile (B) |
| Flow Rate (mL/min) | 1.0 |
| Detection | CAD |

| Gradient | | |
|---|---|---|
| Time (min) | % A | % B |
| 0.0-45 | 83 | 17 |
| 45.01-54 | 50 | 50 |
| 55 | 83 | 17 |

Primary Preparative HPLC Method. The primary processing was performed using a pre-packed Waters Symmetry RP18 column (50×250 mm, 7 μm). The purification process was performed with a Waters Delta Prep LC Model 2000/4000 system coupled to a UV-Vis detector. Details of the preparative method are summarized in Table 4.

TABLE 4

Conditions for primary preparative HPLC method.

| Column | Waters Symmetry Shield RP18 (50 × 250 mm, 7 μm) @ ambient |
|---|---|
| Flow Rate (mL/min) | 105 |
| Detection | UV at 210 nm |
| Mobile Phases | 15% Acetonitrile in water (A) |
| | 25% Acetonitrile in water (B) |
| | 85% Acetonitrile in water (C) |
| Load (g) | 12 |
| Sample preparation | 12 g dissolved in 40 mL of Dimethylsulfoxide, then added 80 mL of A |

| Gradient | | | |
|---|---|---|---|
| Time (min) | % A | % B | % C |
| 0.0-11.0 | 100 | 0 | 0 |
| 30.0-40.0 | 0 | 100 | 0 |
| 41.0-51.0 | 0 | 0 | 100 |
| 52.0 | 100 | 0 | 0 |

Secondary Preparative HPLC Method. The secondary processing was performed using a Phenomenex Synergi Hydro RP 80 (50×250 mm, 10 μm) column. The purification process was performed with a Waters Delta Prep LC Model 2000/4000 system coupled to a UV-Vis detector. Details of the preparative method are summarized in Table 5.

TABLE 5

Conditions for secondary preparative HPLC method.

| Column | Phenomenex Synergi Hydro RP 80 Å (50 × 250 mm, 10 μm) @ 50° C. |
|---|---|
| Flow Rate (mL/min) | 105 |
| Detection | UV at 210 nm |
| Mobile Phases | 18% Acetonitrile in water (A) |
| | 50% Acetonitrile in water (B) |
| Load | 0.5 g in 40 mL of water |
| Sample preparation | 500 mg dissolved in 40 mL of water |

| Gradient | | |
|---|---|---|
| Time (min) | % A | % B |
| 0.0-75.0 | 100 | 0 |
| 75.1-85.1 | 0 | 100 |
| 86.0 | 100 | 0 |

Tertiary Processing Method. The tertiary processing for isolation was conducted on a Waters 2767 Auto-purification system using mass triggering for fraction collection as described in Table 6.

TABLE 6

Conditions for tertiary HPLC process.

| Column | Phenomenex Gemini-NX (10 × 250 mm) @ ambient |
|---|---|
| Mobile Phases | Water (A) |
| | Acetonitrile (B) |
| Gradient | 78% A Isocratic for 15 min followed by column flush |
| Flow Rate (mL/min) | 5 |
| Injection volume (μL) | 950 |
| Detection | Mass Range: 500-2000 m/z, ES(+/−) |

Quaternary Processing Method. The quaternary processing for isolation was conducted on a Waters 2767 Auto-purification system using mass triggering for fraction collection as described in Table 7.

TABLE 7

Conditions for quaternary HPLC process.

| Column | Phenomenex Gemini-NX (10 × 250 mm) @ ambient |
|---|---|
| Mobile Phases | Water (A) |
| | Methanol (B) |
| Gradient | 40% B to 65% B over 20 min followed by column flush |
| Flow Rate (mL/min) | 5 |
| Injection volume (μL) | 950 |
| Detection | Mass Range: 500-2000 m/z, ES(+/−) |

Quinary Processing Method. The quinary processing was conducted on a Waters 2767 Auto-purification system using mass triggering for fraction collection as described in Table 8.

TABLE 8

Conditions for quinary HPLC process.

| Column | Phenomenex Gemini-NX (10 × 250 mm) @ 50° C. |
|---|---|
| Mobile | Water (A) |

TABLE 8-continued

Conditions for quinary HPLC process.

| | |
|---|---|
| Phases | Acetonitrile (B) |
| Gradient | 18% B isocratic for 25 min followed by column flush |
| Flow Rate (mL/min) | 5 |
| Injection volume (µL) | 950 |
| Detection | Mass Range: 500-2000 m/z, ES(+/−) |

Senary Preparative HPLC Method. The senary processing was performed using a Waters Xbridge Phenyl (19×250 mm) column. The purification process was performed with a Waters Delta Prep LC Model 2000/4000 system coupled to a UV-Vis detector. Details of the semi-preparative method are summarized in Table 9.

TABLE 9

Conditions for senary HPLC process.

| | |
|---|---|
| Column | Waters Xbridge Phenyl (19 × 250 mm, 5 µm) @ ambient |
| Flow Rate (mL/min) | 30 |
| Detection | 210 nm |
| Gradient | 16% Acetonitrile in water isocratic for 45 min |
| Load (mL) | 10 |

Isolation Procedure. Fractions collected during the final pre-concentration step were filtered through a stainless steel sieve and concentrated in vacuo using a Buchi® Rotary Evaporator, Model R-114. The concentrated solution was dried for 48-72 h using the Kinetics Flexi-Dry Personal Freeze Dryer, followed by vacuum oven drying at 37° C. for 24 h to remove residual moisture.

MS and MS/MS. MS and MS/MS data were generated with a Waters QTof Micro mass spectrometer equipped with an electrospray ionization source. The sample was analyzed by negative ESI. The sample was diluted to a concentration of 0.25 mg/mL with $H_2O$:MeCN (1:1) and introduced via flow injection for MS data acquisition, tuned for MS/MS and acquired by direct infusion.

NMR. The sample was prepared by dissolving ~1 mg in 200 µL of $CD_3OD$+TMS and NMR data were acquired on a Bruker Avance 500 MHz instrument equipped with a 2.5 mm inverse probe. Selected 2D and the $^{13}C$ NMR data were acquired using Rensselaer Polytechnic Institutes Bruker Avance 800 MHz and 600 MHz instruments equipped with 5 mm cryoprobes, respectively. The $^1H$ and $^{13}C$ NMR spectra were referenced to the TMS signal ($\delta_H$ 0.00 ppm and $\delta_C$ 0.0 ppm).

Results and Discussion

Unless otherwise noted, all solvent ratios are listed as percent by volume (v/v).

Primary Purification. Approximately 300 g of Lot #CB-2977-171 was processed using the primary preparative HPLC method described above. Collected fractions were analyzed by LC-MS using the analytical method summarized in Table 1. According MS analysis, the presence of a target with a [M-H]⁻ ion of m/z 1613 Daltons was identified. Fraction 3 (Lot #JAM-D-10-3) contained the target of interest.

Secondary Purification. Lot #JAM-D-10-3 (and equivalent lots) was reprocessed with conditions summarized above. Fractions were analyzed using the analytical method summarized in Table 2. Direct injection MS (not shown) indicated that Fraction 3 (Lot #JAM-D-40-3) was of interest due to the detection of a target with a [M-H]⁻ ion of m/z 1613.

Tertiary Purification. Fraction Lot #JAM-D-40-3 was reprocessed with conditions summarized above. A [M-H]⁻ ion of m/z 1613 was detected in fraction Lot #CJP-C-123(1). This fraction was concentrated for further processing.

Quaternary Purification. Fraction Lot #CJP-C-123(1) was reprocessed with conditions summarized above. Collected fraction Lot #CJP-C-125(2) was reprocessed to improve purity.

Quinary Purification. Fraction Lot #CJP-C-125(2) was reprocessed with conditions summarized above. CJP-C-127(1) was collected within purity specifications for further spectroscopic analysis.

Senary Purification. A final purification of CJP-C-127(1) was completed as described above. JMP-A-163(1) was collected as pure target compound.

Figure 46:
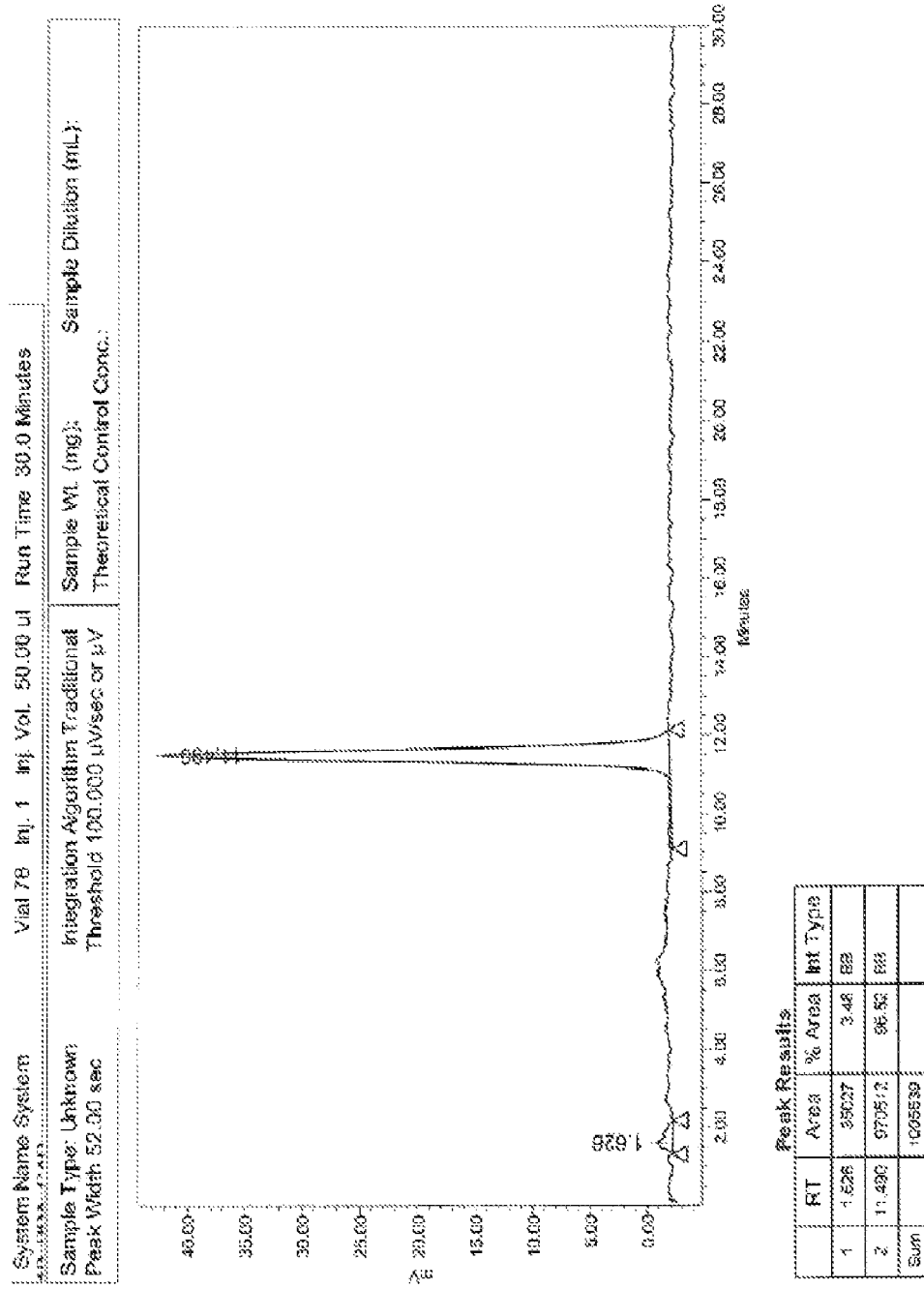
FIG. 46: Shows a HPLC trace of diterpene glycoside 5, final batch preparation, as described in Example 5.

Final Batch Preparation. The purified solution was filtered through a stainless steel sieve to remove particulates. The solution was then concentrated by rotary evaporation and lyophilized for about 72 h. The HPLC analysis was performed using the method summarized in Table 3 and the trace is presented in FIG. 46. The final batch (1.1 mg), at >99% (AUC, CAD) purity, was submitted for structural identification.

Mass Spectrometry. The ESI-TOF mass spectrum showed a [M-H]⁻ ion at m/z 1613.6368. The mass of the [M-H]⁻ ion was in good agreement with the molecular formula $C_{68}H_{110}O_{43}$ (calcd for $C_{68}H_{109}O_{43}$: 1613.6343, error: 1.5 ppm) expected. The MS data confirmed a nominal mass of 1614 Daltons with the molecular formula, $C_{68}H_{110}O_{43}$.

The MS/MS spectrum, selecting the [M-H]⁻ ion at m/z 1613.3 for fragmentation, indicated sequential loss of eight glucose units at m/z 1451.7968, 1289.7245, 1127.6445, 965.5809, 803.4899, 641.4058, 479.2658 and 317.2298.

Figure 47:
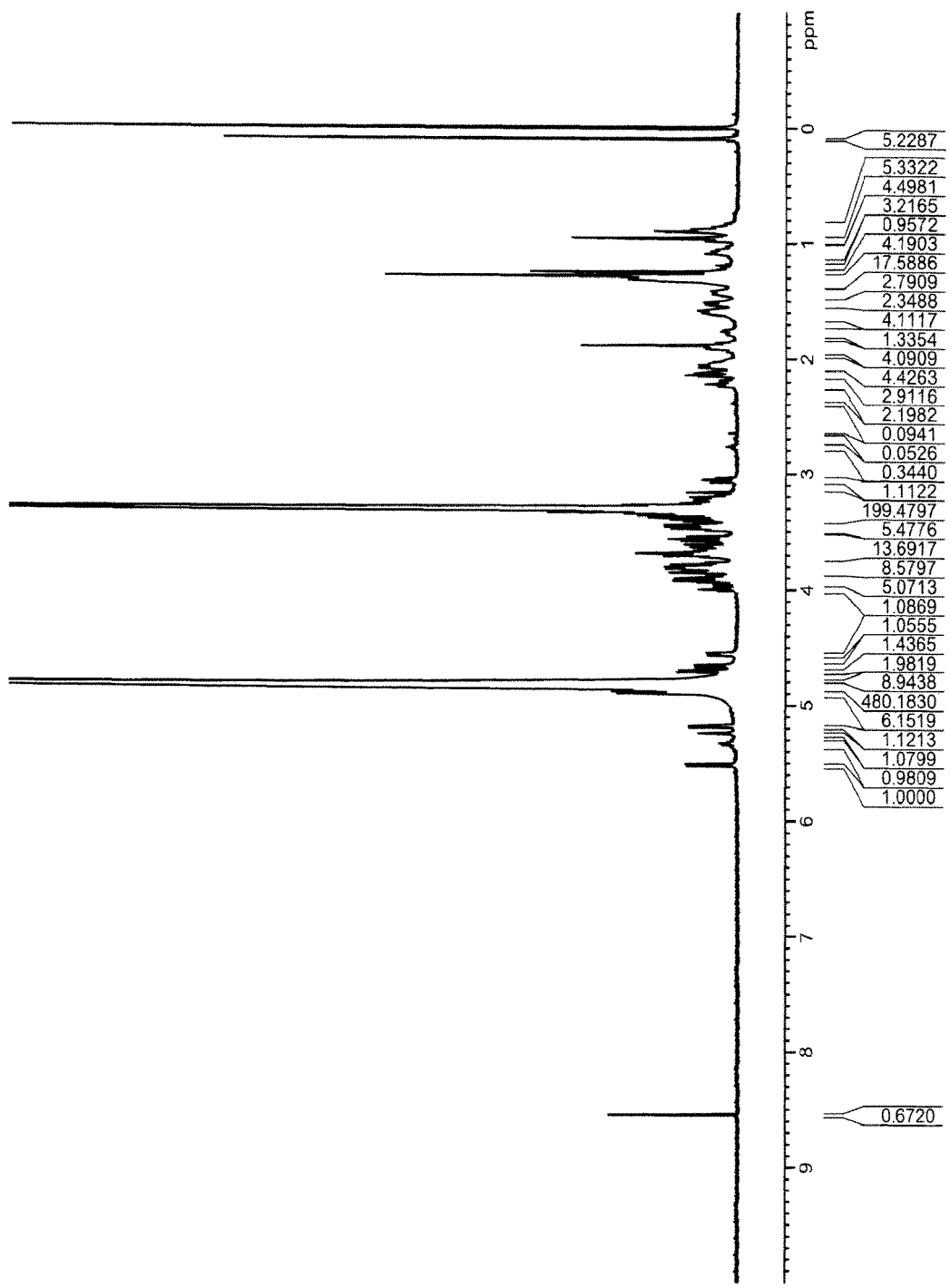
FIG. 47: Shows the $^1$H NMR spectrum (500 MHz, CD$_3$OD) of diterpene glycoside 5 at 300K.
Figure 48:
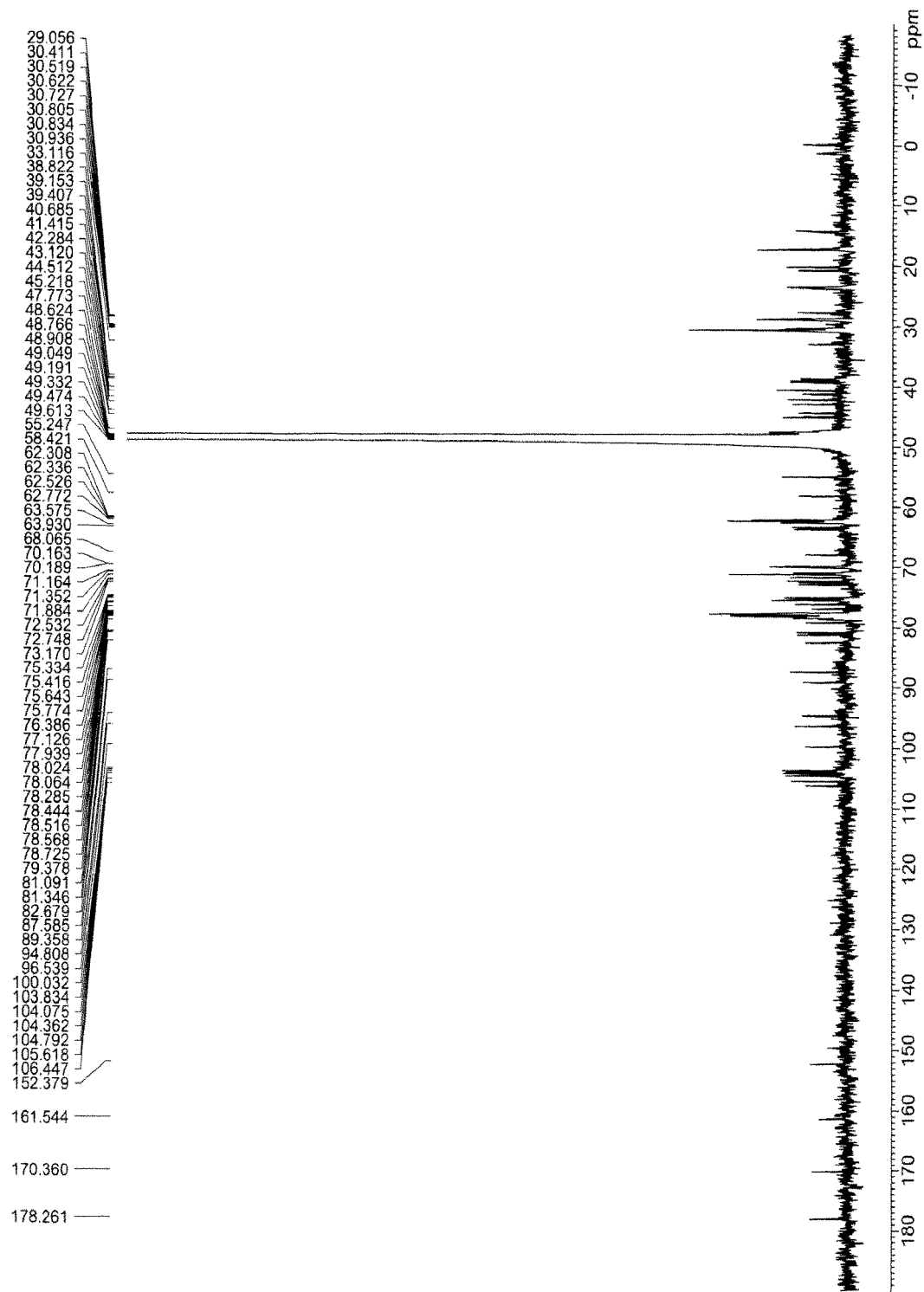
FIG. 48: Shows the $^{13}$C NMR spectrum (150 MHz, CD$_3$OD) of diterpene glycoside 5 at 300K.
Figure 49:
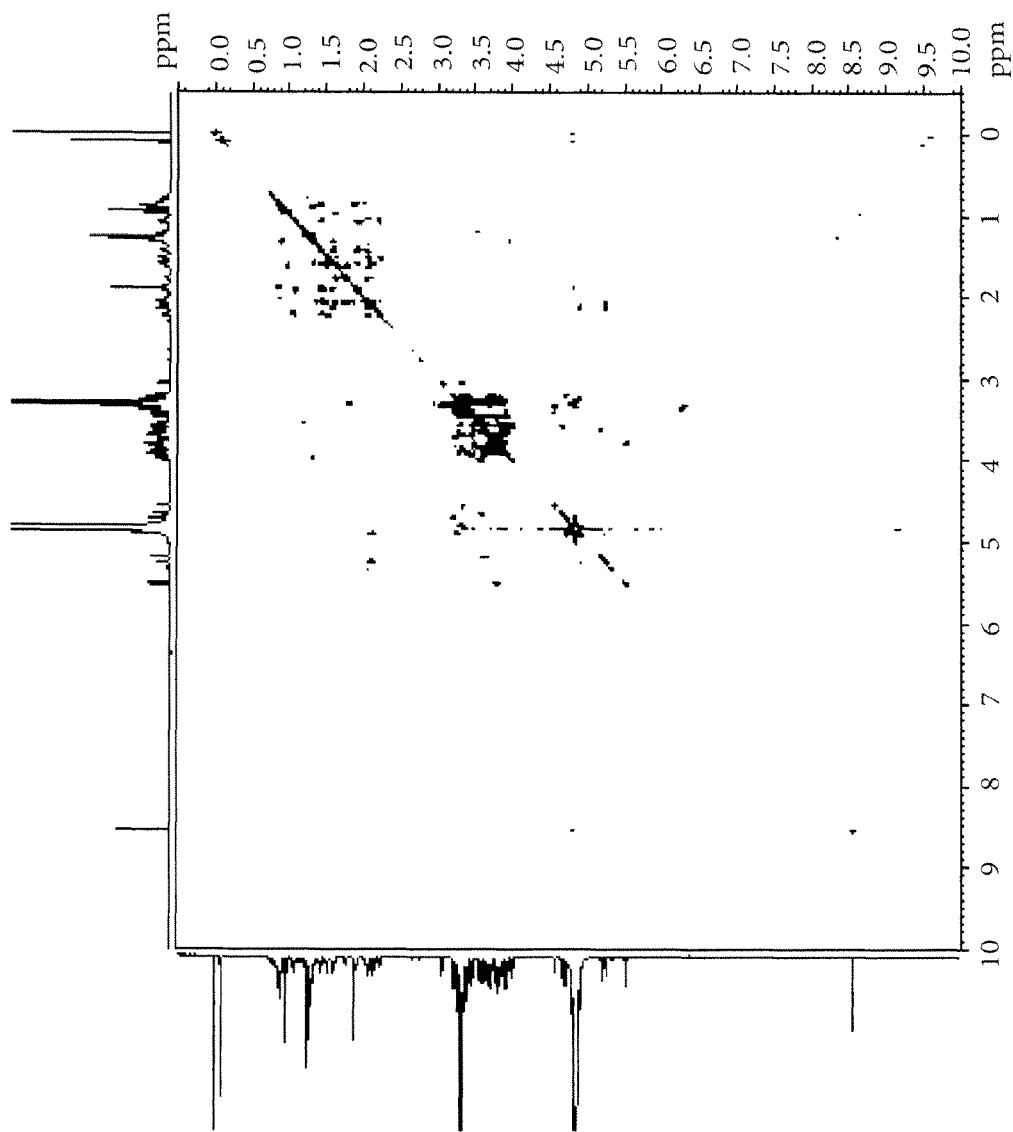
FIG. 49: Shows the $^1$H-$^1$H COSY spectrum (500 MHz, CD$_3$OD) of diterpene glycoside 5 at 300K.
Figure 50:
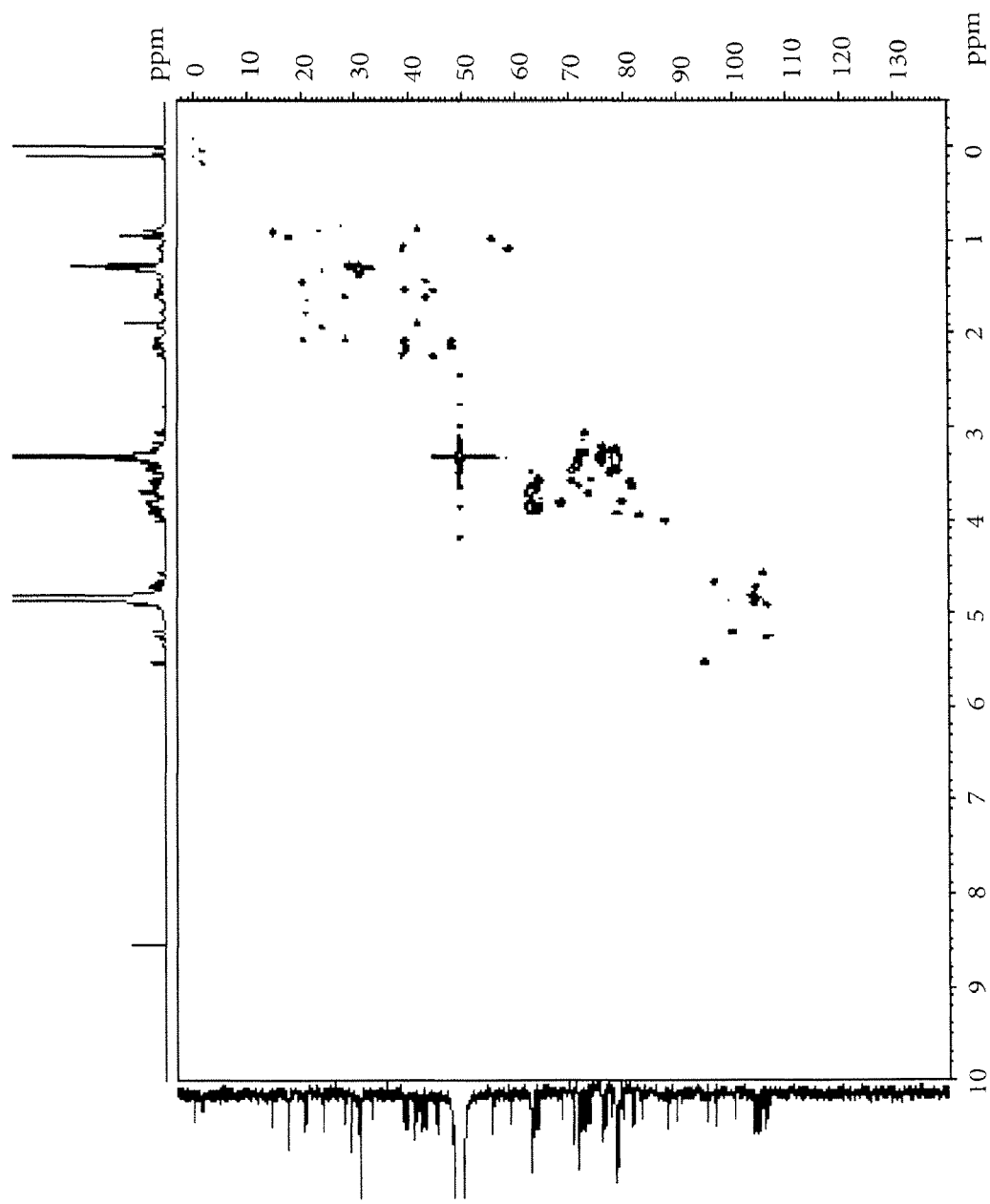
FIG. 50: Shows the HSQC-DEPT spectrum (500 MHz, CD$_3$OD) of diterpene glycoside 5 at 300K.
Figure 51:
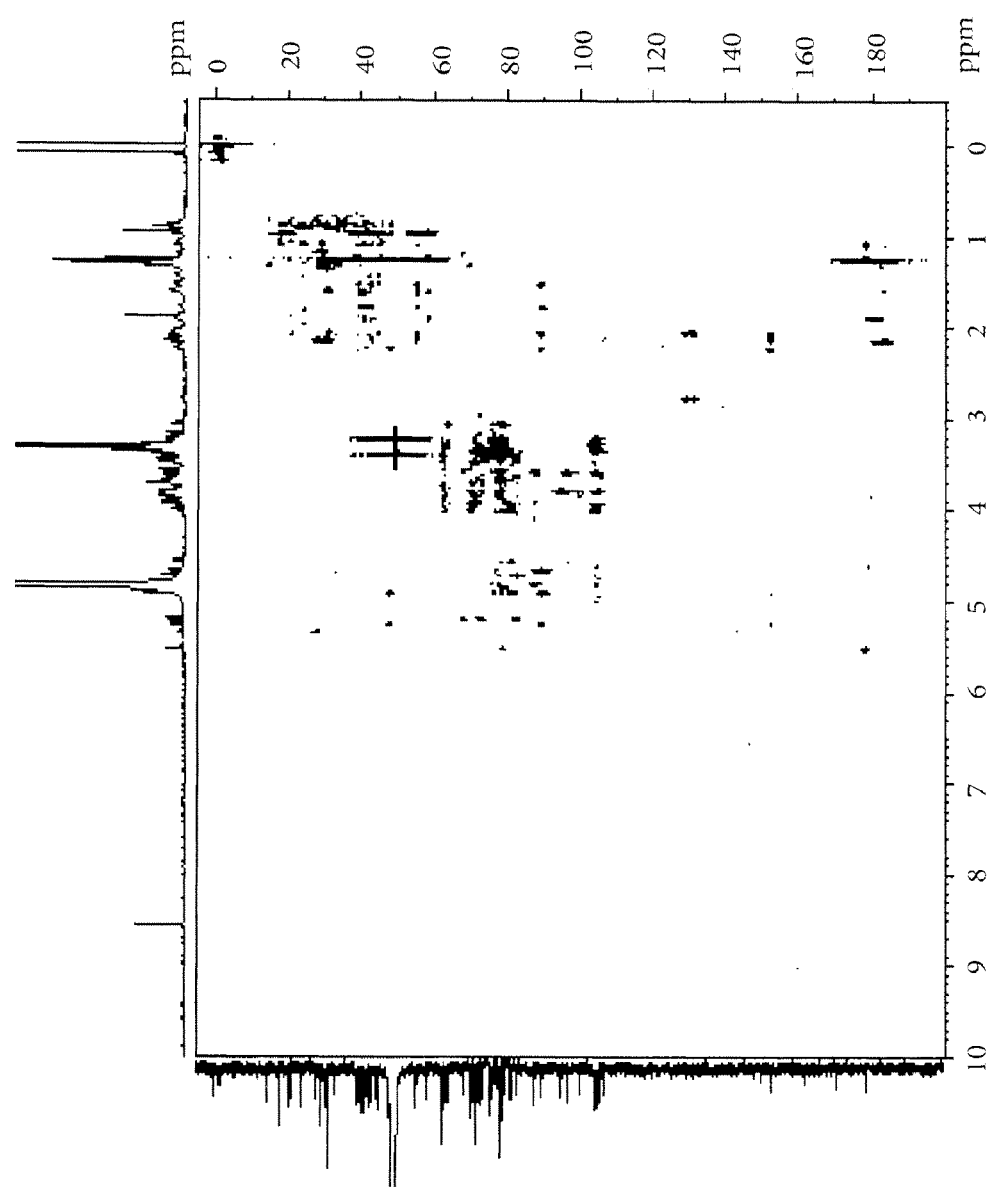
FIG. 51: Shows the HMBC spectrum (800 MHz, CD$_3$OD) of diterpene glycoside 5 at 300 K.
Figure 52:
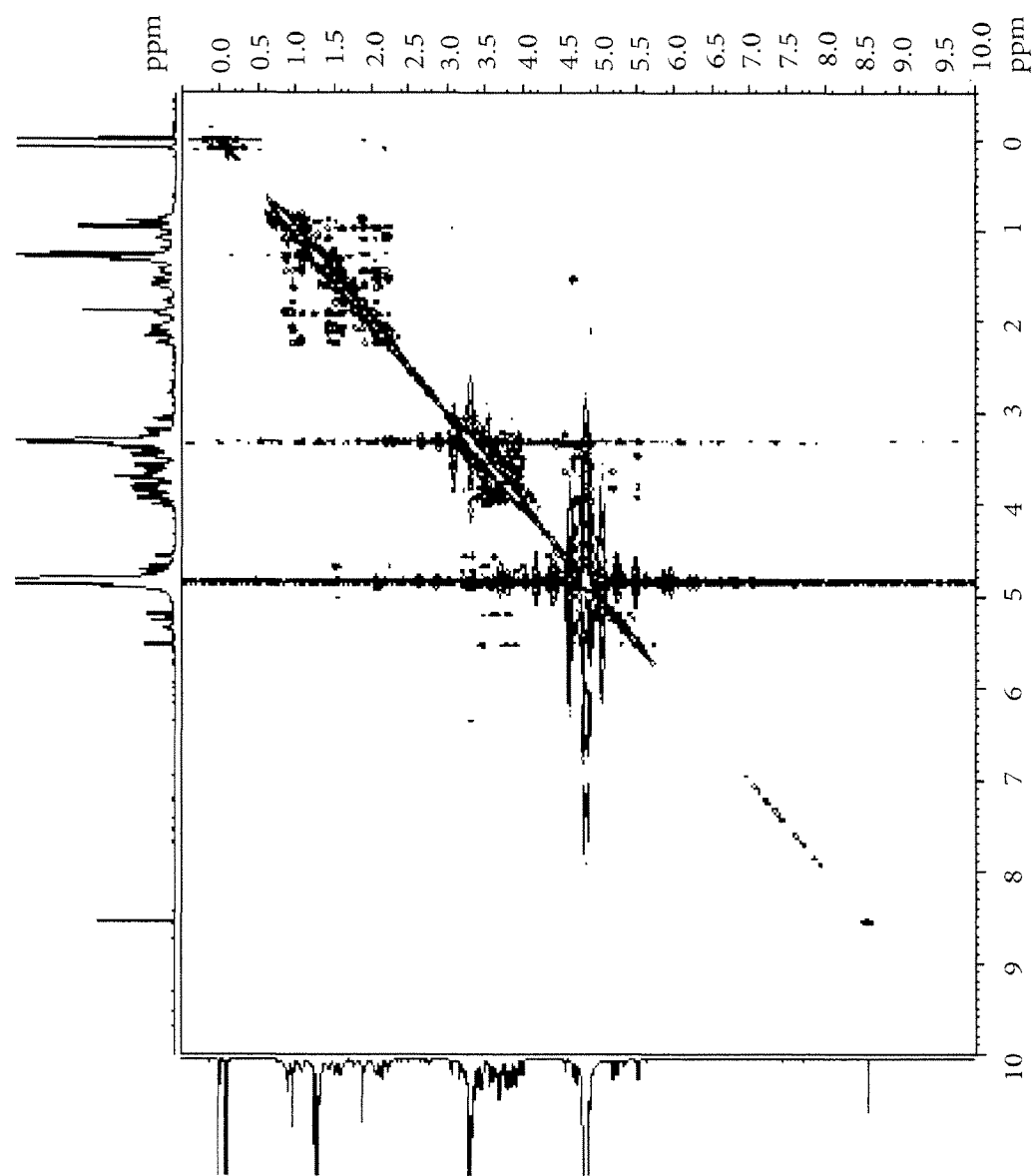
FIG. 52: Shows the NOESY spectrum (500 MHz, CD$_3$OD) of diterpene glycoside 5 at 300K.

NMR Spectroscopy. A series of NMR experiments including $^1H$ NMR (FIG. 47), $^{13}C$ NMR (FIG. 48), $^1H$-$^1H$ COSY (FIG. 49), HSQC-DEPT (FIG. 50), HMBC (FIG. 51), NOESY (FIG. 52), and 1D TOCSY (not shown) were performed.

The 1D and 2D NMR data indicated that the central core of the glycoside is a diterpene. An HMBC correlation from the methyl protons at $\delta_H$ 1.25 to the carbonyl at $\delta_C$ 178.3 allowed assignment of one of the tertiary methyl groups (C-18) as well as C-19 and provided a starting point for the assignment of the rest of the aglycone. Additional HMBC correlations from the methyl protons (H-18) to carbons at $\delta_C$ 38.8, 45.2, and 58.4 allowed assignment of C-3, C-4, and C-5. Analysis of the $^1H$-$^{13}C$ HSQC-DEPT data indicated that the carbon at $\delta_C$ 38.8 was a methylene group and the carbon at $\delta_C$ 58.4 was a methine which were assigned as C-3 and C-5, respectively. This left the carbon at $\delta_C$ 45.2, which did not show a correlation in the HSQC-DEPT spectrum, to be assigned as the quaternary carbon, C-4. The $^1H$ chemical shifts for C-3 ($\delta_H$ 1.06 and 2.21) and C-5 ($\delta_H$ 1.07) were assigned using the HSQC-DEPT data. A COSY correlation between one of the H-3 protons ($\delta_H$ 1.06) and a proton at $\delta_H$ 1.44 allowed assignment of one of the H-2 protons which in turn showed a correlation with a proton at $\delta_H$ 0.86 which was assigned to H-1. The remaining $^1H$ and $^{13}C$ chemical shifts for C-1 and C-2 were then assigned on the basis of additional COSY and HSQC-DEPT correlations.

The other tertiary methyl singlet, observed at $\delta_H$ 0.95, showed HMBC correlations to C-1 ($\delta_C$ 41.4) and C-5 and was assigned as H-20. The methyl protons showed additional HMBC correlations to a quaternary carbon ($\delta_C$ 40.7) and a methine carbon ($\delta_C$ 55.2) which were assigned as C-10 and C-9, respectively. COSY correlations between H-5 ($\delta_H$ 1.07) and protons at $\delta_H$ 1.32 and 1.92 then allowed assignment of the H-6 protons which in turn showed correlations to protons at $\delta_H$ 1.43 and 1.60 which were assigned to H-7. The $^{13}$C chemical shifts for C-6 ($\delta_C$ 23.7) and C-7 ($\delta_C$ 43.1) were then determined from the HSQC-DEPT data. COSY correlations between H-9 ($\delta_H$ 0.98) and protons at $\delta_H$ 1.62 and 1.77 allowed assignment of the H-11 protons which in turn showed COSY correlations to protons at $\delta_H$ 1.52 and 2.08 which were assigned as the H-12 protons. The HSQC-DEPT data was then used to assign C-11 ($\delta_C$ 20.9) and C-12 ($\delta_C$ 39.2). The olefinic protons observed at $\delta_H$ 4.90 and 5.25 showed HMBC correlations to a carbon at $\delta_C$ 89.4 (C-13) and were assigned to H-17 ($\delta_C$ 106.4 via HSQC-DEPT). The methine proton H-9 showed HMBC correlations to carbons at $\delta_C$ 42.3 and 44.5 which were assigned as C-8 and C-14, respectively. An additional HMBC correlation from H-9 to a carbon at $\delta_C$ 47.8 allowed assignment of C-15. The $^1$H chemical shifts at C-14 ($\delta_H$ 1.53 and 2.23) and C-15 ($\delta_H$ 2.06 and 2.13) were assigned using the HSQC-DEPT data. HMBC correlation from H-14 ($\delta_H$ 2.23) to a quaternary carbon at $\delta_C$ 152.4 allowed assignment of C-16. In addition the H-14 ($\delta_H$ 2.23) and the olefinic protons (H-17) showed HMBC correlations to C-15 which further confirmed the assignments made above to complete the assignment of the central core.

Figure 53:
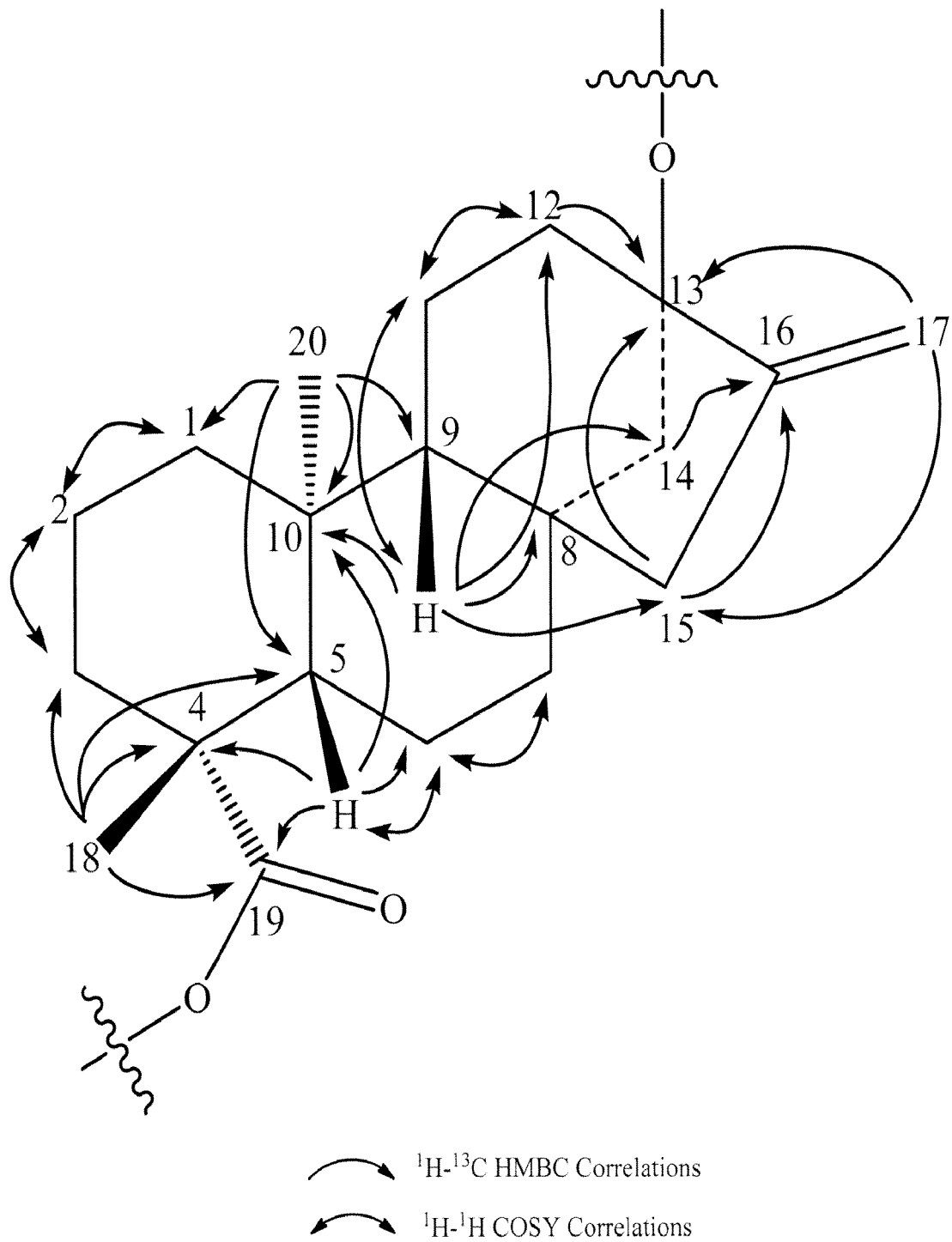
FIG. 53: Shows a summary of key HMBC and COSY correlations used to assign the aglycone region of diterpene glycoside 5.

Correlations observed in the NOESY spectrum were analyzed to assign the relative stereochemistry of the central diterpene core. In the NOESY spectrum, NOE correlations were observed between H-5 and H-18 indicating that H-5 and H-18 are on the same face of the rings. Due to very close chemical shift of H-9 ($\delta_H$ 0.95) and H-20 ($\delta_H$ 0.96), it was not possible to unambiguously assign the relative stereochemistry of H-9, H-14 and H-20. However, based on relative stereochemistry of reported Stevia glycosides central diterpene core and their $^1$H and $^{13}$C chemical shifts comparison, the relative stereochemistry of H-9, H-14 and H-20 are proposed as presented in FIG. 53.

Analysis of the $^1$H-$^{13}$C HSQC-DEPT data confirmed the presence of eight anomeric protons. Five of the anomeric protons were well resolved at $\delta_H$ 5.52 ($\delta_C$ 94.8), 5.19 ($\delta_C$ 100.0), 4.71 ($\delta_C$ 104.4), 4.66 ($\delta_C$ 96.5), and 4.56 ($\delta_C$ 105.6) in the $^1$H NMR spectrum acquired at 300K, while those at $\delta_H$ 4.89 ($\delta_C$ 104.1) and 4.80 ($\delta_C$ 103.8) were partially overlapped by H-17 and the water resonance, respectively. One anomeric proton which was completely obscured by the water resonance in the $^1$H NMR spectrum acquired at 300K was sufficiently resolved in the $^1$H NMR spectrum acquired at 296K at $\delta_H$ 4.84 ($\delta_C$ 104.7). An anomeric proton at $\delta_H$ 5.19 had a small coupling (3.5 Hz) indicating that it had an α-configuration. The remaining seven anomeric protons had large couplings (7.4 Hz-8.1 Hz) indicating that they had β-configurations. The anomeric proton observed at $\delta_H$ 5.52 showed an HMBC correlation to C-19 which indicated that it corresponded to the anomeric proton of Glc$_I$. Similarly, the anomeric proton observed at $\delta_H$ 4.66 showed an HMBC correlation to C-13 allowing it to be assigned as the anomeric proton of Glc$_{II}$.

The Glc$_I$ anomeric proton ($\delta_H$ 5.52) showed a COSY correlation to a proton at $\delta_H$ 3.79 which was assigned as Glc$_I$ H-2 and in turn showed a COSY correlation to a proton at $\delta_H$ 3.91 (Glc$_I$ H-3) which showed a correlation with a proton at $\delta_H$ 3.40 (Glc$_I$ H-4). Due to overlap in the data the COSY spectrum did not allow assignment of the H-5 or H-6 protons. Therefore, a series of 1D TOCSY experiments were performed using selective irradiation of the Glc$_I$ anomeric proton with several different mixing times (not shown). In addition to confirming the assignments for Glc$_I$ H-2 through H-4, the TOCSY data showed a proton at $\delta_H$ 3.46 assigned as Glc$_I$ H-5 and protons at $\delta_H$ 3.67 and 3.85 assigned as Glc$_I$ H-6 protons. The $^{13}$C chemical shifts for Glc$_I$ C-2 ($\delta_C$ 79.4), C-3 ($\delta_C$ 78.5), C-4 ($\delta_C$ 71.4), C-5 ($\delta_C$ 77.9-78.7), and C-6 ($\delta_C$ 62.3-62.8) were assigned using the HSQC-DEPT data. HMBC correlations from H-1 to C-3, H-2 to C-1, C-3 and H-3 to C-1, C-2 further confirmed that assignments made above to complete the assignment of Glc$_I$.

Of the seven remaining unassigned glucose moieties one was assigned as substituent at C-2 of Glc$_I$ on the basis of HMBC correlations. The anomeric proton observed at $\delta_H$ 4.84 showed an HMBC correlation to Glc$_I$ C-2 and was assigned as the anomeric proton of Glc$_V$. The reciprocal HMBC correlation from Glc$_I$ H-2 to the anomeric carbon of Glc$_V$ was also observed.

The anomeric proton of Glc$_V$ ($\delta_H$ 4.84) showed a COSY correlation with a proton at $\delta_H$ 3.35 which was assigned as Glc$_V$ H-2. Glc$_V$ C-2 ($\delta_C$ 75.3 or 75.4) was then assigned using the HSQC-DEPT data. Due to overlap in the data the COSY spectrum did not allow assignment of the remaining protons. In addition, the anomeric proton was completely obscured by water resonance in the $^1$H NMR acquired at 300K. Therefore, a series of 1D TOCSY experiments were performed using selective irradiation of the Glc$_V$ anomeric proton with several different mixing times at 296K (not shown). In addition to confirming the assignments for Glc$_V$ H-2, the TOCSY data allowed assignment of Glc$_V$ H-3 ($\delta_H$ 3.38), H-4 ($\delta_H$ 3.28), and H-5 ($\delta_H$ 3.37). In the TOCSY data the protons observed at $\delta_H$ 3.67 and $\delta_H$ 3.92 were assigned as the Glc$_V$ H-6 protons. The $^{13}$C chemical shifts for Glc$_V$ C-3 ($\delta_C$ 77.9-78.7), C-4 ($\delta_C$ 71.9 or 72.5 or 72.7), C-5 ($\delta_C$ 77.9-78.7) and C-6 ($\delta_C$ 63.6) were assigned using the HSQC-DEPT data to complete the assignment of Glc$_V$.

Figure 54:
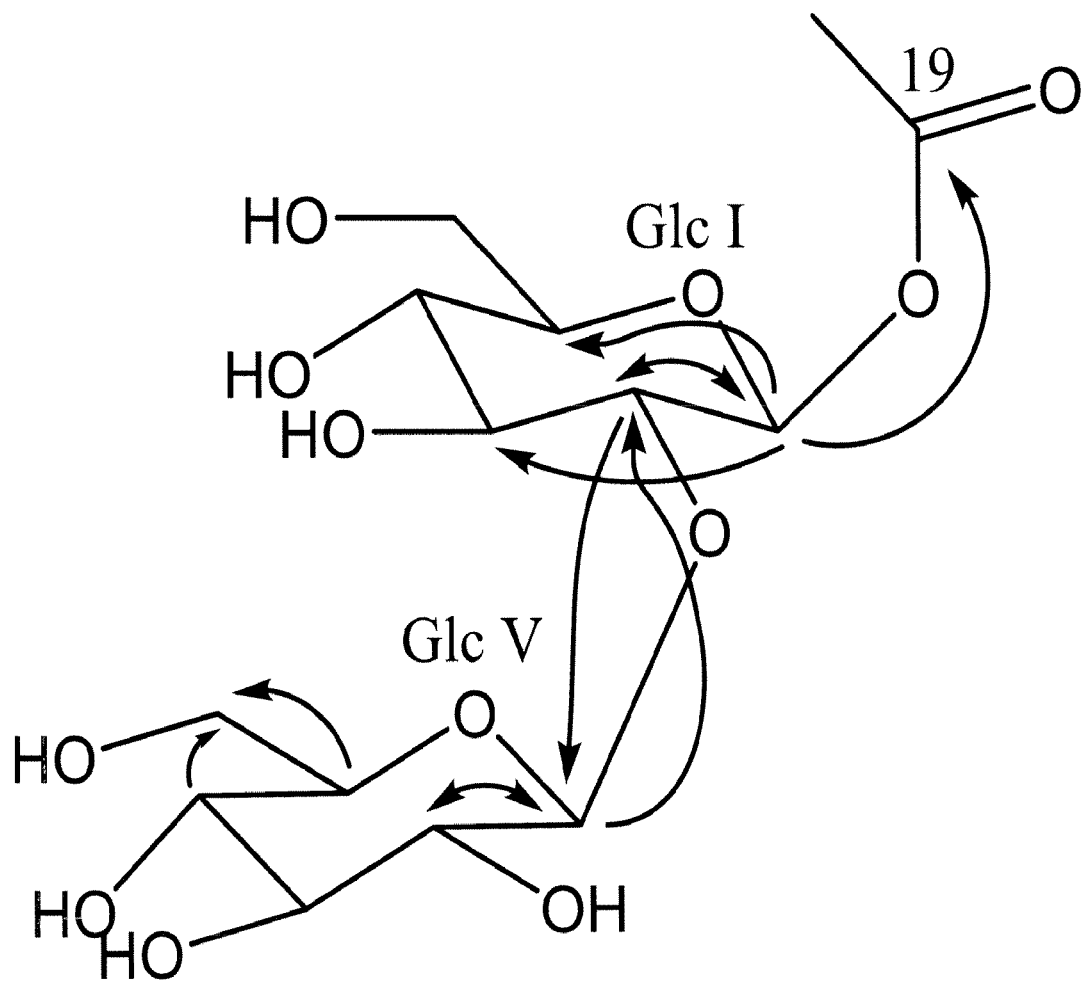
FIG. 54: Shows a summary of key HMBC and COSY correlations used to assign the C-19 glycoside region of diterpene glycoside 5.

A summary of the key HMBC and COSY correlations used to assign the C-19 glycoside region are provided in FIG. 54.

Assignment of Glc$_{II}$ was carried out in a similar manner. The Glc$_{II}$ anomeric proton ($\delta_H$ 4.66) showed a COSY correlation to a proton at $\delta_H$ 3.58 which was assigned as Glc$_{II}$ H-2 and in turn showed a COSY correlation to a proton at $\delta_H$ 4.00 (Glc$_{II}$ H-3). Due to overlap in the data the COSY spectrum did not allow assignment of the remaining protons. Therefore, a series of 1D TOCSY experiments were performed using selective irradiation of the Glc$_{II}$ anomeric proton with several different mixing times (not shown). In addition to confirming the assignments for Glc$_V$ H-2, the TOCSY data allowed assignment of H-4 ($\delta_H$ 3.57), and H-5 ($\delta_H$ 3.48). In the TOCSY data the protons observed at $\delta_H$ 3.80 and 3.81 were assigned as the Glc$_{II}$ H-6 protons. 1D-TOCSY experiments were also performed using selective irradiation of the Glc$_{II}$ H-3 with several different mixing times (not shown) which further confirmed the assignments made above. Assignment of the $^{13}$C chemical shifts for Glc$_{II}$ C-2 ($\delta_C$ 81.1), C-3 ($\delta_C$ 87.6), C-4 ($\delta_C$ 70.2), C-5 ($\delta_C$ 77.1) and C-6 ($\delta_C$ 68.1) was based on HSQC-DEPT data. HMBC correlations from Glc$_{II}$ H-3 to C-2 and C-4, Glc$_{II}$ H-2 to C-1 and from Glc$_{II}$ H-1 to C-3 and C-5 further confirmed the assignments of Glc$_{II}$. In addition HMBC correlations observed from Glc$_{II}$ H-4 to C-6 and the reciprocal HMBC from Glc$_{II}$ H-6 to C-4 further confirmed the assignments made above. The relatively downfield shift of the C-6 methylene carbon indicated a 146 glycoside linkage at Glc$_{II}$ C-6.

Of the five remaining unassigned glucose moieties, two were assigned as substituents at C-2 and C-3 of Glc$_{II}$ on the basis of HMBC correlations. The anomeric proton observed at δ$_H$ 4.89 showed an HMBC correlation to Glc$_{II}$ C-2 and was assigned as the anomeric proton of Glc$_{II}$. The anomeric proton observed at δ$_H$ 4.80 showed an HMBC correlation to Glc$_{II}$ C-3 and was assigned as the anomeric proton of Glc$_{IV}$. The reciprocal HMBC correlations from Glc$_{II}$ H-2 to the anomeric carbon of Glc$_{III}$ and from Glc$_{II}$ H-3 to the anomeric carbon of Glc$_{IV}$ were also observed.

The anomeric proton of Glc$_{III}$ (δ$_H$ 4.89) showed a COSY correlation with a proton at δ$_H$ 3.25 which was assigned as Glc$_{III}$ H-2. Glc$_{III}$ C-2 (δ$_C$ 76.4) was then assigned using the HSQC-DEPT data. Due to overlap in the data the COSY spectrum did not allow assignment of the remaining protons. Therefore, a series of 1D TOCSY experiments were performed using selective irradiation of the Glc$_{III}$ anomeric proton with several different mixing times (not shown). In addition to confirming the assignments for Glc$_{III}$ H-2, the TOCSY data allowed assignment of Glc$_{III}$ H-3 (δ$_H$ 3.34), H-4 (δ$_H$ 3.06) and H-5 (δ$_H$ 3.30). In the TOCSY data the protons observed at δ$_H$ 3.57 and δ$_H$ 3.85 were assigned as the Glc$_{III}$ H-6 protons. 1D-TOCSY experiments were also performed using selective irradiation of the Glc$_{III}$ H-4 with several different mixing times (not shown) which further confirmed the assignments made above. The $^{13}$C chemical shifts for C-3 (δ$_C$ 77.9-78.7), C-4 (δ$_C$ 72.5 or 72.7), C-5 (δ$_C$ 77.9-78.7) and C-6 (δ$_C$ 63.9) were assigned using the HSQC-DEPT data to complete the assignment of Glc$_{III}$.

The anomeric proton of Glc$_{IV}$ (δ$_H$ 4.80) showed a COSY correlation with a proton at δ$_H$ 3.30 which was assigned as Glc$_{IV}$ H-2. Glc$_{IV}$ C-2 (δ$_C$ 75.4 or 75.6) was then assigned using the HSQC-DEPT data. Due to overlap in the data, the COSY spectrum did not allow assignment of the remaining protons. Therefore, a series of 1D TOCSY experiments were performed using selective irradiation of the Glc$_{IV}$ anomeric proton with several different mixing times (not shown). In addition to confirming the assignments for Glc$_{IV}$ H-2, the 1D TOCSY data allowed assignment of H-3 (δ$_H$ 3.38), H-4 (δ$_H$ 3.28), H-5 (δ$_H$ 3.48) and H-6 (δ$_H$ 3.63 and 3.92). The $^{13}$C chemical shifts for C-3 (δ$_C$ 77.9-78.7), C-4 (δ$_C$ 71.9 or 72.5 or 72.7), C-5 (δ$_C$ 77.9-78.7) and C-6 (δ$_C$ 62.3-62.8) were assigned using the HSQC-DEPT data to complete the assignment of Glc$_{IV}$.

The anomeric proton of Glc$_{VII}$ at δ$_H$ 5.19 (δ$_C$ 100.0) showed HMBC correlations to the carbon at δ$_C$ 68.1 ppm (Glc$_{II}$ C-6) indicating that it was attached to Glc$_{II}$ via an 1→6 linkage. The reciprocal HMBC correlation was also observed from the methylene protons of Glc$_{II}$ (δ$_H$ 3.80 and 3.81) to the anomeric carbon of Glc$_{VII}$ at δ$_C$ 100.0 confirming the 1→6 linkage between Glc$_{VII}$ and Glc$_{II}$. Assignment of Glc$_{VII}$ was done using a combination of COSY, HSQC-DEPT, HMBC and 1D TOCSY data. The anomeric proton of Glc$_{VII}$ (δ$_H$ 5.19) showed a COSY correlation with a proton at δ$_H$ 3.63 which was assigned as Glc$_{VII}$ H-2 and showed a COSY correlation with a proton at δ$_H$ 3.94 which was assigned as Glc$_{VII}$ H-3. Glc$_{VII}$ C-2 (δ$_C$ 81.3) and C-3 (δ$_C$ 82.7) were then assigned using the HSQC-DEPT data. Due to overlap in the data the COSY spectrum did not allow unambiguous assignment of the remaining protons. Therefore, a series of 1D TOCSY experiments were performed using selective irradiation of the Glc$_{VII}$ anomeric proton with several different mixing times (not shown). In addition to confirming the assignments for Glc$_{VII}$ H-2 and H-3, the TOCSY data allowed assignment of Glc$_{VII}$ H-4 (δ$_H$ 3.46), and H-5 (δ$_H$ 3.70). In the TOCSY data the protons observed at δ$_H$ 3.72 and δ$_H$ 3.78/3.80 were assigned as the Glc$_{III}$ H-6 protons. The $^{13}$C chemical shifts for Glc$_{VII}$ C-4 (δ$_C$ 70.2), C-5 (δ$_C$ 73.2) and C-6 (δ$_C$ 62.3-62.8) were assigned using the HSQC-DEPT data. HMBC correlations observed from Glc$_{VII}$ H-1 to C-3, H-2 to C-3, H-3 to C-2 and H-4 to C-3, C-5 further confirmed the assignments made above.

The two remaining glucose moieties with anomeric protons at δ$_H$ 4.56 (δ$_C$ 105.6) and δ$_H$ 4.71 (δ$_C$ 104.4) were assigned as substituents at C-2 and C-3 of Glc$_{VII}$ on the basis of HMBC correlations. The anomeric proton observed at δ$_H$ 4.56 showed an HMBC correlation to Glc$_{VII}$ C-2 and was assigned as the anomeric proton of Glc$_{VIII}$. The anomeric proton observed at δ$_H$ 4.71 showed an HMBC correlation to Glc$_{VII}$ C-3 and was assigned as the anomeric proton of Glc$_{IX}$. The reciprocal HMBC correlations from Glc$_{VII}$ H-2 to the anomeric carbon of Glc$_{VIII}$ and from Glc$_{VII}$ H-3 to the anomeric carbon of Glc$_{VI}$ were also observed.

The anomeric proton of Glc$_{VIII}$ (δ$_H$ 4.56) showed a COSY correlation with a proton at δ$_H$ 3.33 which was assigned as Glc$_{VIII}$ H-2. Due to overlap in the data the COSY spectrum did not allow assignment of the remaining protons. Therefore, a series of 1D TOCSY experiments were performed using selective irradiation of the Glc$_{VIII}$ anomeric proton with several different mixing times (not shown). In addition to confirming the assignments for Glc$_{VIII}$ H-2, the TOCSY data allowed assignment of Glc$_{VIII}$ H-3 (δ$_H$ 3.55), H-4 (δ$_H$ 3.41) and H-5 (δ$_H$ 3.22). In the TOCSY data the protons observed at δ$_H$ 3.72 and δ$_H$ 3.84 were assigned as the Glc$_{VIII}$ H-6 protons. Assignment of the $^{13}$C chemical shifts for Glc$_{VIII}$ C-2 (δ$_C$ 75.3-75.8), C-3 (δ$_C$ 77.9-78.7), C-4 (δ$_C$ 71.2 or 71.4), C-5 (δ$_C$ 77.9-78.7), and C-6 (δ$_C$ 62.3-62.8) was determined using the HSQC-DEPT data to complete the assignment of Glc$_{VIII}$.

The anomeric proton of Glc$_{IV}$ (δ$_H$ 4.71) showed a COSY correlation with a proton at δ$_H$ 3.21 which was assigned as Glc$_{IX}$ H-2. The Glc$_{IX}$ H-2 in turn showed a COSY correlation to Glc$_{IX}$ H-3 (δ$_H$ 3.36). Due to overlap in the data the COSY spectrum did not allow assignment of the remaining protons. Therefore, a series of 1D TOCSY experiments were performed using selective irradiation of the Glc$_{IX}$ anomeric proton with several different mixing times (not shown). In addition to confirming the assignments for Glc$_{IX}$ H-2 and H-3, the TOCSY data allowed assignment of Glc$_{IX}$ H-4 (δ$_H$ 3.34), H-5 (δ$_H$ 3.33) and H-6 (δ$_H$ 3.69 and 3.87). Assignment of the $^{13}$C chemical shifts for Glc$_{IX}$ C-2 (δ$_C$ 75.6-75.8), C-3 (δ$_C$ 77.9-78.7), C-4 (δ$_C$ 71.2 or 71.4), C-5 (δ$_C$ 77.9-78.7), and C-6 (δ$_C$ 62.3-62.8) was determined using the HSQC-DEPT data to complete the assignment of Glc$_{IX}$.

Figure 55:
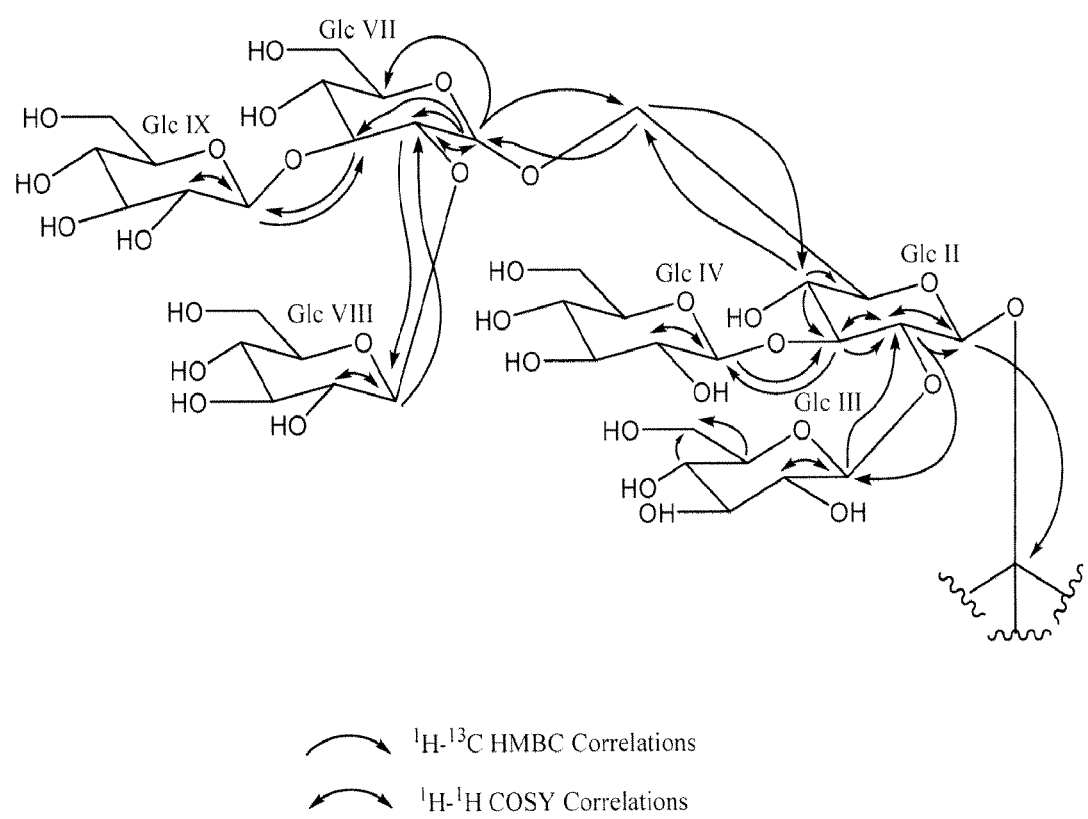
FIG. 55: Shows a summary of key HMBC and COSY correlations used to assign the C-13 glycoside region of diterpene glycoside 5.

A summary of the key HMBC and COSY correlations used to assign the C-13 glycoside region are provided in FIG. 55.

Figure 45:
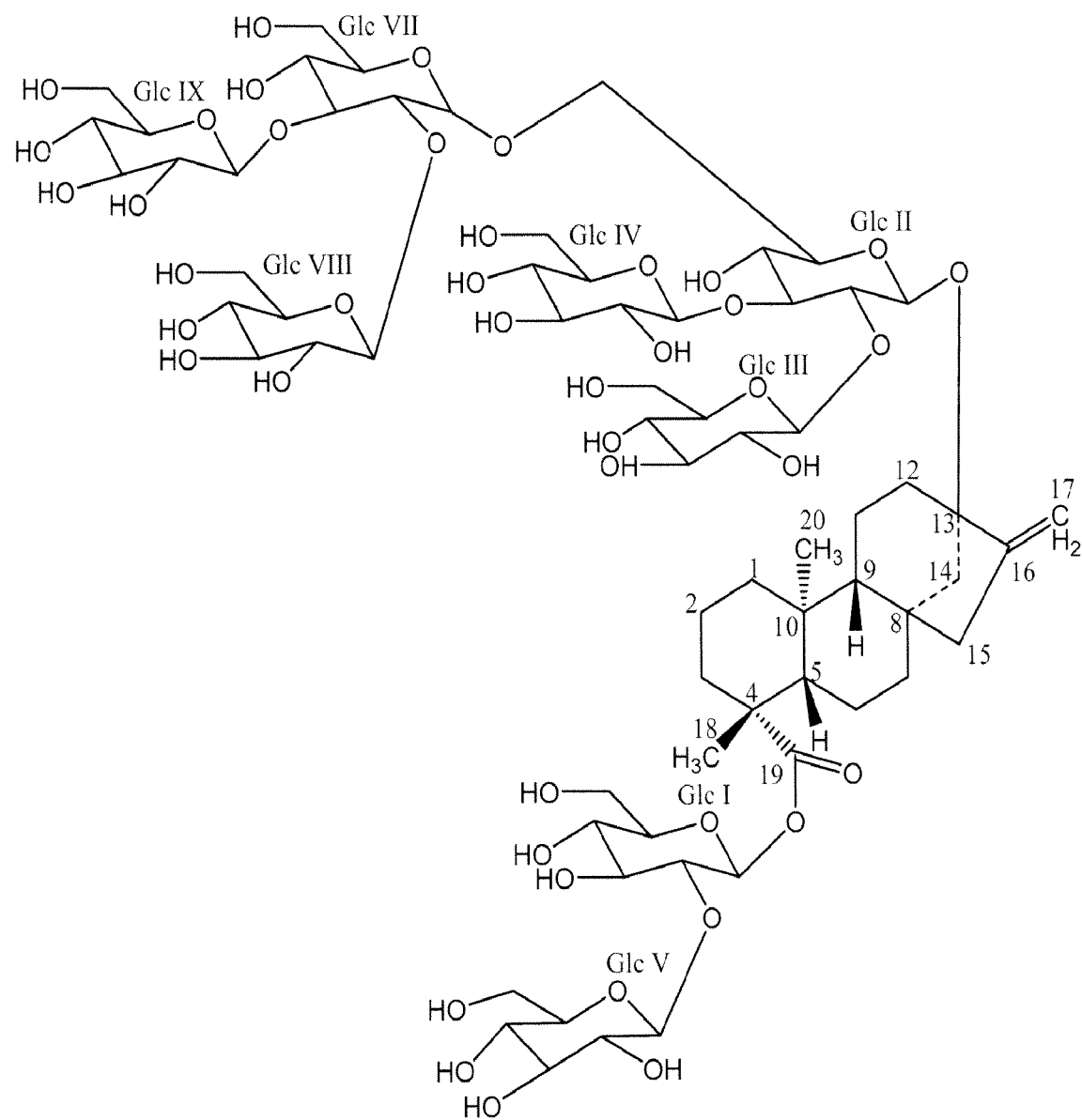
FIG. 45: Shows the structure of diterpene glycoside 5, i.e, (13-[(2-O-β-D-glucopyranosyl-3-O-β-D-glucopyranosyl-6-O-α-D-glucopyranosyl-(2-O-β-D-glucopyranosyl-3-O-β-D-glucopyranosyl)-β-D-glucopyranosyl)oxy] ent-kaur-16-en-19-oic acid-[(2-O-β-D-glucopyranosyl)-β-D-glucopyranosyl) ester].

The structure was determined to be (13-[(2-O-β-D-glucopyranosyl-3-O-β-D-glucopyranosyl-6-O-α-D-glucopyranosyl-(2-O-α-D-glucopyranosyl-3-O-β-D-glucopyranosyl)-β-D-glucopyranosyl)oxy] ent-kaur-16-en-19-oic acid-[(2-O-β-D-glucopyranosyl)-β-D-glucopyranosyl) ester] as shown in FIG. 45.

Example 6

Isolation and Characterization of 6

Materials: The material used for the isolation was a *Stevia* extract, Lot #CB-2977-171, received from The Coca-Cola Company.

Analytical HPLC Method: Preliminary HPLC analyses of samples were performed using a Waters 2695 Alliance System with the following method: Phenomenex Synergi Hydro-RP 80A, 4.6×250 mm, 4 μm (s/n 695639-21); Column Temp: 55° C.; Mobile Phase A: 0.00284% NH$_4$OAc and 0.0116% HOAc in water; Mobile Phase B: Acetonitrile (MeCN); Flow Rate: 1.0 mL/min; Injection volume: 10 μL. Detection was by UV (210 nm) and CAD.

TABLE 1

Gradient method

| Time (min) | % A | % B |
|---|---|---|
| 0.0-5.0 | 85 | 15 |
| 5.1 | 85 | 15 |
| 15.0 | 75 | 25 |
| 30.0 | 75 | 25 |
| 31.0 | 25 | 75 |
| 36.0 | 25 | 75 |
| 36.1 | 85 | 15 |

HPLC Analysis—Secondary Process. HPLC analyses of samples were performed using a Waters 2695 Alliance System with the following method: Phenomenex Synergi Hydro-RP 80A, 4.6×250 mm, 4 μm (s/n 695639-21); Column Temp: 50° C.; Mobile Phase A: Water; Mobile Phase B: MeCN; Flow Rate: 1.0 mL/min; Injection volume: 10 μL. Detection was by UV (210 nm) and CAD.

TABLE 2

Gradient method

| Time (min) | % A | % B |
|---|---|---|
| 0.0 | 80 | 20 |
| 35.0 | 80 | 20 |
| 35.1 | 50 | 50 |
| 45.0 | 50 | 50 |
| 45.1 | 80 | 20 |

Primary Preparative HPLC Method. The primary processing of Lot #CB-2977-171 was performed using a pre-packed Waters Symmetry RP18 column (50×250 mm, 7 μm). The purification process was performed with a Waters Delta Prep LC Model 2000/4000 system coupled to a UV-Vis detector. Details of the preparative method are summarized in Table 3.

TABLE 3

Conditions for Primary Preparative HPLC Method.

Primary HPLC Parameters

| Column | Waters Symmetry Shield RP18 (50 × 250 mm, 7 μm) @ ambient |
|---|---|
| Flow Rate (mL/min) | 105 |
| Detection | UV at 210 nm |
| Mobile Phases | (A) 15% MeCN in water |
| | (B) 25% MeCN in water |
| | (C) 85% MeOH in water |
| Load (g) | 12 g |
| Sample preparation | 12 g dissolved in 40 mL of DMSO, then added 80 mL of MP-A |

Gradient

| Time (min) | % A | % B | % C |
|---|---|---|---|
| 0.0-11.0 | 100 | 0 | 0 |
| 30.0-40.0 | 0 | 100 | 0 |
| 41.0-51.0 | 0 | 0 | 100 |
| 52.0 | 100 | 0 | 0 |

Secondary Preparative HPLC Method. The secondary processing was performed using a Phenomenex Synergi Hydro RP 80 (50×250 mm, 10 μm) column. The purification process was performed with a Waters Delta Prep LC Model 2000/4000 system coupled to a UV-Vis detector. Details of the preparative method are summarized in Table 4.

TABLE 4

Conditions for Secondary Preparative HPLC Method.

| Parameter | Description |
|---|---|
| Column | Phenomenex Synergi Hydro RP 80 Å (50 × 250 mm, 10 μm) @ 50° C. |
| Flow Rate (mL/min) | 105 |
| Detection | UV at 210 nm |
| Mobile Phases | (A) 18% MeCN in water |
| | (B) 50% MeCN in water |
| Load (g) | 0.5 g in 40 mL of water |
| Sample preparation | 500 mg of JAM-D-1-3, or JAM-D-10-3, or JAM-D-14-3 dissolved in 40 mL of water |

Gradient

| Time (min) | % A | % B |
|---|---|---|
| 0.0-75.0 | 100 | 0 |
| 75.1-85.1 | 0 | 100 |
| 86.0 | 100 | 0 |

Tertiary Processing Method. Tertiary processing was conducted on a Waters 2767 Auto-purification system using mass triggering for fraction collection as described in Table 5.

TABLE 5

Conditions for Tertiary HPLC Process.

| Parameter | Description |
|---|---|
| Column: | Phenomenex Gemini-NX, 10 × 250 mm |
| Column Temp: | Ambient |
| Mobile Phases: | (A) Water |
| | (B) MeCN |
| Gradient: | 80% A Isocratic for 25 min followed by column flush |
| Flow: | 5 mL/min |
| Load (μL): | 950 |
| Detection: | Mass Range: 500-2000 m/z, ES(+/−) |

Quaternary Processing Method. Quaternary processing was conducted on a Waters 2767 Auto-purification system using mass triggering for fraction collection as described in Table 6.

TABLE 6

Conditions for Quaternary HPLC Process.

| Parameter | Description |
|---|---|
| Column: | Phenomenex Gemini-NX, 10 × 250 mm |
| Column Temp: | Ambient |
| Mobile Phases: | (A) Water |
| | (B) Methanol (MeOH) |
| Gradient: | 60% B to 65% B over 20 min followed by column flush |
| Flow: | 5 mL/min |
| Load (μL): | 950 |
| Detection: | Mass Range: 500-2000 m/z, ES(+/−) |

Quinary Processing Method. Quinary processing was conducted on a Waters 2767 Auto-purification system using mass triggering for fraction collection as described in Table 7.

TABLE 7

Conditions for Quinary HPLC Process.

| Parameter | Description |
| --- | --- |
| Column: | Phenomenex Gemini-NX, 10 × 250 mm |
| Column Temp: | Ambient |
| Mobile Phases: | (A) Water |
|  | (B) MeOH |
| Gradient: | 40% B to 65% B over 26 min followed by column flush |
| Flow: | 5 mL/min |
| Load (µL): | 950 |
| Detection: | Mass Range: 500-2000 m/z, ES(+/−) |

Senary Processing. Senary processing was conducted on a Waters 2767 Auto-purification system using mass triggering for fraction as described in Table 8 below.

TABLE 8

Conditions for Senary HPLC Process.

| Parameter | Description |
| --- | --- |
| Column: | Phenomenex Prodigy ODS, 10 × 250 mm |
| Flow Rate (mL/min): | 5 |
| Detection: | ES(−) 500-2000 Da |
| Mass Triggers: | 1305, 1452, 1614, 1776 m/z ± 1Da |
| Mobile Phases: | (A) 0.2% Acetic Acid in Water |
|  | (B) MeCN |
| Load (µL): | 950 |
| Gradient: | Gradient from 20% B to 26% B over 25 min, followed by flush and re-equilibration |

Septenary Processing. Septenary processing was conducted on a Waters 2767 Auto-purification system using mass triggering for fraction as described in Table 9 below.

TABLE 9

Conditions for Septenary HPLC Process.

| Parameter | Description |
| --- | --- |
| Column: | Phenomenex Gemini-NX, 10 × 250 mm |
| Flow Rate (mL/min): | 5 |
| Detection: | ES(−) 500-2000Da |
| Mass Triggers: | 1305, 1452, 1614, 1776 m/z ± 1Da |
| Mobile Phases: | (A) Water |
|  | (B) MeCN |
| Load (µL): | 950 |
| Gradient: | 20% B for 30 min, followed by flush and re-equilibration |

Octonary Processing. Octonary processing was conducted on a Waters Delta Prep LC Model 2000/4000 system coupled to a UV-Vis detector as described in Table 10 below.

TABLE 10

Conditions for Octonary HPLC Process.

| Parameter | Description |
| --- | --- |
| Column: | Waters Xbridge Phenyl, 30 × 150 mm |
| Flow Rate (mL/min): | 40 |
| Detection: | UV at 210 nm |
| Mobile Phases: | (A) 95:5 Water/MeCN |
|  | (B) 12.5:87.5 Water/Acetonitrile |

TABLE 10-continued

Conditions for Octonary HPLC Process.

| Parameter | Description |
| --- | --- |
| Load (mL): | 10 |
| Gradient: | 100% A for 10 min, followed by flush and re-equilibration |

Isolation Procedure. Fractions collected during the final pre-concentration step were filtered through a stainless steel sieve and concentrated in vacuo using a Buchi® Rotary Evaporator, Model R-114. The concentrated solution was dried for 48-72 h using the Kinetics Flexi-Dry Personal Freeze Dryer, followed by vacuum oven drying at 37° C. for 24 h to remove residual moisture.

HPLC analysis of Isolated Target. Final analysis was completed as described in Table 11 below using a Waters Xbridge Phenyl 4.6×150 mm column.

TABLE 11

HPLC Chromatographic Conditions.

| Parameter | Description |
| --- | --- |
| Column: | Waters Xbridge Phenyl, 4.6 × 150 mm |
| Flow Rate (mL/min): | 1 |
| Detection: | CAD |
| Mobile Phases: | (A) Water |
|  | (B) MeCN |
| Load (mL): | 950 |
| Gradient: | 5% B to 25% B over 20 min, followed by flush and re-equilibration |

MS and MS/MS. MS and MS/MS data were generated with a Waters QTof Micro mass spectrometer equipped with an electrospray ionization source. The sample was analyzed by negative ESI. The sample (0.3 mg) was diluted with $H_2O$ to a concentration of 0.3 mg/mL for HRMS and the sample (0.2 mg) was diluted with $ACN:H_2O$ (1:1)+0.1% $NH_4OH$ to a concentration of 0.04 mg/mL for MS/MS. Both samples were introduced via direct infusion.

NMR. An attempt was made to dissolve 3.8 mg of the sample in 250 µL of $CD_3OD$. The sample did not dissolve completely in the solvent, a portion of the sample settled at the bottom of the NMR tube. However, the soluble portion of the sample was sufficient to acquire all NMR data except for 1D-TOCSY data of $Glc_{IV}$ H-6 ($\delta_H$ 3.92) which was obtained using a subsequent preparation utilizing an aliquot of the original NMR solution (~2.0 mg/150 µL $CD_3OD$). All NMR data were acquired on Bruker Avance 500 MHz instruments with either a 2.5 mm inverse probe or a 5 mm broad band probe. The $^1H$ and $^{13}C$ NMR spectra were referenced to the solvent resonance at $\delta_H$ 3.30 ppm and $\delta_C$ 49.0 ppm, respectively.

Results and Discussion

Unless otherwise noted, all solvent ratios are listed as percent by volume (v/v).

Primary Purification. Approximately 300 g of Lot #CB-2977-171 was processed using the primary preparative HPLC method described above. Collected fractions were analyzed by LC-MS using the analytical method summarized in Table 1. According MS analysis, the presence of the [2M-H]⁻ charged state, 887 m/z suggested the presence of a target with molecular weight of 1776 Da. Fraction 3 (Lot #JAM-D-10-3) contained the target of interest.

Secondary Purification. The Lot #JAM-D-10-3 (and equivalent lots JAM-D-1-3 and JAM-D-14-3) was reprocessed with conditions summarized above. Fractions were analyzed using the analytical method summarized in Table 2.

Tertiary Purification. Material obtained from secondary processing was reprocessed with conditions summarized above. Fractions with 1776 m/z targets were collected as CJP-C-185(3). This fraction was concentrated for additional processing to remove other target impurities.

Quaternary Purification. Fraction Lot #CJP-C-185(3) was reprocessed as described above. Fraction CJP-C-193(4) was isolated containing several strong signals for 1776 m/z. This fraction was concentrated for additional processing.

Quinary Purification. Fraction Lot #CJP-C-193(4) was reprocessed as described above. CJP-C-196(5) was isolated and concentrated for additional processing.

Senary Purification. Fraction Lot #CJP-C-196(4) was reprocessed as described above. CJP-C-200(2) was isolated and analyzed as described above.

Septenary Purification. Fraction Lot #CJP-C-201(1) was reprocessed as described above. CJP-C-204(2) was isolated in 100% purity.

Octonary Purification. Fraction Lot #CJP-C-204(2) was reprocessed as described above. CJP-G-57 was isolated in 100% purity.

Final Batch Preparation. CJP-G-57 was concentrated by rotary evaporation for final isolation. The concentrated solution was further dried via lyophilization for 48 h. The final yield of the batch, CJP-G-57, was 3.8 mg. The purity was >99% (AUC, CAD).

Mass Spectrometry. The ESI-TOF mass spectrum was acquired by infusion. A [M-H]$^-$ ion at m/z 1775.6925 was found. The mass of the [M-H]$^-$ ion was in good agreement with the molecular formula $C_{74}H_{120}O_{48}$ (calcd for $C_{74}H_{119}O_{48}$: 1775.6871, error: 3.0 ppm) expected for 6. The MS data confirmed a nominal mass of 1776 Daltons with the molecular formula, $C_{74}H_{120}O_{48}$.

The MS/MS spectrum, selecting the [M-H]$^-$ ion at m/z 1775.7 for fragmentation, indicated loss of one glucose unit at m/z 1613.6771. Although very weak, the ions at m/z 1451.6040, 1289.4744, and 1127.4987 correspond to sequential loss of three glucose units followed by the loss of two glucose units at m/z 803.3750 and sequential loss of three glucose units at m/z 641.3215, 479.2698, and 317.2214. The ion at m/z 971.3156 likely corresponds to cleavage of the ester linkage and subsequent loss of water from one of the six sugar units.

Figure 57:
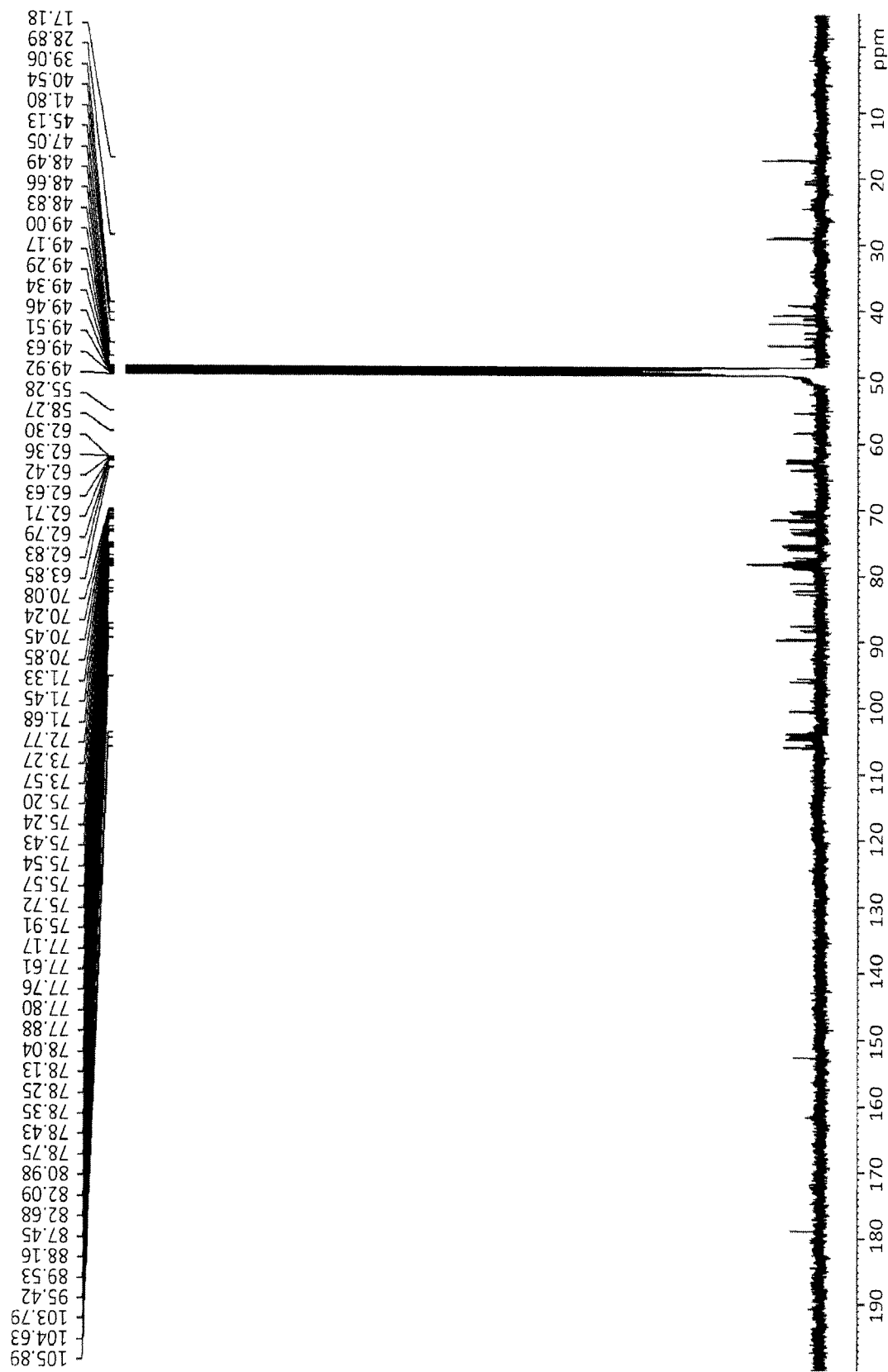
FIG. 57: Shows the $^{13}$C NMR spectrum (150 MHz, CD$_3$OD) of diterpene glycoside 6 at 292K.
Figure 58:
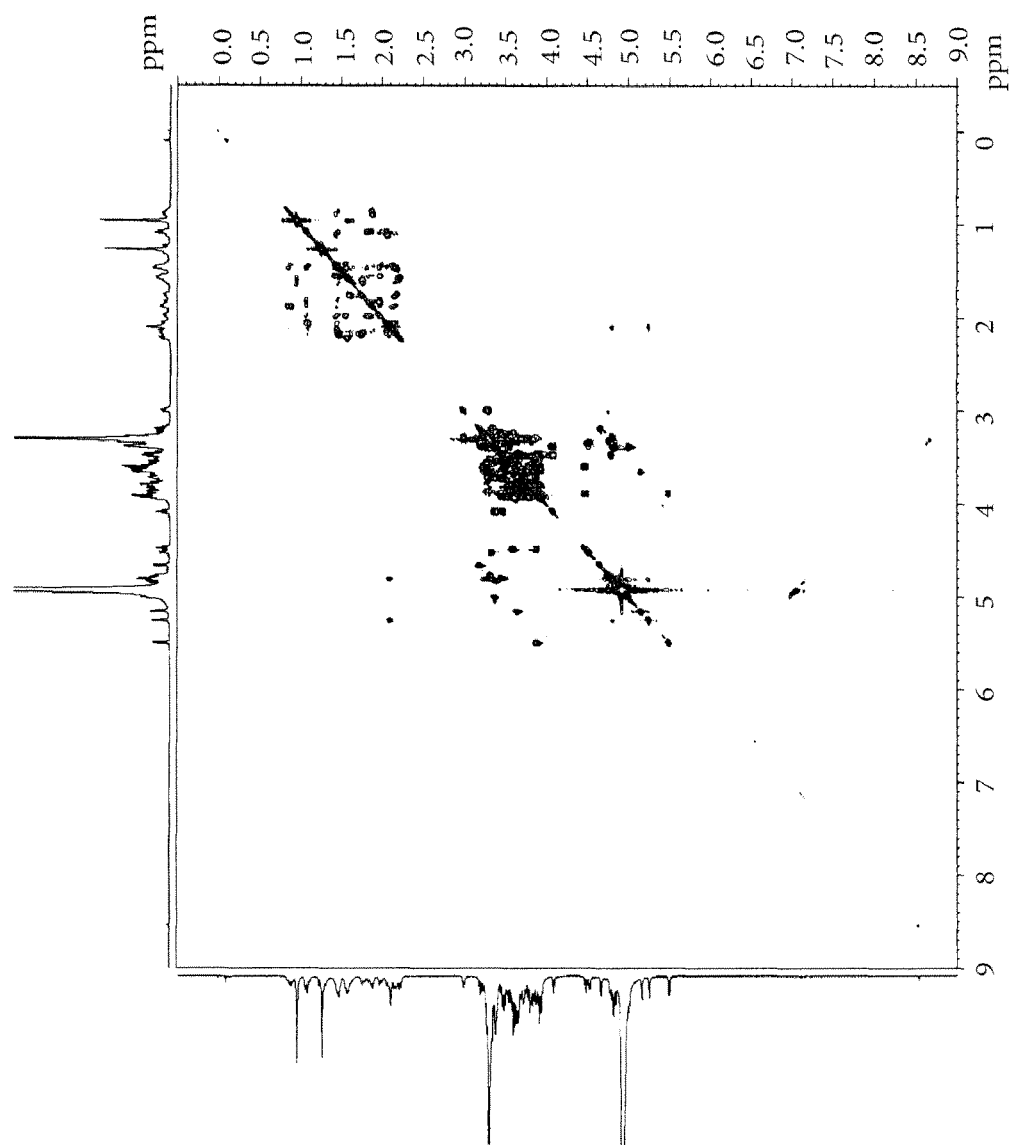
FIG. 58: Shows the $^1$H-$^1$H COSY spectrum (500 MHz, CD$_3$OD) of diterpene glycoside 6 at 292K.
Figure 59:
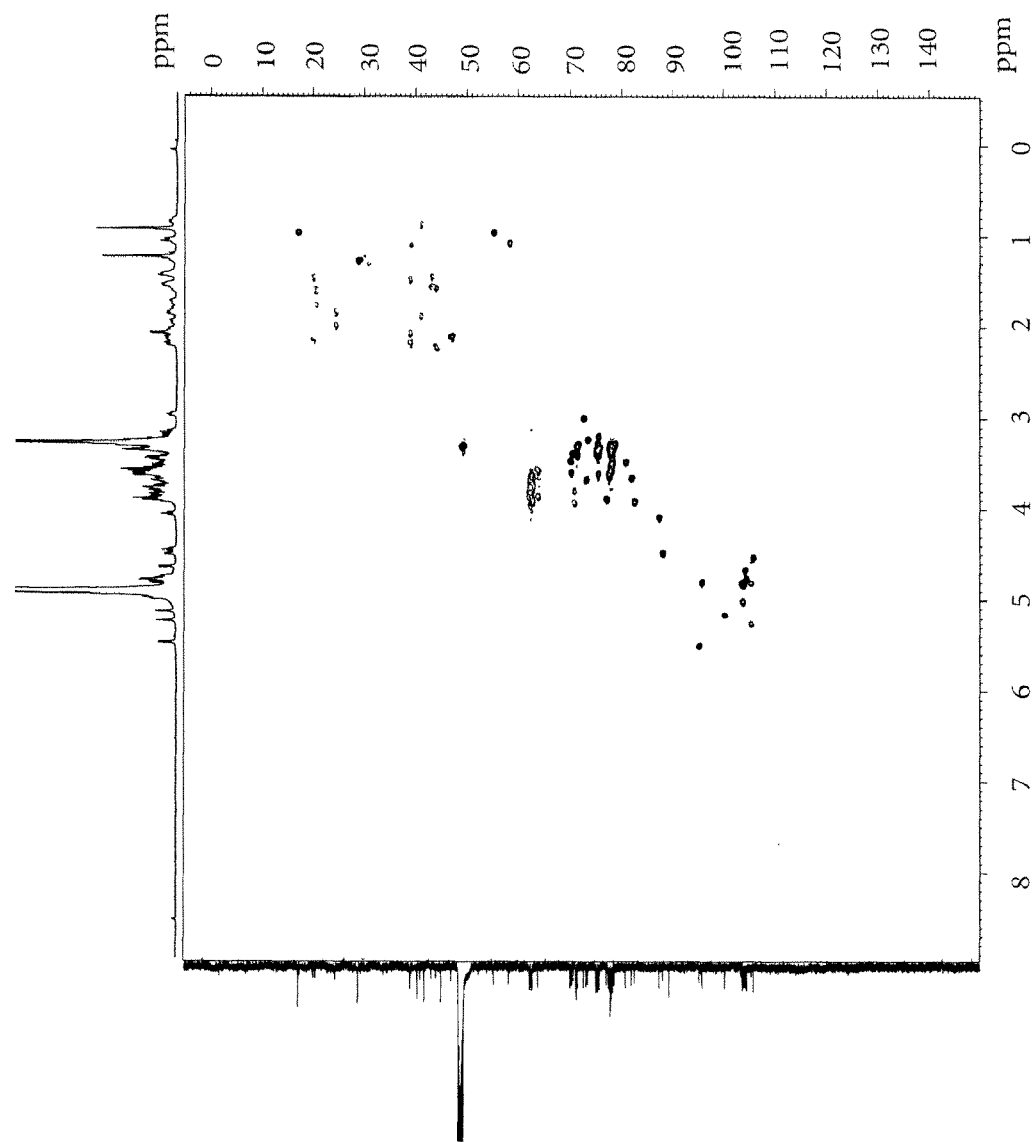
FIG. 59: Shows the HSQC-DEPT spectrum (500 MHz, CD$_3$OD) of diterpene glycoside 6 at 292K.
Figure 60:
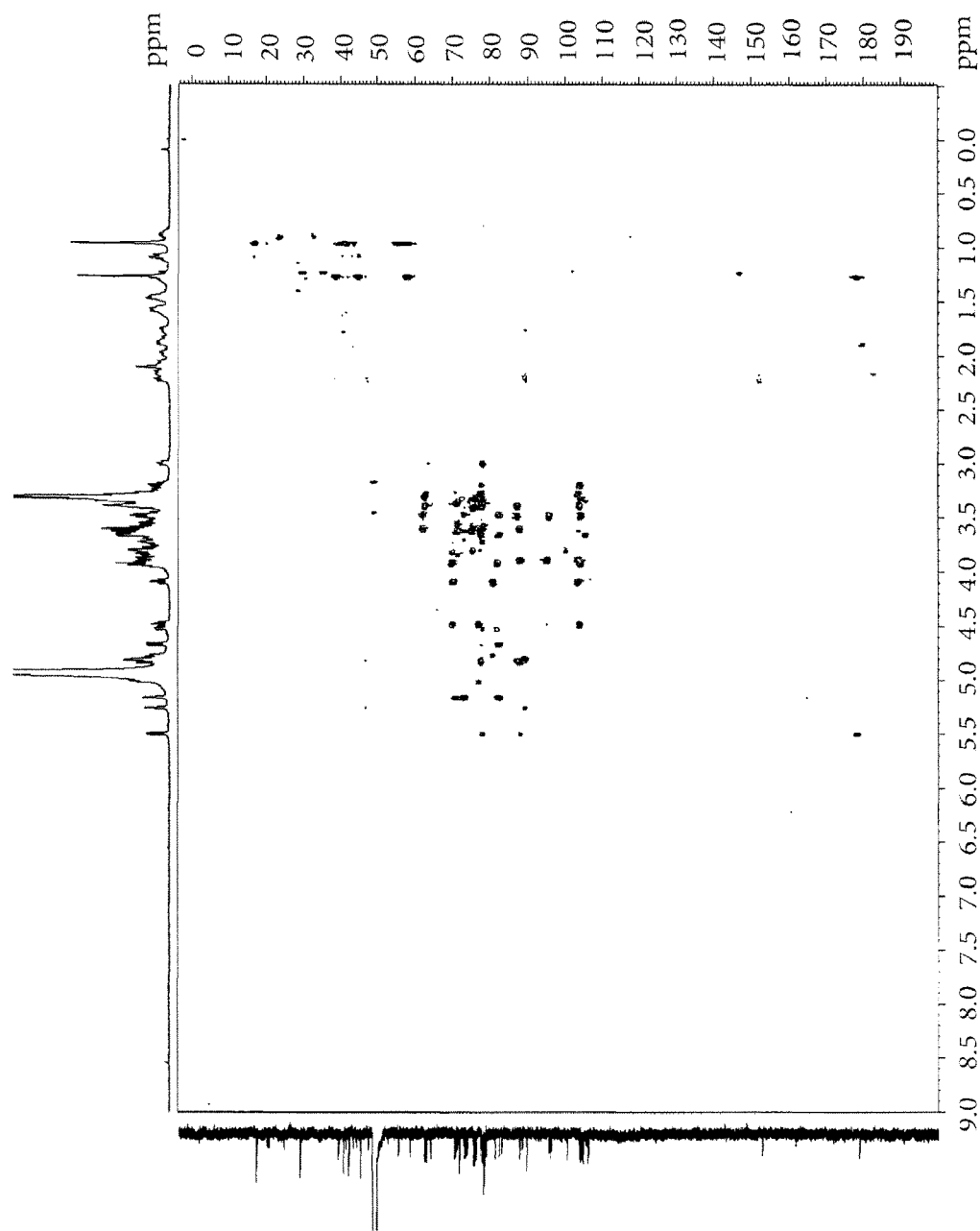
FIG. 60: Shows the HMBC spectrum (600 MHz, CD$_3$OD) of diterpene glycoside 6 at 292 K.
Figure 61:
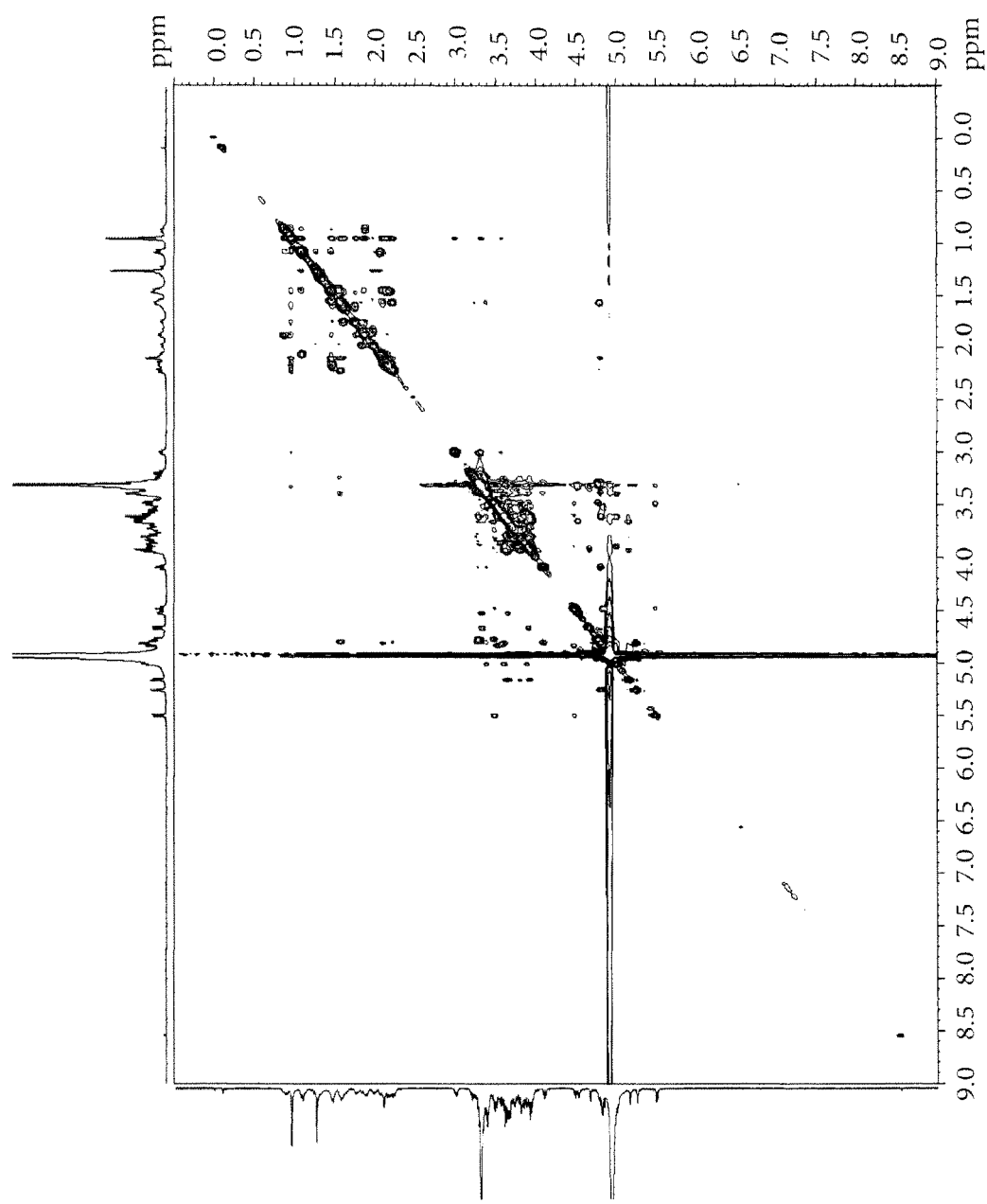
FIG. 61: Shows the NOESY spectrum (500 MHz, CD$_3$OD) of diterpene glycoside 6 at 292K.

NMR Spectroscopy. In the $^1$H NMR spectrum acquired at 300 K, some anomeric protons were obscured by water resonance. Therefore it was decided to acquire $^1$H NMR spectrum under variable temperature. In the $^1$H NMR spectrum acquired at 292 K (FIG. 56), the anomeric protons obscured by water resonance were resolved. Therefore, all NMR data were acquired at 292 K including $^{13}$C NMR (FIG. 57), $^1$H-$^1$H COSY (FIG. 58), HSQC-DEPT (FIG. 59), HMBC (FIG. 60), NOESY (FIG. 61), and 1D TOCSY (not shown).

The 1D and 2D NMR data indicated that the central core of the glycoside is a diterpene. An HMBC correlation from the methyl protons at $\delta_H$ 1.26 to the carbonyl at $\delta_C$ 178.8 allowed assignment of one of the tertiary methyl groups (C-18) as well as C-19 and provided a starting point for the assignment of the rest of the aglycone. Additional HMBC correlations from the methyl protons (H-18) to carbons at $\delta_C$ 39.1, 45.1, and 58.3 allowed assignment of C-3, C-4, and C-5. Analysis of the $^1$H-$^{13}$C HSQC-DEPT data indicated that the carbon at $\delta_C$ 39.1 was a methylene and the carbon at $\delta_C$ 58.3 was a methine which were assigned as C-3 and C-5, respectively. This carbon at $\delta_C$ 45.1, which did not show a correlation in the HSQC-DEPT spectrum, was assigned as the quaternary carbon, C-4. The $^1$H chemical shifts for C-3 ($\delta_H$ 1.09 and 2.06) and C-5 ($\delta_H$ 1.07) were assigned using the HSQC-DEPT data. A COSY correlation between one of the H-3 protons ($\delta_H$ 1.09) and a proton at $\delta_H$ 1.45 allowed assignment of one of the H-2 protons which in turn showed a correlation with a proton at $\delta_H$ 0.87 which was assigned to H-1. The remaining $^1$H and $^{13}$C chemical shifts for C-1 and C-2 were then assigned on the basis of additional COSY and HSQC-DEPT correlations.

The other tertiary methyl singlet, observed at $\delta_H$ 0.95 ($\delta_C$ 17.2), showed HMBC correlations to C-1 and C-5 and was assigned as H-20. The methyl protons showed additional HMBC correlations to a quaternary carbon ($\delta_C$ 40.5) and a methine carbon ($\delta_C$ 55.3) which were assigned as C-10 and C-9, respectively. COSY correlations between H-5 ($\delta_H$ 1.07) and protons at $\delta_H$ 1.84 and 1.98 then allowed assignment of the H-6 protons which in turn showed correlations to protons at $\delta_H$ 1.44 and 1.55 which were assigned to H-7. The $^{13}$C chemical shifts for C-6 ($\delta_C$ 24.5) and C-7 ($\delta_C$ 43.2) were then determined from the HSQC-DEPT data. COSY correlations between H-9 ($\delta_H$ 0.95) and proton at $\delta_H$ 1.59 allowed assignment of one of the H-11 protons. The $^1$H chemical shift for remaining proton at C-11 ($\delta_H$ 1.75) was assigned using the HSQC-DEPT data. COSY correlations from H-11 protons ($\delta_H$ 1.59 and 1.75) to a proton at $\delta_H$ 2.16 allowed assignment of one of the H-12 protons. The $^1$H chemical shift for remaining proton at C-12 ($\delta_H$ 1.47) was assigned using the HSQC-DEPT data. The HSQC-DEPT data was also used to assign C-11 ($\delta_C$ 20.6) and C-12 ($\delta_C$ 39.1). The olefinic protons observed at $\delta_H$ 4.81 (partially overlapped by an anomeric proton) and 5.25 showed HMBC correlations to a carbon at $\delta_C$ 89.5 (C-13) and were assigned to H-17 ($\delta_C$ 105.5 via HSQC-DEPT). The methine proton H-9 showed HMBC correlations to the carbons at $\delta_C$ 41.8 and 44.0 which were assigned as C-8 and C-14, respectively. HMBC correlation from H-17 to a carbon at $\delta_C$ 47.1 allowed assignment of C-15. The $^1$H chemical shifts at C-14 ($\delta_H$ 1.56 and 2.26) and C-15 ($\delta_H$ 2.09 and 2.12) were assigned using the HSQC-DEPT data. HMBC correlations from H-14 ($\delta_H$ 2.22) and H-17 ($\delta_H$ 4.81 and 5.25) to a quaternary carbon at $\delta_C$ 152.6 allowed assignment of C-16 to complete the assignment of the central core.

The relative stereochemistry of the central diterpene core could not be assigned unambiguously due to overlap of H-9 and H-20 at $\delta_H$ 0.95 as well as very close chemical shift of H-5 ($\delta_H$ 1.07) and H-3 ($\delta_H$ 1.09). However, since the proton and carbon chemical shifts for central diterpene core of CC-00319 are consistent with the proton and carbon chemical shifts for central diterpene core of previously reported Stevia compounds, the relative stereochemistry of central diterpene core is considered to be the same (FIG. 62) as for previously reported Stevia compounds.

Figure 62:
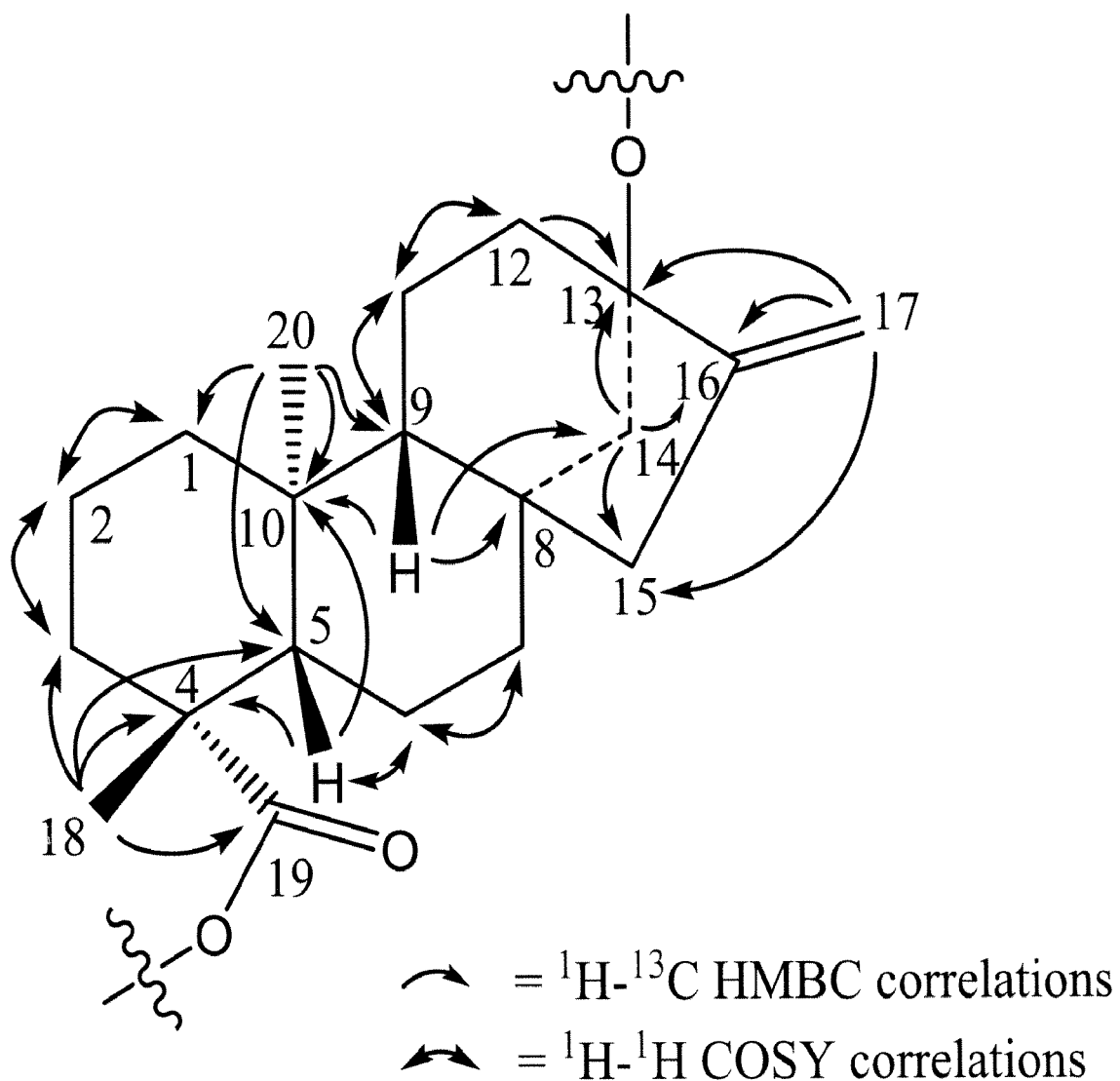
FIG. 62: Shows a summary of key HMBC and COSY correlations used to assign the aglycone region of diterpene glycoside 6.

A summary of the key HMBC and COSY correlations used to assign the aglycone region is provided in FIG. 62.

Figure 56:
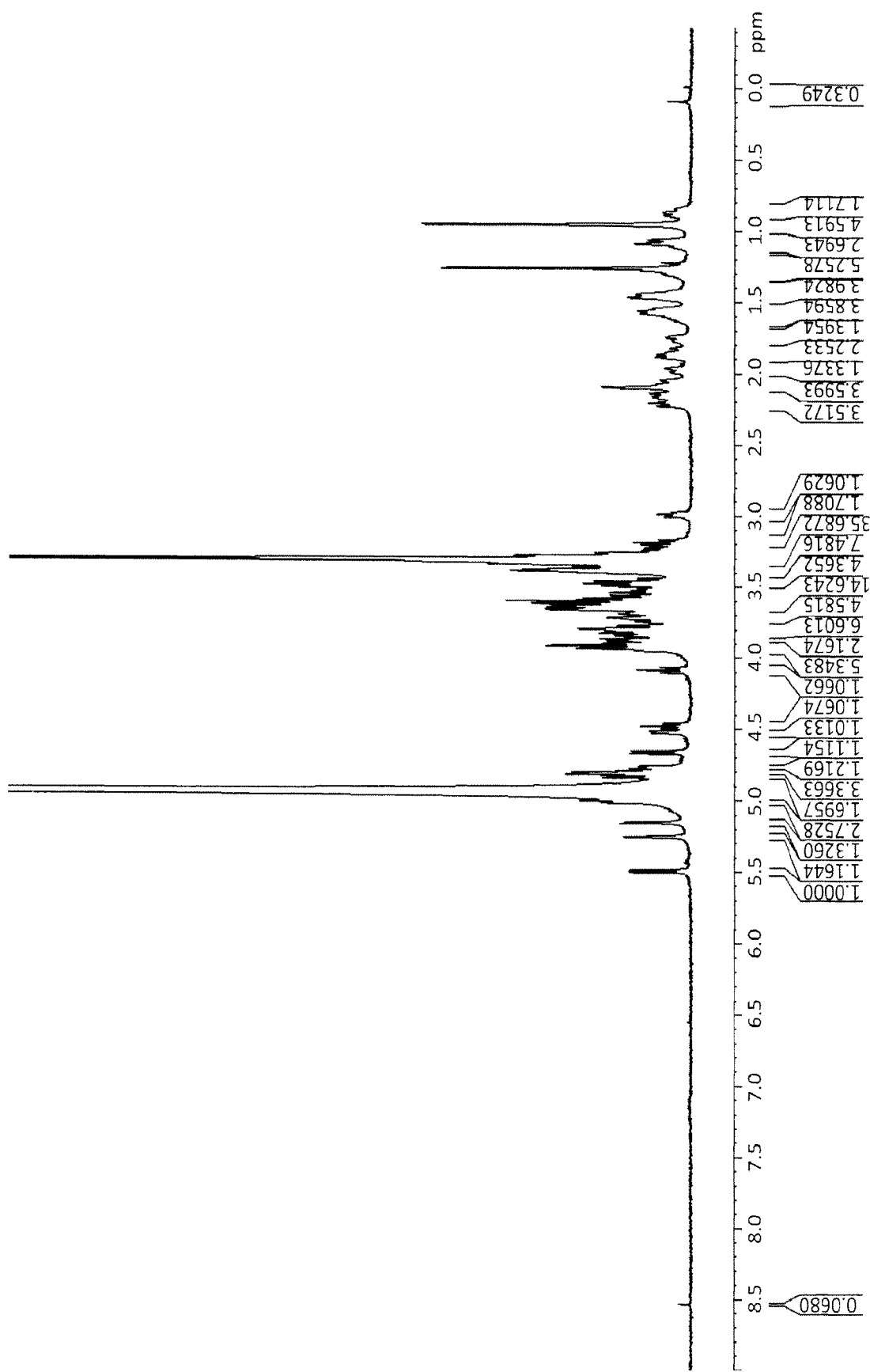
FIG. 56: Shows the $^1$H NMR spectrum (500 MHz, CD$_3$OD) of diterpene glycoside 6 at 292K.

Analysis of the $^1$H-$^{13}$C HSQC-DEPT data confirmed the presence of nine anomeric protons. Seven of the anomeric protons were well resolved at $\delta_H$ 5.49 ($\delta_C$ 95.4), 5.15 ($\delta_C$ 100.3), 5.00 ($\delta_C$ 104.0), 4.83 ($\delta_C$ 104.2), 4.77 ($\delta_C$ 104.6), 4.66 ($\delta_C$ 104.4), and 4.52 ($\delta_C$ 105.9) and two were partially overlapped at $\delta_H$ 4.80 ($\delta_C$ 103.8) and $\delta_H$ 4.79 ($\delta_C$ 96.0) in the $^1$H NMR spectrum acquired at 292 K. Some of the anomeric protons obscured by the water resonance in the $^1$H NMR spectrum acquired at 300 K were observed in the $^1$H NMR spectrum acquired at 292 K (FIG. 56). The anomeric proton at $\delta_H$ 5.15 had a small coupling (3.6 Hz) indicating that it had an α-configuration. The other anomeric protons had large couplings (7.2-8.3 Hz) indicating that they had β-configurations. The anomeric proton observed at $\delta_H$ 5.49 showed an HMBC correlation to C-19 which indicated that it corresponded to the anomeric proton of Glc$_I$. Similarly, the anomeric proton observed at $\delta_H$ 4.79 showed an HMBC correlation to C-13 allowing it to be assigned as the anomeric proton of Glc$_{II}$.

The Glc$_I$ anomeric proton ($\delta_H$ 5.49) showed a COSY correlation to a proton at $\delta_H$ 3.88 which was assigned as Glc$_I$ H-2 and in turn showed a COSY correlation to a proton at $\delta_H$ 4.48 (Glc$_I$ H-3). Due to data overlap the COSY spectrum did not allow assignment of the H-4, H-5 and H-6 protons. Therefore, a series of 1D TOCSY experiments were performed using selective irradiation of the Glc$_I$ anomeric proton with several different mixing times. In addition to confirming the assignments for Glc$_I$ H-2 through H-3, the TOCSY data showed protons at $\delta_H$ 3.59 assigned as Glc$_I$ H-4, at $\delta_H$ 3.48 assigned as Glc$_I$ H-5 and the protons at $\delta_H$ 3.73 and 3.82 assigned as the Glc$_I$ H-6. The $^{13}$C chemical shifts for Glc$_I$ C-2 ($\delta_C$ 77.2), C-3 ($\delta_C$ 88.2), C-4 ($\delta_C$ 70.2), C-5 ($\delta_C$ 77.6-78.4), and C-6 ($\delta_C$ 62.3-62.8) were assigned using the HSQC-DEPT data. The HMBC correlations observed from the Glc$_I$ H-1 to C-3 and C-5, H-2 to C-1 and C-3, H-3 to C-3 and C-4, H-4 to C-3 and H-6 ($\delta_H$ 3.82) to C-4 further confirmed the assignments made above to complete the assignment of Glc$_I$. A coupling value of 8.3 Hz in the $^1$H NMR spectrum indicated β-configuration for Glc$_I$.

Of the eight remaining unassigned glucose moieties two were assigned as substituents at C-2 and C-3 of Glc$_I$ on the basis of HMBC correlations. The anomeric proton observed at $\delta_H$ 5.00 showed an HMBC correlation to Glc$_I$ C-2 and was assigned as the anomeric proton of Glc$_V$. The reciprocal HMBC correlation from Glc$_I$ H-2 to the anomeric carbon of Glc$_V$ was also observed. The anomeric proton observed at $\delta_H$ 4.83 showed an HMBC correlation to Glc$_I$ C-3 and was assigned as the anomeric proton of Glc$_{VI}$. The reciprocal HMBC correlation from Glc$_I$ H-3 to the anomeric carbon of Glc$_{VI}$ was also observed.

Assignment of Glc$_{VI}$ was carried out in a similar manner. The anomeric proton of Glc$_{VI}$ ($\delta_H$ 4.83) showed a COSY correlation with a proton at $\delta_H$ 3.39 which was assigned as Glc$_{VI}$ H-2 and in turn showed a COSY correlation to a proton at $\delta_H$ 3.54 (Glc$_{VI}$ H-3). Glc$_{VI}$ C-2 ($\delta_C$ 75.2-75.9) and C-3 ($\delta_C$ 77.6-78.4) were then assigned using the HSQC-DEPT data. Due to data overlap the COSY spectrum did not allow assignment of the remaining protons. Therefore, a series of 1D TOCSY experiments were performed using selective irradiation of the Glc$_{VI}$ anomeric proton with several different mixing times. In addition to confirming the assignments for Glc$_{VI}$ H-2 and H-3, the TOCSY data allowed assignment of Glc$_{VI}$ H-4 ($\delta_H$ 3.31), and H-5 ($\delta_H$ 3.60). The protons observed at $\delta_H$ 3.63 and $\delta_H$ 3.94 in the TOCSY spectrum were assigned as the Glc$_{VI}$ H-6 protons. The additional resonances at $\delta_H$ 4.81 and 5.25 ppm observed in the TOCSY spectra are due to H-17 since one of the H-17 protons at $\delta_H$ 4.81 being very close to Glc$_{VI}$ H-1 was also impacted by the TOCSY irradiation pulse. In the TOCSY spectra, the resonance at 4.91 ppm is due to water. Other minor resonances are due to TOCSY correlations from Glc$_{IV}$ proton at $\delta_H$ 4.80. The $^{13}$C chemical shifts for C-4 ($\delta_C$ 71.3 or 71.5), C-5 ($\delta_C$ 77.6-78.4), and C-6 ($\delta_C$ 62.3-62.8) were assigned using the HSQC-DEPT data. The HMBC correlations observed from the Glc$_{VI}$ H-1 to C-3 and/or C-5, H-2 to C-1, H-3 to C-4 and H-6 ($\delta_H$ 3.63) to C-4 further confirmed the assignments made above to complete the assignment of Glc$_{VI}$. A coupling value of 8.0 Hz in the $^1$H NMR spectrum indicated β-configuration for Glc$_{VI}$.

The anomeric proton of Glc$_V$ ($\delta_H$ 5.00) showed a COSY correlation with a proton at $\delta_H$ 3.38 which was assigned as Glc$_V$ H-2. Glc$_V$ C-2 ($\delta_C$ 75.2-75.9) was then assigned using the HSQC-DEPT data. Due to data overlap the COSY spectrum did not allow assignment of the remaining protons. Therefore, a series of 1D TOCSY experiments were performed using selective irradiation of the Glc$_V$ anomeric proton with several different mixing times. In addition to confirming the assignments for Glc$_V$ H-2, the TOCSY data allowed assignment of Glc$_V$ H-3 ($\delta_H$ 3.38), H-4 ($\delta_H$ 3.23), and H-5 ($\delta_H$ 3.60). The protons observed at $\delta_H$ 3.79 and $\delta_H$ 3.92 in the TOCSY spectrum were assigned as the Glc$_V$ H-6 protons. These assignments were further confirmed by COSY correlations between Glc$_V$ H-3/H-4, H-4/H-5 and H-5/H-6 ($\delta_H$ 3.92). The $^{13}$C chemical shifts for Glc$_V$ C-3 ($\delta_C$ 77.6-78.4), C-4 ($\delta_C$ 73.6), C-5 ($\delta_C$ 75.5 or 75.6) and C-6 ($\delta_C$ 70.8) were assigned using the HSQC-DEPT data. HMBC correlations from Glc$_V$ H-4 to C-6 and H-6 ($\delta_H$ 3.79) to C-5 confirmed the assignments made above to complete the assignment of Glc$_V$. A coupling value of 7.2 Hz in the $^1$H NMR spectrum indicated β-configuration for Glc$_V$. The downfield chemical shift of C-6 indicated that the hydroxyl group at C-6 is replaced by a sugar linkage. This was confirmed by HMBC correlations discussed below.

The anomeric proton of Glc$_{VII}$ at $\delta_H$ 5.15 ($\delta_C$ 100.3) showed an HMBC correlation to the carbon at $\delta_C$ 70.8 ppm (Glc$_V$ C-6) indicating that it was attached to Glc$_V$ via a 1→6 linkage. The reciprocal HMBC correlation was also observed from the methylene proton of Glc$_V$ ($\delta_H$ 3.79) to the anomeric carbon of Glc$_{VII}$ at $\delta_C$ 100.3 confirming the 1→6 linkage between Glc$_{VII}$ and Glc$_V$. The anomeric proton of Glc$_{VII}$ ($\delta_H$ 5.15) showed a COSY correlation with a proton at $\delta_H$ 3.65 which was assigned as Glc$_{VII}$ H-2. Glc$_{VII}$ C-2 ($\delta_C$ 82.1) was then assigned using the HSQC-DEPT data. Due to data overlap the COSY spectrum did not allow unambiguous assignment of the remaining protons. Therefore, a series of 1D TOCSY experiments were performed using selective irradiation of the Glc$_{VII}$ anomeric proton with several different mixing times. In addition to confirming the assignments for Glc$_{VII}$ H-2, the TOCSY data allowed assignment of Glc$_{VII}$ H-3 ($\delta_H$ 3.91), H-4 ($\delta_H$ 3.46), and H-5 ($\delta_H$ 3.67). The protons observed at $\delta_H$ 3.71 and 3.80 in the TOCSY spectrum were assigned as the Glc$_{VII}$ H-6 protons. The $^{13}$C chemical shifts for Glc$_{VII}$ C-3 ($\delta_C$ 82.7), C-4 ($\delta_C$ 70.1), C-5 ($\delta_C$ 73.3) and C-6 ($\delta_C$ 62.3-62.8) were assigned using the HSQC-DEPT data. The HMBC correlations observed from the Glc$_{VII}$ H-1 to C-2 and C-5 and H-2 to C-3 further confirmed the assignments made above to complete the assignments of Glc$_{VII}$. A coupling value of 3.6 Hz in the $^1$H NMR spectrum indicated α-configuration for Glc$_{VII}$.

Of the five remaining unassigned glucose moieties, two glucose moieties with anomeric protons at $\delta_H$ 4.52 ($\delta_C$ 105.9) and $\delta_H$ 4.66 ($\delta_C$ 104.4) were assigned as substituents at C-2 and C-3 of $Glc_{VII}$ on the basis of HMBC correlations. The anomeric proton observed at $\delta_H$ 4.52 showed an HMBC correlation to $Glc_{VII}$ C-2 and was assigned as the anomeric proton of $Glc_{VIII}$. The anomeric proton observed at $\delta_H$ 4.66 showed an HMBC correlation to $Glc_{VII}$ C-3 and was assigned as the anomeric proton of $Glc_{IX}$. The reciprocal HMBC correlations from $Glc_{VII}$ H-2 to the anomeric carbon of $Glc_{VIII}$ and from $Glc_{VII}$ H-3 to the anomeric carbon of $Glc_{IX}$ were also observed.

The anomeric proton of $Glc_{VIII}$ ($\delta_H$ 4.52) showed a COSY correlation with a proton at $\delta_H$ 3.33 which was assigned as $Glc_{VIII}$ H-2. Due to data overlap the COSY spectrum did not allow assignment of the remaining protons. Therefore, a series of 1D TOCSY experiments were performed using selective irradiation of the $Glc_{VIII}$ anomeric proton with several different mixing times. In addition to confirming the assignments for $Glc_{VIII}$ H-2, the TOCSY data allowed assignment of $Glc_{VIII}$ H-4 ($\delta_H$ 3.39) and H-6 ($\delta_H$ 3.71 and $\delta_H$ 3.88). The partially overlapping protons observed at $\delta_H$ ~3.30-~3.32 were due to H-3 and H-5. Although H-3 and H-5 could not be unambiguously assigned based on TOCSY data, the assignment of H-5 was confirmed by the correlations observed from $Glc_{VIII}$ H-6 ($\delta_H$ 3.71) to $Glc_{VIII}$ H-5 ($\delta_H$ ~3.30) in COSY spectrum and thus the remaining proton at $\delta_H$ ~3.32 was assigned as H-3. In the TOCSY spectrum additional resonances at $\delta_H$ 4.48 and $\delta_H$ 5.49 corresponding to $Glc_I$ protons were also observed since $Glc_I$ H-3 at $\delta_H$ 4.48 is close to $Glc_{VIII}$ H-1 ($\delta_H$ 4.52) and the TOCSY irradiation also impacted the proton at $\delta_H$ 4.48 consequently correlation from this proton was also observed. Assignment of the $^{13}C$ chemical shifts for $Glc_{VIII}$ C-2 ($\delta_C$ 75.2-75.9), C-3 ($\delta_C$ 77.6-78.4), C-4 ($\delta_C$ 71.3 or 71.5), C-5 ($\delta_C$ 77.6-78.4), and C-6 ($\delta_C$ 62.3-62.8) was determined using the HSQC-DEPT data. The HMBC correlations observed from the $Glc_{VIII}$ H-1 to C-3 and/or C-5 and H-4 to C-6 further confirmed the assignments made above to complete the assignment of $Glc_{VIII}$. A coupling value of 7.2 Hz in the $^1H$ NMR spectrum indicated β-configuration for $Glc_{VIII}$.

The anomeric proton of $Glc_{IX}$ ($\delta_H$ 4.66) showed a COSY correlation with a proton at $\delta_H$ 3.19 which was assigned as $Glc_{IX}$ H-2. The $Glc_{IX}$ H-2 in turn showed a COSY correlation to $Glc_{IX}$ H-3 ($\delta_H$ 3.36). Due to data overlap the COSY spectrum did not allow assignment of the remaining protons. Therefore, a series of 1D TOCSY experiments were performed using selective irradiation of the $Glc_{IX}$ anomeric proton with several different mixing times. In addition to confirming the assignments for $Glc_{IX}$ H-2 and H-3, the TOCSY data allowed assignment of $Glc_{IX}$ H-6 ($\delta_H$ 3.65 and 3.84). The partially overlapped resonances observed in the TOCSY spectrum at $\delta_H$ ~3.30-~3.32 were due to H-4 and H-5 protons. Although, H-4 and H-5 could not be unambiguously assigned based on TOCSY data, the assignment of H-5 was confirmed by the correlations observed from $Glc_{IX}$ H-6 ($\delta_H$ 3.65 and 3.84) to $Glc_{IX}$ H-5 ($\delta_H$ ~3.32) in COSY spectrum and thus the remaining proton at $\delta_H$ ~3.30 was assigned as H-4. Assignment of the $^{13}C$ chemical shifts for $Glc_{IX}$ C-2 ($\delta_C$ 75.5 or 75.6), C-3 ($\delta_C$ 77.6-78.4), C-4 ($\delta_C$ 71.3 or 71.5), C-5 ($\delta_C$ 77.6-78.4), and C-6 ($\delta_C$ 62.3-62.8) was determined using the HSQC-DEPT data. HMBC correlations from $Glc_{IX}$ H-2 to C-1 and C-3 and H-6 ($\delta_H$ 3.84) to C-4 confirmed the assignments made above to complete the assignment of $Glc_{IX}$. A coupling value of 8.1 Hz in the $^1H$ NMR spectrum indicated β-configuration for $Glc_{IX}$.

Figure 63:
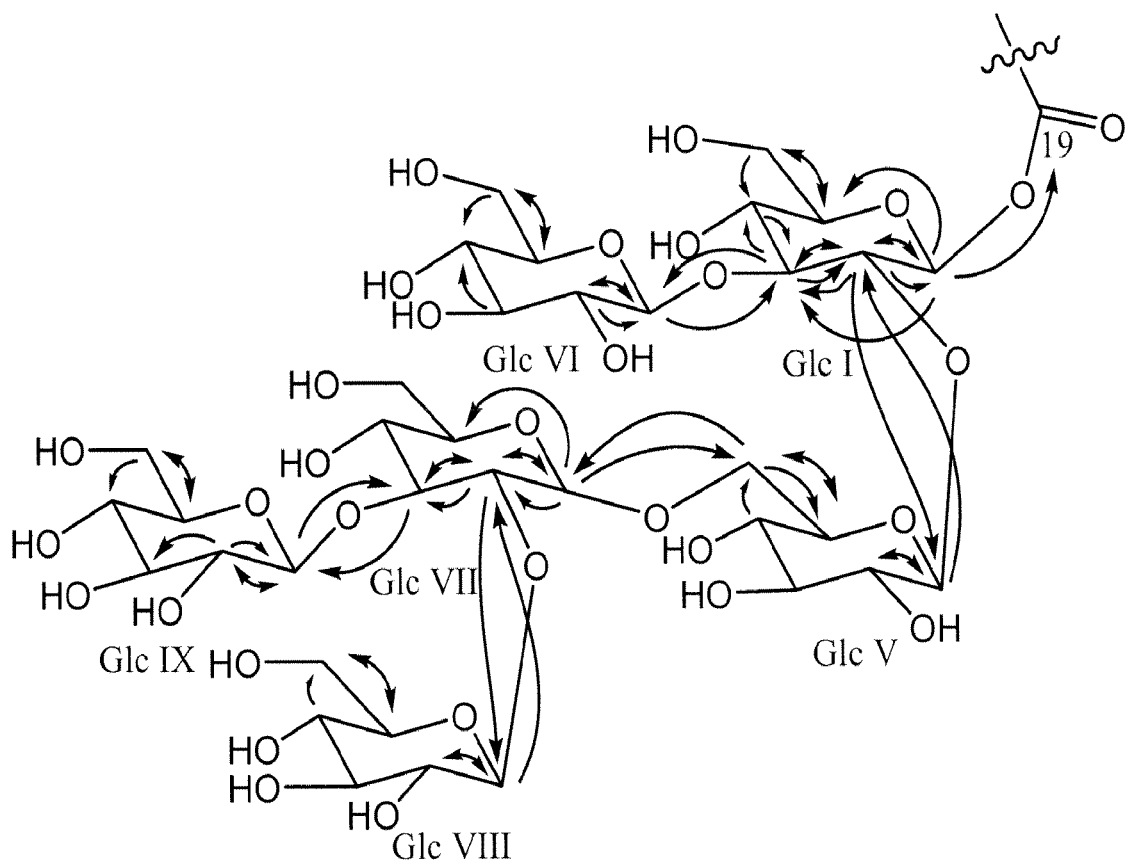
FIG. 63: Shows a summary of key HMBC and COSY correlations used to assign the C-19 glycoside region of diterpene glycoside 6.

A summary of the key HMBC and COSY correlations used to assign the C-19 glycoside region is provided in FIG. 63.

Assignment of $Glc_{II}$ was carried out in a similar manner. The $Glc_{II}$ anomeric proton ($\delta_H$ 4.79) showed a COSY correlation to a proton at $\delta_H$ 3.47 which was assigned as $Glc_{II}$ H-2 and in turn showed a COSY correlation to a proton at $\delta_H$ 4.08 ($Glc_{II}$ H-3). This latter proton showed an additional correlation with a proton at $\delta_H$ 3.38 ($Glc_{II}$ H-4). Due to data overlap the COSY spectrum did not allow assignment of the remaining protons. Since $Glc_{II}$ H-1 ($\delta_H$ 4.79) was partially overlapped with $Glc_{IV}$ H-1 ($\delta_H$ 4.80) and $Glc_{II}$ H-3 ($\delta_H$ 4.08) was well resolved, 1D TOCSY experiments were performed using selective irradiation of the $Glc_{II}$ H-3 proton with several different mixing times. In addition to confirming the assignments for $Glc_{II}$ H-1 and H-2, the TOCSY data allowed assignment of $Glc_{VII}$ H-4 ($\delta_H$ 3.38) and H-5 ($\delta_H$ 3.28). The protons observed at $\delta_H$ 3.65 and 3.78 in the TOCSY spectrum were assigned as the $Glc_{II}$ H-6 protons. Since $Glc_{II}$ H-1 ($\delta_H$ 4.79) was partially overlapped with $Glc_{IV}$ H-1 ($\delta_H$ 4.80), the coupling constant of $Glc_{II}$ H-1 at $\delta_H$ 4.79 could not be determined from the $^1H$ NMR spectrum. However in the 1D TOCSY spectrum of $Glc_{II}$ H-3 ($\delta_H$ 4.08) the $Glc_{II}$ anomeric proton was well resolved and thus coupling was determined to be 8.0 Hz indicating a β-orientation of $Glc_{II}$. Assignment of the $^{13}C$ chemical shifts for $Glc_{II}$ C-2 ($\delta_C$ 81.0), C-3 ($\delta_C$ 87.5), C-4 ($\delta_C$ 70.5), C-5 ($\delta_C$ 77.6-78.4) and C-6 ($\delta_C$ 62.3-63.8) was based on HSQC-DEPT data. COSY correlations between $Glc_{II}$ H-5 and both protons of H-6 together with the HMBC correlations from $Glc_{II}$ H-1 to C-3 and C-5, H-2 to C-1 and C-3 and also from $Glc_{II}$ H-4 to C-3 confirmed the assignments made above to complete the assignment of $Glc_{II}$.

The remaining two unassigned glucose moieties were assigned as substituents at C-2 and C-3 of $Glc_{II}$ on the basis of HMBC correlations. The anomeric proton observed at $\delta_H$ 4.77 showed an HMBC correlation to $Glc_{II}$ C-2 and was assigned as the anomeric proton of $Glc_{III}$. The anomeric proton observed at $\delta_H$ 4.80 showed an HMBC correlation to $Glc_{II}$ C-3 and was assigned as the anomeric proton of $Glc_{IV}$. The reciprocal HMBC correlations from $Glc_{II}$ H-2 to the anomeric carbon of $Glc_{III}$ and from $Glc_{II}$ H-3 to the anomeric carbon of $Glc_{IV}$ were also observed.

The anomeric proton of $Glc_{III}$ ($\delta_H$ 4.77) showed a COSY correlation with a proton at $\delta_H$ 3.31 which was assigned as $Glc_{III}$ H-2. $Glc_{III}$ C-2 ($\delta_C$ 75.2-75.9) was then assigned using the HSQC-DEPT data. Due to data overlap the COSY spectrum did not allow assignment of the remaining protons. Since chemical shift of $Glc_{III}$ H-1 ($\delta_H$ 4.77) was very close to $Glc_{II}$ H-1 ($\delta_H$ 4.79) and $Glc_{IV}$ H-1 ($\delta_H$ 4.80), the 1D TOCSY experiments using selective irradiation of the $Glc_{III}$ H-1 would give correlations for all three anomeric protons. Therefore, 1D TOCSY experiments were performed using selective irradiation of the well resolved $Glc_{III}$ H-4 proton at $\delta_H$ 2.99 with several different mixing times. In addition to confirming the assignments for $Glc_{III}$ H-2, the TOCSY data allowed assignment of $Glc_{III}$ H-3 ($\delta_H$ 3.27) and H-5 ($\delta_H$ ~3.31). The protons observed at $\delta_H$ 3.56 and $\delta_H$ 3.85 in the TOCSY spectrum were assigned as the $Glc_{III}$ H-6 protons.

The chemical shift of H-5 ($\delta_H$ ~3.31) was further confirmed by COSY correlations between H-5 and H-6 ($\delta_H$ 3.56 and $\delta_H$ 3.85). The $^{13}$C chemical shifts for C-3 ($\delta_C$ 78.7), C-4 ($\delta_C$ 72.8), C-5 ($\delta_C$ 77.6-78.4) and C-6 ($\delta_C$ 63.8) were assigned using the HSQC-DEPT data. The HMBC correlation observed from the Glc$_{III}$ H-4 to C-6 further confirmed the assignments made above to complete the assignment of Glc$_{III}$. A coupling value of 7.2 Hz in the $^1$H NMR spectrum indicated β-configuration for Glc$_{III}$.

The anomeric proton of Glc$_{IV}$ ($\delta_H$ 4.80) showed a COSY correlation with a proton at $\delta_H$ 3.27 which was assigned as Glc$_{IV}$ H-2 which in turn showed a COSY correlation with a proton at $\delta_H$ ~3.60 which was assigned as Glc$_{IV}$ H-3. Due to data overlap the COSY spectrum did not allow assignment of the remaining protons. Therefore, a series of 1D TOCSY experiments were performed using selective irradiation of the Glc$_{IV}$ anomeric proton with several different mixing times. Since Glc$_{IV}$ H-1 ($\delta_H$ 4.80) and Glc$_{II}$ H-1 ($\delta_H$ 4.79) have very close chemical shift and Glc$_{III}$ H-1 ($\delta_H$ 4.77) and Glc$_{VI}$ H-1 ($\delta_H$ 4.83) chemical shifts are also very close to Glc$_{IV}$ H-1, the irradiation of the proton at $\delta_H$ 4.80 impacted the protons of all four glucose moieties and TOCSY correlations for all four glucose moieties were observed in the spectra. However, since proton assignments for Glc$_{II}$, Glc$_{III}$, and Glc$_{VI}$ have already been made, the protons of Glc$_{IV}$ were assigned based on elimination of other glucose protons. Hence, in addition to confirming the assignments for Glc$_{IV}$ H-2 and H-3, the TOCSY data allowed assignment of Glc$_{IV}$ H-4 ($\delta_H$ ~3.29), H-5 ($\delta_H$ ~3.62) and H-6 ($\delta_H$ 3.78 and 3.92). The chemical shift of H-5 ($\delta_H$ ~3.62) was further confirmed by COSY correlations between H-5 and H-6 ($\delta_H$ 3.92). The additional resonance at $\delta_H$ 5.25 ppm in the TOCSY spectra are due to H-17 since one of the H-17 protons at $\delta_H$ 4.81 being very close to Glc$_{IV}$ H-1 was also impacted by the TOCSY irradiation pulse. Since Glc$_{IV}$ H-1 ($\delta_H$ 4.80) was partially overlapped with Glc$_{II}$ H-1 ($\delta_H$ 4.79), the coupling constant of Glc$_{IV}$ H-1 at $\delta_H$ 4.80 could not be determined from $^1$H NMR spectrum. Therefore 1D TOCSY experiment was performed using selective irradiation of the Glc$_{IV}$ proton at $\delta_H$ 3.92 (H-6). While in the resulting spectrum, TOCSY correlation from several other sugars (Glc$_I$, Glc$_V$, Glc$_{VI}$, Glc$_{VII}$, and Glc$_{VIII}$) were observed (since these glucose also have proton chemical shift either at $\delta_H$ 3.92 or very close to $\delta_H$ 3.92) the anomeric proton of Glc$_{IV}$ at $\delta_H$ 4.80 was resolved and the coupling constant was determined to be 8.1 Hz indicating β-orientation for Glc$_{IV}$. Assignment of the $^{13}$C chemical shifts for Glc$_{IV}$ C-2 ($\delta_C$ 75.4), C-3 ($\delta_C$ 77.6-78.4), C-4 ($\delta_C$ 71.7), C-5 ($\delta_C$ 77.6-78.4) and C-6 ($\delta_C$ 62.3-62.8) was based on HSQC-DEPT data. HMBC correlations from Glc$_{IV}$ H-1 to C-3 and/or C-5, H-2 to C-1, H-3 to C-2 and C-4 and H-4 to C-6 confirmed the assignments made above to complete the assignment of Glc$_{VI}$.

Figure 64:
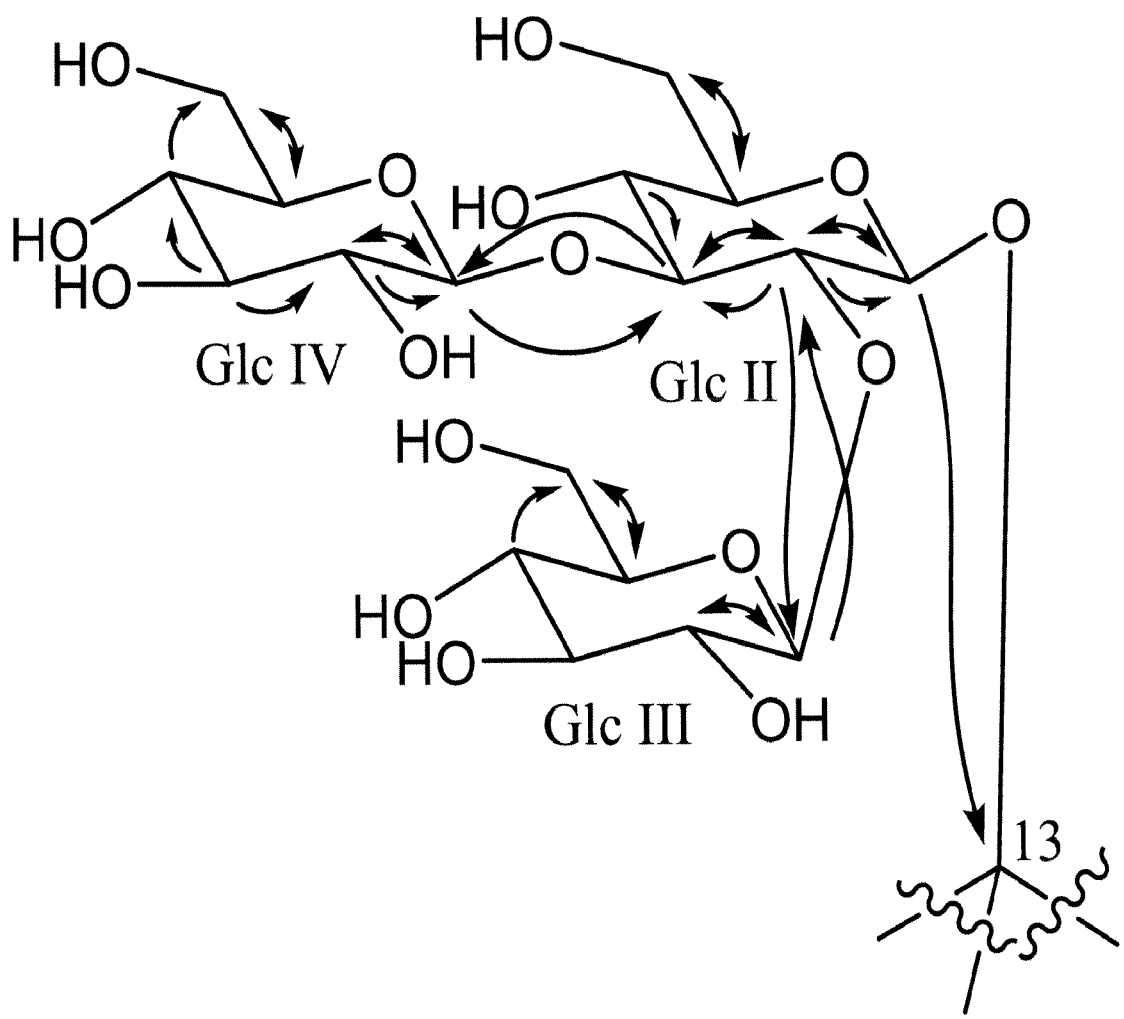
FIG. 64: Shows a summary of key HMBC and COSY correlations used to assign the C-13 glycoside region of diterpene glycoside 6.

A summary of the key HMBC and COSY correlations used to assign the C-13 glycoside region is provided in FIG. 64.

Some impurity(ies) resonances were also observed in $^1$H NMR spectrum at $\delta_H$ −0.01, 0.90, 1.22, and 8.53 ppm.

Figure 65:
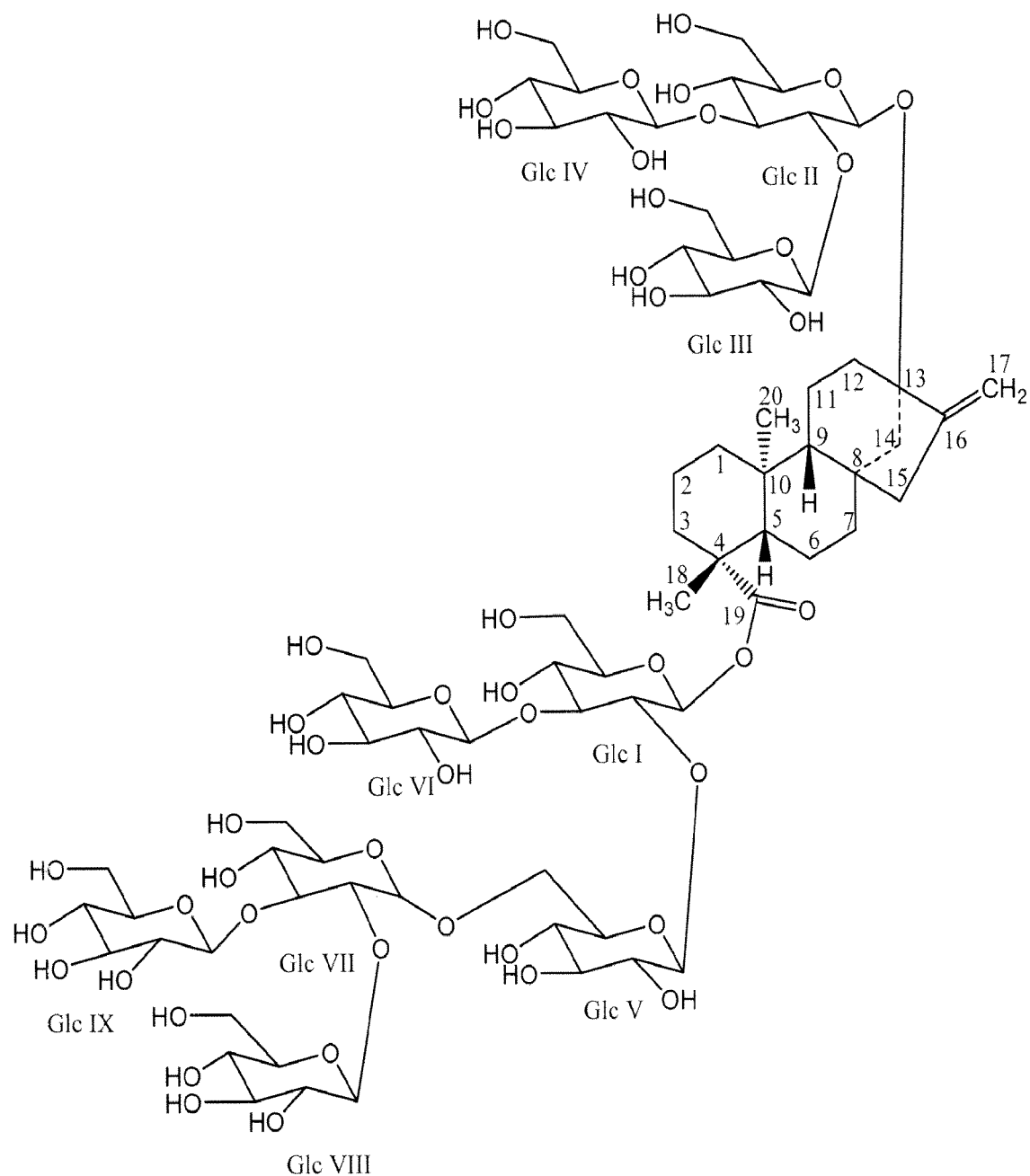
FIG. 65: Shows the structure of diterpene glycoside 6, i.e, (13-[(2-O-β-D-glucopyranosyl-3-O-β-D-glucopyranosyl)-β-D-glucopyranosyl)oxy] ent-kaur-16-en-19-oic acid-[(2-O-β-D-glucopyranosyl-(6-O-α-D-glucopyranosyl-(2-O-β-D-glucopyranosyl-3-O-β-D-glucopyranosyl)-3-O-β-D-glucopyranosyl)-β-D-glucopyranosyl) ester].

The structure was determined to be (13-[(2-O-β-D-glucopyranosyl-3-O-β-D-glucopyranosyl)-β-D-glucopyranosyl)oxy] ent-kaur-16-en-19-oic acid-[(2-O-β-D-glucopyranosyl-(6-O-α-D-glucopyranosyl-(2-O-β-D-glucopyranosyl-3-O-β-D-glucopyranosyl)-3-O-β-D-glucopyranosyl)-β-D-glucopyranosyl) ester] as shown in FIG. 65.

Example 7

Sensory Evaluation of 1 and 3

Samples were prepared as described in Table 1. All samples were served at 4° C.

TABLE 1

| Sample Description | | | |
|---|---|---|---|
| Sweetener | Concentration (ppm) | Matrix | Temperature Tested |
| Reb M (>95%) | 400 | Water | 4° C. |
| 3 | 400 | Water | 4° C. |
| 1 (>95%) | 400 | Water | 4° C. |

Samples were evaluated using a single sip protocol as follows:

Samples were served at approximately 4° C.

Panelists were instructed to take 1 sip of the sample, hold in mouth for 5 seconds, expectorate comfortable with this), and rate the given attributes A 5 minute break was placed between each sample and panelists were instructed to cleanse their palates with at least 1 bite of unsalted cracker and 2 sips of filtered water Due to limited sample quantities, panelists were given the following amounts to test:

a 3 vs Reb M: 1.5 mL 1 vs Reb M: 5 mL

Samples were randomized within each session for each panelist

All samples were presented in replicate in each session

Samples were evaluated for:

Sweet taste intensity: maximum level of sweetness in mouth during 5 seconds

Bitter taste intensity: maximum level of bitterness in mouth during 5 seconds

Overall maximum sweet intensity: maximum sweet intensity experienced from the time the sip is taken up to 1 minute Overall maximum bitter intensity: maximum sweet intensity experienced from the time the sip is taken up to 1 minute Other intensity: Intensity of any aromatic other than sweet and bitter (metallic, plastic, licorice, etc.) or mouthfeel/sensation Sweet linger intensity: sweet intensity 1 minute after tasting the sample Bitter aftertaste intensity: bitter intensity 1 minute after tasting the sample Data Analysis. A 3-way ANOVA was used to compare the sweeteners for each attribute, for 1 only, and significance was determined at p<0.05. Fishers's LSD was used to determine significant differences between mean scores. The results of the test are shown in Table 2.

TABLE 2

| | | Sweet Intensity (In mouth) | Bitter Intensity (In mouth) | Overall Max Sweetness Intensity | Overall Max Bitterness Intensity | Other Intensity | Sweet Linter Intensity | Bitter Aftertaste Intensity |
|---|---|---|---|---|---|---|---|---|
| Sample | N | | | | | | | |
| Reb M 400 ppm | 3 | 7.4 | 0.4 | 6.3 | 1.4 | 0.3 | 2.5 | 0.3 |
| 3 (400 ppm) | 3 | 5.4 | 0.3 | 5.6 | 1.3 | 0.5 | 0.9 | 0.3 |
| Reb M 400 ppm | 6 | 7.8 | 0.7 | 8.4 | 0.8 | 0.8 | 3.6 | 0.5 |
| 1 (400 ppm) | 6 | 0.8 | 0.7 | 1.1 | 0.8 | 10. | 0.0 | 0.8 |

Results and Discussion 3 was slightly lower in Sweet Intensity in Mouth, Overall Max Sweetness, and significantly less Sweet Linger Intensity compared to Reb M. 1 was significantly lower in Sweet Intensity in Mouth, with very little Sweet Intensity being perceived. The Overall Max Sweetness and Sweet Linger were also significantly lower for 1 compared to Reb M.

We claim:

1. A beverage comprising at least one diterpene glycoside of formula (A'):

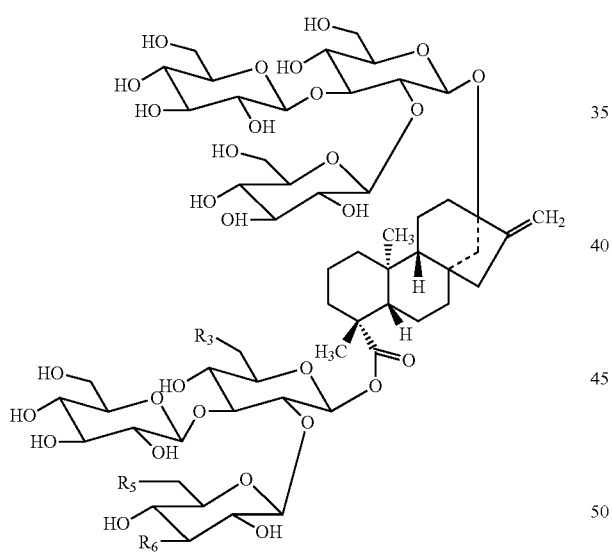

formula (A')

wherein:

$R_3$, $R_5$, and $R_6$ are each independently selected from hydroxyl and an O-linked oligosaccharide comprising from three to six glucoses and the diterpene glycoside has at least nine saccharides; and wherein the concentration of the at least one diterpene glycoside in the beverage is from about 50 ppm to about 600 ppm.

2. The beverage of claim 1, wherein the diterpene glycoside is provided as part of a mixture, and wherein the diterpene glycoside is present in the mixture in an amount greater than about 95% or greater by weight on a dry basis.

3. The beverage of claim 1, wherein the diterpene glycoside is selected from the following:
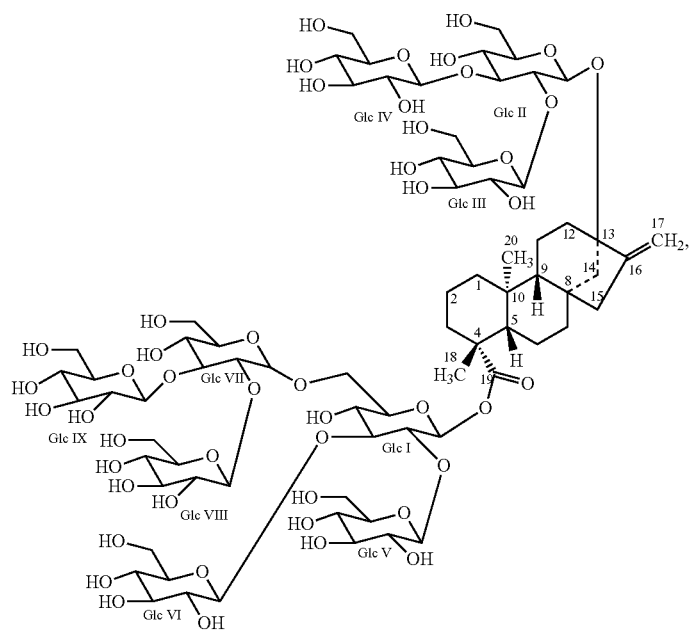
3
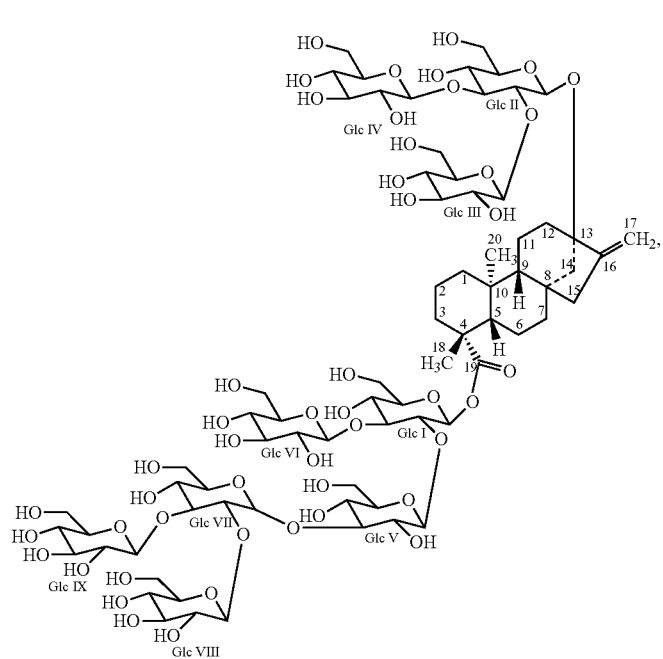
4

-continued

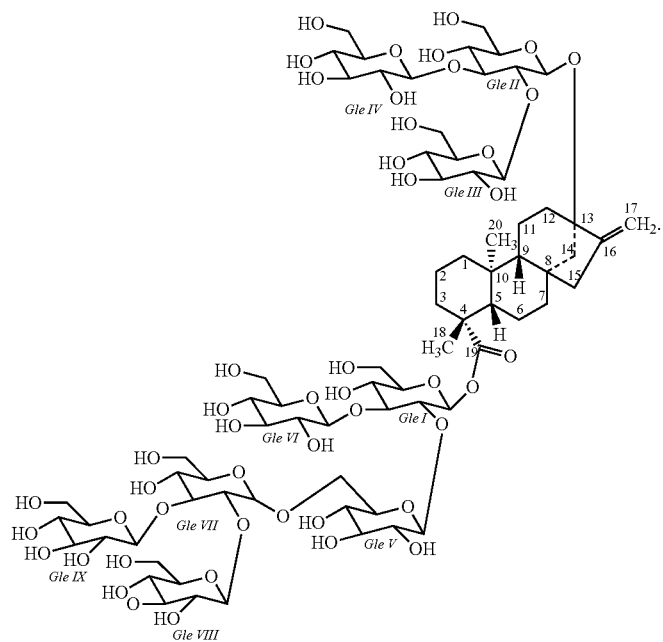

6

4. The beverage of claim 1, wherein beverage is a non-carbonated beverage selected from the group consisting of sports drinks, energy drinks, enhanced water drinks, enhanced water with vitamins, near water drinks, and coconut water.

5. The beverage of claim 4, wherein the beverage is an enhanced water drink.

6. The beverage of claim 5, wherein the beverage further comprises at least one vitamin.

7. The beverage of claim 1, wherein the beverage is a carbonated beverage selected from the group consisting of enhanced sparkling beverages, cola, lemon-lime flavored sparkling beverage, orange flavored sparkling beverage, grape flavored sparkling beverage, strawberry flavored sparkling beverage, pineapple flavored sparkling beverage, ginger-ale, soft drink and root beer.

* * * * *